US012551451B2

(12) United States Patent
Li et al.

(10) Patent No.: US 12,551,451 B2
(45) Date of Patent: Feb. 17, 2026

(54) COMPOSITIONS AND METHODS FOR DELIVERING MOLECULES

(71) Applicant: SunVax mRNA Therapeutics Inc., Beverly, MA (US)

(72) Inventors: Yingzhong Li, Reading, MA (US); Libin Zhang, Lynnfield, MA (US)

(73) Assignee: SUNVAX MRNA THERAPEUTICS INC., Beverly, MA (US)

( * ) Notice: Subject to any disclaimer, the term of this patent is extended or adjusted under 35 U.S.C. 154(b) by 0 days.

(21) Appl. No.: 18/765,147

(22) Filed: Jul. 5, 2024

(65) Prior Publication Data

US 2025/0025428 A1 Jan. 23, 2025

Related U.S. Application Data

(60) Provisional application No. 63/512,154, filed on Jul. 6, 2023.

(51) Int. Cl.

| | |
|---|---|
| ***A61K 9/51*** | (2006.01) |
| ***A61K 47/42*** | (2017.01) |
| ***A61K 48/00*** | (2006.01) |
| ***C07D 251/04*** | (2006.01) |
| ***C07D 295/00*** | (2006.01) |
| ***C12N 15/88*** | (2006.01) |

(52) U.S. Cl.

CPC ............ *A61K 9/5123* (2013.01); *A61K 47/42* (2013.01); *A61K 48/0008* (2013.01); *C07D 251/04* (2013.01); *C07D 295/00* (2013.01); *C12N 15/88* (2013.01)

(58) Field of Classification Search

None

See application file for complete search history.

(56) References Cited

U.S. PATENT DOCUMENTS

| | | | | |
|---|---|---|---|---|
| 2023/0322689 | A1* | 10/2023 | Zhang | B82Y 40/00 |
| 2024/0261223 | A1* | 8/2024 | Zhang | C07C 231/02 |

FOREIGN PATENT DOCUMENTS

| | | | |
|---|---|---|---|
| DE | 31 40 635 | A1 | 4/1983 |
| WO | 2015/199952 | A1 | 12/2015 |
| WO | 2019/152557 | A1 | 8/2019 |
| WO | 2023/196527 | A2 | 10/2023 |
| WO | 2024/145290 | A2 | 7/2024 |

OTHER PUBLICATIONS

Billingsley, et al. (2020) "Ionizable Lipid Nanoparticle-Mediated mRNA Delivery for human CAR T Cell Engineering", Nano Letters, 20: 1578-89. (Year: 2020).*

Singh, et al. (2014) "Differences in control of local versus disseminated neuroblastoma by transiently-modified GD2 CAR T cells due to variability in tumor penetration", Cancer Immunological Research 2(11): 1059-70. (Year: 2014).*

Qin, et al. (2022) "mRNA-based therapeutics: powerful and versatile tools to combat diseases", Signal Transduction and Targeted Therapy, 7: 166; https://doi.org/10.1038/s41392-022-01007-w; 35 pages long. (Year: 2022).*

Moot, et al. (2016) "Genetic engineering of chimeric antigen receptors using lamprey derived variable lymphocyte receptors", Molecular Therapy—Oncolytics, 3: 16026 (7 pages). (Year: 2016).*

Authors unknown, downloaded Jun. 11, 2025, "Isomer", https://en.wikipedia.org/wiki/Isomer, No Journal/Volume/Issue, 9 page PDF version. (Year: 2025).*

International Search Report and Written Opinion for PCT/US2024/036941 mailed Feb. 3, 2025 (21 pages).

Hou Xucheng et al: "Lipid nanoparticles for mRNA delivery", Nature Reviews Materials, Aug. 10, 2021, 9 pages.

* cited by examiner

*Primary Examiner* — Robert M Kelly

(74) *Attorney, Agent, or Firm* — ROTHWELL, FIGG, ERNST & MANBECK, P.C.

(57) ABSTRACT

Compositions comprising mRNA, self-amplifying mRNA (sa-mRNA), modified mRNA, or circular RNA constructs comprising a gene-of-interest, and lipids and LNPs for use in therapy are disclosed. A method of delivering a payload to immune cells ex vivo by contacting immune cells with a lipid nanoparticle (LNP) encapsulating a payload encoding at least one polypeptide of interest, wherein the polypeptide of interest is an antigen receptor or an antibody.

27 Claims, 20 Drawing Sheets

Specification includes a Sequence Listing.

| | heart | liver | spleen | lung | kidney |
|---|---|---|---|---|---|
| P1D4-d1 | 1.75E+05 | 6.53E+07 | 3.03E+07 | 8.59E+05 | 3.94E+05 |
| P51C12-d1 | 9.39E+04 | 4.59E+06 | 1.30E+07 | 5.50E+05 | 1.77E+05 |
| P161F6-d1 | 1.93E+06 | 1.01E+09 | 2.63E+08 | 3.56E+08 | 1.06E+07 |

COMPOSITIONS AND METHODS FOR DELIVERING MOLECULES

SEQUENCE LISTING STATEMENT

The instant application contains a Sequence Listing in electronic format which has been submitted via EFS-Web. Said Sequence Listing, created on Jul. 3, 2024, is named "ST26-5292-108PCT.xml" and is 104,049 bytes in size. The information in the electronic format of the Sequence Listing is part of the present application and is incorporated herein by reference in its entirety.

TECHNICAL FIELD

The present disclosure provides methods for immunotherapy and compositions comprising mRNA, including self-amplifying mRNA (sa-mRNA), modified mRNA, and circular mRNA (circRNA) encoding a protein of the immune system and novel ionizable lipids and lipid nanoparticles (LNPs).

BACKGROUND

Cell therapy is intended to utilize living cells to treat various diseases and conditions. It involves the transplantation or manipulation of cells to restore, repair, or replace damaged or dysfunctional tissues or organs within the body. The cells used in cell therapy can be derived from a variety of sources, including embryonic stem cells, adult stem cells, or immune cells. Ex vivo cell therapy involves harvesting cells from patients or donors, genetically modifying the cells outside of the body to produce the desired therapeutic factors and their subsequent injection back into patients in need thereof.

For example, chimeric antigen receptor T-cell (CAR-T) therapy, a treatment for cancer and autoimmune diseases, generally comprise isolating T-cells from a patient, activating the T-cells, and genetically altering them, for example by using a lentivirus, to express CARs against tumor specific antigens for a known cancer (e.g., a tumor). Following amplification ex vivo to a sufficient number of genetically modified T-cells, the autologous cells are infused back into the patient, resulting in the antigen-specific destruction of the target (e.g. cancer). However, like all cancer treatments, CAR-T cell therapies can cause severe side effects. Furthermore, a challenge associated with CAR-T cell therapy is that it can be very expensive due to the requirement of culturing autologous T-cells ex vivo for engineering using lentiviruses and expansion in animal free media.

There exists a need to develop compounds, compositions, and methods that improve stability, facilitate internalization, and reduce safety concerns in ex vivo cell therapy, such as the engineering of human primary T cells using lentiviruses. The present invention provides nucleic acid based compounds (e.g., modified mRNA, sa-mRNA and circRNA), which encode at least one gene of interest (GOI), such as a CAR-related polypeptide of interest, and which can be delivered with higher transfection efficiency compared to existing mRNA to address one or more of the problems in the art.

There also exists a need to develop compounds, compositions, and methods that deliver the nucleic acid based compounds (e.g., modified mRNA, sa-mRNA and circRNA), which encode at least one gene of interest (GOI), such as a CAR-related polypeptide of interest, in vivo to decrease costs associated with ex vivo expansion and increase accessibility of cell therapy treatments that are currently only available ex vivo. The present invention provides methods for transfecting and activating cells, such as human primary T cells, in vivo.

SUMMARY OF THE INVENTION

The present disclosure includes novel mRNA, including sa-mRNA, modified mRNA and circRNA, and LNP compositions comprising novel ionizable lipids, which improve stability, facilitate internalization, and reduce safety issues associated with increased administrations and cytotoxic effects, and therapeutic applications thereof.

In one aspect, the present disclosure provides a method of delivering a payload to immune cells ex vivo comprising contacting immune cells with a lipid nanoparticle (LNP) encapsulating a payload encoding at least one polypeptide of interest, wherein the polypeptide of interest is an antigen receptor or antibody.

In one aspect, the present disclosure provides a method of delivering at least one mRNA molecule encoding a CAR to a subject in need thereof, comprising administering a LNP of the present disclosure to the subject, wherein the LNP delivers the mRNA molecule encoding CAR to a cell or target in the subject. In some aspects, the target may be selected from the group consisting of an immune cell, T cell, resident T cells, B cell, natural killer (NK) cell, monocytes, macrophages, cancerous cell, cell associated with a disease or disorder, tissue associated with a disease or disorder, brain tissue, central nervous system tissue, pulmonary tissue, apical surface tissue, epithelial cell, endothelial cell, liver tissue, intestine tissue, colon tissue, small intestine tissue, large intestine tissue, feces, bone marrow, macrophages, spleen tissue, muscles tissue, joint tissue, tumor cells, diseased tissues, lymph node tissue, lymphatic circulation, and any combination thereof.

In one aspect, the present disclosure provides a method of delivering a payload to immune cells in vivo comprising administering an LNP encapsulating a payload encoding at least one polypeptide of interest to a subject, wherein the polypeptide of interest is antigen receptor or antibody.

In one aspect, the immune cells are T-cells, natural killer (NK) cells, or monocytes. In some aspects, the immune cells are human T-cells. In some aspects, the antigen receptor is a chimeric antigen receptor (CAR), T-cell receptor (TCR), growth factor receptor (GFR), or hormone receptor (HR). In some aspects, the antibody is a natural antibody or a synthetic antibody. In some aspects, the synthetic antibody is a nanobody (Nb).

In one aspect, the present disclosure provides an ionizable lipid compound, wherein the compound is a compound of Formula I:

(I)

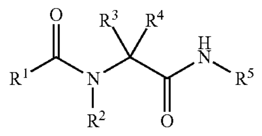

or a salt or isomer thereof, wherein each $R^1$, $R^2$, $R^3$, $R^4$ and $R^5$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

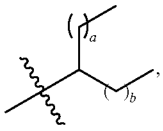,
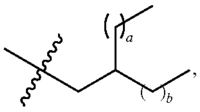,
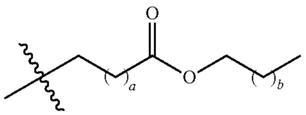
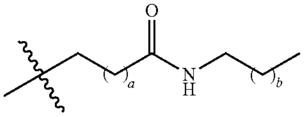,
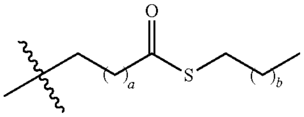,
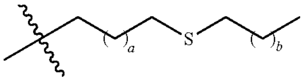,
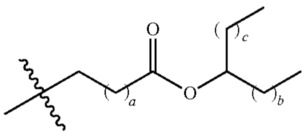,
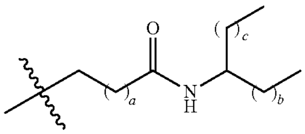,
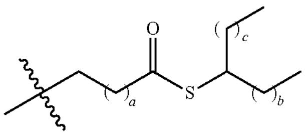,
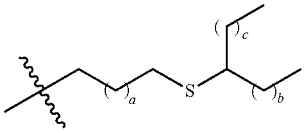,
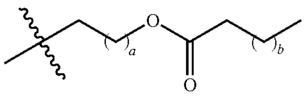,
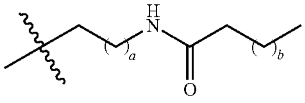,
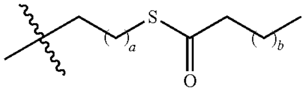,
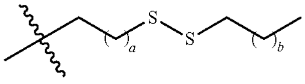,
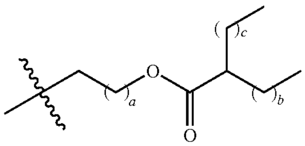,
-continued
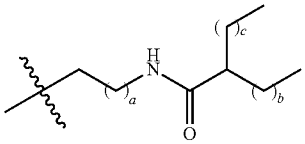,
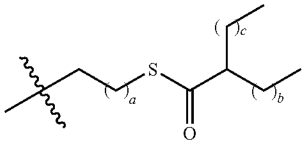,
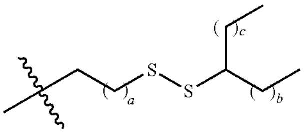,
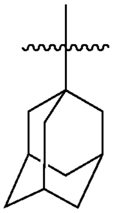,
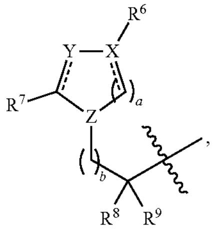,
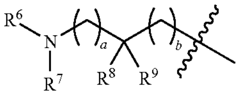
a, b and c are each independently an integer from 0-24; each $R^6$, $R^7$, $R^8$ and $R^9$ are independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,
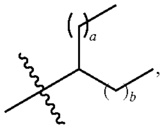,
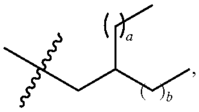,
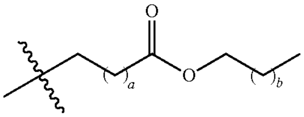,
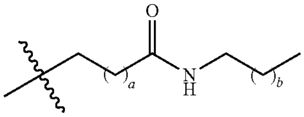,
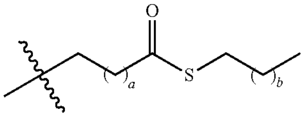,
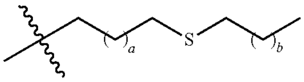,
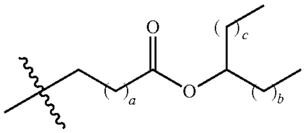, -continued
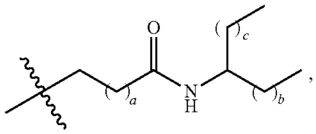
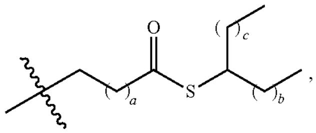
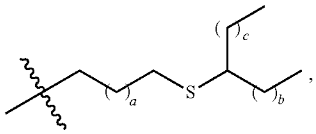
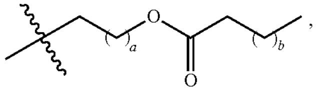
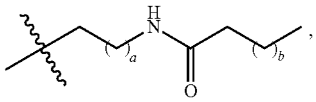
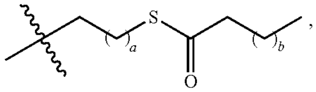
-continued
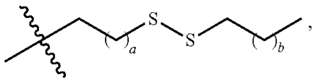
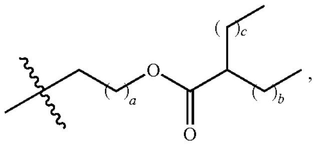
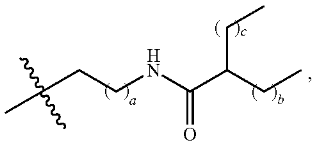
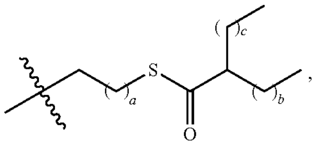
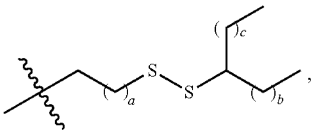
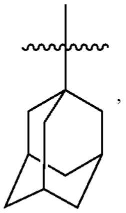
a, b and c are each independently an integer from 0-24; each X is independently selected from CH, N; each Y is independently selected from $CH_2$, NH, O, or S; each Z is independently selected from CH or N.
In some aspects, the compound is:
(I) or P6A2
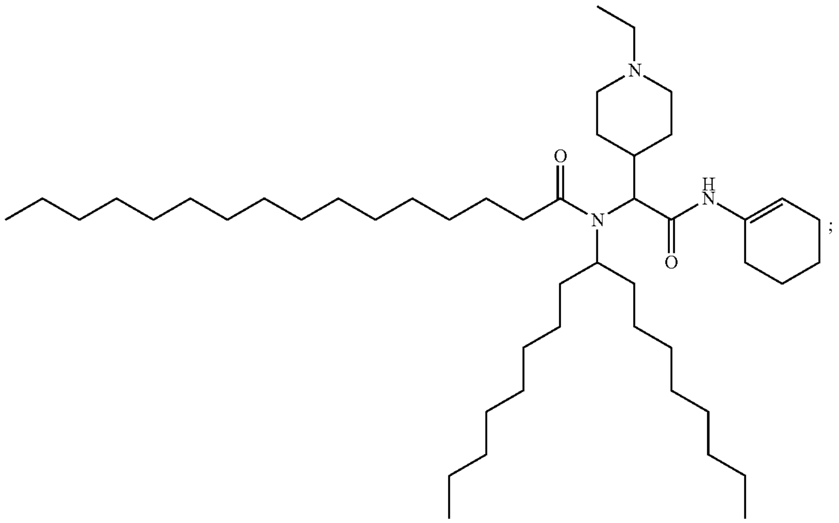

-continued
(II) or P1D4
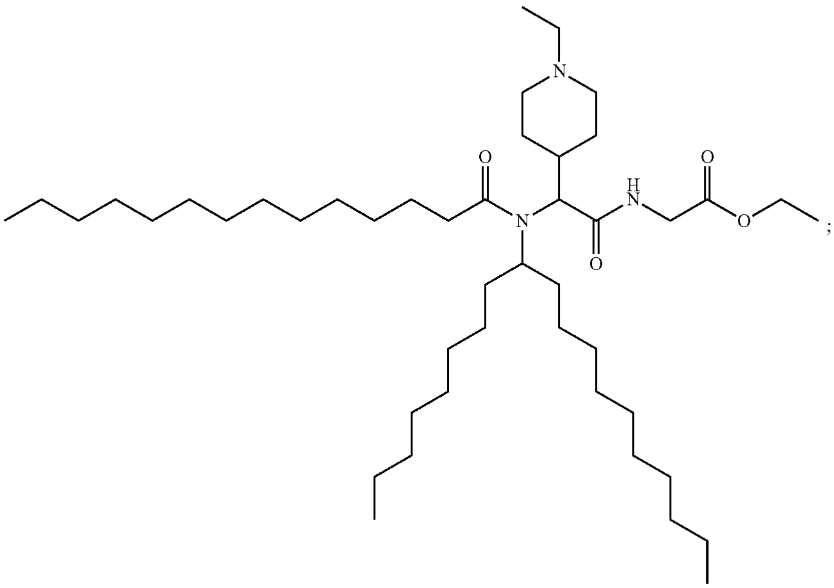
;
(III) or P30B7
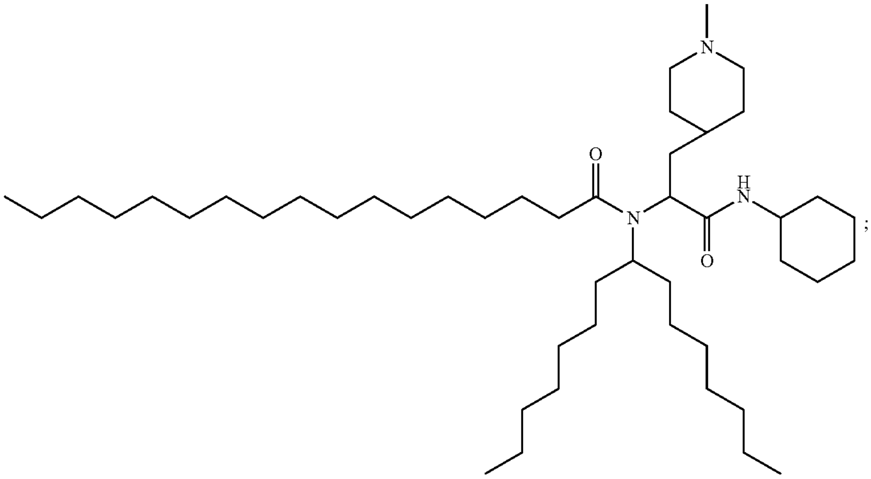
;
(IV) or P30A1
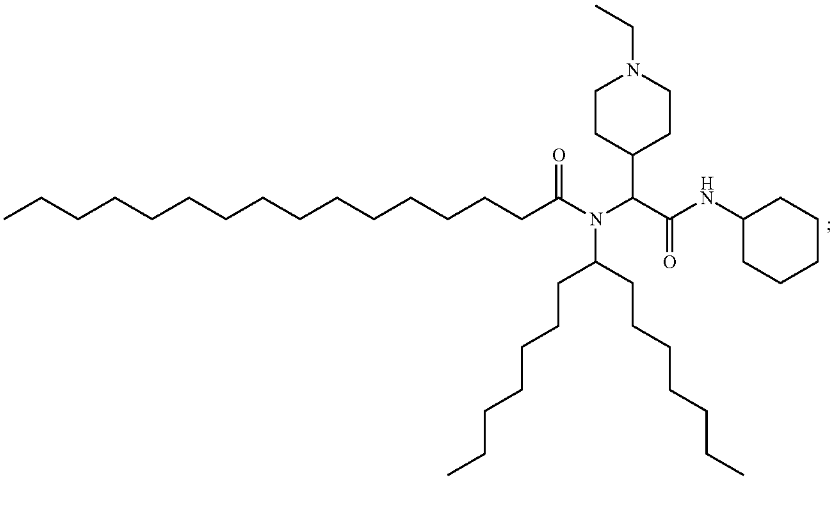
;

-continued
(V) or P54B6
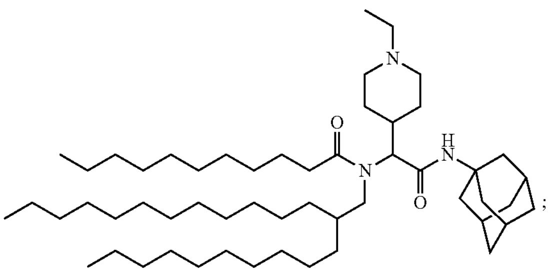
;
(VI) or P38D1
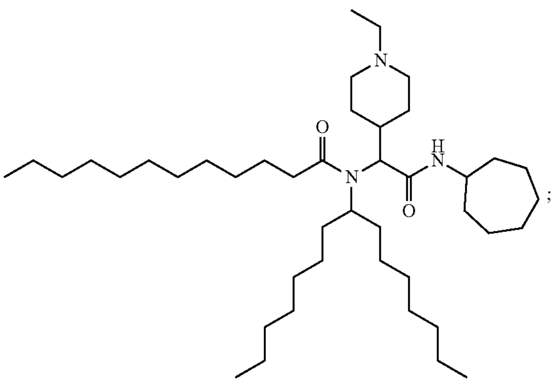
;
(VII) or P51C12
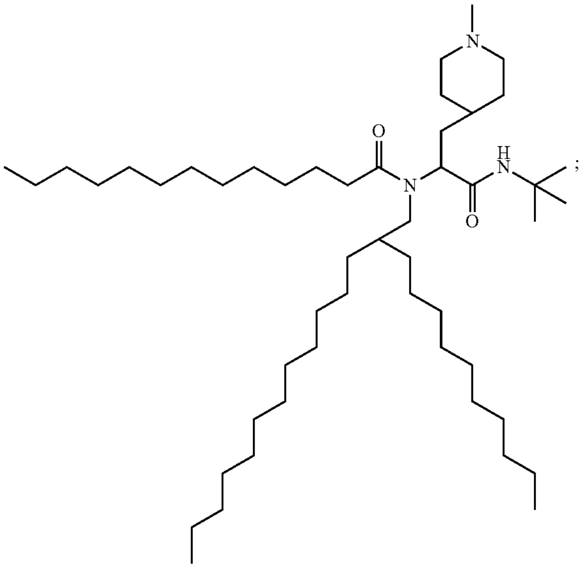
;
(VIII) or P53A6
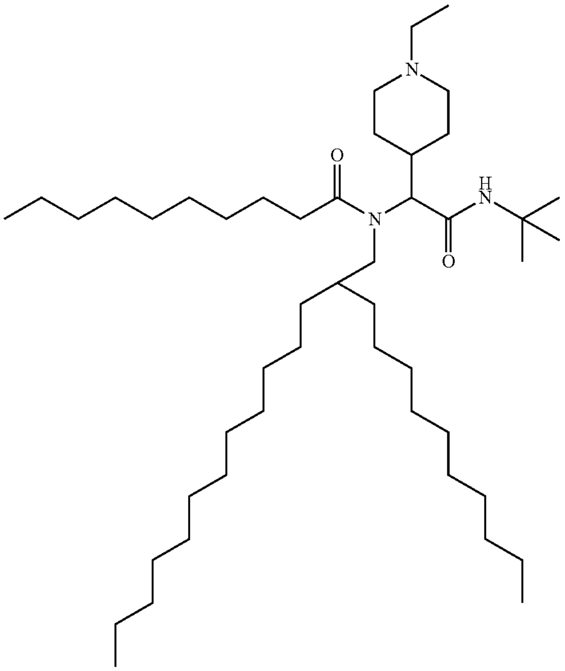
;
(IX) or P40D7
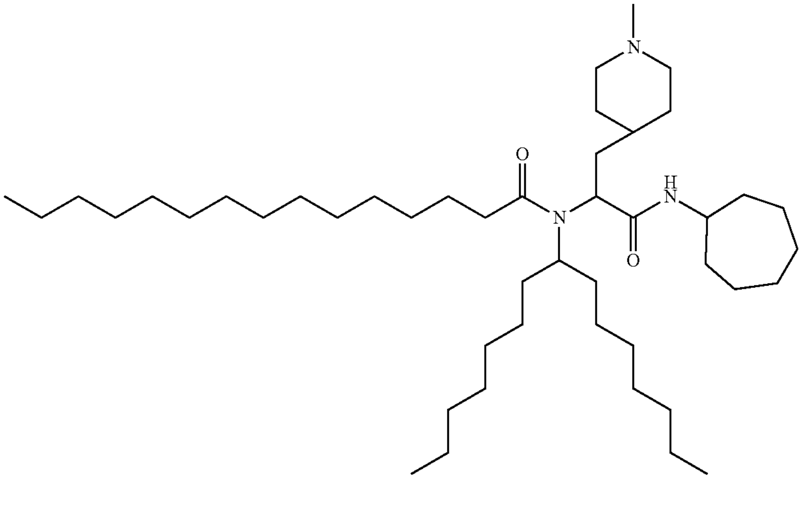
;

-continued
(X) or P149A2
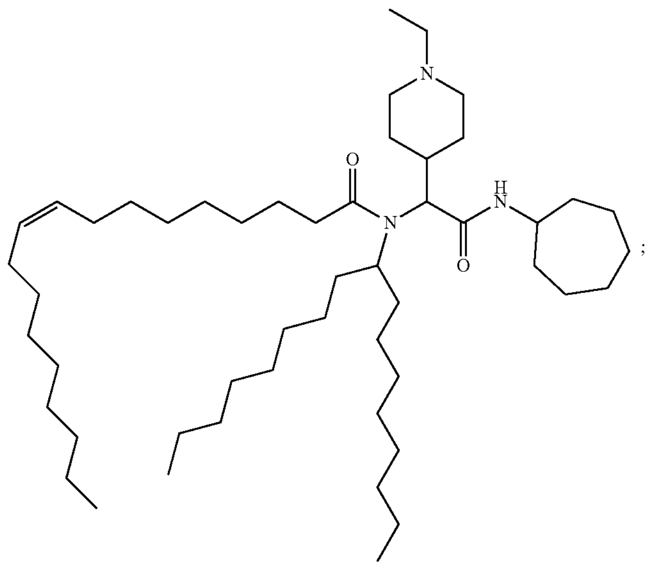
(XI) or P153C3
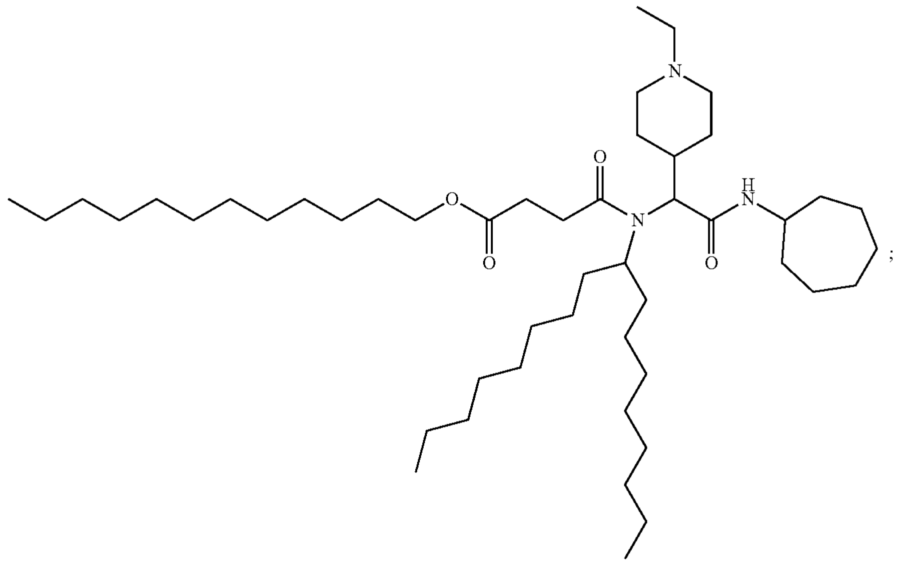

-continued
(XII) or P153C5
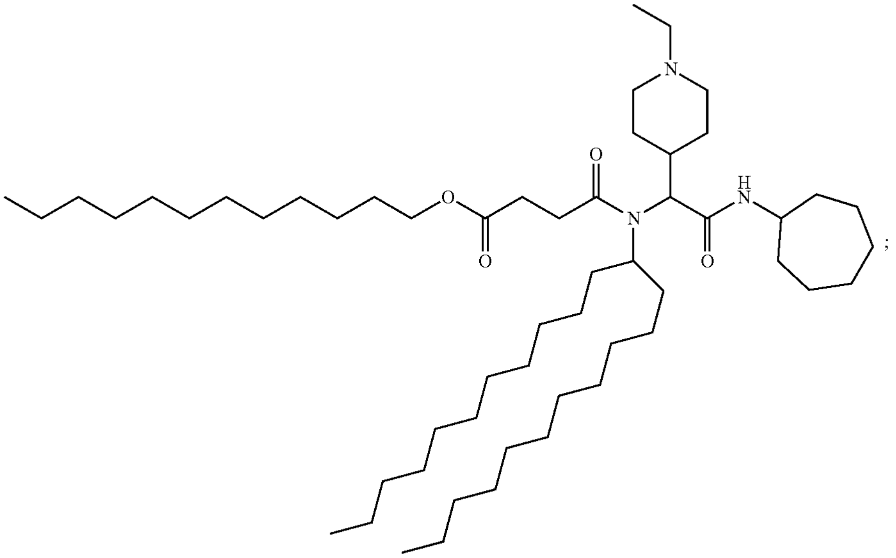
(XIII) or P30C7
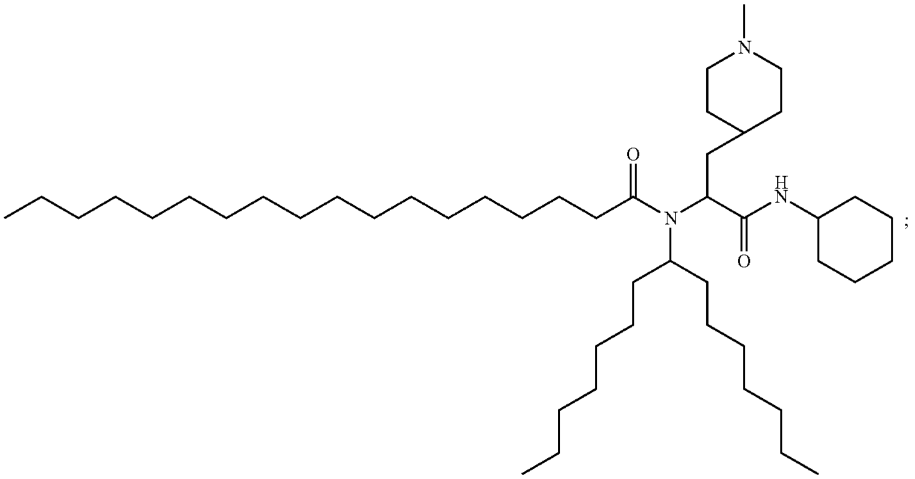
(XIV) or P30C7
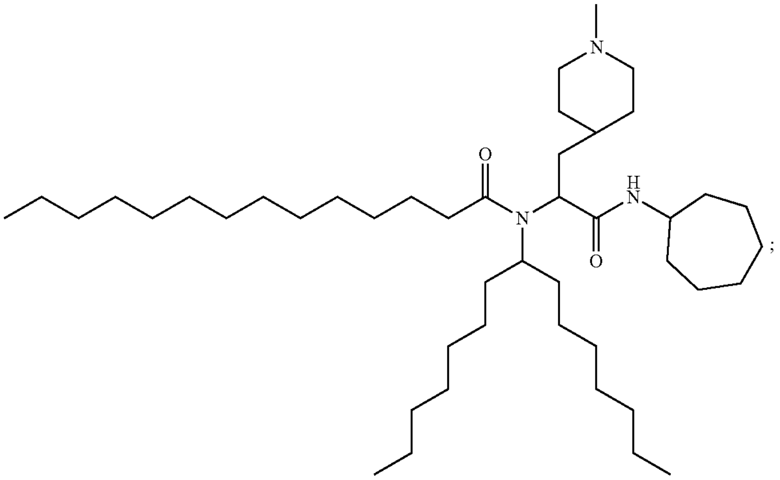
or P38D7

-continued
(XV) or P38D8
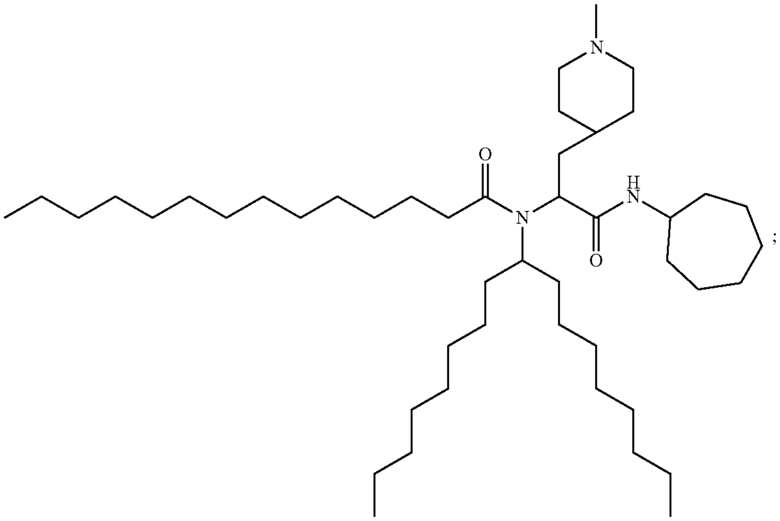
or P38D8
(XVI) or P56A1
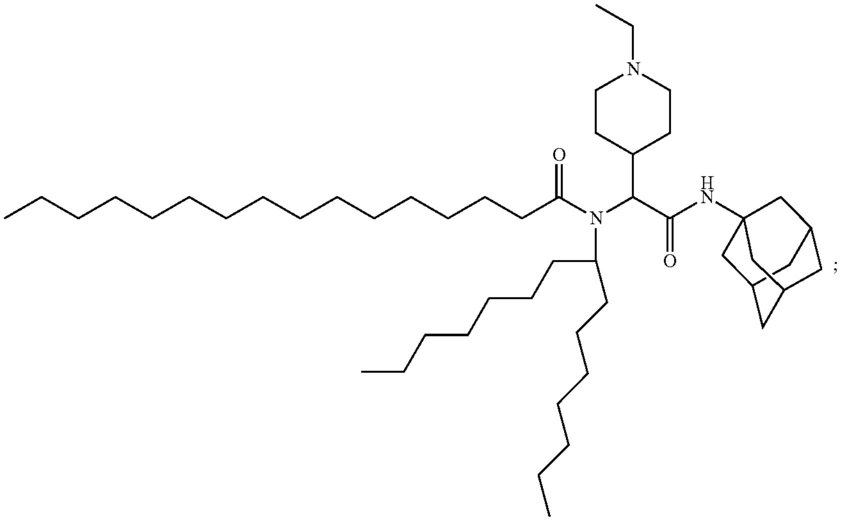

(XVII) or P56B1
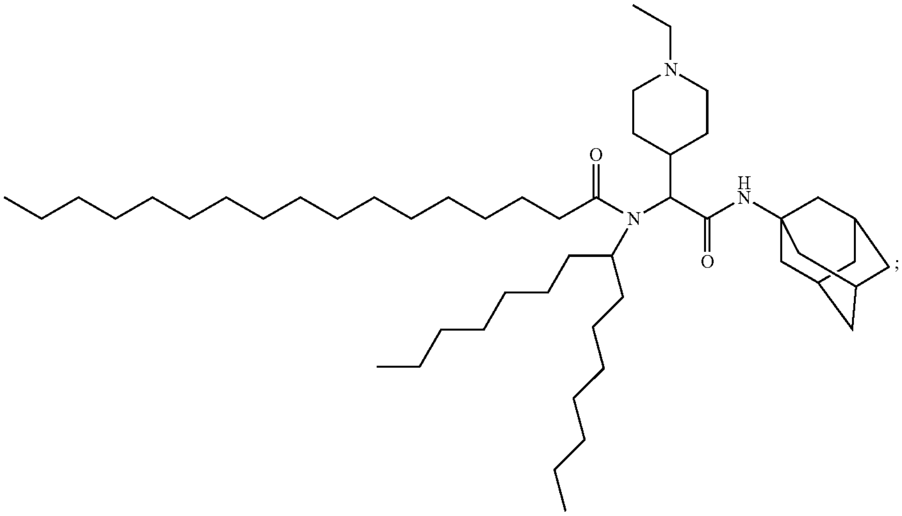
;
(XVIII) or P28D10
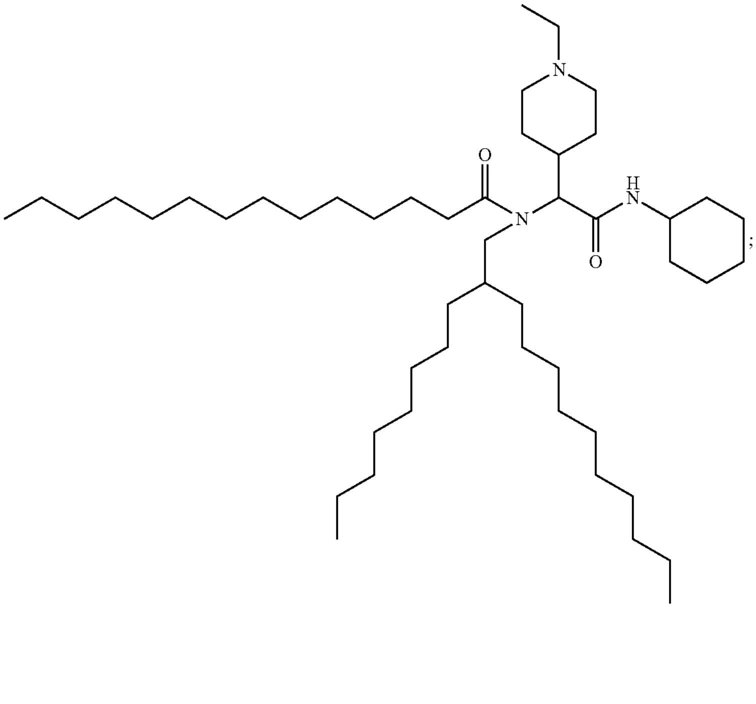
;

-continued
(XIX) or P56A2
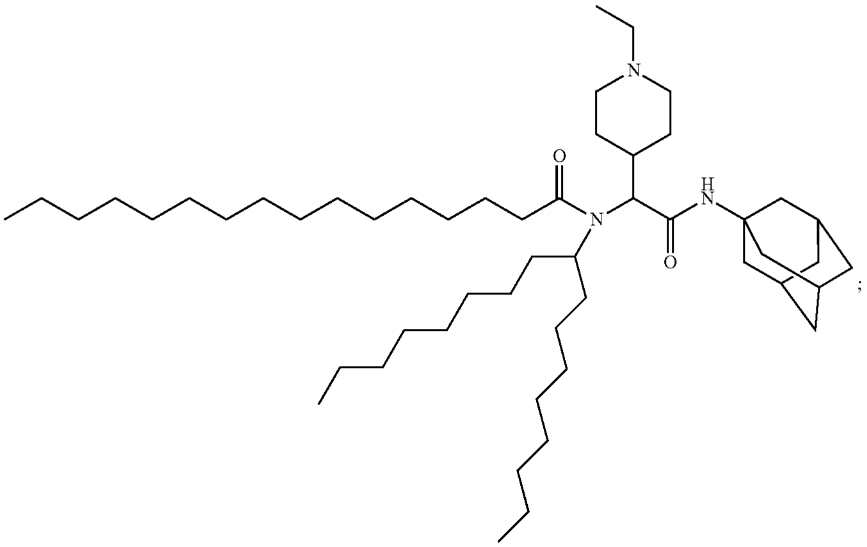
(XX) or P38D4
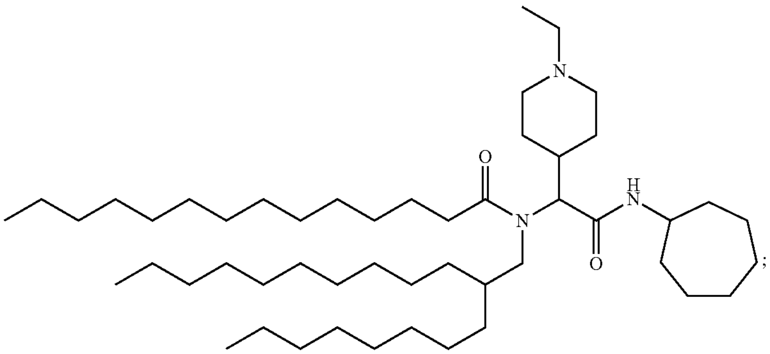
(XXI) or P161F10
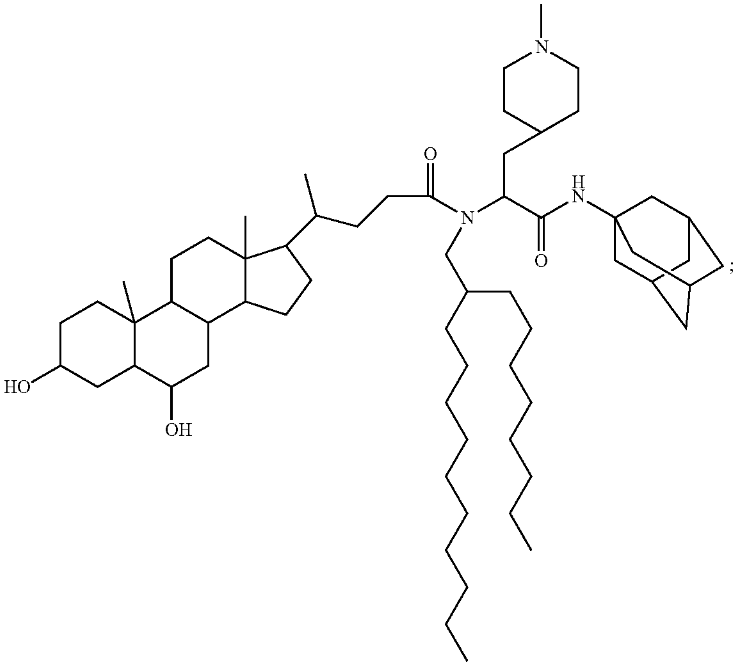

-continued
(XXII) or P159C10
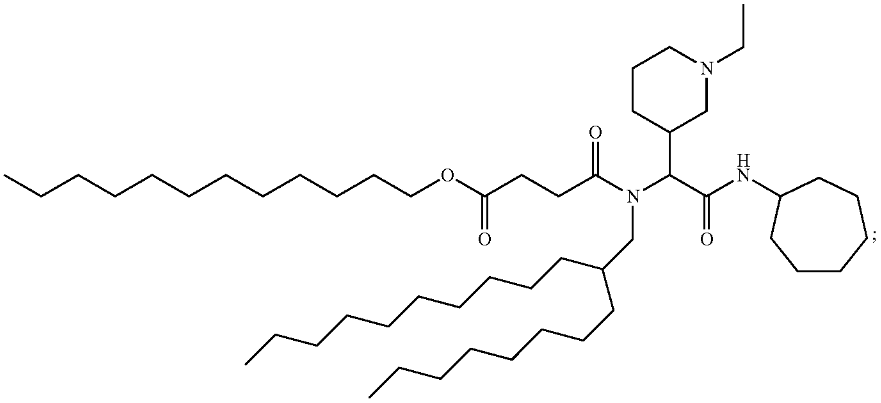
(XXIII) or P149A1
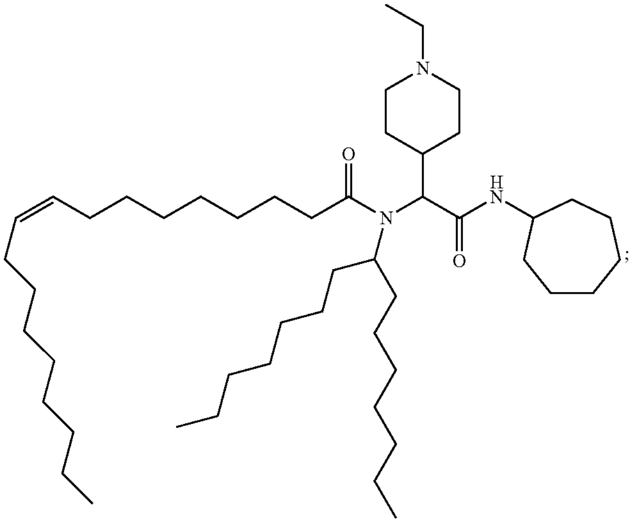
(XXIV) or P153C1
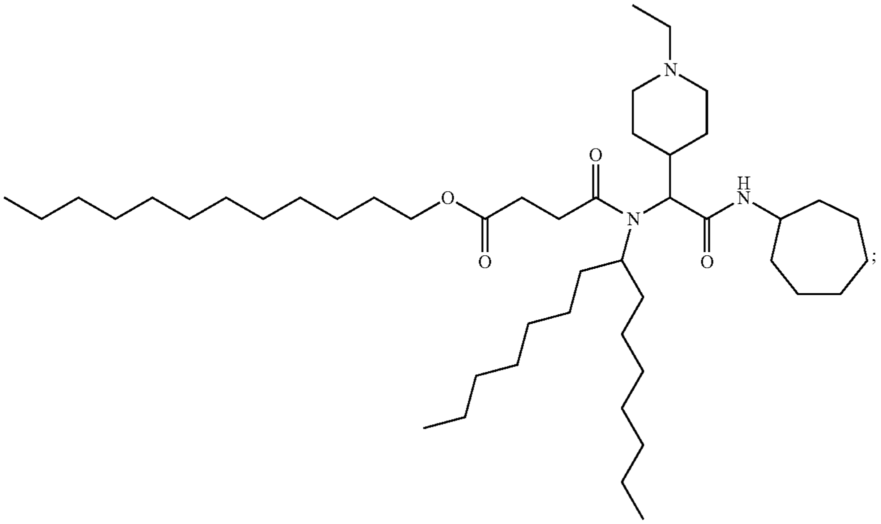

-continued
(XXV) or P40B10
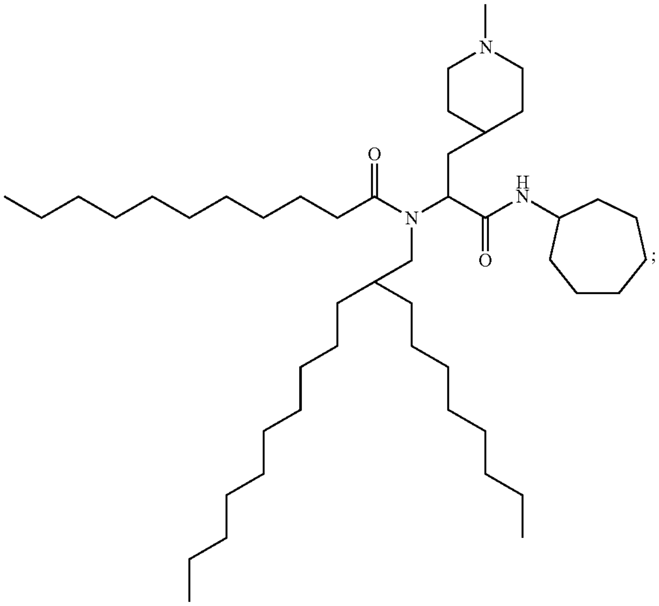
(XXVI) or P40C11
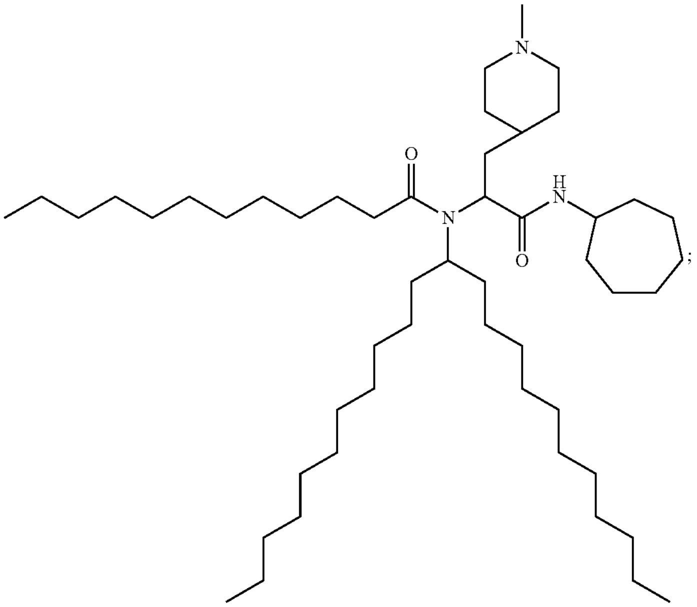

-continued
(XXVII) or P53A5
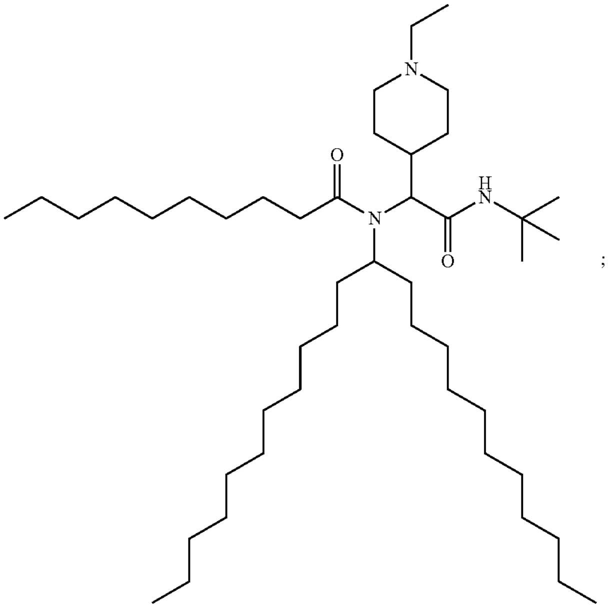
;
(XXVIII) or P40C10
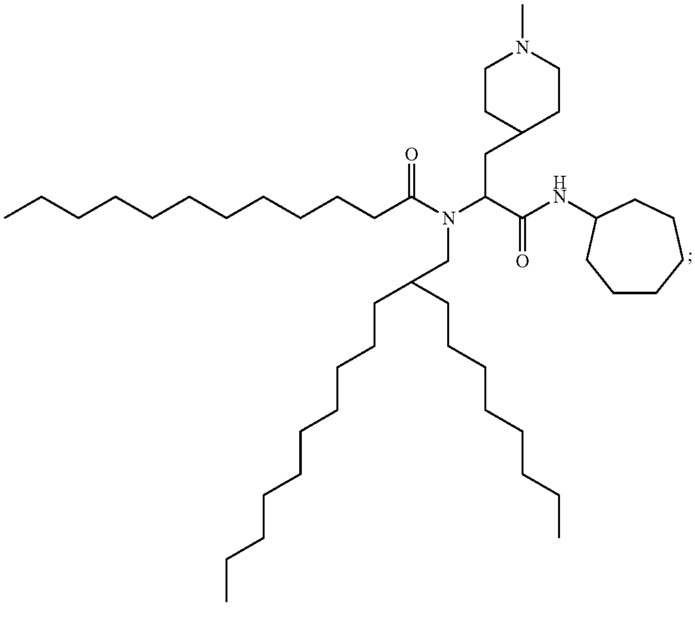
;

(XXIX)
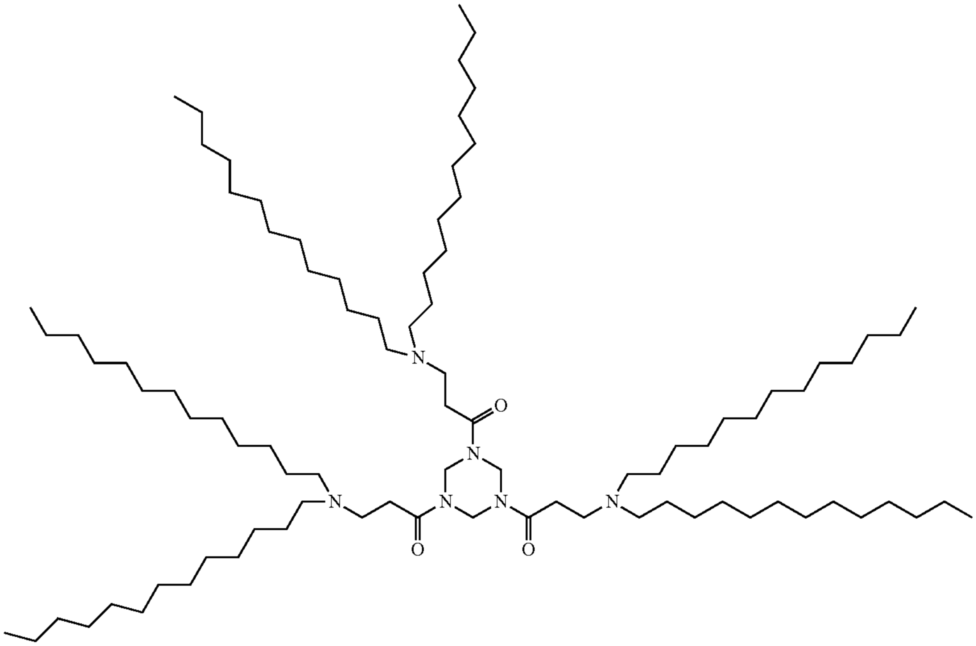
or E6;
(XXX)
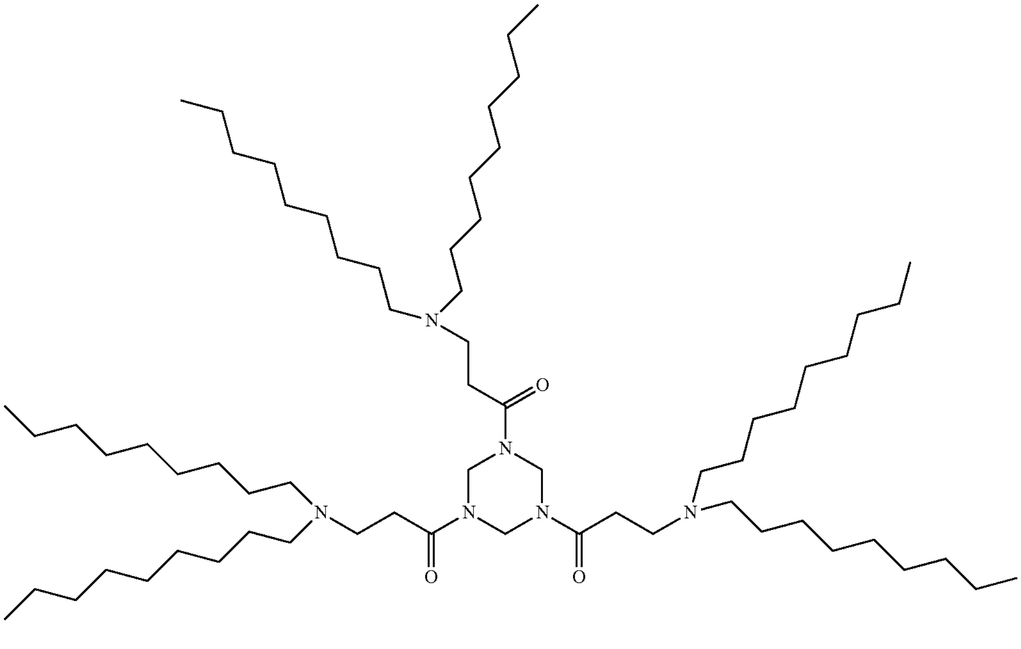
or E2;

-continued (XXXI)

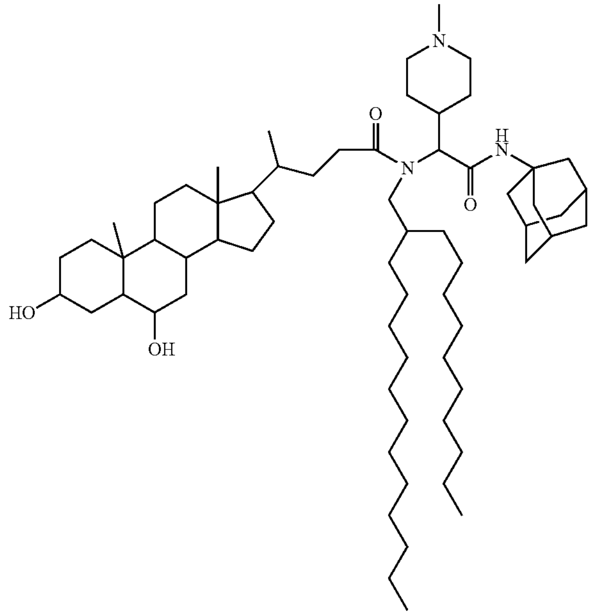

or P161F6;

(XXXII)

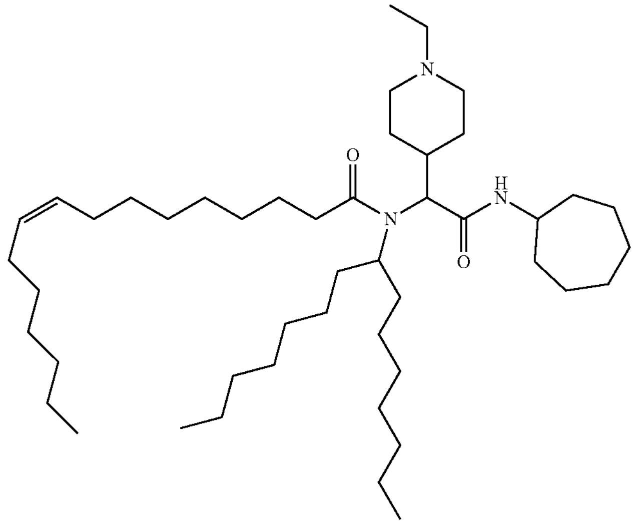

or P149C2;

or a salt or isomer thereof.

In one aspect, the payload is an mRNA comprising a nucleic acid sequence encoding from 5' to 3':

LP-Nb wherein, LP is a leading peptide; and Nb is a nanobody.

In one aspect, the payload is an mRNA comprising a nucleic acid sequence encoding from 5' to 3':

LP-AR wherein, LP is a leading peptide; and AR is an antigen receptor.

In one aspect, the payload is an mRNA comprising a nucleic acid sequence encoding from 5' to 3':

LP-CAR wherein, LP is a leading peptide; and CAR encodes from 5' to 3': VH-LK-VL-CD8-CD28-CD3z wherein, VH is the variable region of a immunoglobulin heavy chain, LK is a linker, VL is the variable region of an immunoglobulin light chain, CD8 is the hinge region of a CD8 alpha chain, CD28 is a CD28 activation domain, and CD3z is a CD3 zeta cytoplasmic domain.

The molecules of the present disclosure may encode one or more GOIs. In one aspect, the GOI encodes more than one gene of interest. In one aspect, the GOI is a reporter gene. In one aspect, the reporter gene encodes a green fluorescent protein (GFP) or an epitope tag. In one aspect, the epitope tag is a Myc-tag. In one aspect, the GOI encodes a CAR. In one aspect, the GOI encodes a therapeutic polypeptide. In one aspect, the GOI encodes a prophylactic polypeptide. In one aspect, the GOI encodes a helper protein.

In one aspect, the payload is an mRNA comprising a nucleic acid sequence encoding from 5' to 3':

LP-VH-LK-VL-MyC-CD8-CD28-CD3z wherein, LP is a leading peptide; VH is the variable region of a immunoglobulin heavy chain; LK is a linker; VL is the variable region of an immunoglobulin light chain; MyC is a Myc tag; CD8 is the hinge region of a CD8 alpha chain; CD28 is a CD28 activation domain; and CD3z is a CD3 zeta cytoplasmic domain.

In one aspect, the LP encodes an amino acid sequence with at least about 85, 90, 95, 98, or 99% sequence identity to SEQ ID NO: 1. In one aspect, the LK encodes an amino acid sequence with at least about 85, 90, 95, 98, or 99% sequence identity to SEQ ID NO: 2. In one aspect, the Myc encodes an amino acid sequence with at least about 85, 90, 95, 98, or 99% sequence identity to SEQ ID NO: 3. In one aspect, the CD8 encodes an amino acid sequence with at least about 85, 90, 95, 98, or 99% sequence identity to SEQ ID NO: 4 or SEQ ID NO: 7. In one aspect, the CD28 encodes an amino acid sequence with at least about 85, 90, 95, 98, or 99% sequence identity to SEQ ID NO: 5 or SEQ ID NO: 8. In one aspect, the CD3z encodes an amino acid sequence with at least about 85, 90, 95, 98, or 99% sequence identity to SEQ ID NO: 6 or SEQ ID NO: 9.

In one aspect, the mRNA encodes from 5' to 3': (SEQ ID NO: 1)-VH-(SEQ ID NO: 2)-VL- (SEQ ID NO: 3)- (SEQ ID NO: 4)- (SEQ ID NO: 5)- (SEQ ID NO: 6). In one aspect, the mRNA encodes from 5' to 3': (SEQ ID NO: 1)-VH-(SEQ ID NO: 2)-VL- (SEQ ID NO: 3)- (SEQ ID NO: 7)- (SEQ ID NO: 8)- (SEQ ID NO: 9).

In one aspect, the mRNA is a self-amplifying mRNA, a modified mRNA, or a circular RNA. In one aspect, the modified mRNA is a modified mRNA, a modified self-amplifying mRNA, or a modified circular RNA.

In one aspect, the payload is a sa-mRNA comprising a nucleic acid sequence from 5' to 3':

a) 5'UTR-nsP-L-GOI-L-3'UTR-PolyA b) 5'UTR-nsP-GOI-L-3'UTR-PolyA;

c) 5'UTR-nsP-L-GOI-3'UTR-PolyA; or d) 5'UTR-nsP-SGP-GOI-3'UTR-PolyA wherein 5'UTR is a 5' untranslated region, nsP is a plurality of non-structural replicase domain sequences, L is a linker, SGP is a subgenomic promoter, GOI is one or more genes of interest, 3'UTR is a 3' untranslated region, and poly-A is a 3' poly-adenylated tail (poly-A tail).

In one aspect, at least one GOI is a reporter gene. In some aspects, the reporter gene is green fluorescent protein (GFP) or an epitope tag. In some aspects, the epitope tag is a Myc-tag. In some aspects, at least one GOI encodes a CAR, a TCR, a GFR, a HR, or a Nb. In one aspect, SGP is a viral promoter that is recognized by viral RNA dependent RNA polymerase.

In one aspect, the plurality of non-structural replicase domain sequences are obtained from a Group IV positive single strand RNA virus selected from the group comprising Picornaviridae, Togaviridae, Coronaviridae, Hepeviridae, Caliciviridae, Flaviviridae, and Astroviridae. In one aspect, the plurality of non-structural replicase domain sequences are obtained from an alphavirus selected from the group comprising Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus. In one aspect. the plurality of non-structural replicase domain sequences are alphavirus nonstructural proteins 1-4 (nsP1-4). In one aspect, the plurality of non-structural replicase domain sequences are obtained from the TC-83 strain of Venezuelan Equine Encephalitis virus (VEE).

In one aspect, uridine (U) nucleotide residues of the mRNA, including sa-mRNA of the disclosure are substituted with nucleotide residues selected from the group consisting of 1-methylpseudouridine (m1Ψ) or pseudouridine (Ψ) to produce a modified mRNA.

In one aspect, the present disclosure provides a method of increasing transfection efficiency of mRNA, wherein the mRNA comprise at least one GOI encoding a CAR, a TCR, a GFR, a HR, a Nb, scFv or a reporter said method comprising substituting uridine (U) nucleotide residues of a reference mRNA with nucleotide residues selected from the group consisting of 1-methylpseudouridine (m1Ψ) and pseudouridine (Ψ), thereby rendering modified mRNA, wherein the modified mRNA shows increased transfection efficiency than the reference mRNA. In some aspects, the reference mRNA is a sa-mRNA. In some aspects, the reference mRNA is a circRNA. In some aspects, the modified mRNA is a sa-mRNA. In some aspects, the modified mRNA is a circRNA.

In some aspects, the modified mRNA exhibits enhanced ability to produce a CAR, a TCR, a GFR, a HR, a nanobody, or a reporter in an immune cell compared to the same quantity of a reference mRNA that exhibit same sequence but with uridine in place of said at least one modified nucleoside selected from the group consisting of 1-methylpseudouridine and pseudouridine, wherein said enhanced ability to produce said the CAR, TCR, GFR, HR, Nb, or reporter is determined by measuring a higher level of either the amount of the CAR, TCR, GFR, HR, Nb, or reporter or other biological effect produced at one or more times after said contacting of said cell with said modified mRNA compared to the corresponding amount of the CAR, TCR, GFR, HR, Nb, or reporter or other biological effect produced in the same or equivalent immune cell at the same times after contacting with the same quantity of the reference mRNA. In one aspect, the immune cell is a T-cell, a NK cells, or a monocyte. In one aspect, the immune cell is a human T-cell.

In one aspect, the sa-mRNA, modified mRNA, or circRNA, is delivered to the T-cell using a lipid nanoparticle (LNP). In one aspect, the lipid nanoparticle comprise an ionizable lipid compound of the disclosure.

In one aspect, the LNP further comprises a phospholipid selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

In one aspect, the LNP further comprises a structural lipid selected from the group consisting of cholesterol, fecosterol, sitosterol, ergosterol, campesterol, stigmasterol, brassicasterol, tomatidine, ursolic acid, alpha-tocopherol, and mixtures thereof. In some aspects, the structural lipid is cholesterol.

In one aspect, the LNP further comprises a PEG lipid selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, a PEG-modified myristoyl diglyceride, and mixtures thereof.

In one aspect, the present disclosure provides a method of treating a subject in need of CAR-T therapy, comprising modifying a T-cell by (i) delivering a sa-mRNA or modified mRNA, including a modified sa-mRNA, encoding CAR to a T-cell, (ii) maintaining the T-cell under conditions suitable for expression of CAR, and (iii) administering the modified T-cell of (ii) to the subject. In one aspect, the T-cell is isolated from the subject. In one aspect, the sa-mRNA or modified mRNA, including modified sa-mRNA, encoding CAR is delivered using an LNP comprising at least one ionizable lipid of the disclosure.

In one aspect, the present disclosure provides a method of treating a subject in need of cell therapy, comprising modifying an immune cell by (i) delivering a mRNA encoding at least one polypeptide of interest, wherein the polypeptide of interest is an antigen receptor or antibody, (ii) maintaining the immune cell under conditions suitable for expression of the polypeptide of interest to produce a modified immune cell, and (iii) administering the modified immune cell to the subject.

In one aspect, the present disclosure provides a method of treating a subject in need of CAR-T therapy, comprising modifying a T-cell by (i) delivering a mRNA encoding CAR to the T-cell, (ii) maintaining the T-cell under conditions suitable for expression of CAR to produce a modified T-cell, and (iii) administering the modified T-cell to the subject. In one aspect, the T-cell is isolated from the subject. In some aspects, the mRNA encoding CAR is delivered using an LNP comprising at least one ionizable lipid of the disclosure. In some aspects, the mRNA is a self-amplifying mRNA, a modified mRNA, or a circular RNA. In some aspects, the modified mRNA is a modified mRNA, a modified self-amplifying mRNA, or a modified circular RNA. In some aspects, the LNP comprises the ionizable lipid, the phospholipid, the cholesterol, and the PEG lipid in a mole ratio of 15 to 40:15 to 40:30 to 55:0.5 to 5. In some aspects, the LNP comprises the ionizable lipid, the phospholipid, the cholesterol, and the PEG lipid in a mole ratio of 20 to 35:20 to 35:35 to 50:1 to 4. In some aspects, the LNP comprises the ionizable lipid, the phospholipid, the cholesterol, and the PEG lipid in a mole ratio of 25 to 35:25 to 35:40 to 50:1.5 to 3.

In some aspects, the nanoparticle composition of the present invention are employed with another therapeutic compound separate from the nanoparticle for treatment of the same indication in the subject. In particular cases, the LNPs and the therapeutic agent are delivered separately or together. When delivered together, they may or may not be in the same formulation, and they may or may not be delivered by the same route.

Each of the aspects of the present disclosure can encompass various elements of the present disclosure. It is, therefore, anticipated that each of the aspects of the present disclosure involving any one element or combinations of elements can be included in each aspect of the present disclosure. This disclosure is not limited in its application to the details of construction and the arrangement of components set forth in the following detailed description or illustrated in the drawings.

BRIEF DESCRIPTION OF THE DRAWINGS

FIG. 11A shows the FACS gating strategies used, and FIG. 11B shows percentages of transfected CD8, CD4, and CD4/CD8 double positive T cells (DP).

Figure 1:
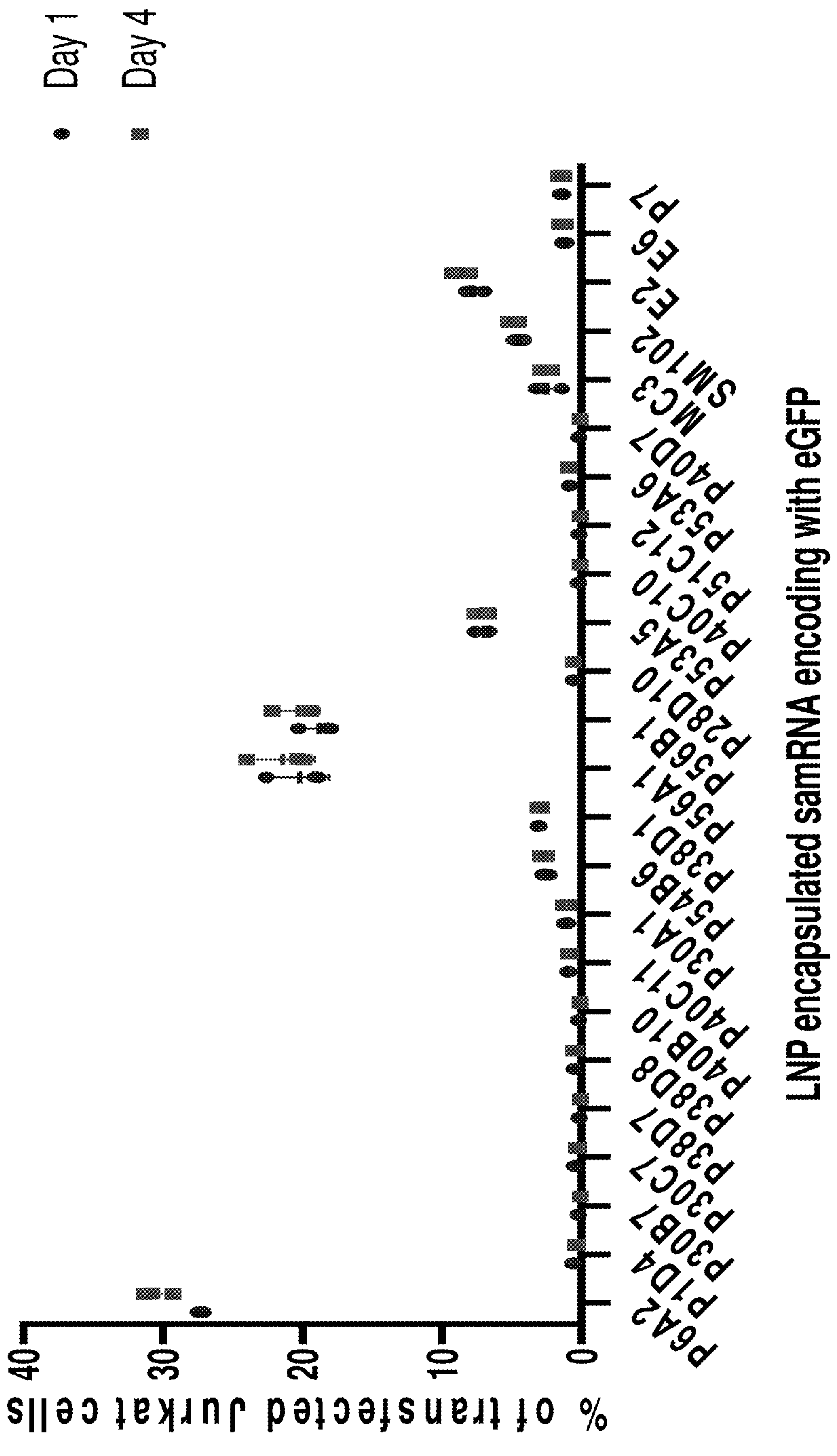
FIG. 1 show the transfection efficiency of the sa-mRNA of the disclosure encoding eGFP delivered into human Jurkat T cells using LNPs formulated using the novel ionizable lipids of the disclosure compared to two control LNP formulations (MC3 and SM102). The ionizable lipids are used for LNPs are as indicated on the x-axis. Shown are percentages of transfected cells (Y-axis) versus LNPs at 1 and 4 days post transfection.
Figure 2A:
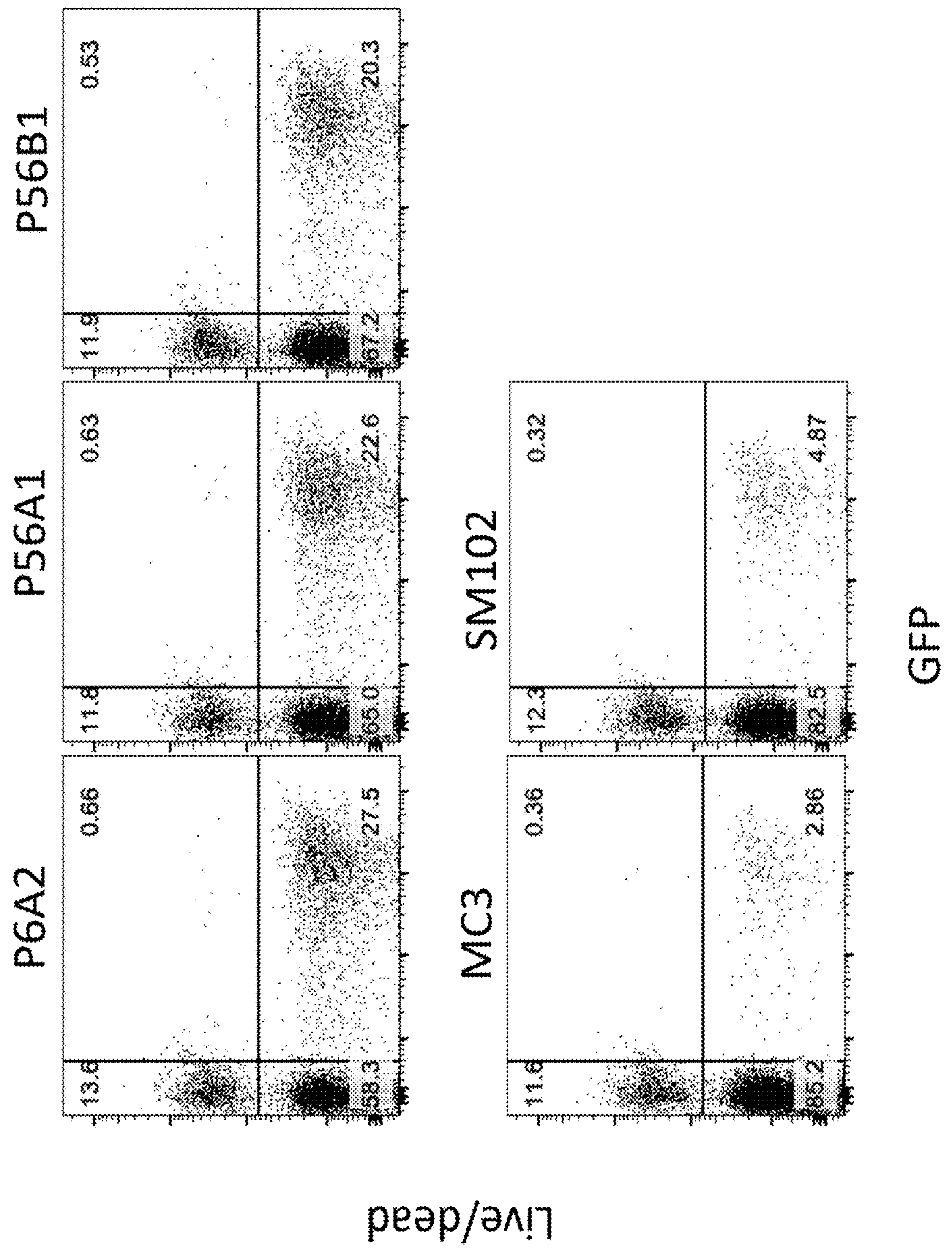
FIG. 2A shows FACS of the sa-mRNA of the disclosure encoding eGFP delivered into human Jurkat T cells using LNPs formulated using the novel ionizable lipids of the disclosure compared to two control LNP formulations (MC3 and SM102). The GFP positive live cells are as indicated in Q3. GFP expression is shown on the x-axis, live/dead cells are shown on the y-axis at 1 day post-transfection.
Figure 2B:
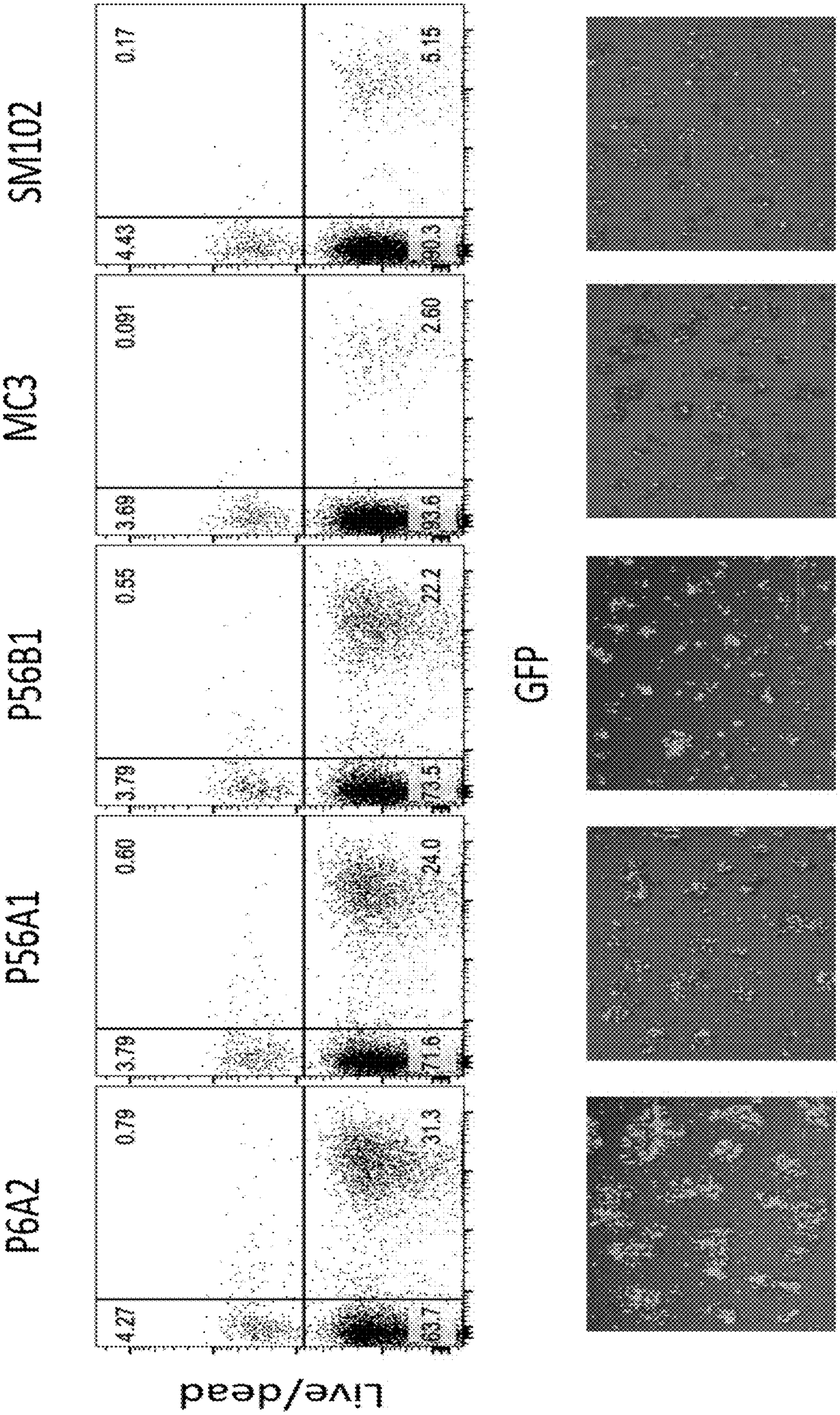
FIG. 2B shows GFP expression at 4 day post transfection.
Figure 3A:
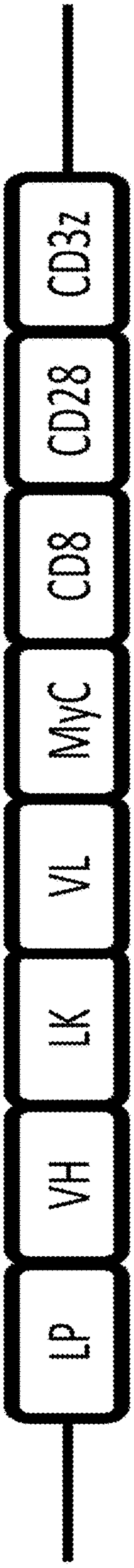
FIG. 3A shows a schematic of the GOI of a sa-mRNA, wherein, LP is a leading peptide; VH is the variable region of a immunoglobulin heavy chain; LK is a linker; VL is the variable region of an immunoglobulin light chain; MyC is a Myc tag; CD8 is the hinge region of a CD8 alpha chain; CD28 is a CD28 activation domain; and CD3z is a CD3 zeta cytoplasmic domain. The VH, VL, CD8, CD28, CD3z, and optionally LK regions represent CAR.
Figure 3B:
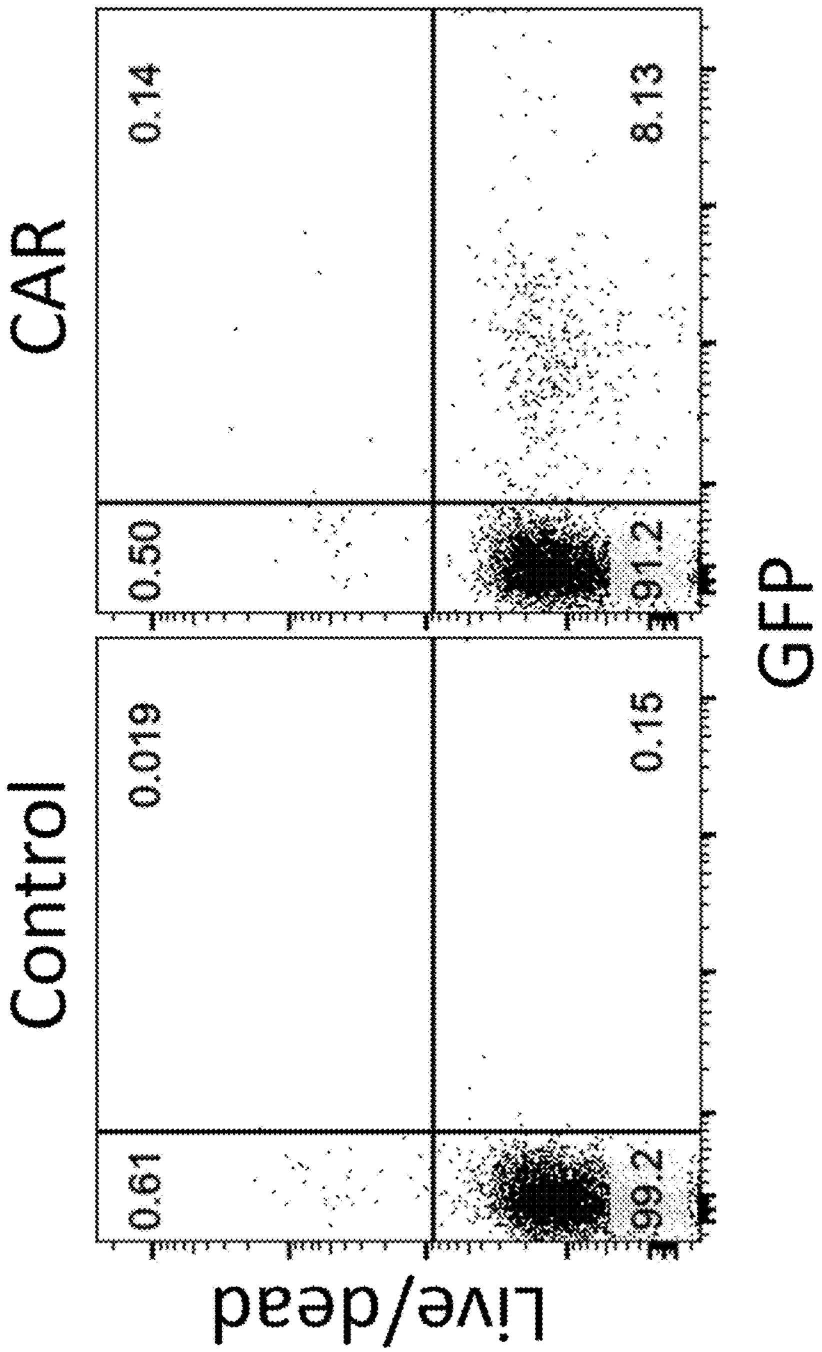
FIG. 3B shows FACS of novel ionizable lipid P6 formulated LNPs encapsulating a self-amplifying m-RNA encoding chimeric antigen receptor (CAR) according to the schematic shown in FIG. 3A, transfected into human Jurkat T cells. After transfection, the Jurkat cells express CAR with a MyC tag. The transfected cells were stained with antibody against Myc tag which is conjugated with FITC. The CAR positive live cells are as indicated in Q3. CAR expression is shown on the x-axis, live/dead cells are shown on the y-axis.
Figure 4A:
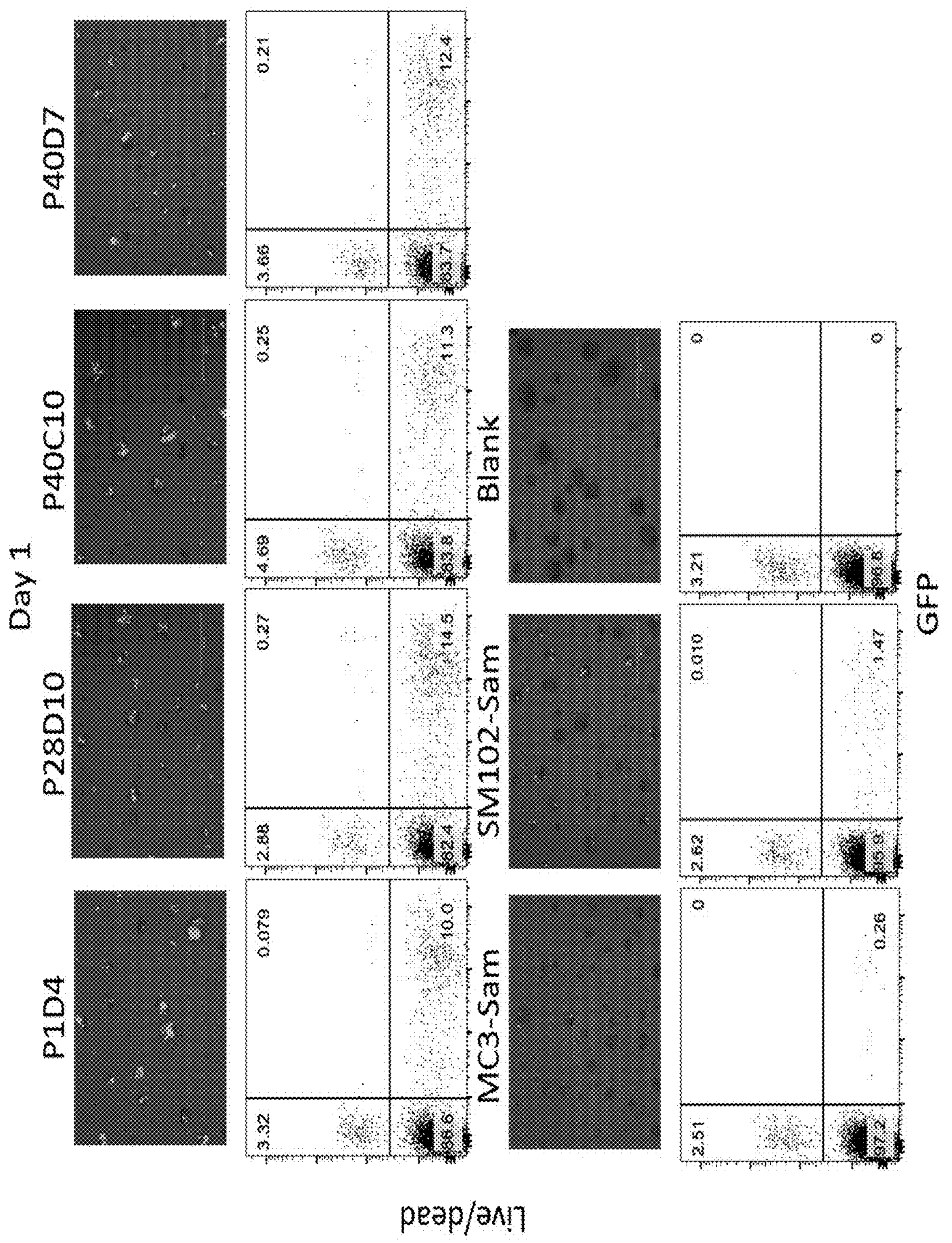
FIGS. 4A-4B show FACS of sa-mRNA of the disclosure encoding eGFP, which transfect and express GFP-mRNA in human primary T-cells isolated from leukopac (Stemcell) and activated by a-CD3/CD28/CD2. The sa-mRNA was delivered LNPs formulated using the novel ionizable lipids of the disclosure compared to two control LNP formulations (MC3 and SM102). The GFP positive live cells are as indicated in Q3. GFP expression is shown on the x-axis and live/dead cells are shown on the y-axis at 1 day (FIG. 4A) and 3 days (FIG. 4B) post-transfection.
Figure 4B:
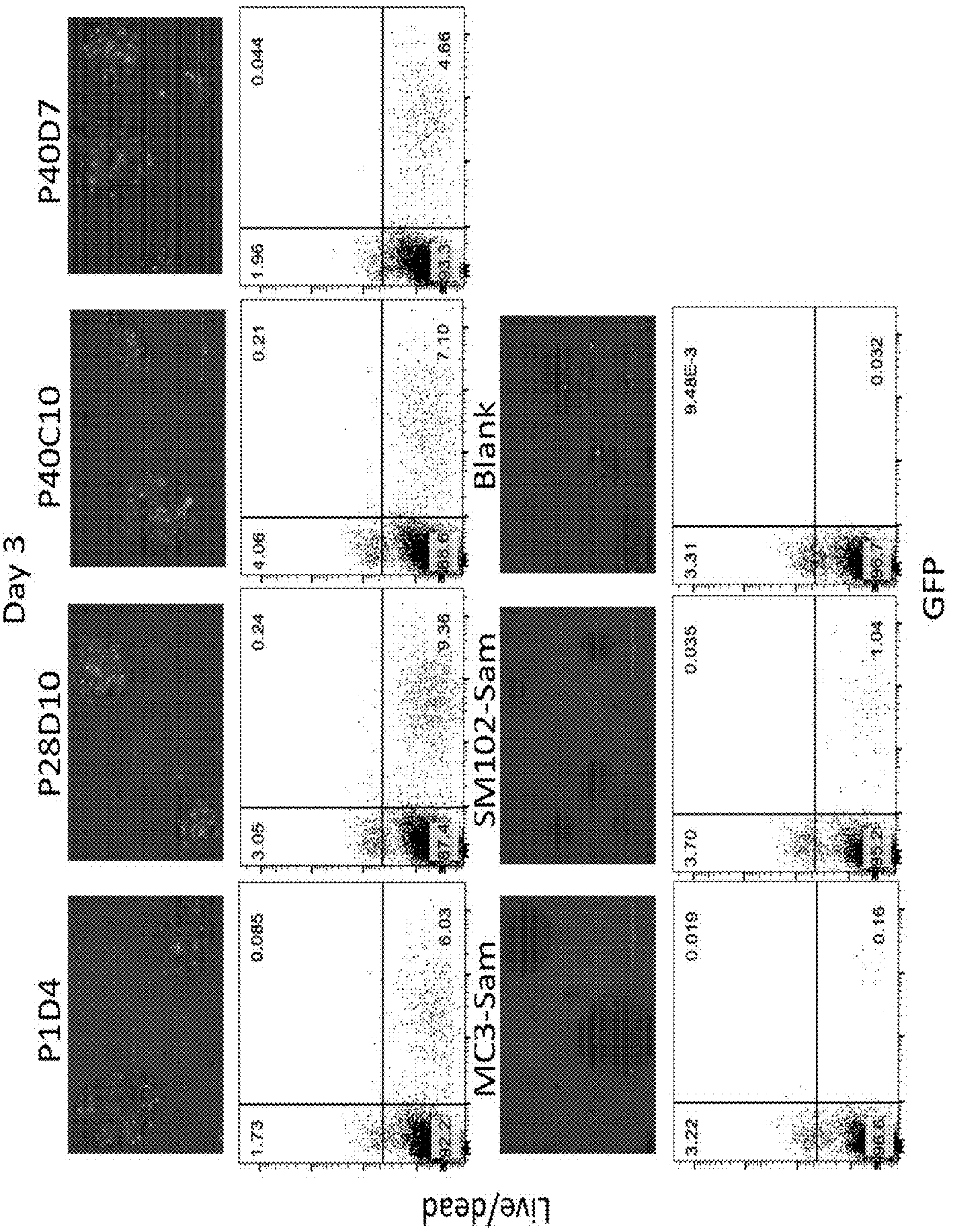
Figure 5:
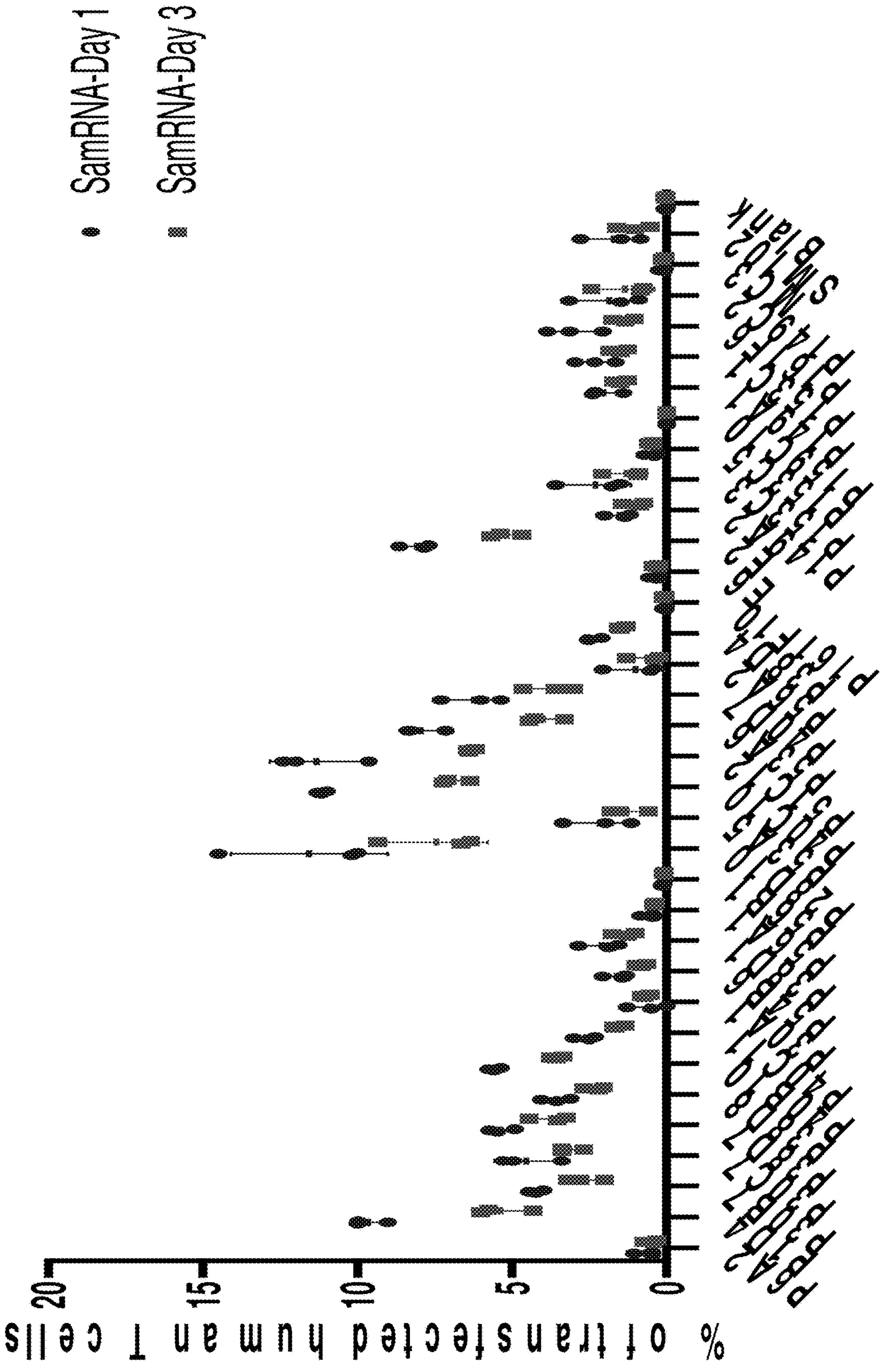
FIG. 5 shows the transfection efficiency of sa-mRNA of the disclosure encoding eGFP delivered into human primary T-cells using LNPs formulated using the novel ionizable lipids of the disclosure compared to two control LNP formulations (MC3 and SM102). The ionizable lipids used to formulate each LNP are indicated on the x-axis. Shown are percentages of transfected cells (Y-axis) versus LNPs at 1 and 3 days post transfection.
Figure 6A:
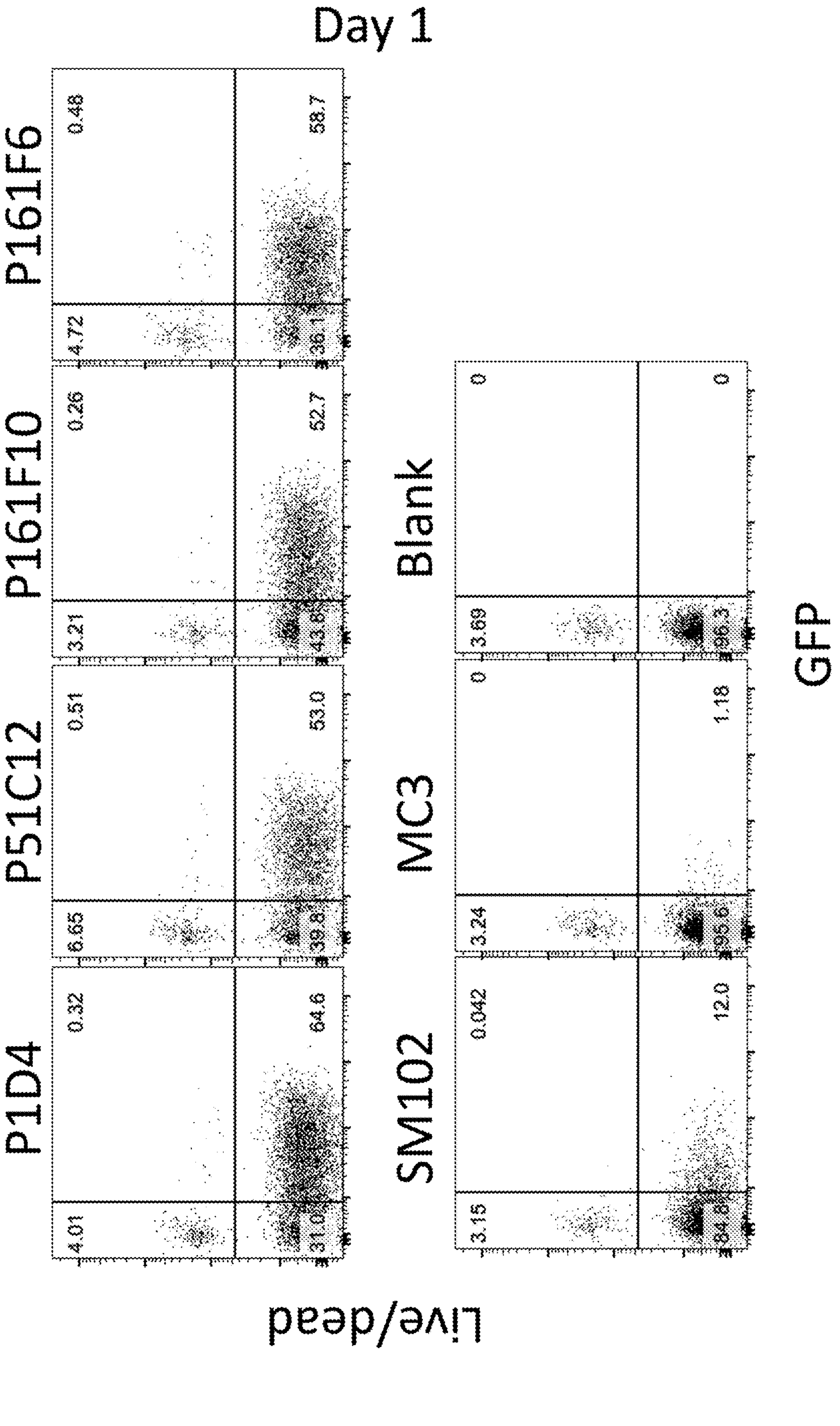
FIGS. 6A-6B show FACS of modified mRNA of the disclosure encoding eGFP, which transfect and express GFP-mRNA in human primary T-cells. The sa-mRNA was delivered LNPs formulated using the novel ionizable lipids of the disclosure compared to two control LNP formulations (MC3 and SM102). The GFP positive live cells are as indicated in Q3. GFP expression is shown on the x-axis, live/dead cells are shown on the y-axis at 1 day (FIG. 6A) and 3 days (FIG. 6B) post-transfection.
Figure 6B:
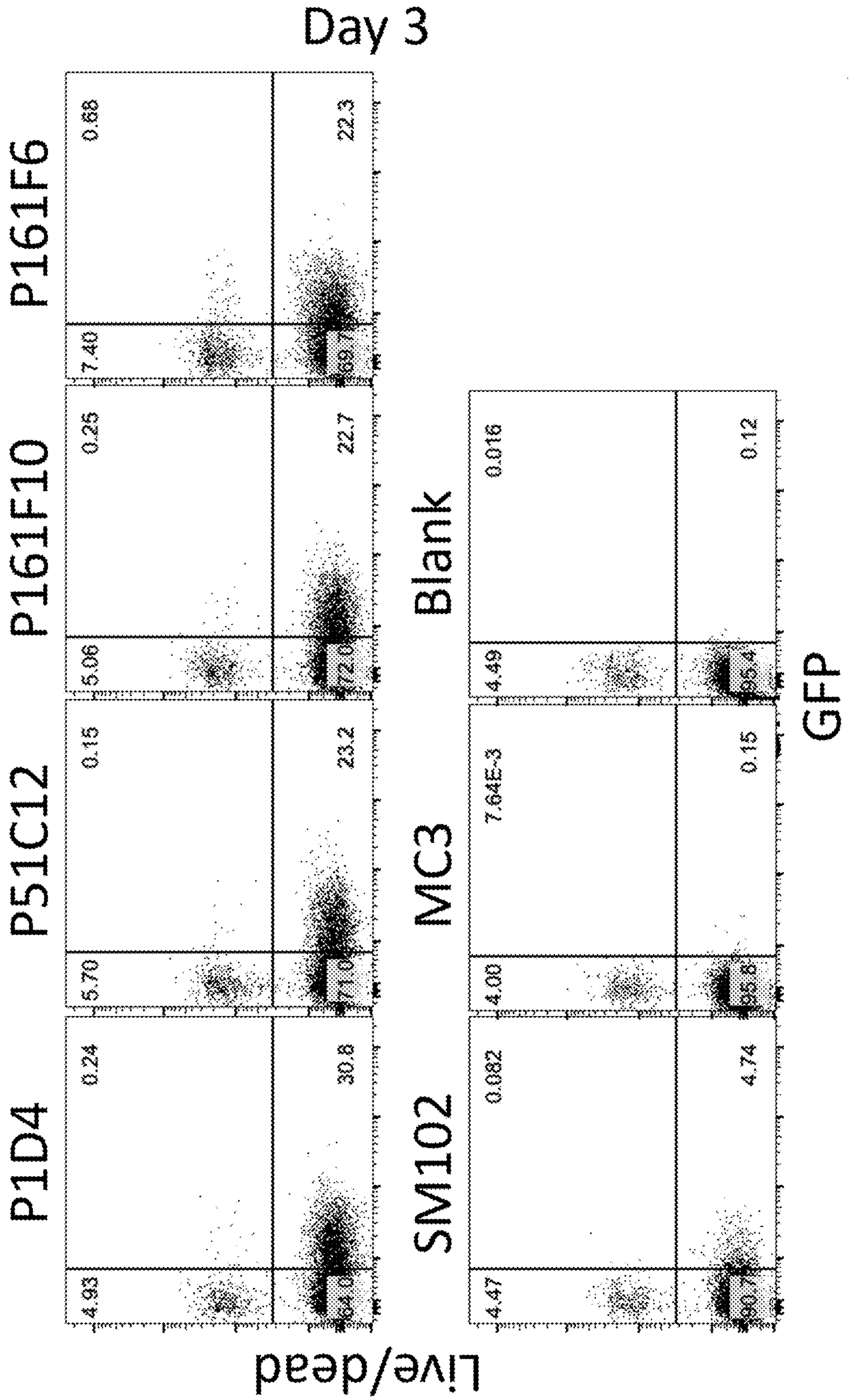
Figure 7:
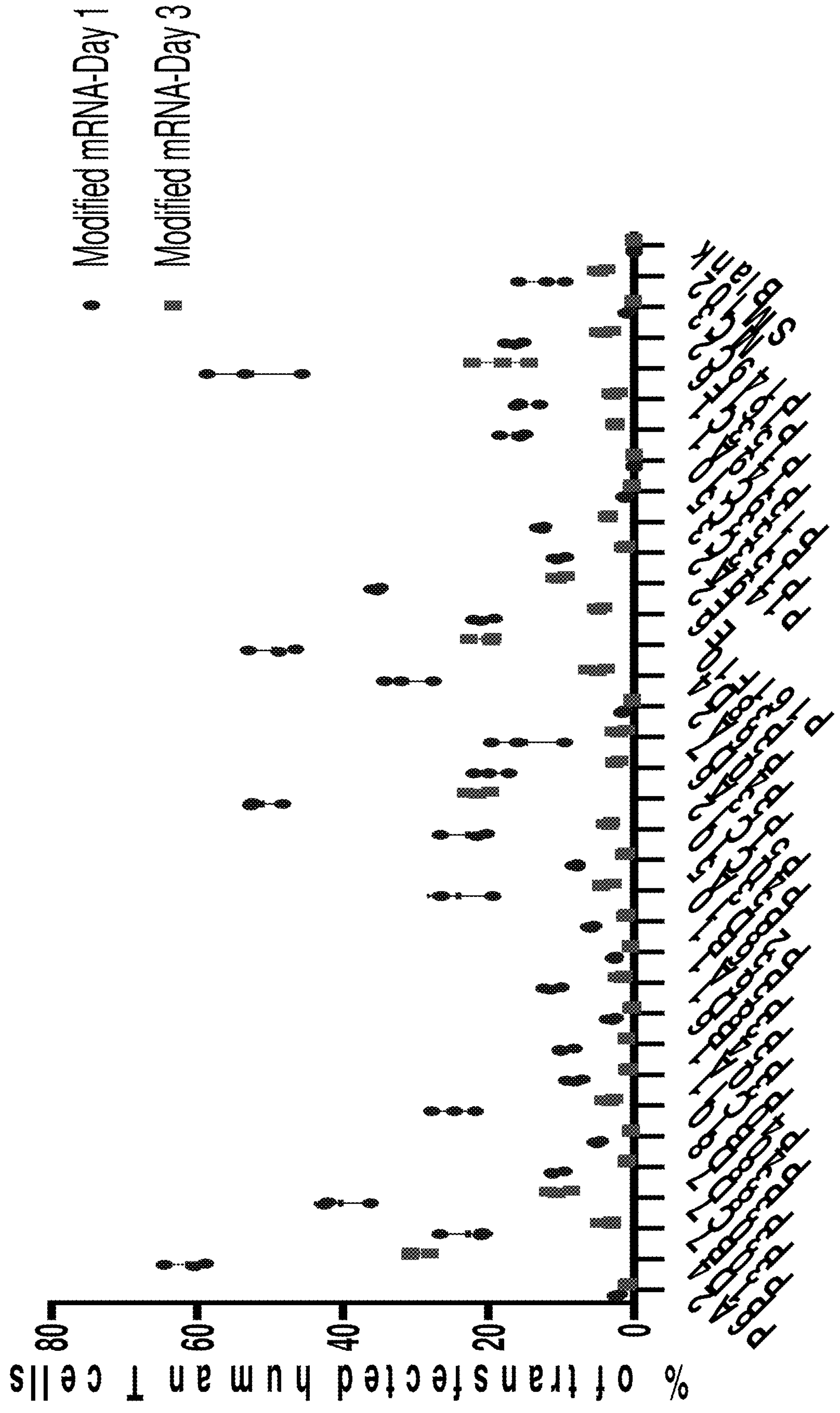
FIG. 7 shows the transfection efficiency of modified mRNA encoding eGFP delivered into human T-cells isolated from leukopac (Stemcell) and activated by a-CD3/CD28/CD2 using LNPs formulated using the novel ionizable lipids of the disclosure compared to two control LNP formulations (MC3 and SM102). The ionizable lipids are used for LNPs are as indicated on the x-axis. Shown are percentages of transfected cells (Y-axis) versus LNPs at 1 and 3 days post transfection.

Note that any one or more of the illustrative components of the molecules or methods are optional and the present disclosure includes aspects that contain fewer than all of the illustrated elements including any parts thereof.

DETAILED DESCRIPTION

The disclosure relates to novel methods and compositions for delivering molecules ex vivo or in vivo, including novel sa-mRNA, modified mRNA, circRNA, and LNP compositions comprising novel ionizable lipids, which improve stability, facilitate internalization, and reduce safety issues associated with increased administrations and cytotoxic effects, and therapeutic applications thereof. The payloads of the disclosure are synthetic nucleic acids that are capable of reprogramming immune responses for treatment of diseases, such as cancer. The nucleic acids of the disclosure encode synthetic proteins including chimeric antigen receptor (CAR), T-cell receptor (TCR), growth factor receptor (GFR), hormone receptor (HR), and nanobodies. Other payloads useful for immunotherapy comprising genetic reprogramming of immune cells are also contemplated.

In one aspect, the present disclosure provides a method of delivering a payload to primary immune cells, such as T-cells, including human T-cells, ex vivo comprising delivering a sa-mRNA, modified mRNA or circRNA encoding a polypeptide of interest using an LNP comprising an ionizable lipid of the disclosure. In one aspect, the modified mRNA is a modified sa-mRNA or a modified circRNA. In one aspect, the present disclosure provides a method of delivering a payload to T-cells, including human T-cells, in vivo comprising delivering a sa-mRNA, modified mRNA or circRNA encoding CAR, TCR, GFR, HR or nanobodies using an LNP comprising an ionizable lipid of the disclosure.

Although the present disclosure is described in detail below, it is to be understood that this disclosure is not limited to the particular methodologies, protocols and reagents described herein as these may vary. It is also to be understood that the terminology used herein is for the purpose of describing particular aspects only, and is not intended to limit the scope of the present disclosure. Unless defined otherwise, all technical and scientific terms used herein have the same meanings as commonly understood by one of ordinary skill in the art.

Definitions

As used herein, the terms "gene of interest," "genes of interest," "gene or genes of interest," "GOI," or "coding region" refers to the nucleotide sequence which encode the amino acids found in polypeptides and proteins as a result of translation of a mRNA molecule, including from a sa-mRNA, modified mRNA or circRNA. Thus, in some aspects, the GOI encodes a polypeptide to be produced. A GOI, for the purposes of this disclosure, include, but is not limited to, polynucleotides encoding antigen receptors (such as CAR, TCR, GFR and HR) and Nbs. As used herein, "polypeptide of interest" or "polypeptides of interest" refer to one or more polypeptides encoded by one or more gene or genes of interest.

As used herein, the term "immune cells" refer to cells that are part of the immune system. Immune cells include lymphocytes (T cells, B cells, and NK cells), neutrophils, monocytes and macrophages.

As used herein, a "nucleoside" consists of a nucleic acid base (e.g., the canonical nucleic acid bases: guanine (G), adenine (A), thymine (T), uracil (U), and cytosine (C)); or a modified nucleic acid base (e.g., 5-methylcytosine (m5C)), that is covalently linked to a pentose sugar (e.g., ribose or 2'-deoxyribose), whereas and a "nucleotide" consists of a nucleoside that is phosphorylated at one of the hydroxyl groups of the pentose sugar. Linear nucleic acid molecules are said to have a "5' terminus" (5' end) and a "3' terminus" (3' end) because, except with respect to capping or adenylation (e.g., adenylation by a ligase), mononucleotides are joined in one direction via a phosphodiester linkage to make oligonucleotides or polynucleotides, in a manner such that a phosphate on the 5' carbon of one mononucleotide sugar moiety is joined to an oxygen on the 3' carbon of the sugar moiety of its neighboring mononucleotide. Therefore, an end of a linear single-stranded oligonucleotide or polynucleotide or an end of one strand of a linear double-stranded nucleic acid (RNA or DNA) is referred to as the "5' end" if its 5' phosphate is not joined or linked to the oxygen of the 3' carbon of a mononucleotide sugar moiety, and as the "3' end" if its 3' oxygen is not joined to a 5' phosphate that is joined to a sugar of another mononucleotide.

As used herein, the term "modified nucleotide", "modified nucleoside" and "nucleotide analog" refer to a nucleotide or nucleoside that contains one or more chemical modifications (e.g. substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six- membered sugar analog, or open-chain sugar analog), or the phosphate. There are more than 96 naturally occurring modified nucleosides found on mammalian RNA. See, e.g., Limbach et al, Nucleic Acids Research, 22(12):2183-2196 (1994). A modified nucleobase species may include one or more substitutions that are not naturally occurring. The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein.

As used herein, "nucleic acid" refers a nucleic acid molecule. According to the present disclosure, nucleic acids comprise genomic DNA, cDNA, RNA, recombinantly prepared and chemically synthesized molecules. According to the present disclosure, a nucleic acid may be in the form of a single-stranded or double stranded and linear or covalently closed circular molecule. The nucleic acid of the present disclosure may also containing non-natural nucleotides and modified nucleotides. "Nucleic acid" also refers to a consecutive list of abbreviations, letters, characters or words, which represent nucleotides.

As used herein, the term "regulatory element" refers to a nucleotide sequence that controls, at least in part, the transcription of a gene or genes of interest. Regulatory elements may include promoters, enhancers, and other nucleic acid sequences (e.g., polyadenylation signals) that control or help to control nucleic acid transcription or translation. Examples of transcription regulatory elements are described, for example, in Goeddel, Gene Expression Technology: Methods in Enzymology 185 (Academic Press, San Diego, Calif., 1990).

As used herein, the term "non-coding" refers to nucleotide sequences that do not encode a polypeptide or an expressed protein. Non-coding sequences include but are not limited to introns, enhancers, promoter regions, 3' untranslated regions, 5' untranslated regions, linkers and GOI which encode regulatory structures.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a GOI if the promoter modulates transcription of said GOI in a cell. Additionally, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the term "linker" refers to a nucleotide sequence added between two nucleotide sequences to connect said two nucleotide sequences. There is no particular limitation regarding the linker sequence.

As used herein, the term "subgenomic promoter," is a promoter that can be used to transcribe the subgenome of alphaviruses encoding structural proteins by RNA dependent RNA polymerase encoded by nsP. When two or more subgenomic promoters are present in a nucleic acid comprising multiple expression units, the promoters can be the same or different. In certain aspects, subgenomic promoters can be modified using techniques known in the art in order to increase or reduce viral transcription of the proteins, see e.g. U.S. Pat. No. 6,592,874, which is incorporated by reference in its entirety herein.

As used herein, the term "genomic DNA" is referring to the heritable genetic information of a host organism. Said genomic DNA comprises the DNA of the nucleus (also referred to as chromosomal DNA) but also the DNA of the other cellular organelles (e.g., mitochondria). In some aspects, the term genomic DNA refers to the chromosomal DNA of the nucleus.

As used herein, "encoding" refers to a polynucleotide, such as an RNA molecule, that encodes a gene product of interest, such as a protein of interest.

As used herein, the terms "polypeptide," "peptide," "oligopeptide," "gene product," "expression product" and "protein" are used interchangeably herein to refer to a polymer or oligomer of consecutive amino acid residues. The terms "gene product" and "expression product" can also refer to regulatory structures.

As used herein, an "effective amount" of a mRNA, including sa-mRNA, modified mRNA, and circular mRNA, refers to an amount sufficient to elicit expression of a detectable amount of an antigen or protein, e.g., an amount suitable to produce a desired therapeutic, diagnostic or prophylactic effect.

As used herein, the term "naked" refers to nucleic acids that are substantially free of other macromolecules, such as lipids, polymers, and proteins. A "naked" nucleic acid, such as a plasmid or a sa-mRNA, is not formulated with other macromolecules to improve cellular uptake. Accordingly, a naked nucleic acid is not encapsulated in, absorbed on, or bound to a liposome, a microparticle or nanoparticle, a cationic emulsion, and the like.

As used herein, the term "transfection" or "transformation" refers to introducing one or more nucleic acids into an organism or into a host cell. Various methods may be employed in order to introduce nucleic acids into cells in vitro or in vivo. Such methods include transfection of nucleic acid-CaPO4 precipitates, transfection of nucleic acids associated with DEAE, transfection of infection with viruses carrying the nucleic acids of interest, liposome mediated transfection, lipid nanoparticle (LNP) mediated transfection, lipofectamine and the like.

As used herein, the term "reporter" relates to a molecule, typically a peptide or protein, which is encoded by a reporter gene and measured in a reporter assay. Existing systems usually employ an enzymatic reporter (e.g. GFP or Luciferase) and measure the activity of said reporter.

As used herein, the term "recombinant" polypeptides or proteins refer to polypeptides or proteins produced by recombinant DNA techniques. As used herein, the term "synthetic" refers to polynucleotides, polypeptides or proteins prepared by chemical synthesis.

As used herein, the term "payload" refers to a moiety whose biological activity is desired to be delivered (in)to and/or localize at a cell or tissue. Payloads include, but are not limited to a drug, small molecule, diagnostic agent, therapeutic agent, peptide, antibody, antibody fragment, polypeptide, nucleic acid (e.g., mRNA or siRNA) and the like. In some aspects, the payload may be a nucleic acid that encodes a protein or polypeptide. In some aspects, the payload may include or encode a cytokine, a chemokine, an antibody or antibody fragment, a receptor or receptor fragment, an enzyme, an enzyme inhibitor, a hormone, a lymphokine, a plasminogen activator, a natural or modified immunoglobulin or a fragment thereof, an antigen, a chimeric antibody receptor, variable or hypervariable regions of light and/or heavy chains of an antibody ($V_L$, $V_H$), variable fragments (Fv), Fab' fragments, F(ab') 2 fragments, Fab fragments, single chain antibodies (scAb), single chain variable regions (scFv), complementarity determining regions (CDR), domain antibodies (dAbs), single domain heavy chain immunoglobulins of the BHH or BNAR type, nanobodies, single domain light chain immunoglobulins, T-cell receptor, growth factor receptor (e.g., TGF-beta receptor), other polypeptides known in the art containing an antibody capable of binding target proteins or epitopes on target proteins, or any other desired biological macromolecule.

As used herein, the term "nanobody" (Nb) refers to a variable region of a heavy chain of an antibody, and construct a single domain antibody (VHH) consisting of only one heavy chain variable region. It is the smallest antigen-binding fragment with complete function. The small size and unique biophysical properties of Nbs are well suited for the recognition of uncommon or hidden epitopes and for binding into cavities or active sites of protein targets (Hamers-Casterman et al., Nature (1993) 363:446-448). Further, Nbs can be designed as bispecific and bivalent antibodies or attached to reporter molecules (Conrath et al., Antimicrob. Agents Chemother. (2001) 45 (10):2807). Nbs are stable and rigid single domain proteins that can easily be manufactured. Therefore, Nbs can be used in many applications including drug discovery and therapy, and as a tool for purification, functional study and crystallization of proteins (Conrath et al. Protein Sci. (2009) 18(3):619-28).

As used herein, the term "single-chain variable fragment" (scFv) refers to a fusion protein comprising the variable regions of the heavy chain (VH) and the light chain (VL) of immunoglobulins connected by a peptide linker.

As used herein, "encapsulation efficiency" refers to the amount of a payload that becomes part of a nanoparticle composition, relative to the initial total amount of payload used in the preparation of a nanoparticle composition. For example, if 97 mg of a payload are encapsulated in a nanoparticle composition out of a total 100 mg of the payload initially provided to the composition, the encapsulation efficiency may be given as 97%. As used herein, "encapsulation" may refer to complete, substantial, or partial enclosure, confinement, surrounding, or encasement.

As used herein, a "nanoparticle composition" or "LNP formulation" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less. For example, the lipid component of a nanoparticle composition may include one or more cationic/ionizable, PEGylated, structural, or other lipids, such as phospholipids.

As used herein, a "lipid component" is that component of a nanoparticle composition that includes one or more lipids. For example, the lipid component may include one or more cationic/ionizable, PEGylated, structural, or other lipids, such as phospholipids.

As used herein, the term "saccharide lipid" refer to the novel lipids of the present disclosure, which mimics the lipids of the lipid envelopes of certain viral particles. Saccharide lipids are viral envelope lipids with saccharide modifications.

As used herein, the terms "PEG lipid" or "PEGylated lipid" refer to a lipid comprising a polyethylene glycol component. For example, a PEG lipid may be selected from the following non-limiting group: PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

As used herein, the terms "phospholipid" or "helper lipid" refer to a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell. In general, phospholipids may include a phospholipid moiety and one or more fatty acid moieties.

Phospholipids useful in the compositions and methods of the present disclosure may be selected from the following non-limiting group: 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some aspects, a nanoparticle composition includes DSPC. In certain aspects, a nanoparticle composition includes DOPE.

As used herein, "ionizable lipids" and "cationic lipids" are lipids that may have a positive or partial positive charge at physiological pH, such as the lipids disclosed in PCT Patent Application No. PCT/US2023/017777, which is fully incorporated herein by reference.

As used herein, the terms "stain" or "staining" include methods of detecting subpopulations of cells in a cell sample, and in particular, it relates to methods of detecting dead cells in a cell sample using a membrane permeable nucleic acid binding fluorescent label. The staining method can be used in combination with a cell capture system and/or an optical detection system for detecting the presence of live and or dead cells in a cell sample. For example, dead cells can be detected using fluorescent DNA binding dyes such as propidium iodide and 7-aminoactinomycin D (7-AAD) because they have compromised cell membrane integrity compared to live cells (Lecoeur et al., 2002; Gaforio et al., Cytometry 49:8, 2002; Ormerod et al., Cytometry 14:595, 1993; Schmid et al., J. Immunol. Methods 170:145, 1994; Philpott et al., Blood 87:2244, 1996).

As used herein, the term "derived", such as for an RNA (including mRNA) or a polypeptide that is "derived" from a sample, biological sample, cell, tumor, or the like, it is meant that the RNA or polypeptide either was present in the sample, biological sample, cell, tumor, or the like, or was made using the RNA in the sample, biological sample, cell, tumor, or the like by a process such as an in vitro transcription (IVT) reaction, or an RNA amplification reaction, wherein the RNA or polypeptide is either encoded by or a copy of all or a portion of the RNA or polypeptide molecules in the original sample, biological sample, cell, tumor, or the like. By way of example, such RNA can be from an in vitro transcription or an RNA amplification reaction, with or without cloning of cDNA, rather than being obtained directly from the sample, biological sample, cell, tumor, or the like, so long as the original RNA used for the in vitro transcription or an RNA amplification reaction was from the sample, biological sample, cell, tumor, or the like. The terms "sample" and "biological sample" are used in their broadest sense and encompass samples or specimens obtained from any source that contains or may contain eukaryotic cells, including biological and environmental sources. As used herein, the term "sample" when used to refer to biological samples obtained from organisms, includes bodily fluids (e.g., blood or saliva), feces, biopsies, swabs (e.g., buccal swabs), isolated cells, exudates, and the like. The organisms include fungi, plants, animals, and humans. However, these examples are not to be construed as limiting the types of samples or organisms that find use with the present invention. In addition, in order to perform research or study the results related to use of a method or composition of the invention, in some aspects, a "sample" or "biological sample" comprises fixed cells, treated cells, cell lysates, and the like. In some aspects, such as aspects of the method wherein the mRNA is delivered into a cell from an organism that has a known disease or into a cell that exhibits a disease state or a known pathology, the "sample" or "biological sample" also comprises bacteria or viruses.

As used herein, the terms "treat," "treating" or "treatment," may include alleviating, abating or ameliorating disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", may include, but are not limited to, prophylactic, diagnostic and/or therapeutic treatments.

As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions.

As used herein, the terms "biologically active agent" and "therapeutic agent" refer to a characteristic of any substance that has activity in a biological system and/or organism. The terms "biologically active agent" and "therapeutic agent" refer to any agent that, when administered to a subject, has a therapeutic effect and/or elicits a desired biological and/or pharmacological effect. Such agents include, but are not limited to, cytotoxins, radioactive ions, chemotherapeutic agents, small molecule drugs, proteins, and nucleic acids.

As used herein, "expression" of a nucleic acid refers to one or more of the following events: (1) production of an RNA template from a DNA sequence (e.g., by transcription); and (2) translation of an RNA into a polypeptide or protein.

As used herein, the term "contacting" means establishing a physical connection between two or more entities. For example, contacting a cell with a nanoparticle composition comprising a sa-mRNA means that the mammalian cell and a nanoparticle are made to share a physical connection. Methods of contacting cells with external entities both in vivo and ex vivo are well known in the biological arts.

As used herein, the term “delivering” means providing an entity to a destination. For example, delivering a biologically active agent to a subject may involve administering a nanoparticle composition comprising sa-mRNA or modified mRNA including the payload to the subject (e.g., by an intravenous, intranasal, intratracheal, intracerebral, intraventricular, intrathecal, in utero, oral, intratumoral, intraperitoneal, intramuscular, intradermal, or subcutaneous route).

As used herein, the term “in vitro” refers to events that occur in an artificial environment, e.g., in a test tube or reaction vessel, in cell culture, in a Petri dish, etc., rather than within an organism (e.g., animal, plant, or microbe).

As used herein, the term “in vivo” refers to events that occur within an organism (e.g., animal, plant, or microbe).

As used herein, the term “in situ” refers to events that occur in its original place, or in its natural context.

As used herein, the term “ex vivo” refers to events that occur outside an organism. For example, the term ex vivo may refer to a method in which cells (e.g., lymphocytes, T cells, bone marrow aspirates, tissue biopsy) are explanted from a subject then reimplanted into a subject after selecting for cells which have been genetically altered.

As used herein, the term “isolated” refers to a substance or entity that has been (1) separated from at least some of the components with which it was associated when initially produced (whether in nature or in an experimental setting), and/or (2) produced, prepared, and/or manufactured in vitro. Isolated substances and/or entities may be separated from at least about 10%, about 20%, about 30%, about 40%, about 50%, about 60%, about 70%, about 80%, about 90%, or more of the other components with which they were initially associated. In some aspects, isolated agents are more than about 80%, about 85%, about 90%, about 91%, about 92%, about 93%, about 94%, about 95%, about 96%, about 97%, about 98%, about 85, 90, 95, 98, or 99%, or more than about 85, 90, 95, 98, or 99% pure. As used herein, a substance is “pure” if it is substantially free of other components.

As used herein, the term “substantially” refers to the qualitative condition of exhibiting total or near-total extent or degree of a characteristic or property of interest.

As used herein, the term “polypeptide” or “polypeptide of interest” refer to a polymer of amino acid residues typically joined by peptide bonds that can be produced naturally (e.g., isolated or purified) or synthetically.

As used herein, “size” or “mean size” in the context of nanoparticle composition refer to the mean diameter of a nanoparticle composition.

As used herein, the term “subject” or “patient” refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, the term “therapeutically effective amount” means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, “methods of administration” may include intravenous, intranasal, intratracheal, intracerebral, intratumoral, intraperitoneal, intramuscular, intradermal, subcutaneous, or other methods of delivering a composition to a subject. A method of administration may be selected to target delivery (e.g., to specifically deliver) to a specific region or system of a body.

As used herein, “naturally occurring” means existing in nature without artificial aid.

As used herein, the terms “subgenomic” or “subgenome” refers to a nucleotide sequence (e.g. RNA or DNA) of a length or size which is smaller than the genomic nucleotide sequence from which it was derived. For example, a subgenome can be a region encoding VEE structural proteins, subgenomic RNA can be transcribed from the subgenome using an internal subgenomic promoter, whose sequences reside within the genomic viral RNA or its complement. Transcription of a subgenome may be mediated by viral-encoded polymerase(s) associated with host cell-encoded proteins (e.g. nsP1-4). In some aspects of the present disclosure, the subgenomic sa-mRNA is produced from a modified alphavirus replicon (e.g. a modified VEE replicon) as disclosed herein and encodes or expresses one or more gene or genes of interest (GOI).

The phrase “pharmaceutically acceptable” is used herein to refer to those compounds, materials, compositions, and/or dosage forms which are, reasonably suitable for use in contact with the tissues of human beings and animals without excessive toxicity, irritation, allergic response, or other problem or complication.

“Pharmaceutically acceptable compositions” may also include salts of one or more compounds. Salts may be pharmaceutically acceptable salts. As used herein, “pharmaceutically acceptable salts” refers to derivatives of the disclosed compounds wherein the parent compound is altered by converting an existing acid or base moiety to its salt form. Generally, such salts can be prepared by reacting the free acid or base forms of these compounds with a stoichiometric amount of the appropriate base or acid in water or in an organic solvent, or in a mixture of the two. In some aspects, a nonaqueous media like ether, ethyl acetate, ethanol, isopropanol, or acetonitrile may be used. Lists of suitable salts are found in Remington’s Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, the terms “approximately” and “about,” as applied to one or more values of interest, refer to a value that is +/−20% of the recited value.

Sa-mRNA

In some aspects, the payload of the present disclosure is a sa-mRNA molecule.

Sa-mRNAs of the disclosure have the ability to self-replicate in cells and, thus, can be used to induce expression of encoded gene products, such as proteins (e.g., antigen receptors) and regulatory structures (e.g. siRNA, miRNA, saRNA, tRNA, and lincRNA) encoded by the sa-mRNA. In addition, sa-mRNAs are generally based on the genome of an RNA virus (e.g. a Group IV positive single strand RNA virus).

One suitable system for producing a sa-mRNA of the present disclosure is to use an alphavirus-based RNA replicon. Alphavirus-based replicons are positive (+)-single stranded replicons that can be translated after delivery to a cell to give a replicase (or replicase-transcriptase). The replicase is translated as a polyprotein which auto-cleaves to provide a replication complex, comprising plurality of non-structural replicase domain sequences, which creates genomic (−)-strand copies of the (+)-strand delivered RNA. These (−)-strand transcripts can themselves be transcribed to give further copies of the (+)-stranded parent RNA and also to give an mRNA transcript which encodes the desired gene product. Translation of the subgenomic transcript thus leads to in situ expression of the desired gene product by the infected cell.

A sa-mRNA may encode (i) a RNA-dependent RNA polymerase which can replicate RNA from sa-mRNA and transcribe (ii) a GOI of the subgenome. The polymerase can be an alphavirus replicase e.g. comprising alphavirus non-structural proteins 1, 2, 3, and 4.

Whereas natural alphavirus genomes encode structural proteins in addition to the non-structural replicase, in one aspect, an alphavirus based sa-mRNA of the disclosure does not encode alphavirus structural proteins. Thus the sa-mRNA of the disclosure can lead to the production of RNA copies of itself in a cell, but not to the production of RNA-containing alphavirus virions. The inability to produce these virions means that, unlike a wild-type alphavirus, the sa-mRNA cannot perpetuate itself in infectious form. The alphavirus structural proteins which are necessary for perpetuation in wild-type viruses are absent from the sa-mRNAs of the disclosure and their place is taken by the GOI, such that the sa-mRNA transcript encodes the desired gene product rather than the structural alphavirus virion proteins.

Thus, the sa-mRNA of the present disclosure may have more than one coding region. The first (5') coding region encodes a plurality of non-structural replicase domain sequences; the second (3') coding region encodes a gene of interest operably linked to a subgenomic promoter. In some aspects the sa-mRNA may have additional (downstream) coding regions e.g. that encode other desired gene products. A coding region molecule can have a 5' sequence which is compatible with the encoded replicase.

The sa-mRNA of the present disclosure may be derived from or based on a virus other than an alphavirus, including but not limited to a Group IV positive-single stranded RNA virus, for example, picornaviridae, togaviridae, coronaviridae, hepeviridae, caliciviridae, flaviviridae, and astroviridae. Suitable wild-type alphavirus sequences are well-known and are available from sequence depositories, such as the American Type Culture Collection, Rockville, Md. Representative examples of suitable alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

Sa-mRNAs as described herein can amplify themselves and initiate expression of heterologous gene products in the host cell. Sa-mRNAs of the present disclosure, unlike mRNA, use their own encoded viral polymerase to amplify itself. Particular sa-mRNA, such as those based on Group IV RNA viruses such as alphaviruses, generate large amounts of subgenomic mRNAs from which large amounts of proteins (or regulatory structures) can be expressed.

Advantageously, the host cell's own machinery is used by sa-mRNAs to generate an exponential increase of encoded gene products (such as proteins, antigens, or regulatory structures) which can accumulate in the cells or be secreted from the cells. Increased of proteins or antigens by sa-mRNAs takes advantage of the immunostimulatory adjuvant effects, including stimulation of toll-like receptors (TLR) 3, 7 and 8 and non TLR pathways (e.g., RIG-I like receptor, RIG-I, MDA-5, LGP2) by the products of RNA replication and amplification, and translation which induces apoptosis of the transfected cell.

The sa-mRNA of the disclosure may encode any desired gene product, such as a regulatory structure, a polypeptide, a protein or a polypeptide or a fragment of a protein or polypeptide. Additionally, the sa-mRNA of the disclosure may encode a single polypeptide or, optionally, two or more of sequences linked together in a way that each of the sequences retains its identity (e.g., linked in series) when expressed as an amino acid sequence. The polypeptides generated from the sa-mRNAs of the disclosure may then be produced as a fusion protein or engineered in such a manner to result in separate polypeptide or peptide sequences.

The sa-mRNAs described herein may be engineered to express multiple GOI, from two or more coding regions, thereby allowing co-expression of proteins and or regulatory structures, such as a two or more antigens or antigen receptor together with cytokines or other immunomodulators. Such a sa-mRNA might be particularly useful, for example, in the production of various gene products (e.g., proteins) at the same time, for example, as a bivalent or multivalent vaccine, or in gene therapy applications.

In one aspect, the sa-mRNA of the disclosure contains modified nucleotides. Several suitable methods are known in the art for producing sa-mRNA molecules that contain modified nucleotides. For example, a sa-mRNA that contains modified nucleotides can be prepared by transcribing (e.g., in vitro transcription) a nucleic acid that encodes the sa-mRNA using a suitable DNA-dependent RNA polymerase, such as: T7 phage RNA polymerase, SP6 phage RNA polymerase, T3 phage RNA polymerase, T5 phage RNA polymerase, RNA polymerase III, RNA polymerase II, Taq polymerase, Vent polymerase, and the like, or mutants of these polymerases, which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of modified nucleotide into a sa-mRNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

In one aspect, the SGP is a nucleotide sequence selected from

```
                                   SEQ ID NO: 10
(TAACCTGAATGGACTACGACATAGTCTAGTCCGCCAAG) or

                                   SEQ ID NO: 11
(GAACTTCCATCATAGTTATGGCCATGACTACTCTAGCTAGCAGTGTTA

AATCATTCAGCTACCTGAGAGGGGCCCCTATAACTCTCTACGGC).
```

In one aspect, SGP is a viral promoter that is recognized by viral RNA dependent RNA polymerase. In one aspect, L is a nucleotide sequence selected from

SEQ ID NO: 12
(CGCGTGATAACGCAGGAAAGAACATGTGAGCAAAAGGCCAGCAAAAGG

CCAGGAACCGTAAAAAGGCCGCGTTGCTGGCGTT),

SEQ ID NO: 13
(CACATTTCCCCGAAAAGTGCCACCTGAGCTC),

SEQ ID NO: 14
(TTCGAAGGCGCGCCTCTAGAGCCACC), or

SEQ ID NO: 15
(CATCGATGATATCGCGGCCGCATACAGCAGC).

In one aspect, the 5'UTR comprise the nucleic acid sequence ATAGG. In one aspect, the 3'UTR is a nucleotide sequence selected from

SEQ ID NO: 16
(GGATTTTGTTTTTAATATTTC),

SEQ ID NO: 17
(GGATTTTATTTTTAATATTTC),

SEQ ID NO: 18
(AAATTTTGTTTTTAATATTTC),

SEQ ID NO: 19
(AAATTTTATTTTTAATATTTC), or

SEQ ID NO: 31
(TAATACGACTCACTATAGGATAGG).

In one aspect, the present disclosure provides a sa-mRNA comprising a nucleic acid sequence from 5' to 3':

a) 5'UTR-nsP-L-GOI-L-3'UTR-PolyA
b) 5'UTR-nsP-GOI-L-3'UTR-PolyA;
c) 5'UTR-nsP-L-GOI-3'UTR-PolyA; or
d) 5'UTR-nsP-SGP-GOI-3'UTR-PolyA wherein 5'UTR is a 5' untranslated region, nsP is a plurality of non-structural replicase domain sequences, L is a linker, SGP is a subgenomic promoter, GOI is one or more genes of interest, 3'UTR is a 3' untranslated region, and poly-A is a 3' poly-adenylated tail (poly-A tail).

In one aspect, the GOI of the sa-mRNA is a reporter gene. In some aspects, the reporter gene is green fluorescent protein (GFP) or an epitope tag. In one aspect, the epitope tag is a Myc-tag.

In one aspect, the GOI encodes an enzyme, an enzyme inhibitor, a hormone, a lymphokine, a cytokine, a chemokine, a plasminogen activator, an antigen, an antigen receptor, an immunoglobulin, a fragment of an immunoglobulin, or any combinations thereof. In one aspect, the GOI of the sa-mRNA is a chimeric antigen receptor. In some aspects, the GOI is a chimeric T cell receptor (CAR-T). In some aspects, the sa-mRNA further comprises one or more linkers.

In some aspects, at least one non-structural replicase domain sequence comprise sequences selected from Group IV RNA viruses, selected from Picornaviridae, Togaviridae, Coronaviridae, Hepeviridae, Caliciviridae, Flaviviridae, and Astroviridae. In some aspects, at least one non-structural replicase domain sequence comprise sequences selected from Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus. In yet another aspect, at least one non-structural replicase domain sequence is obtained from the TC-83 strain of Venezuelan Equine Encephalitis virus (VEE). In some aspects, the plurality of non-structural replicase domain sequences are alphavirus nonstructural proteins 1-4 (nsP1-4).

In some aspects, SGP is a viral promoter that is recognized by viral RNA dependent RNA polymerase (RdRP). In some aspects, the sa-mRNA of the disclosure comprises one or more linkers.

In one aspect, the sa-mRNA of the present disclosure can incorporate one or more custom GOI built by synthetic methods known in the art, or cloned from cDNA or a genomic library.

CircRNA

Circular RNAs (circRNAs) are a class of single-stranded RNA molecules derived from exonic or intronic sequences by precursor mRNA back-splicing. Unlike linear RNAs, circRNAs form covalently closed, continuous stable loops without a 5'end cap and 3'end poly(A) tail, and therefore are resistant to exonuclease digestion and has a longer half-life. CircRNAs can be synthetic and can exist in nature. In nature, circRNAs can function as microRNA sponges, regulators of gene splicing and transcription, RNA-binding protein sponges and protein/peptide translators. Studies have shown that circRNAs play a role in various human diseases, such as cancers, and may function as predictive biomarkers and therapeutic targets for cancer treatment. Such studies are detailed in Hsu et al., Nature (1979) 280:339-340; Harland & Misher, Development (1988) 102:837-852; Memczak et al. Nature (2013) 495:333-338; Jeck et al., RNA (2013) 19:141-157, which are fully incorporated herein by reference.

The circRNAs of the present invention encode at least one polypeptide of interest, such as a CAR, a TCR, a GFR, a HR, a Nb, a scFv or a reporter.

As used herein, "circular RNA" or "circRNA" means a circular polynucleotide that can encode at least one polypeptide of interest. It is known in the art that a nucleic acid, e.g., a mRNA, may be delivered inside a cell in vitro, in vivo, in situ or ex vivo, to cause intracellular translation of the nucleic acid and production of an encoded polypeptide of interest. Because of their unique closed circular structure, circRNAs are more resistant to the degradation by exonuclease and have a longer half-life compared to their corresponding linear counterparts.

In one aspect, the circular RNAs of the present invention comprise at least one modification, as described herein, in order to avoid at least one of the deficiencies of the linear polynucleotides described and/or known in the art. Hence, in some aspects, the circRNA of the present invention which comprise at least one modification are referred to as modified circular polynucleotides or modified circRNA.

Modified mRNA

In some aspects, mRNA, including linear mRNA, sa-mRNA, and circRNA, of the disclosure can comprise modified nucleotides. Modified mRNAs of the disclosure comprise at least one modified nucleoside selected from the group consisting of a pseudouridine (Ψ), 5-methylcytosine (m5C), 5-methyluridine (m5U), 2'-O-methyluridine (Um or m2'-O U), and 2-thiouridine (s2U) in place of at least a portion of the corresponding unmodified canonical nucleoside of the corresponding unmodified A, C, G, or T canonical nucleoside. In addition, the single-stranded mRNA molecules are preferably purified to be substantially free of RNA contaminant molecules that would activate an unintended response, decrease expression of the single-stranded mRNA, and/or activate RNA sensors in the cells. In certain aspects, the purified RNA preparations are substantially free of RNA contaminant molecules that are: shorter or longer than the full-length single-stranded mRNA molecules, double-stranded, and/or uncapped RNA. In some aspects, the invention provides compositions and methods for reprogramming differentiated eukaryotic cells, including human or other animal somatic cells, by contacting the cells with purified RNA preparations comprising or consisting of one or more different modified mRNA molecules that each encode at least one gene of interest.

In certain aspects, the modified mRNA used in the purified RNA preparations is purified to remove substantially, essentially, or virtually all of the contaminants, including substantially, essentially, or virtually all of the RNA contaminants. The present invention is not limited with respect to the purification methods used to purify the mRNA, and the invention includes use of any method that is known in the art or developed in the future in order to purify the mRNA and remove contaminants, including RNA contaminants, that interfere with the intended use of the mRNA. In some aspects, the purification of the mRNA removes contaminants that are toxic to the cells (e.g., by inducing an innate immune response in the cells, or, in the case of RNA contaminants comprising double-stranded RNA, by inducing RNA interference (RNAi), e.g., via siRNA or long RNAi molecules) and contaminants that directly or indirectly decrease translation of the mRNA in the cells).

The term "pseudouridine" include m1acp3ψ (1-methyl-3-(3-amino-3-carboxypropyl) pseudouridine, m1ψ (1-methylpseudouridine), ψm (2'-O-methylpseudouridine), m5D (5-methyldihydrouridine), m3ψ (3-methylpseudouridine), a pseudouridine moiety that is not further modified, a monophosphate, diphosphate, or triphosphate of any of the above pseudouridines, or any other pseudouridine known in the art. Each possibility represents a separate aspect of the present invention.

In one aspect, between 0.1% and 100% of the residues in the RNA, oligoribonucleotide, or polyribonucleotide molecule of methods and compositions of the present invention are modified (e.g. either by the presence of pseudouridine or a modified nucleoside base). In some aspects, 0.1% of the residues are modified. In some aspects, 0.2%. In some aspects, the fraction is 0.3%. In some aspects, the fraction is 0.4%. In some aspects, the fraction is 0.5%. In some aspects, the fraction is 0.6%. In some aspects, the fraction is 0.8%. In some aspects, the fraction is 1%. In some aspects, the fraction is 1.5%. In some aspects, the fraction is 2%. In some aspects, the fraction is 2.5%. In some aspects, the fraction is 3%. In some aspects, the fraction is 4%. In some aspects, the fraction is 5%. In some aspects, the fraction is 6%. In some aspects, the fraction is 8%. In some aspects, the fraction is 10%. In some aspects, the fraction is 12%. In some aspects, the fraction is 14%. In some aspects, the fraction is 16%. In some aspects, the fraction is 18%. In some aspects, the fraction is 20%. In some aspects, the fraction is 25%. In some aspects, the fraction is 30%. In some aspects, the fraction is 35%. In some aspects, the fraction is 40%. In some aspects, the fraction is 45%. In some aspects, the fraction is 50%. In some aspects, the fraction is 60%. In some aspects, the fraction is 70%. In some aspects, the fraction is 80%. In some aspects, the fraction is 90%. In some aspects, the fraction is 100%.

In another aspect, the fraction is less than 5%. In some aspects, the fraction is less than 3%. In some aspects, the fraction is less than 1%. In some aspects, the fraction is less than 2%. In some aspects, the fraction is less than 4%. In some aspects, the fraction is less than 6%. In some aspects, the fraction is less than 8%. In some aspects, the fraction is less than 10%. In some aspects, the fraction is less than 12%. In some aspects, the fraction is less than 15%. In some aspects, the fraction is less than 20%. In some aspects, the fraction is less than 30%. In some aspects, the fraction is less than 40%. In some aspects, the fraction is less than 50%. In some aspects, the fraction is less than 60%. In some aspects, the fraction is less than 70%.

In one aspect, the present invention provides a method of inducing a cell to produce a polypeptide of interest, comprising contacting the cell with an in vitro-transcribed RNA molecule encoding the polypeptide of interest, the in vitro-transcribed RNA molecule further comprising a pseudouridine or a modified nucleoside, thereby inducing a cell to produce the polypeptide of interest.

In various embodiments, the composition comprises one or more transfection reagent. In another embodiment, the transfection reagent is a lipid-based transfection reagent. In another embodiment, the transfection reagent is a protein-based transfection reagent. In another embodiment, the transfection reagent is a polyethyleneimine based transfection reagent. In another embodiment, the transfection reagent is calcium phosphate. In another embodiment, the transfection reagent is Lipofectin®, Lipofectamine®, or TransIT®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity. In another embodiment, liposomes are hollow spherical vesicles composed of lipids arranged in a similar fashion as those lipids which make up the cell membrane. They have, in another embodiment, an internal aqueous space for entrapping water-soluble compounds and range in size from 0.05 to several microns in diameter. In another embodiment, liposomes can deliver RNA to cells in a biologically active form.

In various embodiments, the compositions of the present invention may comprise any lipid capable of forming a particle to which the one or more nucleic acid molecules are attached, or in which the one or more nucleic acid molecules are encapsulated. The term "lipid" refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In certain embodiments, the composition comprises one or more targeting moieties which are capable of targeting the LNP to a cell, cell population, tissue of interest, or any combination thereof. For example, in one embodiment, the targeting moiety is a ligand which directs the LNP to a receptor found on a cell surface.

In certain embodiments, the composition comprises one or more internalization domains. For example, in one embodiment, the composition comprises one or more domains which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo (e.g., one or more nucleic acid molecules, one or more therapeutic agents, or any combination thereof).

The RNA is produced by in vitro transcription using a plasmid DNA template generated synthetically. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. In one embodiment, the desired template for in vitro transcription is an antigen capable of inducing an adaptive immune response, including for example an antigen associated with a pathogen or tumor, as described elsewhere herein. In one embodiment, the desired template for in vitro transcription is an adjuvant capable of enhancing an adaptive immune response.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. In another embodiment, the DNA to be used for PCR is a gene from a pathogenic or commensal organism, including bacteria, viruses, parasites, and fungi. In another embodiment, the DNA to be used for PCR is from a pathogenic or commensal organism, including bacteria, viruses, parasites, and fungi, including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Examples of genes that can be used as sources of DNA for PCR include genes that encode polypeptides that induce or enhance an adaptive immune response in an organism. Preferred genes are genes which are useful for a short term treatment, or where there are safety concerns regarding dosage or the expressed gene.

In various embodiments, a plasmid is used to generate a template for in vitro transcription of mRNA which is used for transfection.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

In one aspect, the present disclosure provides a method of increasing transfection efficiency of mRNA encoding at least one polypeptide of interest, said method comprising substituting uridine (U) nucleotide residues of a reference mRNA with nucleotide residues selected from the group consisting of 1-methylpseudouridine (m1Ψ) and pseudouridine (Ψ), thereby rendering modified mRNA, wherein the modified mRNA shows increased transfection efficiency than the reference mRNA. In one aspect, the polypeptide of interest is a CAR, a TCR, a GFR, a HR, a Nb, a scFv, or a reporter.

Methods of determining translation efficiency are well known in the art, and include, e.g. measuring the activity or amount of an encoded protein (e.g. luciferase and/or GFP), or measuring radioactive label or epitope tag incorporated into the translated protein (See, e.g., Ngosuwan et al, J Biol Chem (2003) 278(9): 7034-42).

In one aspect, said modified mRNA exhibits enhanced ability to produce a polypeptide of interest encoded by the GOI in a cell compared to the same quantity of a reference mRNA that exhibits the same sequence but with uridine in place of said at least one modified nucleoside selected from the group consisting of 1-methylpseudouridine and pseudouridine, wherein said enhanced ability to produce said protein of interest is determined by measuring a higher level of either the amount of polypeptide or the amount of enzymatic activity or other biological effect produced at one or more times after said contacting of said cell with said modified mRNA compared to the corresponding amount of polypeptide or amount of enzymatic activity or other biological effect produced in the same or equivalent cell at the same times after contacting with the same quantity of the reference mRNA. In some aspects, the cell is an immune cell. In some aspects, the immune cell is a T-cell, a NK cells, or a monocyte. In some aspects, the immune cell is a human T-cell. In some aspects, the polypeptide of interest is a CAR, a TCR, a GFR, a HR, a Nb, a scFv, or a reporter.

In one aspect, said modified RNA further comprises regulatory elements, such as 5' and 3' untranslated regions, which enhance translation and/or reduce cytotoxicity. Studies detailing modified regulatory elements are described in PCT Patent Application No. PCT/US2023/066903, which is fully incorporated herein by reference.

Methods of determining translation efficiency are well known in the art, and include, e.g. measuring the activity of an encoded reporter protein (e.g. luciferase or green fluorescent protein [Wall, et al, J Biol Chem (2005) 280(30): 27670-8]), or measuring radioactive label incorporated into the translated protein (Ngosuwan, et al, J Biol Chem (2003) 278(9): 7034-42). Each method represents a separate aspect of the present invention.

In one aspect, the mRNA of the disclosure (including sa-mRNA, modified mRNA and circRNA) are significantly less immunogenic than a non-self-amplifying, unmodified and/or linear in vitro-synthesized RNA molecule comprising the same sequence. In another aspect, the sa-mRNA or modified mRNA molecule is 2-fold less immunogenic than its traditional mRNA counterpart. In another aspect, immunogenicity is reduced by a 3-fold factor. In another aspect, immunogenicity is reduced by a 5-fold factor. In another aspect, immunogenicity is reduced by a 7-fold factor. In another aspect, immunogenicity is reduced by a 10-fold factor. In another aspect, immunogenicity is reduced by a 15-fold factor. In another aspect, immunogenicity is reduced by a 20-fold factor. In another aspect, immunogenicity is reduced by a 50-fold factor. In another aspect, immunogenicity is reduced by a 100-fold factor. In another aspect, immunogenicity is reduced by a 200-fold factor. In another aspect, immunogenicity is reduced by a 500-fold factor. In another aspect, immunogenicity is reduced by a 1000-fold factor. In another aspect, immunogenicity is reduced by a 2000-fold factor. In another aspect, immunogenicity is reduced by another fold difference.

Methods of determining immunogenicity are well known in the art, and include, e.g. measuring secretion of cytokines (e.g. IL-1β, IA-12, IFN-α, TNF-α, RANTES, MIP-1α or β, IL-6, IFN-β, IFN-γ, or IL-8; Examples herein), measuring expression of DC activation markers (e.g. CD83, HLA-DR, CD80 and CD86; Examples herein), or measuring ability to act as an adjuvant for an adaptive immune response.

mRNA of the present disclosure can be characterized using assays known in the art. These assays can be conducted, for example, by detecting expression of the encoded polypeptide by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular polypeptide involve panning using monoclonal antibodies on a plate or capture using magnetic beads coated with monoclonal antibodies.

Chimeric Antigen Receptor

Chimeric antigen receptor (CAR) comprises a transmembrane domain protein with an antigen recognizing amino terminus, and a transmembrane domain connected to an endodomain which transmits T-cell activation signals. Currently available CAR T-cell therapies are produced by collecting T-cells from a subject and engineering them using recombinant techniques known in the art to produce chimeric antigen receptors (CARs) on the cell surface. The engineered cells are replicated ex vivo and then infused back into the subject.

In one aspect, the sa-mRNA, modified mRNA, or circRNA of the disclosure comprise a GOI encoding from 5' to 3': (SEQ ID NO: 1)-VH-(SEQ ID NO: 2)-VL- (SEQ ID NO: 3)- (SEQ ID NO: 4)- (SEQ ID NO: 5)- (SEQ ID NO: 6). In one aspect, the GOI encodes from 5' to 3': (SEQ ID NO: 1)-VH-(SEQ ID NO: 2)-VL- (SEQ ID NO: 3)- (SEQ ID NO: 7)- (SEQ ID NO: 8)- (SEQ ID NO: 9) or (SEQ ID NO: 1)-VH-(SEQ ID NO: 2)-VL-(SEQ ID NO: 3)-(SEQ ID NO: 7)-(SEQ ID NO: 8)-(SEQ ID NO: 9).

Figure 14:
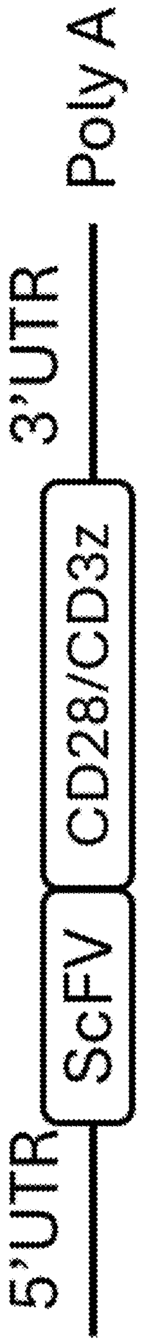
FIG. 14 shows a schematic of a mRNA wherein 5'UTR is a 5' untranslated region, CD8 is the hinge region of a CD8 alpha chain; CD28 is a CD28 activation domain; CD3z is a CD3 zeta cytoplasmic domain; scFv is a single-chain variable fragment, 3'UTR is a 3' untranslated region and poly-A is a a poly A tail.
Figure 15:
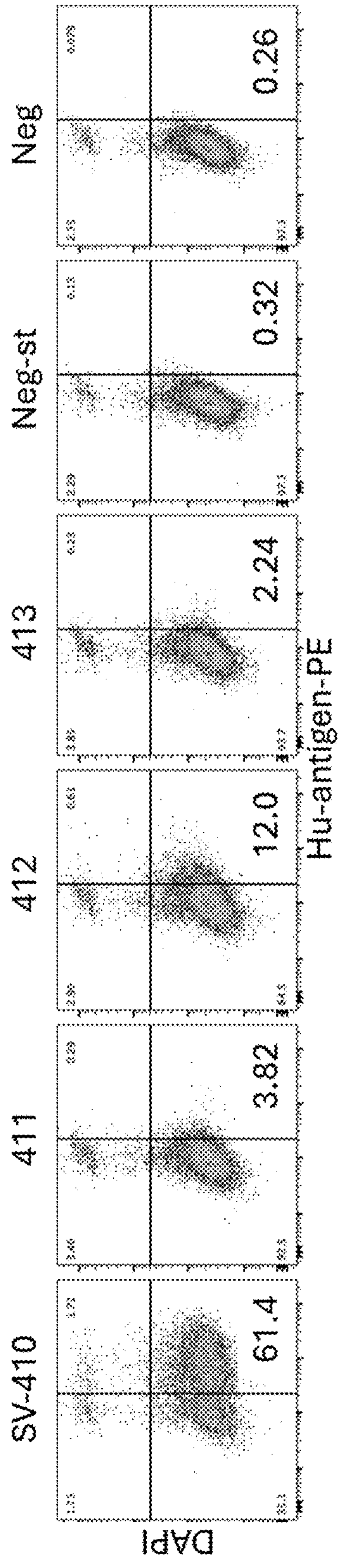
FIG. 15 shows FACS of modified RNA SVP410, SVP411, SVP412, and SVP413 (all comprising a GOI encoding scFv and CAR) delivered into Human Embryonic Kidney (HEK) 293 cells using an LNP of the disclosure.

Studies have indicated that delivering scFv sequences (single-chain variable fragments) in conjunction with CAR show improved cytotoxicity against various aggressive tumors. (See, e.g., Bloemberg et al, S. Mol Ther Methods Clin Dev. (2020) 16: 238-254). FIGS. 14 and 15 show two exemplary mRNA payloads of the disclosure wherein the GOI encodes a scFv and a CAR sequence. In some aspects, the GOI comprises (SEQ ID NO: 30).

In one aspect, the payload of the disclosure is an mRNA comprising a nucleic acid sequence encoding from 5' to 3': LP-AR or LP-scFv-AR, wherein, LP is a leading peptide; scFv is a single-chain variable fragment and AR is an antigen receptor.

In one aspect, the payload is the payload is an mRNA comprising a nucleic acid sequence encoding from 5' to 3': LP-VH-LK-VL-MyC-CD8-CD28-CD3z, wherein, LP is a leading peptide; VH is the variable region of an immunoglobulin heavy chain; LK is a linker; VL is the variable region of an immunoglobulin light chain; MyC is a Myc tag; CD8 is the hinge region of a CD8 alpha chain; CD28 is a CD28 activation domain; and CD3z is a CD3 zeta cytoplasmic domain.

In one aspect, the payload is the payload is an mRNA comprising a nucleic acid sequence encoding from 5' to 3': LP-scFv-CAR, wherein, LP is a leading peptide; and scFv is a single-chain variable fragment; and CAR is a chimeric antigen receptor sequence, wherein scFv-CAR encodes from 5' to 3': VH-LK-VL-CD8-CD28-CD3z, wherein, VH is the variable region of a immunoglobulin heavy chain, LK is a linker, VL is the variable region of an immunoglobulin light chain, CD8 is the hinge region of a CD8 alpha chain, CD28 is a CD28 activation domain, and CD3z is a CD3 zeta cytoplasmic domain.

In one aspect, the mRNA is a self-amplifying mRNA comprising a nucleic acid sequence from 5' to 3': a) 5'UTR-nsP-L-GOI-L-3'UTR-PolyA; b) 5'UTR-nsP-GOI-L-3'UTR-PolyA; c) 5'UTR-nsP-L-GOI-3'UTR-PolyA; or d) 5'UTR-nsP-SGP-GOI-3'UTR-PolyA. In some aspects, the GOI encodes from 5' to 3: scFv-CAR. In some aspects, the GOI comprise SEQ ID NO: 30. In some aspects, the self-amplifying mRNA comprise a nucleic acid sequence with at least about 85, 90, 95, 98, or 99% sequence identity to SEQ ID NO: 24, 25, 26, 27, 28, or 29. In some aspects, scFv comprise a sequence with at least about 85, 90, 95, 98, or 99% sequence identity to SEQ ID NO: 25, 32, 33, 34, 35, 36, 37, 38, 39, 40, or 45. In some aspects, the CAR comprise a nucleic acid sequence with at least about 85, 90, 95, 98, or 99% sequence identity to SEQ ID NO: 26 or 44.

Delivery System

The disclosure also relates to pharmaceutical compositions comprising a sa-mRNA, modified mRNA or circRNA of the present disclosure, a pharmaceutically acceptable carrier and a suitable delivery system, such as liposomes, lipid nanoparticles, nanoemulsions, PLG micro- and nanoparticles, lipoplexes, chitosan micro- and nanoparticles and other polyplexes. If desired other pharmaceutically acceptable components can be included, such as excipients and adjuvants.

In one aspect, the sa-mRNA or modified mRNA of the present disclosure is delivered using an LNP comprising one or more ionizable lipids (e.g., lipids that may have a positive or partial positive charge at physiological pH); one or more PEG or PEG-modified lipids (a lipid modified with polyethylene glycol); one or more structural lipids (e.g. cholesterol, fecosterol, sitosterol, ergosterol, campesterol, stigmasterol, brassicasterol, tomatidine, tomatine, ursolic acid, alpha-tocopherol, and mixtures thereof); and one or more phospholipids (e.g. (poly)unsaturated lipids).

In one aspect, the sa-mRNA or modified mRNA of the present disclosure is delivered to a host cell by an LNP formulated with an ionizable lipid, a helper lipid, a cholesterol, and/or a PEG-lipid. In one aspect, the LNP has a molar ratio of about 2-60% ionizable lipid, about 5-40% helper lipid, about 30-80% cholesterol and about 0.5-30% PEG-lipid. In one aspect, the LNP has a molar ratio of about 5-50% or 8 to 40% or 10 to 30% ionizable lipid, about 10-30% or 13 to 25% or 15 to 20% helper lipid, about 40-70% or 45 to 65% or 50 to 60% cholesterol and about 1-20% or 3-15% or 5 to 10% PEG-lipid. In one aspect, the LNP has a molar ratio of about 2-10% ionizable lipid, about 5-15% helper lipid, about 40-80% cholesterol and about 0.5-3% PEG-lipid.

Ionizable Lipids

In one aspect, the present disclosure provides a method of increasing transfection efficiency and decreasing cytotoxicity of a nanoparticle formulation by using novel ionizable lipids of the present disclosure in the LNP formulation. In some aspects, the nanoparticle compositions may include the ionizable lipid components of PCT Patent Application No. PCT/US2023/017777, which is fully incorporated herein by reference. In some aspects, the nanoparticle compositions may include, but is not limited to the compounds listed in Table 1.

TABLE 1
| Lipid ID | Lipid Structure |
| --- | --- |
| (I) or P6A2 | 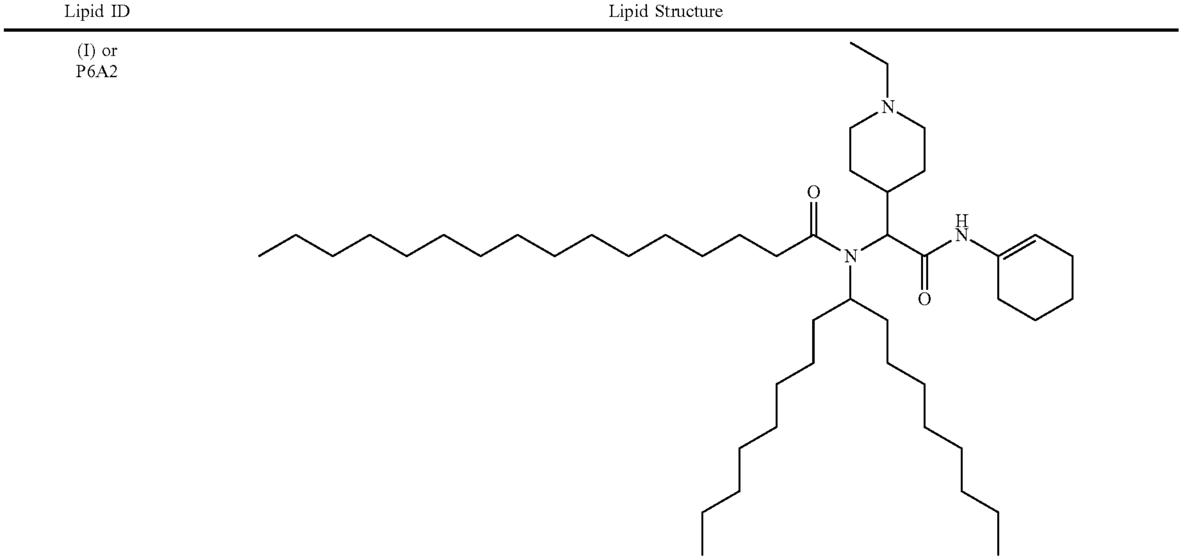 |
| (II) or P1D4 | 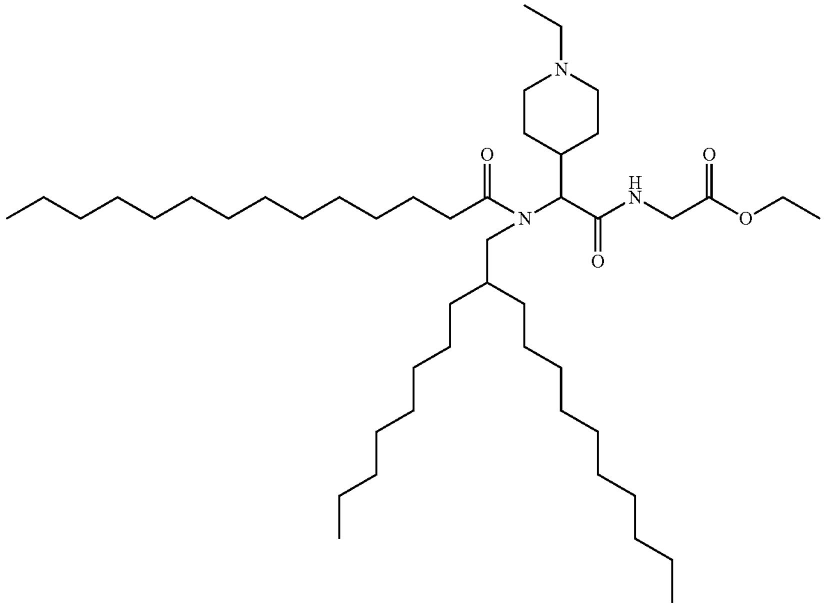 [SMILES: CCCCCCCCCCCCCC(=O)N(CC(CCCCCCCC)CCCCCCCCCC)C(C(=O)NCC(=O)OCC)C1CCN(CC)CC1] |
| (III) or P30B7 | 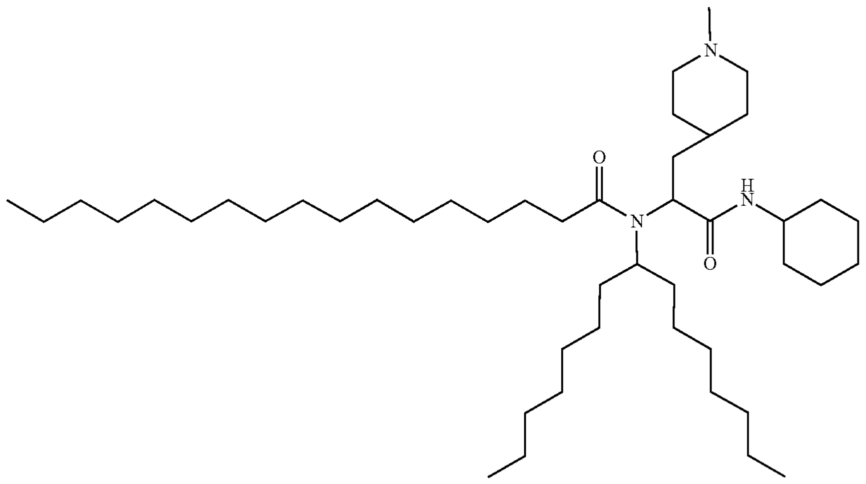 [SMILES: CCCCCCCCCCCCCCCCC(=O)N(C(CCCCCCC)CCCCCCC)C(CC1CCN(C)CC1)C(=O)NC1CCCCC1] |

TABLE 1-continued
| Lipid ID | Lipid Structure |
| --- | --- |
| (IV) or P30A1 | 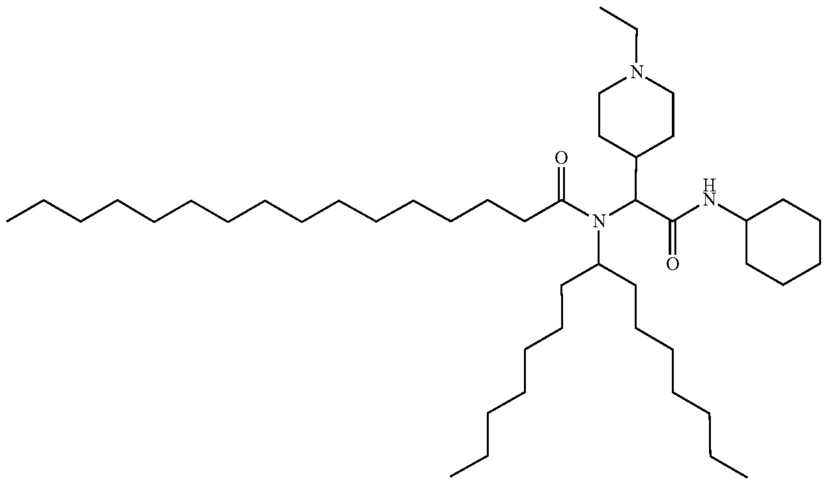 [SMILES: CCCCCCCCCCCCCCCC(=O)N(C(CCCCCCC)CCCCCCC)C(C(=O)NC1CCCCC1)C1CCN(CC)CC1] |
| (V) or P54B6 | 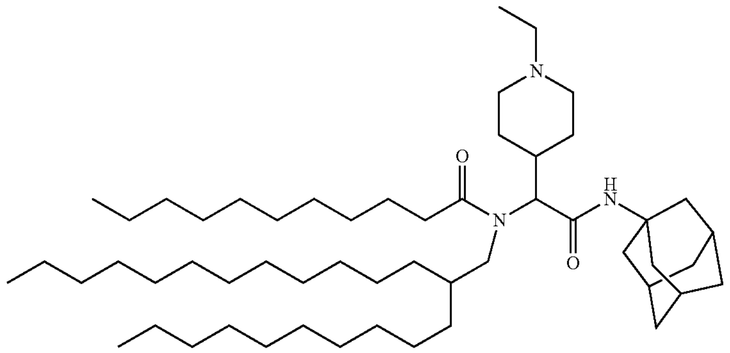 [SMILES: CCCCCCCCCCCCC(CCCCCCCCCC)CN(C(=O)CCCCCCCCCC)C(C(=O)NC12CC3CC(CC(C3)C1)C2)C1CCN(CC)CC1] |
| (VI) or P38D1 | 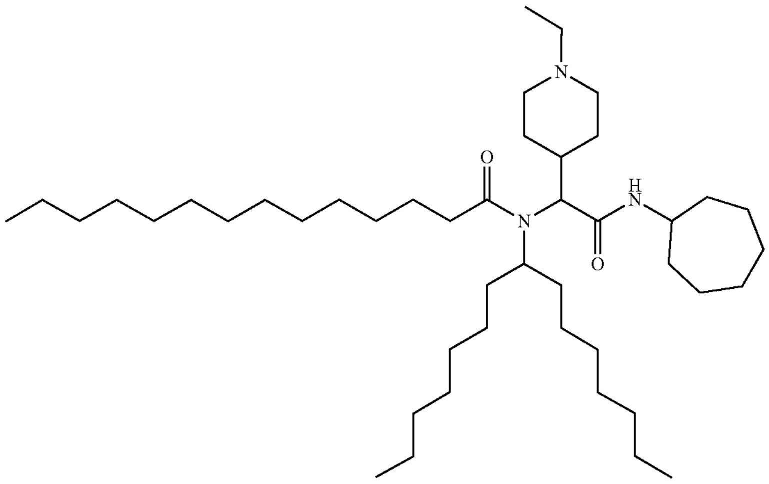 [SMILES: CCCCCCCCCCCCCC(=O)N(C(CCCCCCC)CCCCCCC)C(C(=O)NC1CCCCCC1)C1CCN(CC)CC1] |

TABLE 1-continued
| Lipid ID | Lipid Structure |
| --- | --- |
| (VII) or P51C12 | 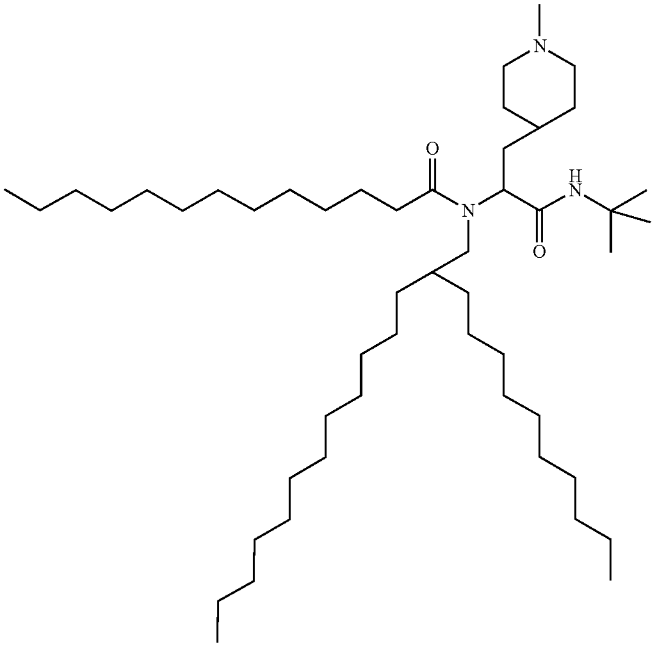 |
| (VIII) or P53A6 | 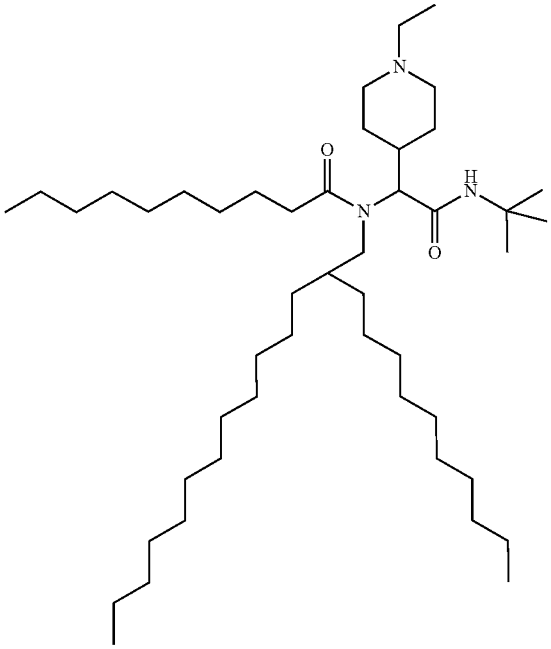 [SMILES: CCCCCCCCCCCCC(CCCCCCCCCC)CN(C(=O)CCCCCCCCC)C(C(=O)NC(C)(C)C)C1CCN(CC)CC1] |

TABLE 1-continued
| Lipid ID | Lipid Structure |
| --- | --- |
| (IX) or P40D7 | 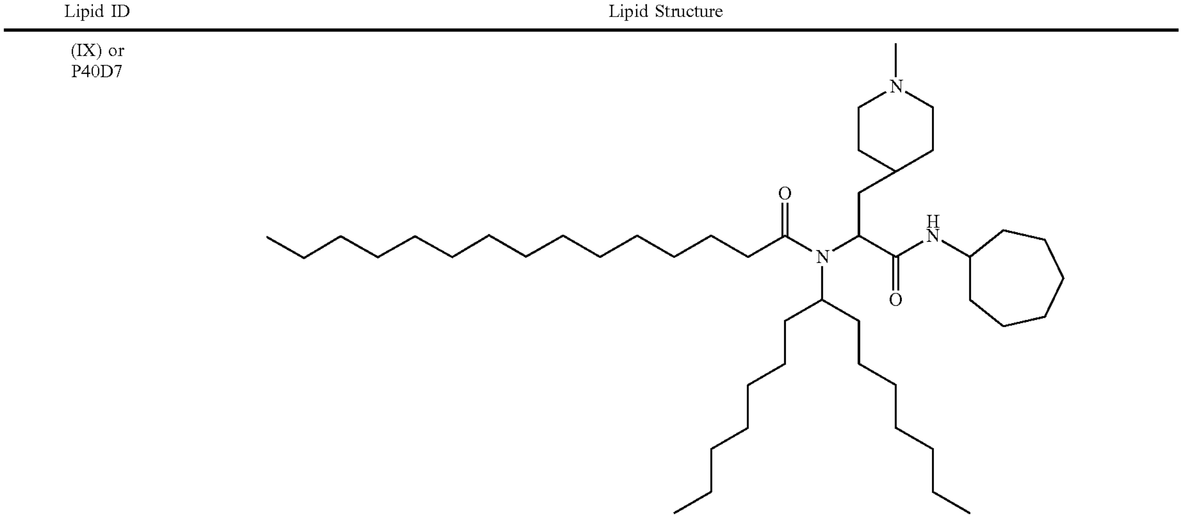 |
| (X) or P149A2 | 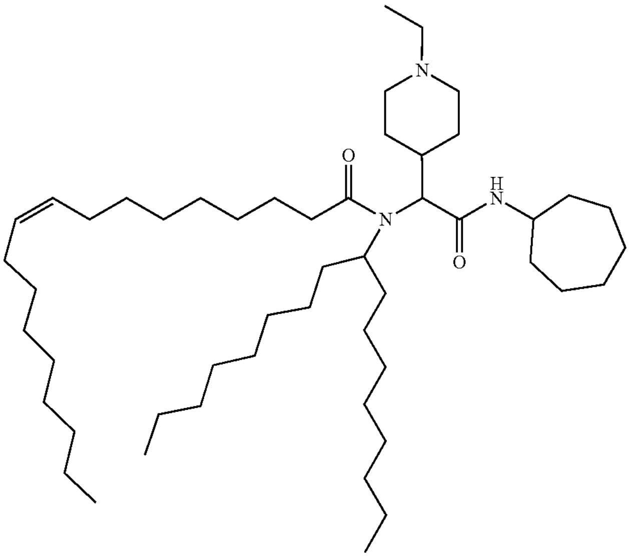 [SMILES: CCCCCCCC/C=C\CCCCCCCC(=O)N(C(CCCCCCCC)CCCCCCCC)C(C(=O)NC1CCCCCC1)C1CCN(CC)CC1] |
| (XI) or P153C3 | 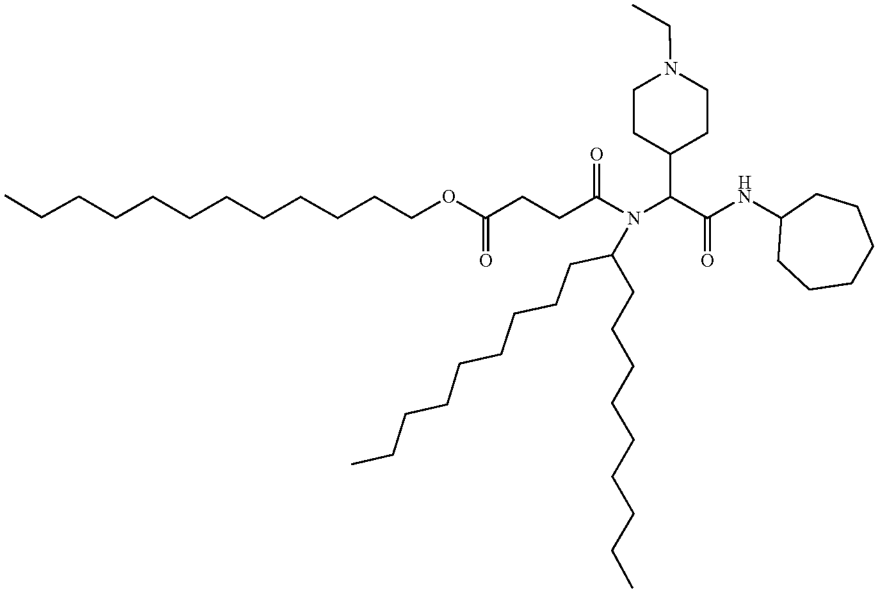 [SMILES: CCCCCCCCCCCCOC(=O)CCC(=O)N(C(CCCCCCCCC)CCCCCCCCC)C(C(=O)NC1CCCCCC1)C1CCN(CC)CC1] |

TABLE 1-continued
| Lipid ID | Lipid Structure |
| --- | --- |
| (XII) or P153C5 | 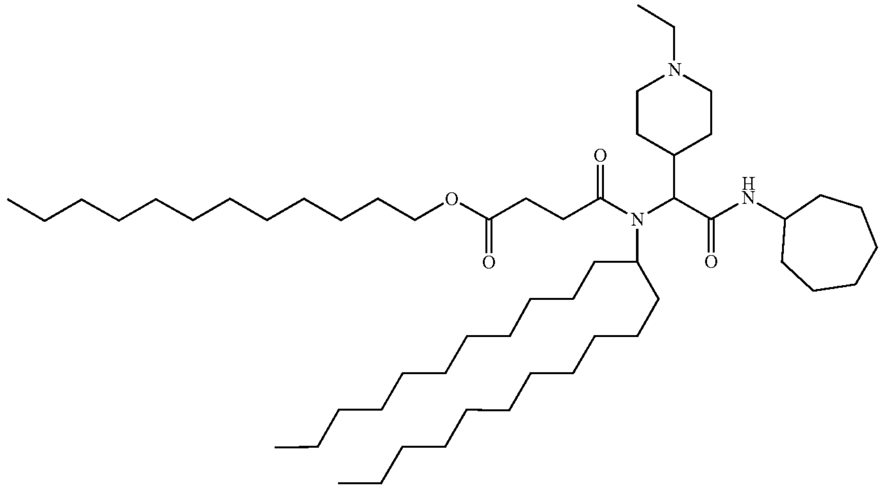 [SMILES: CCCCCCCCCCCCOC(=O)CCC(=O)N(C(CCCCCCCCCCC)CCCCCCCCCCC)C(C(=O)NC1CCCCCC1)C1CCN(CC)CC1] |
| (XIII) or P30C7 | 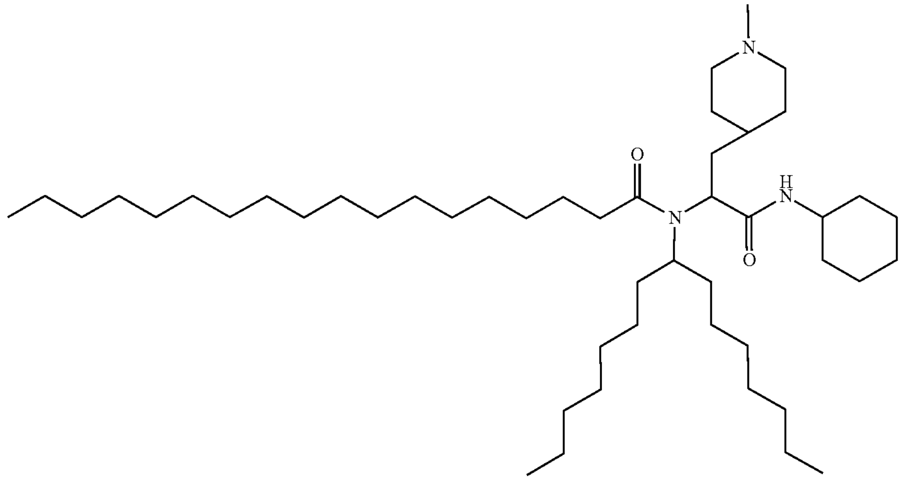 [SMILES: CCCCCCCCCCCCCCCCCC(=O)N(C(CCCCCCC)CCCCCCC)C(CC1CCN(C)CC1)C(=O)NC1CCCCC1] |
| (XIV) or P38D7 | 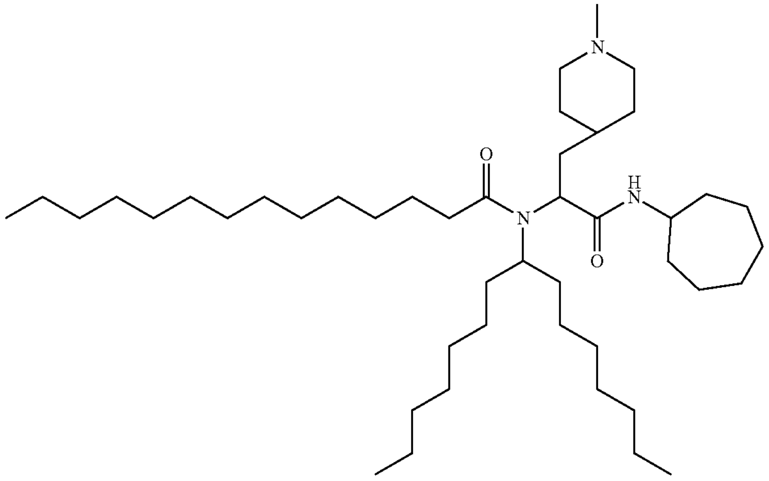 [SMILES: CCCCCCCCCCCCCC(=O)N(C(CCCCCCC)CCCCCCC)C(CC1CCN(C)CC1)C(=O)NC1CCCCCC1] |

TABLE 1-continued
| Lipid ID | Lipid Structure |
|---|---|
| (XV) or P38D8 | 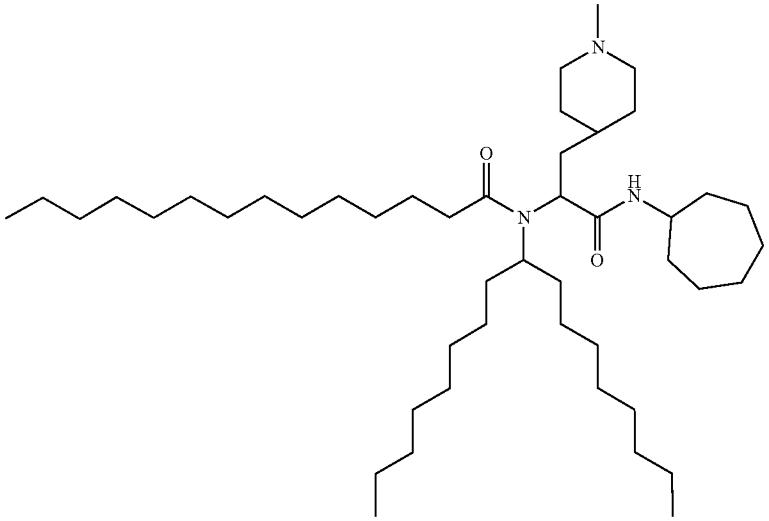 |
| (XVI) or P56A1 | 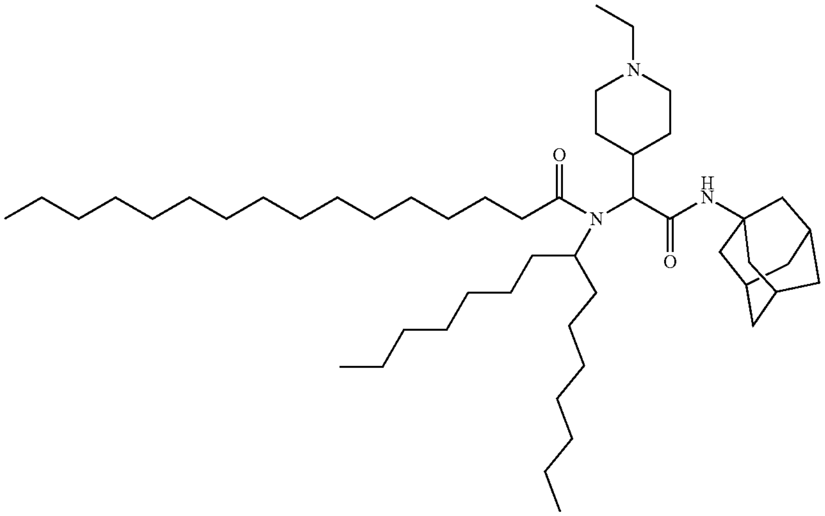 [SMILES: CCCCCCCCCCCCCCCC(=O)N(C(CCCCCCC)CCCCCCC)C(C(=O)NC12CC3CC(CC(C3)C1)C2)C1CCN(CC)CC1] |
| (XVII) or P56B1 | 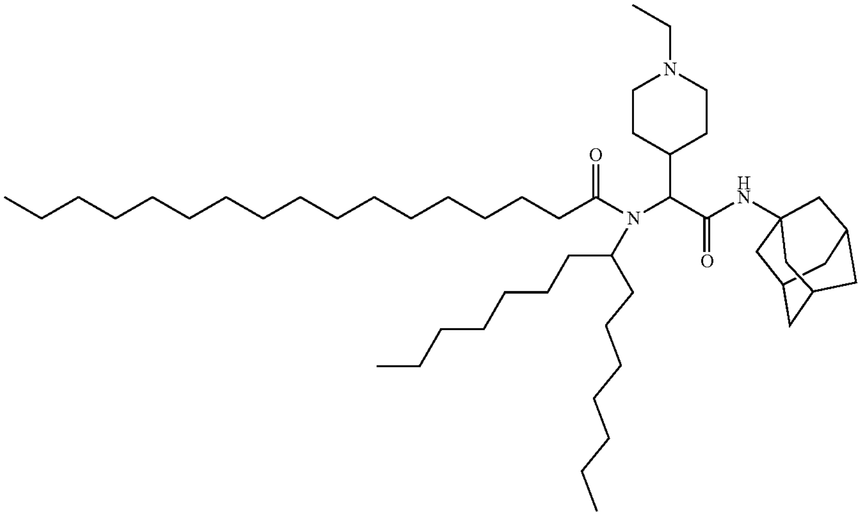 [SMILES: CCCCCCCCCCCCCCCCC(=O)N(C(CCCCCCC)CCCCCCC)C(C(=O)NC12CC3CC(CC(C3)C1)C2)C1CCN(CC)CC1] |

TABLE 1-continued
| Lipid ID | Lipid Structure |
| --- | --- |
| (XVIII) or P28D10 | 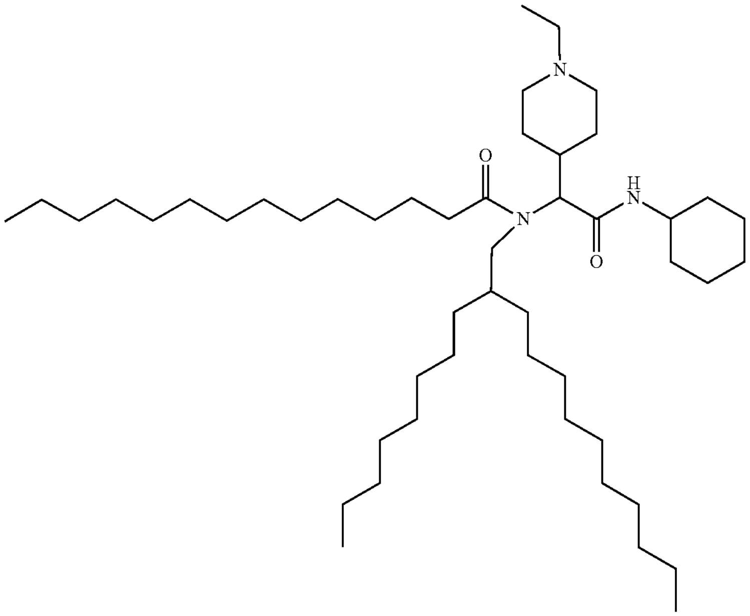 [SMILES: CCCCCCCCCCCCCC(=O)N(CC(CCCCCCCC)CCCCCCCCCC)C(C(=O)NC1CCCCC1)C1CCN(CC)CC1] |
| (XIX) or P56A2 | 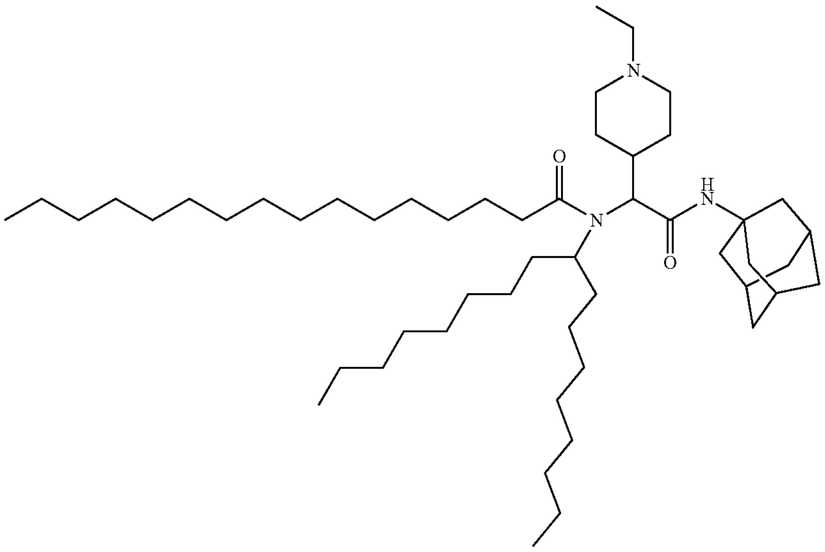 [SMILES: CCCCCCCCCCCCCCCC(=O)N(C(CCCCCCCC)CCCCCCCC)C(C(=O)NC12CC3CC(CC(C3)C1)C2)C1CCN(CC)CC1] |
| (XX) or P38D4 | 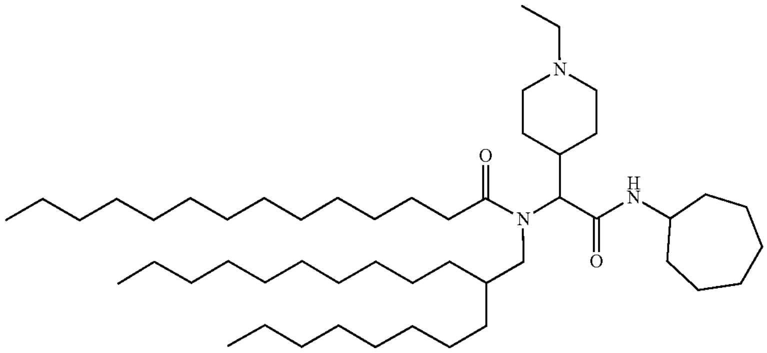 [SMILES: CCCCCCCCCCCCCC(=O)N(CC(CCCCCCCC)CCCCCCCCCC)C(C(=O)NC1CCCCCC1)C1CCN(CC)CC1] |

TABLE 1-continued
| Lipid ID | Lipid Structure |
| --- | --- |
| (XXI) or P161F10 | 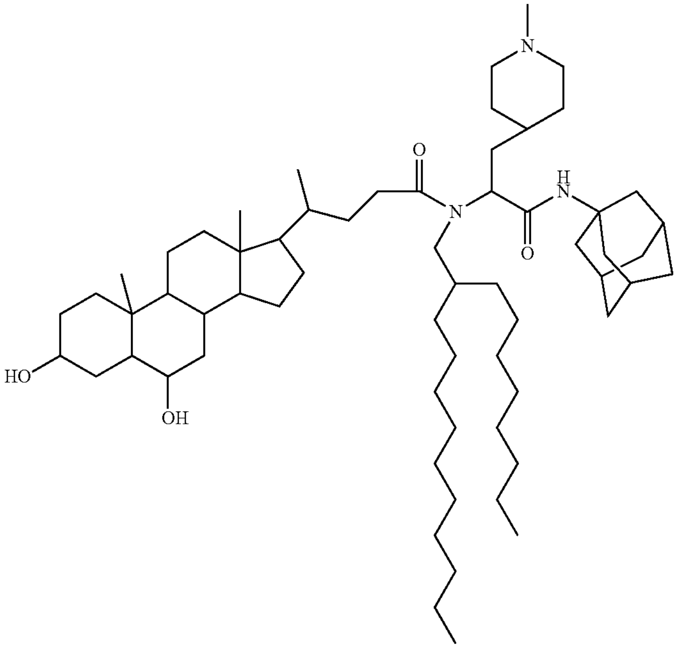 [SMILES: CCCCCCCCCCC(CCCCCCCC)CN(C(=O)CCC(C)C1CCC2C3CC(O)C4CC(O)CCC4(C)C3CCC12C)C(CC1CCN(C)CC1)C(=O)NC12CC3CC(CC(C3)C1)C2] |
| (XXII) or P159C10 | 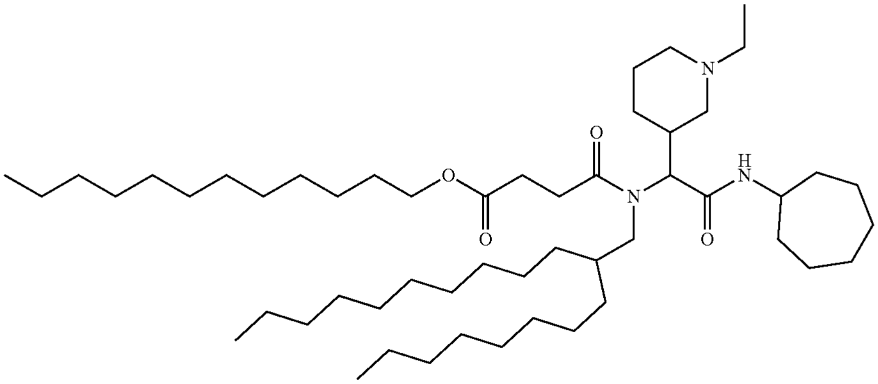 [SMILES: CCCCCCCCCCCCOC(=O)CCC(=O)N(CC(CCCCCCCC)CCCCCCCCCC)C(C(=O)NC1CCCCCC1)C1CCCN(CC)C1] |
| (XXIII) or P149A1 | 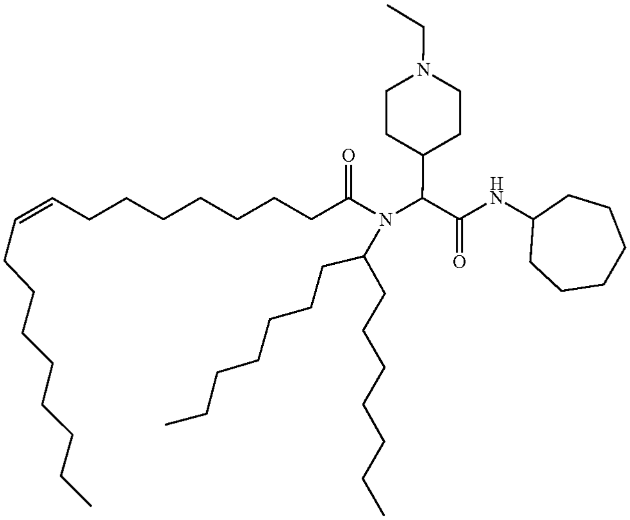 [SMILES: CCCCCCCC/C=C\CCCCCCCC(=O)N(C(CCCCCCC)CCCCCCC)C(C(=O)NC1CCCCCC1)C1CCN(CC)CC1] |

TABLE 1-continued
| Lipid ID | Lipid Structure |
|---|---|
| (XXIV) or P153C1 | 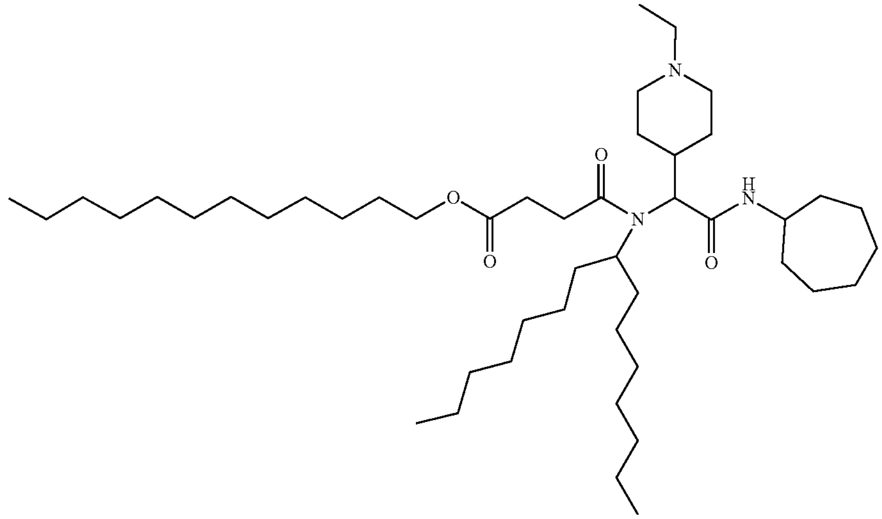 [SMILES: CCCCCCCCCCCCOC(=O)CCC(=O)N(C(CCCCCCC)CCCCCCC)C(C(=O)NC1CCCCCC1)C1CCN(CC)CC1] |
| (XXV) or P40B10 | 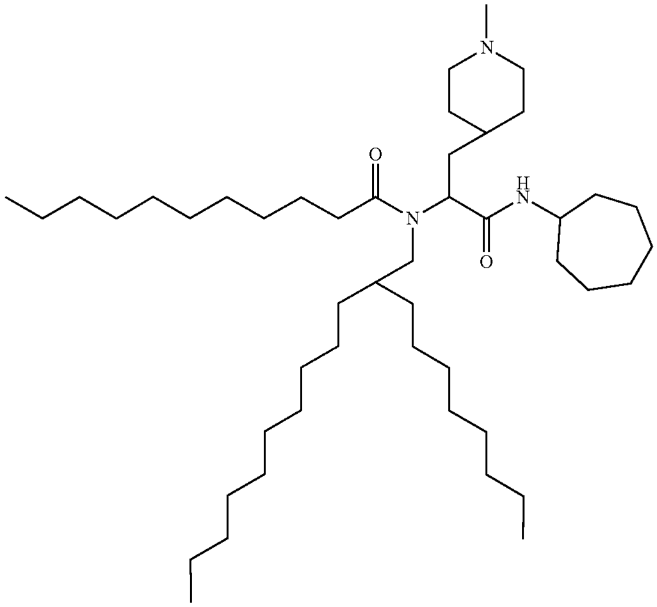 [SMILES: CCCCCCCCCCC(=O)N(CC(CCCCCCCC)CCCCCCCCCC)C(CC1CCN(C)CC1)C(=O)NC1CCCCCC1] |

TABLE 1-continued
| Lipid ID | Lipid Structure |
| --- | --- |
| (XXVI) or P40C11 | 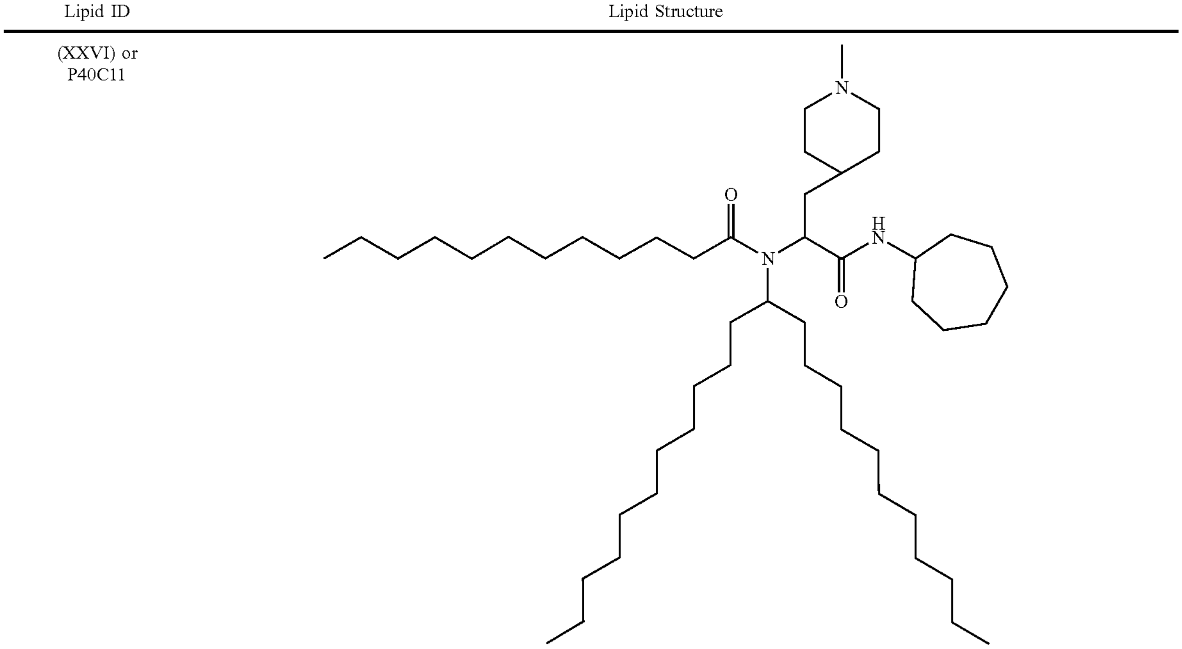 |
| (XXVII) or P53A5 | 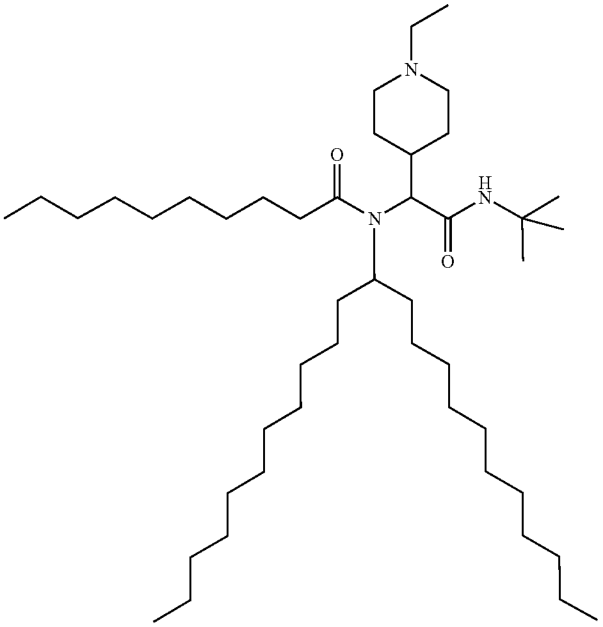 [SMILES: CCCCCCCCCCCC(CCCCCCCCCCC)N(C(=O)CCCCCCCCC)C(C(=O)NC(C)(C)C)C1CCN(CC)CC1] |

TABLE 1-continued
| Lipid ID | Lipid Structure |
|---|---|
| (XXVIII) or P40C10 | 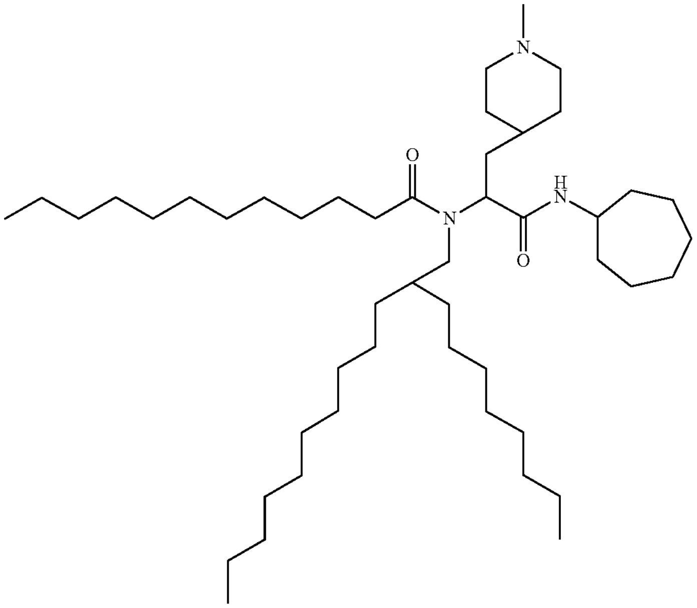 [SMILES: CCCCCCCCCCCC(=O)N(CC(CCCCCCCC)CCCCCCCCCC)C(CC1CCN(C)CC1)C(=O)NC1CCCCCC1] |
| (XXIX) or E6 | 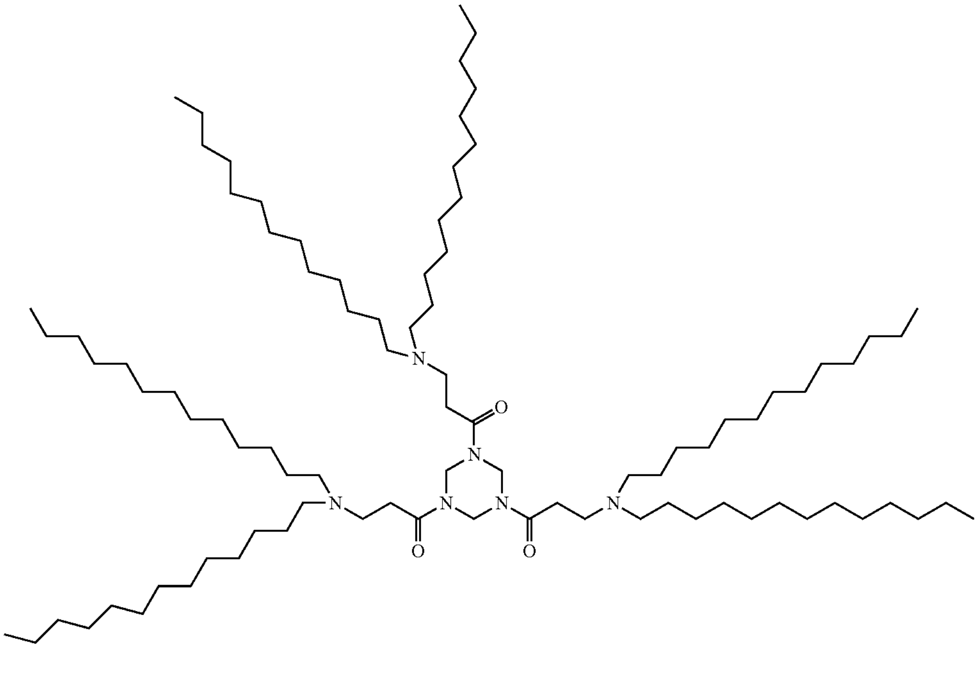 [SMILES: CCCCCCCCCCCCCN(CCCCCCCCCCCCC)CCC(=O)N1CN(C(=O)CCN(CCCCCCCCCCCCC)CCCCCCCCCCCCC)CN(C(=O)CCN(CCCCCCCCCCCCC)CCCCCCCCCCCCC)C1] |

TABLE 1-continued
| Lipid ID | Lipid Structure |
|---|---|
| (XXX) or E2 | 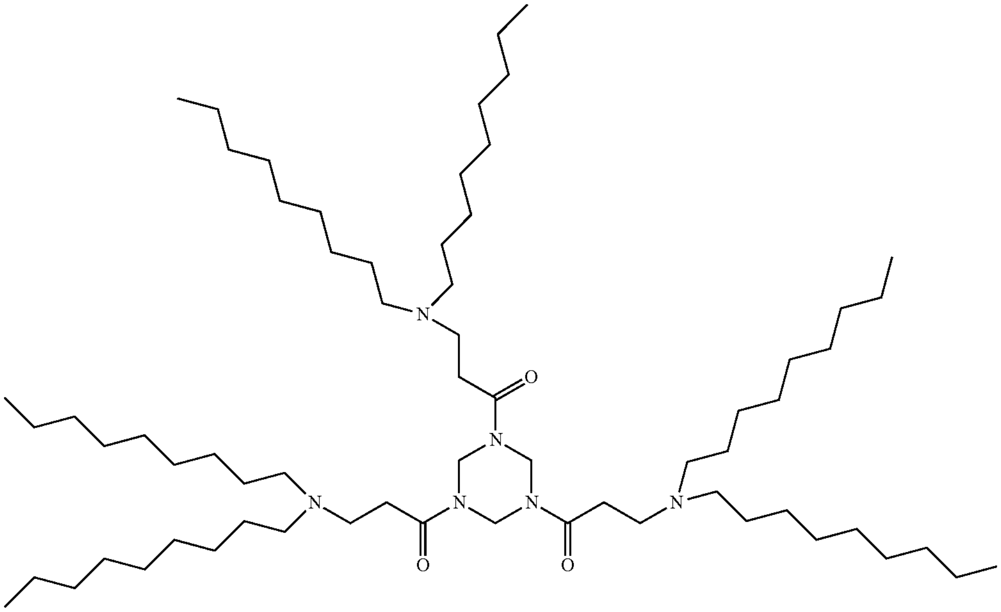 [SMILES: CCCCCCCCCN(CCCCCCCCC)CCC(=O)N1CN(C(=O)CCN(CCCCCCCCC)CCCCCCCCC)CN(C(=O)CCN(CCCCCCCCC)CCCCCCCCC)C1] |
| (XXXI) or P161F6 | 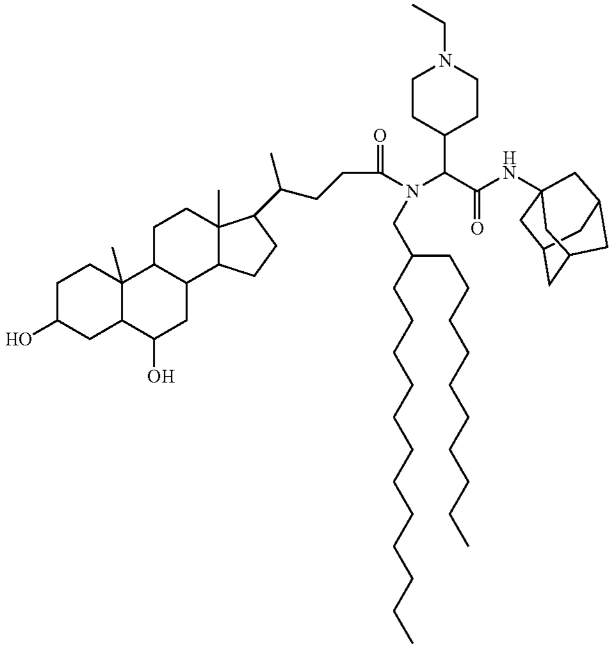 [SMILES: CCCCCCCCCCCCC(CCCCCCCCCC)CN(C(=O)CCC(C)C1CCC2C3CC(O)C4CC(O)CCC4(C)C3CCC12C)C(C(=O)NC12CC3CC(CC(C3)C1)C2)C1CCN(CC)CC1] |

TABLE 1-continued
| Lipid ID | Lipid Structure |
|---|---|
| (XXXII) or P149C2 | 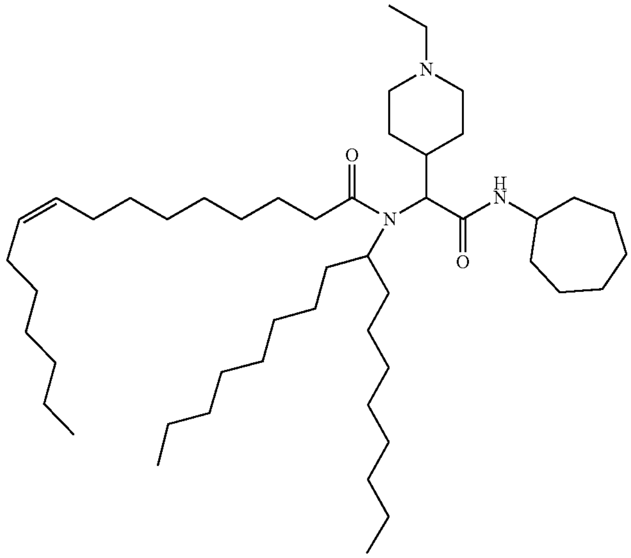 [SMILES: CCCCCC/C=C\CCCCCCCC(=O)N(C(CCCCCCCC)CCCCCCCC)C(C(=O)NC1CCCCCC1)C1CCN(CC)CC1] |
| (XXXIII) or P149A3 | 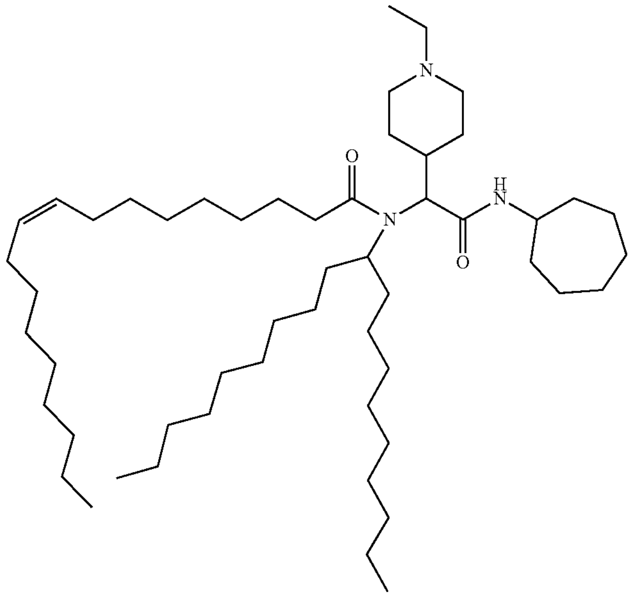 [SMILES: CCCCCCCC/C=C\CCCCCCCC(=O)N(C(CCCCCCCCC)CCCCCCCCC)C(C(=O)NC1CCCCCC1)C1CCN(CC)CC1] |

TABLE 1-continued
| Lipid ID | Lipid Structure |
|---|---|
| (XXXIV) or P149C1 | 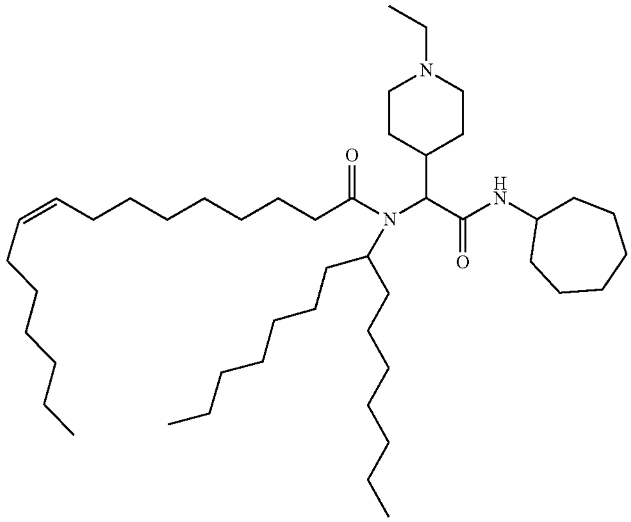 [SMILES: CCCCCC/C=C\CCCCCCCC(=O)N(C(CCCCCCC)CCCCCCC)C(C(=O)NC1CCCCCC1)C1CCN(CC)CC1] |
| (XXXV) or P149C3 | 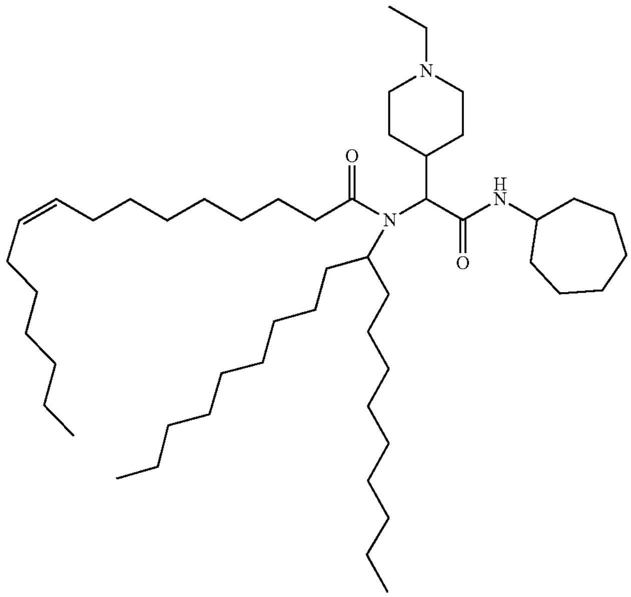 [SMILES: CCCCCC/C=C\CCCCCCCC(=O)N(C(CCCCCCCCC)CCCCCCCCC)C(C(=O)NC1CCCCCC1)C1CCN(CC)CC1] |

TABLE 1-continued
| Lipid ID | Lipid Structure |
|---|---|
| (XXXVI) or P153C2 | 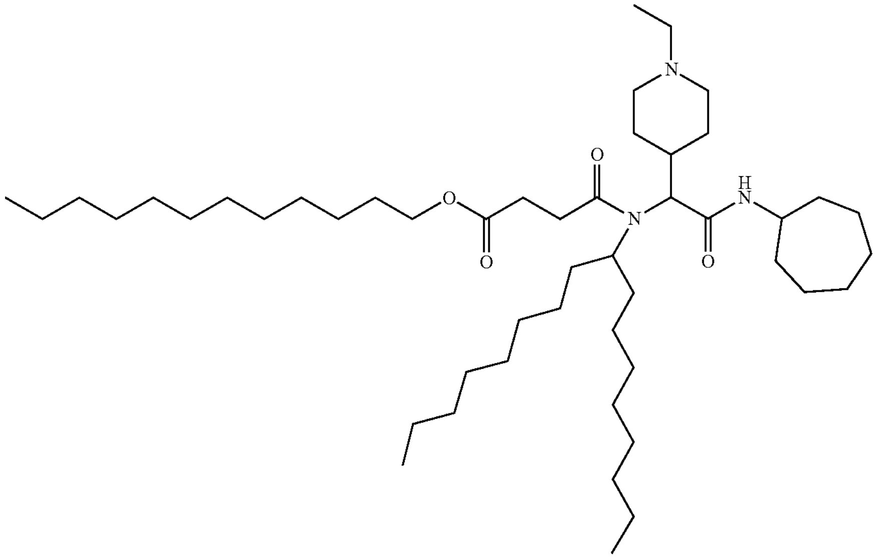 [SMILES: CCCCCCCCCCCCOC(=O)CCC(=O)N(C(CCCCCCCC)CCCCCCCC)C(C(=O)NC1CCCCCC1)C1CCN(CC)CC1] |
| (XXXVII) or P55C12 | 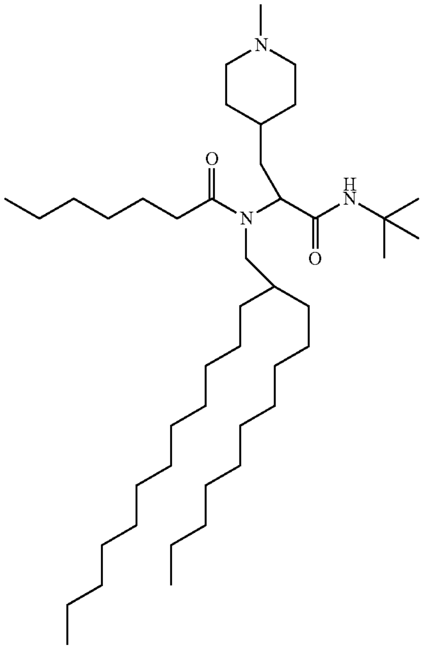 [SMILES: CCCCCCCCCCCCC(CCCCCCCCCC)CN(C(=O)CCCCCC)C(CC1CCN(C)CC1)C(=O)NC(C)(C)C] |

TABLE 1-continued
| Lipid ID | Lipid Structure |
|---|---|
| (XXXVIII) or P319B6 | 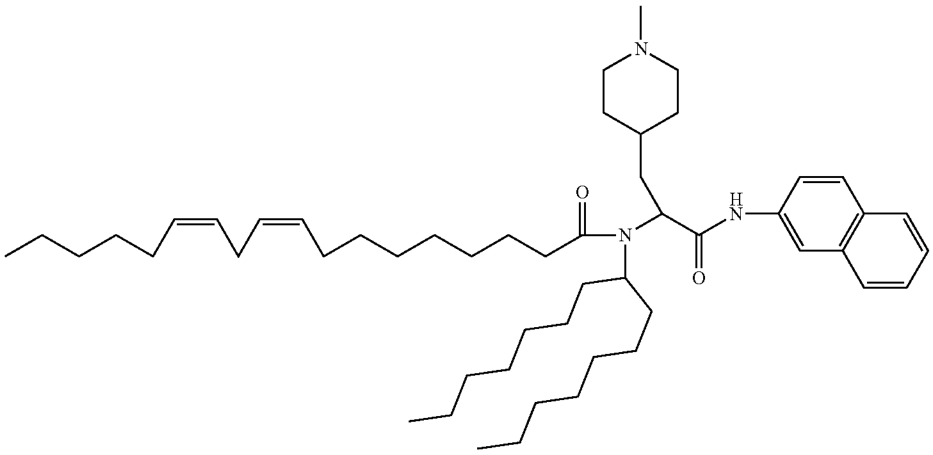 [SMILES: CCCCC/C=C\C/C=C\CCCCCCCC(=O)N(C(CCCCCCC)CCCCCCC)C(CC1CCN(C)CC1)C(=O)Nc1ccc2ccccc2c1] |
| (XXXIX) or P343B6 | 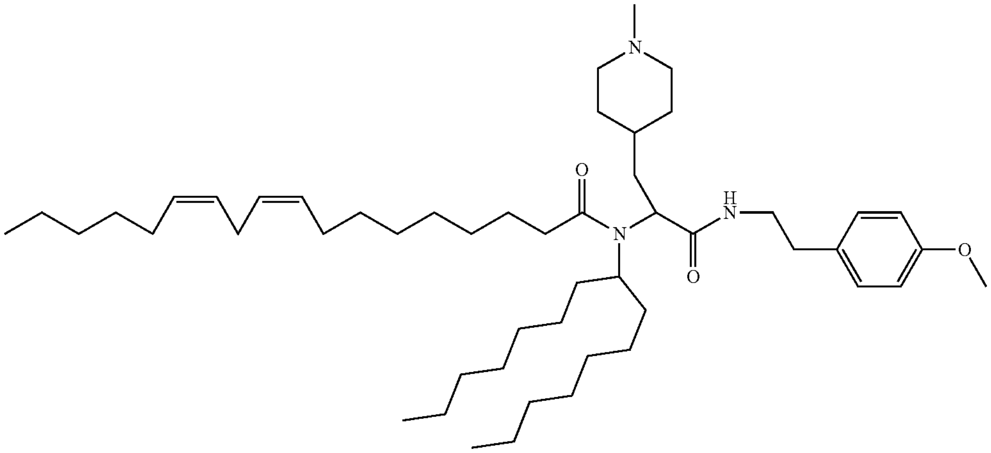 [SMILES: CCCCC/C=C\C/C=C\CCCCCCCC(=O)N(C(CCCCCCC)CCCCCCC)C(CC1CCN(C)CC1)C(=O)NCCc1ccc(OC)cc1] |
| (XL) or P313B7 | 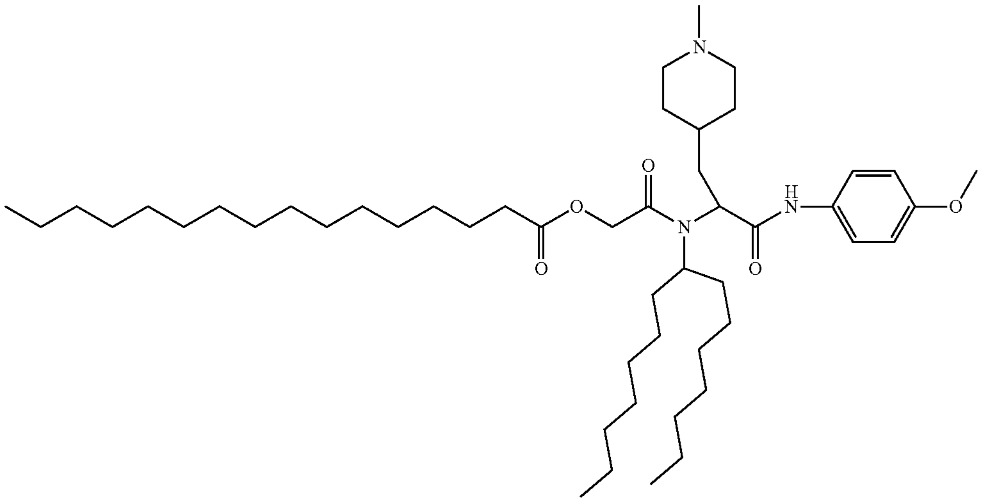 [SMILES: CCCCCCCCCCCCCCCC(=O)OCC(=O)N(C(CCCCCCC)CCCCCCC)C(CC1CCN(C)CC1)C(=O)Nc1ccc(OC)cc1] |

TABLE 1-continued
| Lipid ID | Lipid Structure |
| --- | --- |
| (XLI) or P56B9 | 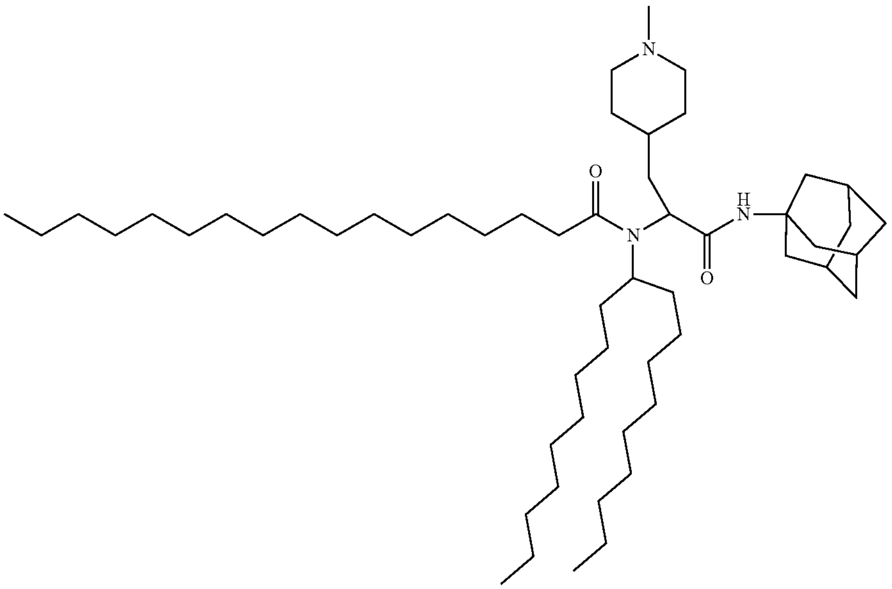 [SMILES: CCCCCCCCCCCCCCCCC(=O)N(C(CCCCCCCCC)CCCCCCCCC)C(CC1CCN(C)CC1)C(=O)NC12CC3CC(CC(C3)C1)C2] |
| (XLII) or P331E4 | 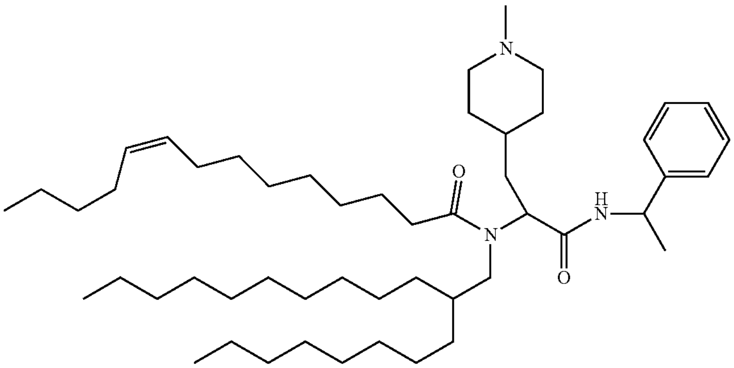 [SMILES: CCCC/C=C\CCCCCCCC(=O)N(CC(CCCCCCCC)CCCCCCCCCC)C(CC1CCN(C)CC1)C(=O)NC(C)c1ccccc1] |
| (XLIII) or P343E5 | 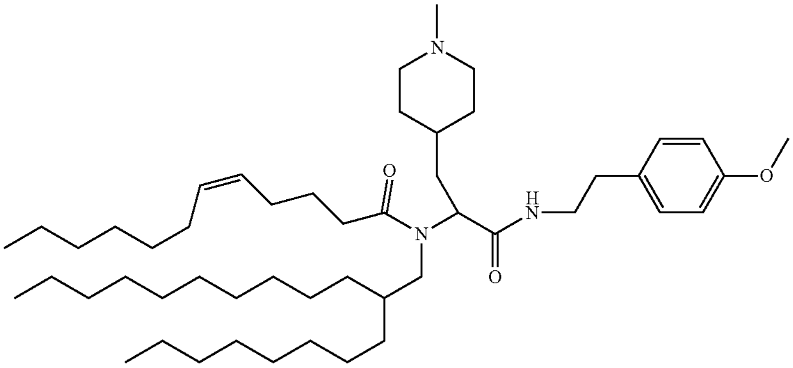 [SMILES: CCCCCC/C=C\CCCC(=O)N(CC(CCCCCCCC)CCCCCCCCCC)C(CC1CCN(C)CC1)C(=O)NCCc1ccc(OC)cc1] |

TABLE 1-continued
| Lipid ID | Lipid Structure |
| --- | --- |
| (XLIV) or P313B6 | 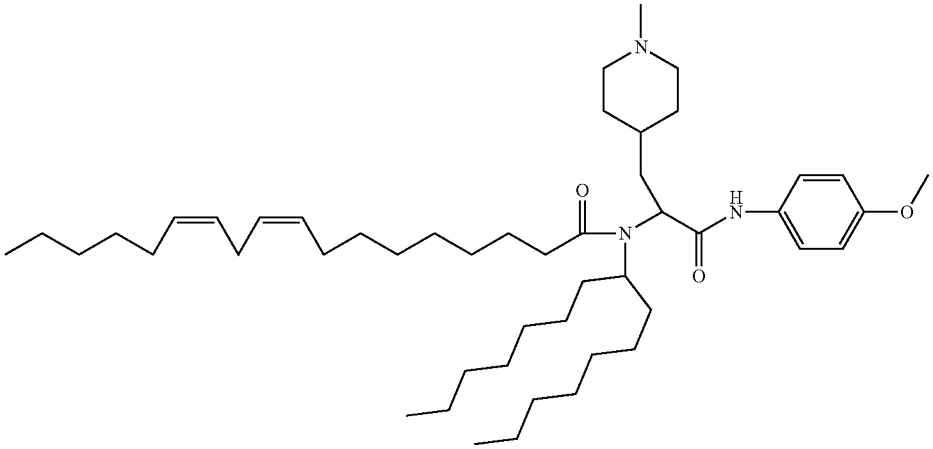 [SMILES: CCCCC/C=C\C/C=C\CCCCCCCC(=O)N(C(CCCCCCC)CCCCCCC)C(CC1CCN(C)CC1)C(=O)Nc1ccc(OC)cc1] |
| (XLV) or P341A10 | 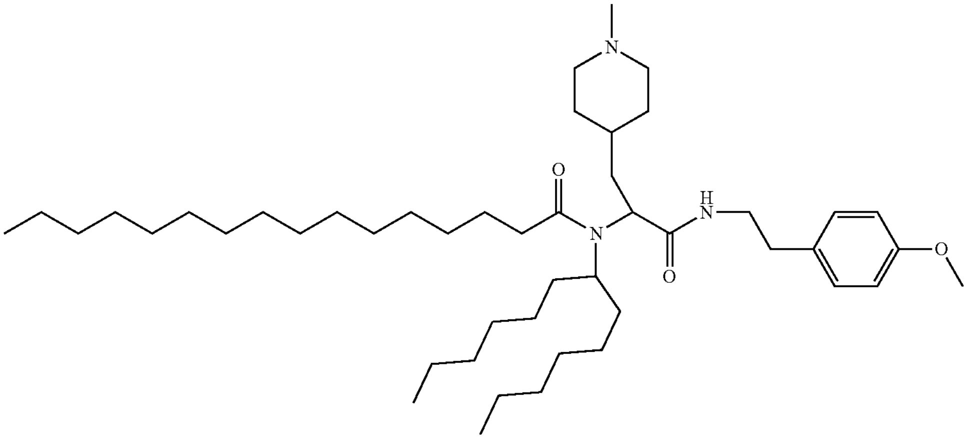 [SMILES: CCCCCCCCCCCCCCCC(=O)N(C(CCCCCC)CCCCCC)C(CC1CCN(C)CC1)C(=O)NCCc1ccc(OC)cc1] |
| (XLVI) or HP13C6 | 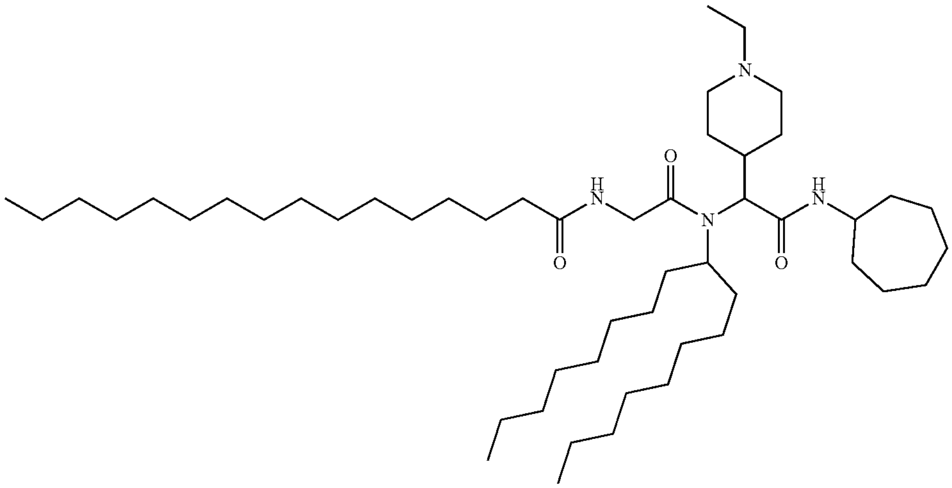 [SMILES: CCCCCCCCCCCCCCCC(=O)NCC(=O)N(C(CCCCCCCC)CCCCCCCC)C(C(=O)NC1CCCCCC1)C1CCN(CC)CC1] |

TABLE 1-continued
| Lipid ID | Lipid Structure |
|---|---|
| (XLVII) or HP16C4 | 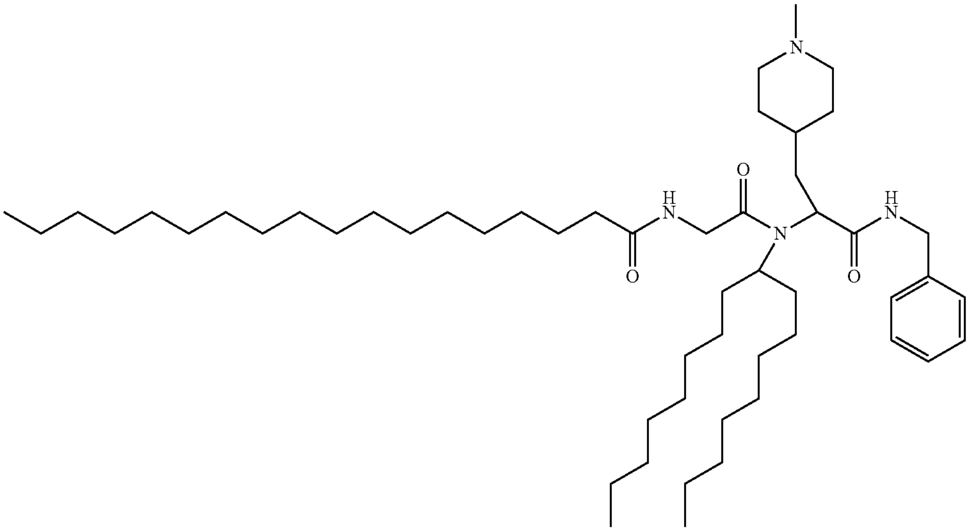 [SMILES: CCCCCCCCCCCCCCCCCC(=O)NCC(=O)N(C(CCCCCCCC)CCCCCCCC)C(CC1CCN(C)CC1)C(=O)NCc1ccccc1] |
| (XLVIII) or HP19G8 | 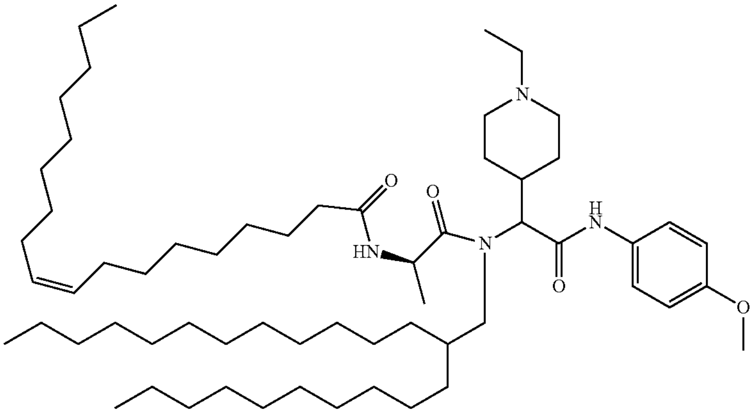 [SMILES: CCCCCCCC/C=C\CCCCCCCC(=O)N[C@H](C)C(=O)N(CC(CCCCCCCCCC)CCCCCCCCCCCC)C(C(=O)Nc1ccc(OC)cc1)C1CCN(CC)CC1] |
| (XLIX) or HP11E8 | 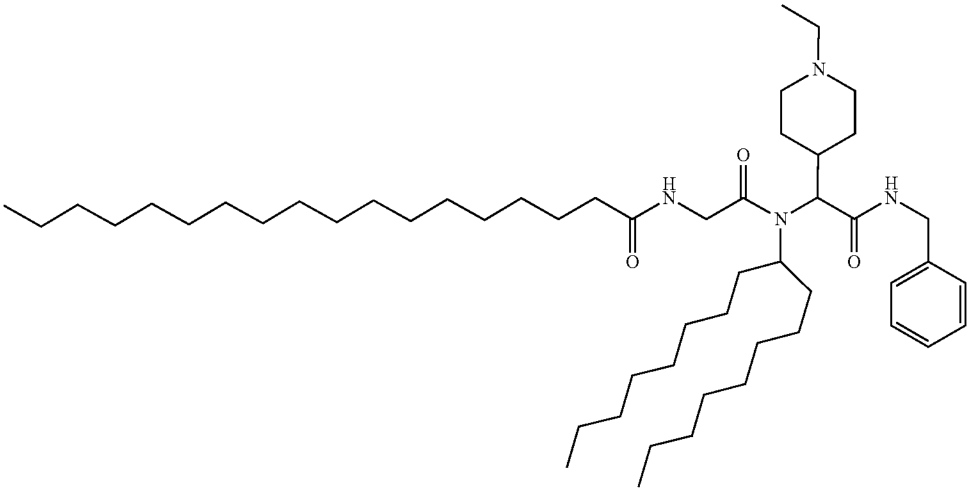 [SMILES: CCCCCCCCCCCCCCCCCC(=O)NCC(=O)N(C(CCCCCCCC)CCCCCCCC)C(C(=O)NCc1ccccc1)C1CCN(CC)CC1] |

TABLE 1-continued
| Lipid ID | Lipid Structure |
|---|---|
| (L) or HP15C4 | 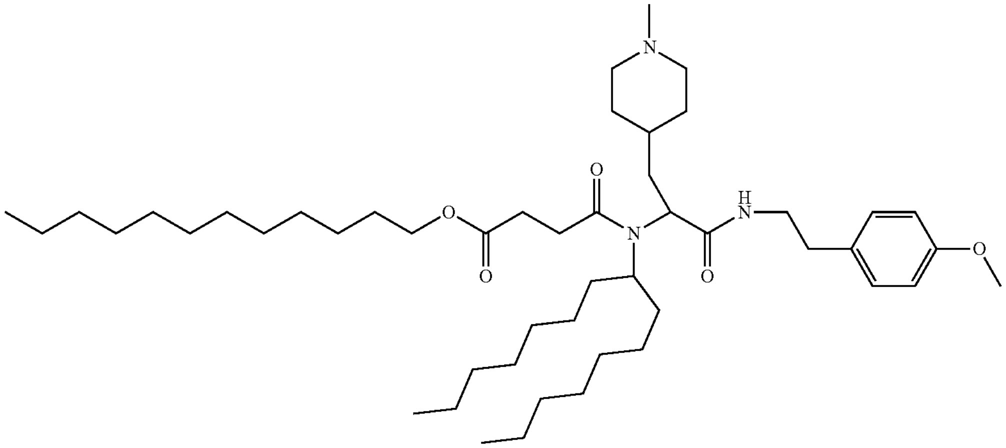 [SMILES: CCCCCCCCCCCCOC(=O)CCC(=O)N(C(CCCCCCC)CCCCCCC)C(CC1CCN(C)CC1)C(=O)NCCc1ccc(OC)cc1] |
| (LI) or P344D3 | 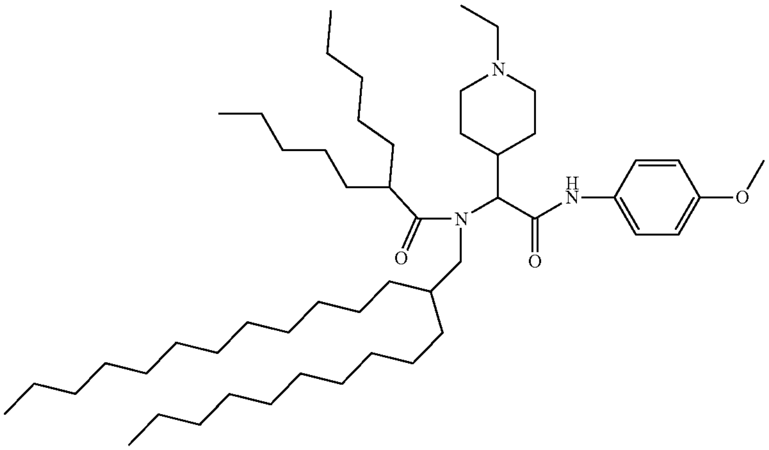 [SMILES: CCCCCCCCCCCCC(CCCCCCCCCC)CN(C(=O)C(CCCCC)CCCCC)C(C(=O)Nc1ccc(OC)cc1)C1CCN(CC)CC1] |
| (LII) or P343B8 | 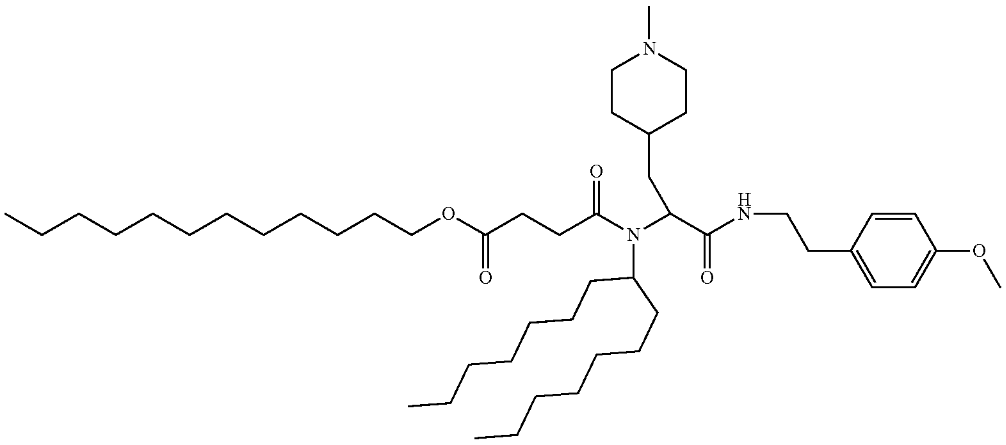 [SMILES: CCCCCCCCCCCCOC(=O)CCC(=O)N(C(CCCCCCC)CCCCCCC)C(CC1CCN(C)CC1)C(=O)NCCc1ccc(OC)cc1] |

TABLE 1-continued
| Lipid ID | Lipid Structure |
| --- | --- |
| (LIII) or P314E1 | 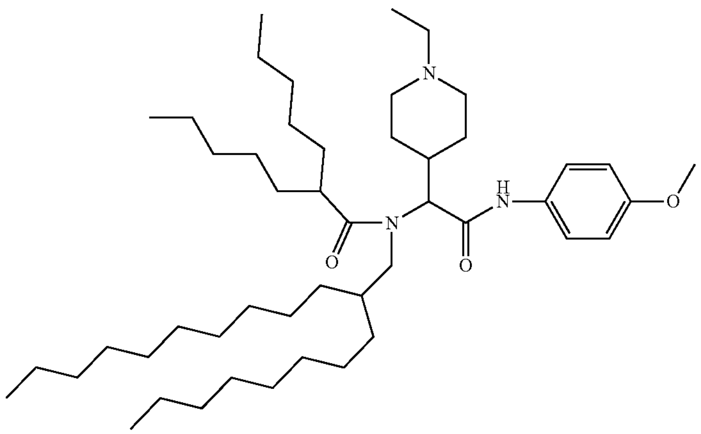 [SMILES: CCCCCCCCCCC(CCCCCCCC)CN(C(=O)C(CCCCC)CCCCC)C(C(=O)Nc1ccc(OC)cc1)C1CCN(CC)CC1] |
| (LIV) or P314G1 | 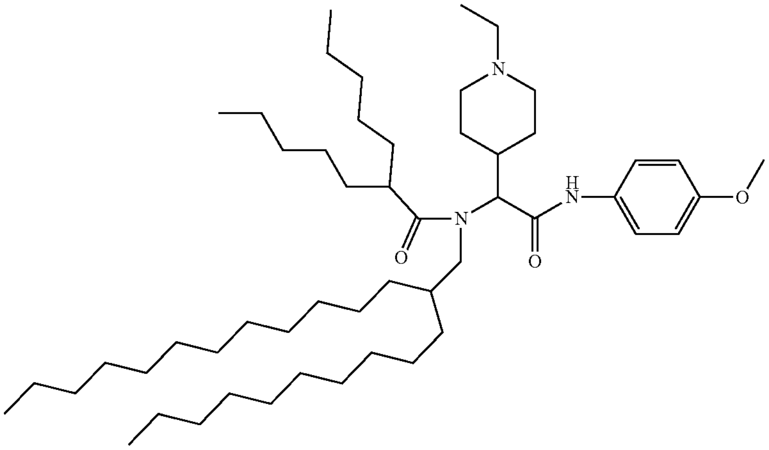 [SMILES: CCCCCCCCCCCCC(CCCCCCCCCC)CN(C(=O)C(CCCCC)CCCCC)C(C(=O)Nc1ccc(OC)cc1)C1CCN(CC)CC1] |
| (LV) or P161F5 | 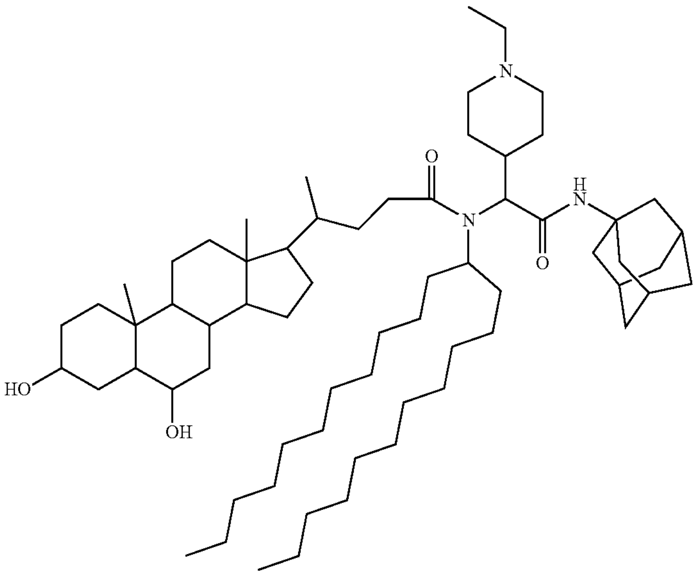 [SMILES: CCCCCCCCCCCC(CCCCCCCCCCC)N(C(=O)CCC(C)C1CCC2C3CC(O)C4CC(O)CCC4(C)C3CCC12C)C(C(=O)NC12CC3CC(CC(C3)C1)C2)C1CCN(CC)CC1] |

TABLE 1-continued
| Lipid ID | Lipid Structure |
| --- | --- |
| (LVI) or P161F12 | 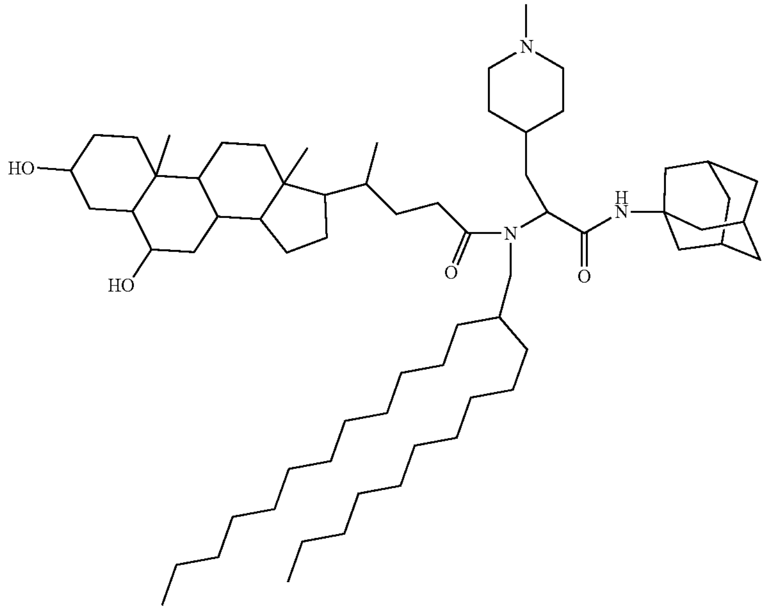 [SMILES: CCCCCCCCCCCCC(CCCCCCCCCC)CN(C(=O)CCC(C)C1CCC2C3CC(O)C4CC(O)CCC4(C)C3CCC12C)C(CC1CCN(C)CC1)C(=O)NC12CC3CC(CC(C3)C1)C2] |
| (LVII) or P287A12 | 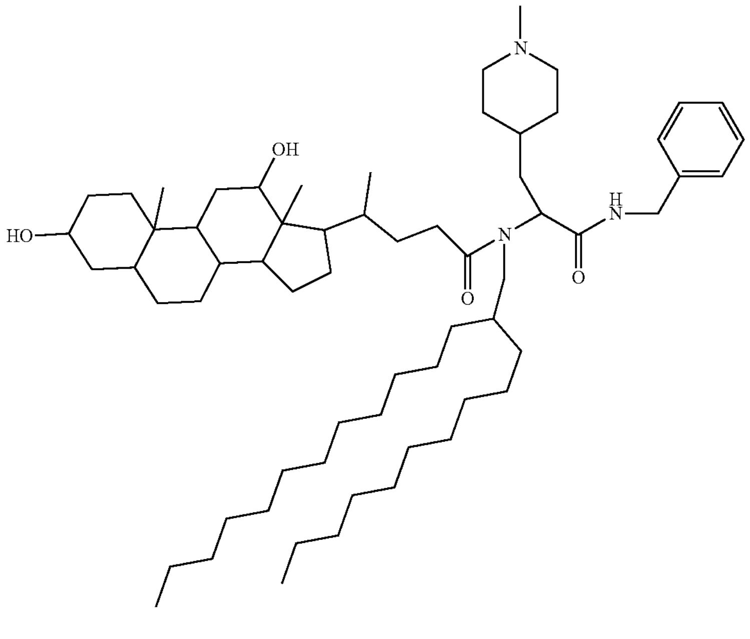 [SMILES: CCCCCCCCCCCCC(CCCCCCCCCC)CN(C(=O)CCC(C)C1CCC2C3CCC4CC(O)CCC4(C)C3CC(O)C12C)C(CC1CCN(C)CC1)C(=O)NCc1ccccc1] |

TABLE 1-continued
| Lipid ID | Lipid Structure |
|---|---|
| (LVIII) or P287C12 | 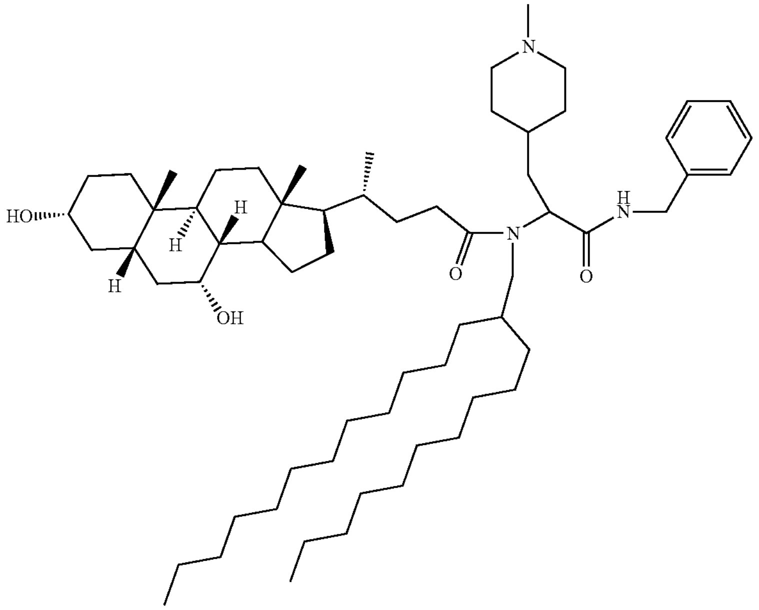 |
| (LIX) or P504D7 | 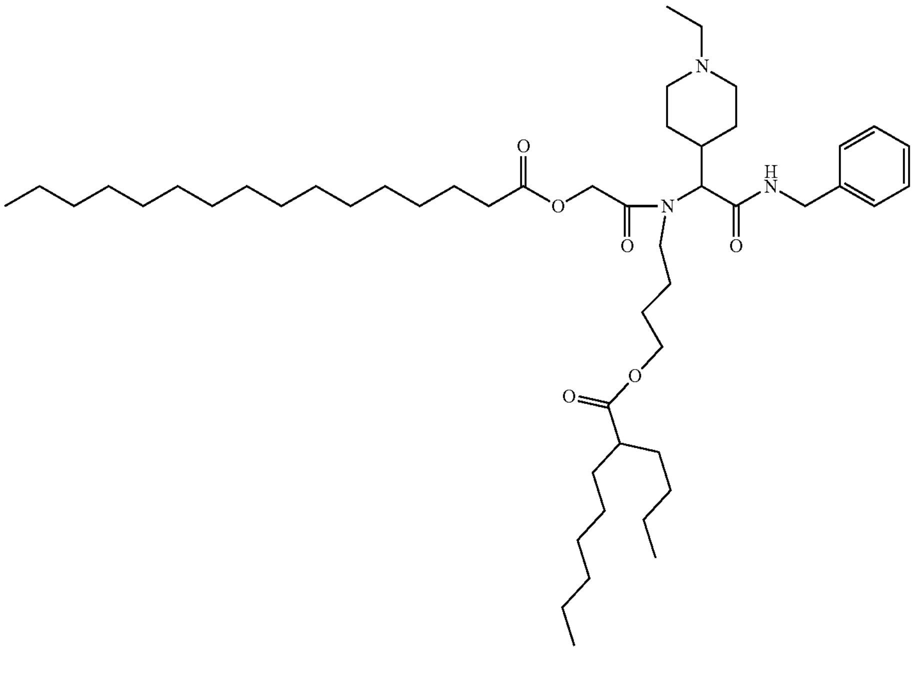 [SMILES: CCCCCCCCCCCCCCCC(=O)OCC(=O)N(CCCCOC(=O)C(CCCC)CCCCCC)C(C(=O)NCc1ccccc1)C1CCN(CC)CC1] |

TABLE 1-continued
| Lipid ID | Lipid Structure |
|---|---|
| (LX) or P505B7 | 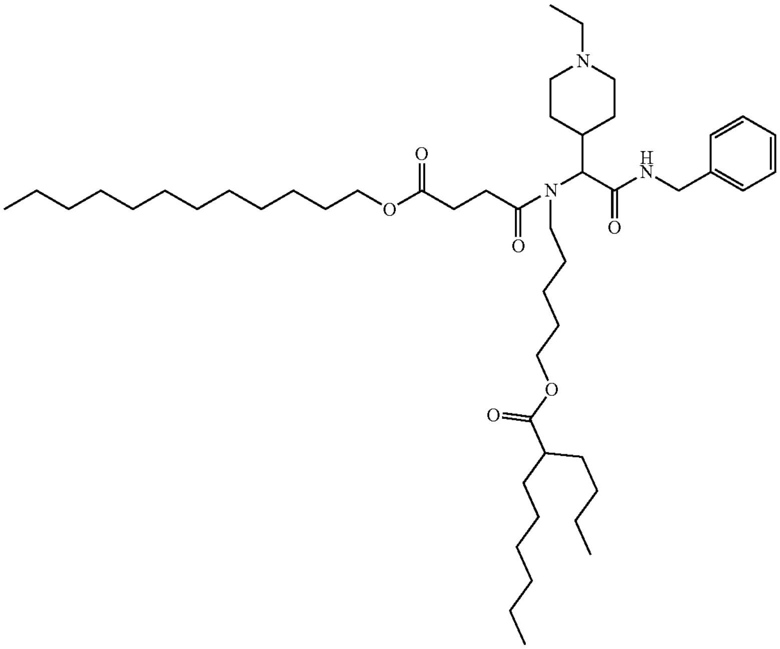 [SMILES: CCCCCCCCCCCCOC(=O)CCC(=O)N(CCCCCOC(=O)C(CCCC)CCCCCC)C(C(=O)NCc1ccccc1)C1CCN(CC)CC1] |
| (LXI) or P505B9 | 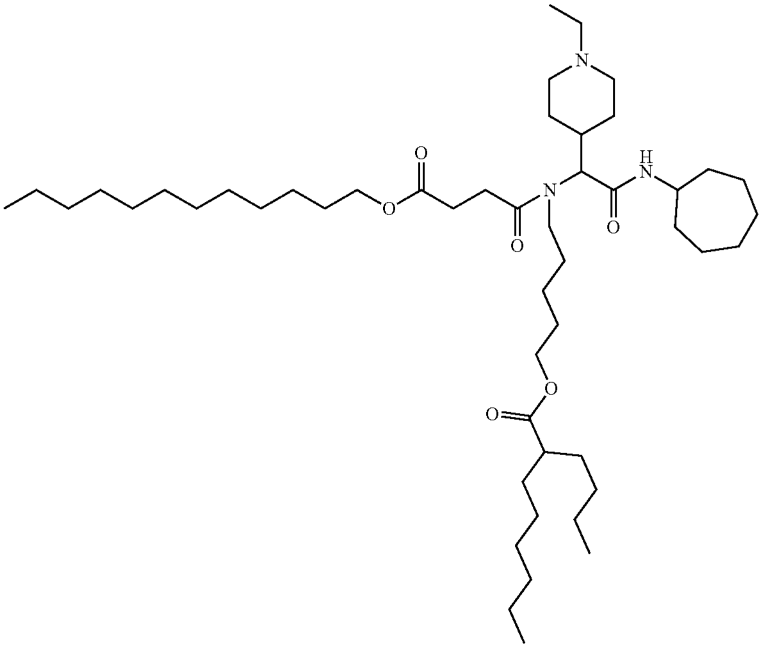 [SMILES: CCCCCCCCCCCCOC(=O)CCC(=O)N(CCCCCOC(=O)C(CCCC)CCCCCC)C(C(=O)NC1CCCCCC1)C1CCN(CC)CC1] |

TABLE 1-continued

| Lipid ID | Lipid Structure |
| --- | --- |
| (LXII) or P505B10 | 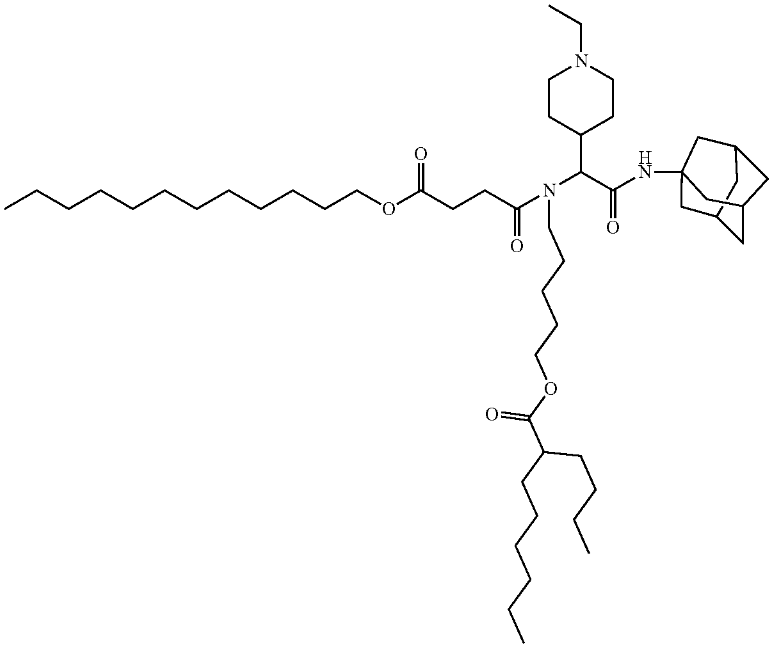 [SMILES: CCCCCCCCCCCCOC(=O)CCC(=O)N(CCCCCOC(=O)C(CCCC)CCCCCC)C(C(=O)NC12CC3CC(CC(C3)C1)C2)C1CCN(CC)CC1] |

The structures of the ionizable lipids (I)-(LXII) can be confirmed using techniques known in the art, for example, nuclear magnetic resonance spectra of 1H and LC-Mass spectrometry.

Adjuvants

In some aspects, a pharmaceutical composition that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Pharmaceutical Compositions

Pharmaceutical compositions may include a biologically active sa-mRNA or modified mRNA and one or more additional components, such as a lipid component and one or more additional components. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The amount of a biologically active mRNA may depend on the size, composition, desired target and/or application, or other properties of the therapeutic, diagnostic and/or prophylactic. Generally, the size of sa-mRNA is always larger than 7 kilo nucleotides.

The relative amounts of the biologically active agent, such as sa-mRNA and modified mRNA, and other elements (e.g., lipids) in a pharmaceutical composition may vary. In some aspects, the wt/wt ratio of the lipid component to a sa-mRNA in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a sa-mRNA or modified mRNA may be from about 1:1 to about 40:1. In certain aspects, the wt/wt ratio is about 20:1. The amount of a biologically active agent in a nanoparticle composition may, for example, be measured using absorption spectroscopy (e.g., ultraviolet-visible spectroscopy).

Pharmaceutical compositions may include one or different therapeutic agents (e.g. sa-mRNA and modified mRNA) and delivery systems. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy,* 21st Edition, A. R. Gennaro; Lippincott, Williams & Wilkins, Baltimore, Md., 2006. Excipients and accessory ingredients may be used in any pharmaceutical composition, except insofar as any excipient or accessory ingredient may be incompatible with one or more components of a sa-mRNA delivery system. An excipient or accessory ingredient may be incompatible if its combination with the component may result in any undesirable biological effect or otherwise deleterious effect.

In some aspects, one or more excipients or accessory ingredients may make up greater than 50% of the total mass or volume of a pharmaceutical composition. For example, the one or more excipients or accessory ingredients may make up 50%, 60%, 70%, 80%, 90%, or more of a pharmaceutical composition. In some aspects, a pharmaceutically acceptable excipient is at least 95%, at least 96%, at least 97%, at least 98%, at least 99%, or 100% pure. In some aspects, an excipient is approved for use in humans and for veterinary use. In some aspects, an excipient is approved by United States Food and Drug Administration. In some aspects, an excipient is pharmaceutical grade. In some aspects, an excipient meets the standards of the United States Pharmacopoeia (USP), the European Pharmacopoeia (EP), the British Pharmacopoeia, and/or the International Pharmacopoeia.

Relative amounts of the one or more delivery systems, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered.

In certain aspects, the pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. For example, the pharmaceutical composition comprising the sa-mRNA or modified mRNA of the present disclosure is a solution that is refrigerated for storage and/or shipment at, for example, about −20° C., −30° C., −40° C., −50° C., −60° C., −70° C., or −80° C. In certain aspects, the disclosure also relates to a method of increasing stability of pharmaceutical compositions comprising sa-mRNA or modified mRNA and a delivery system by storing the pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one aspect, the formulation is stabilized for at least 4 weeks at about 4° C.

In certain aspects, the pharmaceutical composition of the disclosure comprises a sa-mRNA or modified mRNA disclosed herein, a nanoparticle composition delivery system, and a pharmaceutically acceptable carrier selected from one or more of Tris, an acetate (e.g., sodium acetate), an citrate (e.g., sodium citrate), saline, PBS, and sucrose. In certain aspects, the pharmaceutical composition of the disclosure has a pH value between about 5 and 8 (e.g., 5, 5.5, 6. 6.5, 6.8 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a sa-mRNA disclosed herein, a nanoparticle composition delivery system, Tris, saline and sucrose, and has a pH of about 7.5-8, which is suitable for storage and/or shipment at, for example, about −20° C. For example, a pharmaceutical composition of the disclosure comprises a sa-mRNA or modified mRNA, including a modified sa-mRNA, disclosed herein, a nanoparticle composition delivery system, and PBS and has a pH of about 7-7.8, suitable for storage and/or shipment at, for example, about 4° C. or lower.

"Stability," "stabilized," and "stable" in the context of the present disclosure refers to the resistance of pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

Pharmaceutical compositions of the disclosure may be administered to any patient or subject, including those patients or subjects that may benefit from a therapeutic effect provided by the delivery of a biologically active agent to one or more particular cells, tissues, organs, or systems or groups thereof, such as the renal system. In one aspect, the pharmaceutical composition of the present disclosure could be administered directly to a patient rather than engineering T-cells expressing CAR ex vivo.

Although the descriptions provided herein of pharmaceutical compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition of the present disclosure may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., sa-mRNA). The amount of the active ingredient is generally equal to the dosage of the active ingredient which would be administered to a subject and/or a convenient fraction of such a dosage such as, for example, one-half or one-third of such a dosage.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils may be employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Methods of Producing Polypeptides in Cells

The present disclosure provides methods of producing a polypeptide of interest, such as CAR, in a cell. Methods of producing a polypeptide of interest in a cell involve contacting a cell with sa-mRNA, modified mRNA, or circRNA, (either as naked RNA, or in combination with a delivery system), comprising one or more gene or genes of interest. Upon contacting the cell, the sa-mRNA, modified mRNA or circRNA may be taken up and translated in the cell to produce the gene product, such as a CAR, a TCR, a GFR, a HR, a Nb, a scFv or a reporter.

In general, the step of contacting a cell with a mRNA of the disclosure (including sa-mRNA, modified mRNA and circRNA) comprising a gene or genes of interest may be performed in vivo, ex vivo, in culture, or in vitro. The amount of mRNA, may depend on the type of cell or tissue being contacted, the means of administration, the physiochemical characteristics of the mRNA and delivery system (e.g., size, charge, and chemical composition), and other factors. In general, an effective amount of the mRNA will allow for efficient polypeptide production in the cell. Metrics for efficiency may include polypeptide translation (indicated by polypeptide expression), level of mRNA degradation, and immune response indicators.

The step of contacting a nanoparticle composition containing an mRNA with a cell may involve or cause transfection. A phospholipid including in the lipid component of a nanoparticle composition may facilitate transfection and/or increase transfection efficiency, for example, by interacting and/or fusing with a cellular or intracellular membrane. Transfection may allow for the transcription and translation of the mRNA within the cell.

Method of Treatment

The present disclosure provides methods of delivering a payload to human T cells ex vivo or to a patient in vivo comprising delivering an mRNA of the disclosure (including sa-mRNA, modified mRNA and circRNA) using LNP formulations comprising at least one ionizable lipid of the present disclosure, which improve stability, facilitate internalization, and reduce safety issues associated with increased administrations and cytotoxic effects.

In one aspect, the present disclosure provides a method of delivering a payload to immune cells, including human T-cells, ex vivo comprising delivering a sa-mRNA or a modified mRNA encoding a chimeric antigen receptor (CAR) using an LNP. In one aspect, the present disclosure provides a method of delivering a payload to immune cells ex vivo comprising contacting immune cells with a lipid nanoparticle (LNP) encapsulating a payload encoding at least one polypeptide of interest, wherein the polypeptide of interest is an antigen receptor or antibody.

In one aspect, the present disclosure provides a method of delivering a payload to a patient in need thereof, in vivo comprising delivering a payload to immune cells in vivo comprising administering an LNP encapsulating a payload encoding at least one polypeptide of interest to a subject, wherein the polypeptide of interest is antigen receptor or antibody.

In one aspect, the immune cells are T-cells, natural killer (NK) cells, or monocytes. In one aspect, the immune cells are human T-cells. In one aspect, the antigen receptor is a CAR, a TCR, a GFR, or a HR. In one aspect, the antibody is a natural antibody or a synthetic antibody. In one aspect, the synthetic antibody is a nanobody.

In one aspect, the present disclosure provides a method of treating a subject in need of cell therapy, comprising modifying an immune cell by (i) delivering a mRNA encoding at least one polypeptide of interest, wherein the polypeptide of interest is an antigen receptor or antibody, (ii) maintaining the immune cell under conditions suitable for expression of the polypeptide of interest to produce a modified immune cell, and (iii) administering the modified immune cell to the subject.

In one aspect, the present disclosure provides a method of treating a subject in need of CAR-T therapy, comprising modifying a T-cell by (i) delivering a sa-mRNA or modified mRNA, including a modified sa-mRNA encoding CAR to a T-cell, (ii) maintaining the T-cell under conditions suitable for expression of CAR, and (iii) administering the modified T-cell of (ii) to the subject. In one aspect, the T-cell is autologous to the subject. In one aspect, the sa-mRNA or modified mRNA, including modified sa-mRNA, encoding CAR is delivered using an LNP comprising at least one ionizable lipid of the disclosure.

In certain aspects, LNP compositions comprising an ionizable lipid of the present disclosure and sa-mRNA or modified mRNA of the disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a payload (e.g., a sa-mRNA or modified sa-mRNA) in a given dose, where a dose of 1 mg/kg (mpk) provides 1 mg of the payload per 1 kg of subject body weight. In some aspects, a dose of about 0.001 mg/kg to about 10 mg/kg of the payload may be administered. In other aspects, a dose of about 0.005 mg/kg to about 2.5 mg/kg of the payload may be administered. In certain aspects, a dose of about 0.1 mg/kg to about 1 mg/kg may be administered. In other aspects, a dose of about 0.05 mg/kg to about 0.25 mg/kg may be administered. A dose may be administered one or more times per day, in the same or a different amount, to obtain a desired level of mRNA expression and/or biological, or imaging effect.

The desired dosage may be delivered, for example, three times a day, two times a day, once a day, every other day, every third day, every week, every two weeks, every three weeks, or every four weeks. In certain aspects, the desired dosage may be delivered using multiple administrations (e.g., two, three, four, five, six, seven, eight, nine, ten, eleven, twelve, thirteen, fourteen, or more administrations). In some aspects, a single dose may be administered, for example, prior to or after a surgical procedure or in the instance of an acute disease, disorder, or condition.

In some aspects, the nanoparticle composition of the present invention are used in combination with another therapeutic compound separate from the nanoparticle for treatment of the same indication in the subject. By "in combination with," it is not intended to imply that the compounds must be administered at the same time and/or formulated for delivery together, although these methods of delivery are within the scope of the present disclosure. For example, one or more pharmaceutical compositions including one or more different biologically active agents may be administered in combination. Compositions can be administered concurrently with, prior to, or subsequent to, one or more other desired therapeutics or medical procedures. In general, each agent will be administered at a dose and/or on a time schedule determined for that agent. In some aspects, the present disclosure encompasses the delivery of imaging, therapeutic, diagnostic, or prophylactic compositions thereof in combination with agents that improve their bioavailability, reduce and/or modify their metabolism, inhibit their excretion, and/or modify their distribution within the body.

It will further be appreciated that biologically active or imaging active agents utilized in combination may be administered together in a single composition or administered separately in different compositions. When delivered together, they may or may not be in the same formulation, and they may or may not be delivered by the same route. In general, it is expected that agents utilized in combination will be utilized at levels that do not exceed the levels at which they are utilized individually. In some aspects, the levels utilized in combination may be lower than those utilized individually.

The particular combination of therapies to employ in a combination regimen will take into account compatibility of the desired therapeutic procedure and the desired biological effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions). Nucleic and Amino Acid Sequences The following exemplary sequences, represent exemplary amino acid sequences encoded by the sa-mRNA, modified mRNA and circRNA, of the disclosure that may be replaced with any other amino acid sequences. It is important to note that there is degeneracy of the genetic code, meaning that that most amino acids are specified by more than one codon. Thus, since numerous distinct codons define the same amino acid, more than one polynucleotide sequence can code for the same amino acid sequence. Therefore, the amino acid sequences listed below represent multiple nucleic acid sequences. Any permutations and combinations of all described elements in this application should be considered as disclosed by the description of the present application, unless the context indicates otherwise. Persons skilled in the art will recognize that the sequences listed in Tables 2 and 3 are exemplary and not limiting disclosures that support and serve as proof of the concepts disclosed and claimed herein.

TABLE 2

| Description | SEQ ID NO. | Sequence |
|---|---|---|
| Leading peptide | SEQ ID NO: 1 | MDWTWRILFLVAAATGTHA |
| Linker (LK) | SEQ ID NO: 2 | SSGGGGSGGGGSGGGGS |
| Myc tag (Myc) | SEQ ID NO: 3 | EQKLISEEDL |
| Mouse CD8 alpha chain | SEQ ID NO: 4 | TTTKPVLRTPSPVHPTGTSQPQRPEDCRPRGSV KGTGLDFACDIYIWAPLAGICVALLLSLIITLI |
| Mouse CD28 activation domain | SEQ ID NO: 5 | NSRRNRLLQSDYMNMTPRRPGLTRKPYQPYAP ARDFAAYRP |
| Mouse CD3 zeta activation domain | SEQ ID NO: 6 | RAKFSRSAETAANLQDPNQLYNELNLGRREEY DVLEKKRARDPEMGGKQQRRRNPQEGVYNAL QKDKMAEAYSEIGTKGERRRGKGHDGLYQGL STATKDTYDALHMQTLAPR |
| Human CD8 alpha chain | SEQ ID NO: 7 | TTTPAPRPPTPAPTIASQPLSLRPEACRPAAGGA VHTRGLDFACDIYIWAPLAGTCGVLLLSLVITL Y |
| Human CD28 activation domain | SEQ ID NO: 8 | RSKRSRLLHSDYMNMTPRRPGPTRKHYQPYAP PRDFAAYRS |
| Human CD3 zeta activation domain | SEQ ID NO: 9 | RVKFSRSADAPAYQQGQNQLYNELNLGRREEY DVLDKRRGRDPEMGGKPQRRKNPQEGLYNEL QKDKMAEAYSEIGMKGERRRGKGHDGLYQGL STATKDTYDALHMQALPPR |

The following exemplary sequences disclose sa-mRNA comprising an exemplary GOI that may be replaced with any other GOT Persons skilled in the art will recognize that these sequences are exemplary and not limiting disclosures that support and serve as proof of the concepts disclosed and claimed herein. In one aspect, any of the nucleic acid sequences disclosed herein has or may have one or more "T" replaced with "U". In one aspect, any of the nucleic acid sequences disclosed herein including one or more of the sequences of SEQ ID NOs: 10-12 has "T" replaced with m1Ψ or Ψ.

TABLE 3

| Description | SEQ ID NO. | Sequence |
|---|---|---|
| Exemplary subgenomic promoter (SGP) sequences | SEQ ID NO: 10 | TAACCTGAATGGACTACGACATAGTCTAGTC CGCCAAG |
| | SEQ ID NO: 11 | GAACTTCCATCATAGTTATGGCCATGACTACT CTAGCTAGCAGTGTTAAATCATTCAGCTACCT GAGAGGGGCCCCTATAACTCTCTACGGC |
| | SEQ ID NO: 31 | TAATACGACTCACTATAGGATAGG |
| Exemplary linker sequences (L) | SEQ ID NO: 12 | CGCGTGATAACGCAGGAAAGAACATGTGAG CAAAAGGCCAGCAAAAGGCCAGGAACCGTA AAAAGGCCGCGTTGCTGGCGTT |
| | SEQ ID NO: 13 | CACATTTCCCCGAAAAGTGCCACCTGAGCTC |
| | SEQ ID NO: 14 | TTCGAAGGCGCGCCTCTAGAGCCACC |
| | SEQ ID NO: 15 | CATCGATGATATCGCGGCCGCATACAGCAGC |
| 5'UTR' | intentionally skipped sequence | ATAGG |
| Exemplary 3'UTR sequences | SEQ ID NO: 16 (3'UTR conserved sequence) | GGATTTTGTTTTTAATATTTC |
| | SEQ ID NO: 17 | GGATTTTATTTTTAATATTTC |
| | SEQ ID NO: 18 | AAATTTTGTTTTTAATATTTC |
| | SEQ ID NO: 19 | AAATTTTATTTTTAATATTTC |

SAM001

(SEQ ID NO: 20)

AAAAAAAAAACGCGTGATAACGCAGGAAAGAACATGTGAGCAAAAGGCCAGCAAA

AGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGT

AGCGGTTTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACTCACGTTA

AGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTA

CCAATGCTTAATCAGTGAGGCACCTATCTCAGCGATCTGTCTATTTCGTTCATCCATA

GTTGCCTGACTCCCCGTCGTGTAGATAACTACGATACGGGAGGGCTTACCATCTGGC

CCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGC

CTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTT

GGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAG

TTGGCCGCAGTGTTATCACTCATGGTTATGGCAGCACTGCATAATTCTCTTACTGTCA

-continued

TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGAGCTCTAATACGACTCACTATAGgATaGGCGGCGCATG
AGAGAAGCCCAGACCAATTACCTACCCAAAATGGAGAAAGTTCACGTTGACATCGA
GGAAGACAGCCCATTCCTCAGAGCTTTGCAGCGGAGCTTCCCGCAGTTTGAGGTAGA
AGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAA
GTGCGCCCGCCCGCAGAATGTATTCTAAGCACAAGTATCATTGTATCTGTCCGATGA
GATGTGCGGAAGATCCGGACAGATTGTATAAGTATGCAACTAAGCTGAAGAAAAAC
TGTAAGGAAATAACTGATAAGGAATTGGACAAGAAAATGAAGGAGCTGGCCGCCGT
CATGAGCGACCCTGACCTGGAAACTGAGACTATGTGCCTCCACGACGACGAGTCGT
GTCGCTACGAAGGGCAAGTCGCTGTTTACCAGGATGTATACGCGGTTGACGGACCG
ACAAGTCTCTATCACCAAGCCAATAAGGGAGTTAGAGTCGCCTACTGGATAGGCTTT
GACACCACCCCTTTTATGTTTAAGAACTTGGCTGGAGCATATCCATCATACTCTACC
AACTGGGCCGACGAAACCGTGTTAACGGCTCGTAACATAGGCCTATGCAGCTCTGA
CGTTATGGAGCGGTCACGTAGAGGGATGTCCATTCTTAGAAAGAAGTATTTGAAACC
ATCCAACAATGTTCTATTCTCTGTTGGCTCGACCATCTACCACGAGAAGAGGGACTT
ACTGAGGAGCTGGCACCTGCCGTCTGTATTTCACTTACGTGGCAAGCAAAATTACAC
ATGTCGGTGTGAGACTATAGTTAGTTGCGACGGGTACGTCGTTAAAAGAATAGCTAT
CAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCG
TGTGCACGTATGTGCCAGCTACATTGTGTGACCAAATGACTGGCATACTGGCAACAG
ATGTCAGTGCGGACGACGCGCAAAAACTGCTGGTTGGGCTCAACCAGCGTATAGTC
GTCAACGGTCGCACCCAGAGAAACACCAATACCATGAAAAATTACCTTTTGCCCGT
AGTGGCCCAGGCATTTGCTAGGTGGGCAAAGGAATATAAGGAAGATCAAGAAGATG
AAAGGCCACTAGGACTACGAGATAGACAGTTAGTCATGGGGTGTTGTTGGGCTTTTA
GAAGGCACAAGATAACATCTATTTATAAGCGCCCGGATACCCAAACCATCATCAAA
GTGAACAGCGATTTCCACTCATTCGTGCTGCCCAGGATAGGCAGTAACACATTGGAG
ATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAG
GAGGTGCGTGAAGCCGAGGAGTTGCGCGCAGCTCTACCACCTTTGGCAGCTGATGTT
GAGGAGCCCACTCTGGAAGCCGATGTCGACTTGATGTTACAAGAGGCTGGGGCCGG
CTCAGTGGAGACACCTCGTGGCTTGATAAAGGTTACCAGCTACGATGGCGAGGACA
AGATCGGCTCTTACGCTGTGCTTTCTCCGCAGGCTGTACTCAAGAGTGAAAAATTAT

-continued

CTTGCATCCACCCTCTCGCTGAACAAGTCATAGTGATAACACACTCTGGCCGAAAAG

GGCGTTATGCCGTGGAACCATACCATGGTAAAGTAGTGGTGCCAGAGGGACATGCA

ATACCCGTCCAGGACTTTCAAGCTCTGAGTGAAAGTGCCACCATTGTGTACAACGAA

CGTGAGTTCGTAAACAGGTACCTGCACCATATTGCCACACATGGAGGAGCGCTGAA

CACTGATGAAGAATATTACAAAACTGTCAAGCCCAGCGAGCACGACGGCGAATACC

TGTACGACATCGACAGGAAACAGTGCGTCAAGAAAGAACTAGTCACTGGGCTAGGG

CTCACAGGCGAGCTGGTGGATCCTCCCTTCCATGAATTCGCCTACGAGAGTCTGAGA

ACACGACCAGCCGCTCCTTACCAAGTACCAACCATAGGGGTGTATGGCGTGCCAGG

ATCAGGCAAGTCTGGCATCATTAAAAGCGCAGTCACCAAAAAAGATCTAGTGGTGA

GCGCCAAGAAAGAAAACTGTGCAGAAATTATAAGGGACGTCAAGAAAATGAAAGG

GCTGGACGTCAATGCCAGAACTGTGGACTCAGTGCTCTTGAATGGATGCAAACACCC

CGTAGAGACCCTGTATATTGACGAAGCTTTTGCTTGTCATGCAGGTACTCTCAGAGC

GCTCATAGCCATTATAAGACCTAAAAAGGCAGTGCTCTGCGGGGATCCCAAACAGT

GCGGTTTTTTTAACATGATGTGCCTGAAAGTGCATTTTAACCACGAGATTTGCACAC

AAGTCTTCCACAAAAGCATCTCTCGCCGTTGCACTAAATCTGTGACTTCGGTCGTCTC

AACCTTGTTTTACGACAAAAAAATGAGAACGACGAATCCGAAAGAGACTAAGATTG

TGATTGACACTACCGGCAGTACCAAACCTAAGCAGGACGATCTCATTCTCACTTGTT

TCAGAGGGTGGGTGAAGCAGTTGCAAATAGATTACAAAGGCAACGAAATAATGACG

GCAGCTGCCTCTCAAGGGCTGACCCGTAAAGGTGTGTATGCCGTTCGGTACAAGGTG

AATGAAAATCCTCTGTACGCACCCACCTCAGAACATGTGAACGTCCTACTGACCCGC

ACGGAGGACCGCATCGTGTGGAAAACACTAGCCGGCGACCCATGGATAAAAACACT

GACTGCCAAGTACCCTGGGAATTTCACTGCCACGATAGAGGAGTGGCAAGCAGAGC

ATGATGCCATCATGAGGCACATCTTGGAGAGACCGGACCCTACCGACGTCTTCCAG

AATAAGGCAAACGTGTGTTGGGCCAAGGCTTTAGTGCCGGTGCTGAAGACCGCTGG

CATAGACATGACCACTGAACAATGGAACACTGTGGATTATTTTGAAACGGACAAAG

CTCACTCAGCAGAGATAGTATTGAACCAACTATGCGTGAGGTTCTTTGGACTCGATC

TGGACTCCGGTCTATTTTCTGCACCCACTGTTCCGTTATCCATTAGGAATAATCACTG

GGATAACTCCCCGTCGCCTAACATGTACGGGCTGAATAAAGAAGTGGTCCGTCAGCT

CTCTCGCAGGTACCCACAACTGCCTCGGGCAGTTGCCACTGGAAGAGTCTATGACAT

GAACACTGGTACACTGCGCAATTATGATCCGCGCATAAACCTAGTACCTGTAAACAG

AAGACTGCCTCATGCTTTAGTCCTCCACCATAATGAACACCCACAGAGTGACTTTTC

TTCATTCGTCAGCAAATTGAAGGGCAGAACTGTCCTGGTGGTCGGGGAAAAGTTGTC

CGTCCCAGGCAAAATGGTTGACTGGTTGTCAGACCGGCCTGAGGCTACCTTCAGAGC

TCGGCTGGATTTAGGCATCCCAGGTGATGTGCCCAAATATGACATAATATTTGTTAA

TGTGAGGACCCCATATAAATACCATCACTATCAGCAGTGTGAAGACCATGCCATTAA

GCTTAGCATGTTGACCAAGAAAGCTTGTCTGCATCTGAATCCCGGCGGAACCTGTGT

CAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGG

AAGTTCTGTTTGTATTCATTGGGTACGATCGCAAGGCCCGTACGCACAATcCTTACAA

GCTTTCATCAACCTTGACCAACATTTATACAGGTTCCAGACTCCACGAAGCCGGATG

TGCACCCTCATATCATGTGGTGCGAGGGGATATTGCCACGGCCACCGAAGGAGTGA

-continued

TTATAAATGCTGCTAACAGCAAAGGACAACCTGGCGGAGGGGTGTGCGGAGCGCTG

TATAAGAAATTCCCGGAAAGCTTCGATTTACAGCCGATCGAAGTAGGAAAAGCGCG

ACTGGTCAAAGGTGCAGCTAAACATATCATTCATGCCGTAGGACCAAACTTCAACA

AAGTTTCGGAGGTTGAAGGTGACAAACAGTTGGCAGAGGCTTATGAGTCCATCGCT

AAGATTGTCAACGATAACAATTACAAGTCAGTAGCGATTCCACTGTTGTCCACCGGC

ATCTTTTCCGGGAACAAAGATCGACTAACCCAATCATTGAACCATTTGCTGACAGCT

TTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCG

ACGACTCTTCAGTGACAGAACCTGATGCAGAGCTGGTGAGGGTGCATCCGAAGAGT

TCTTTGGCTGGAAGGAAGGGCTACAGCACAAGCGATGGCAAAACTTTCTCATATTTG

GAAGGGACCAAGTTTCACCAGGCGGCCAAGGATATAGCAGAAATTAATGCCATGTG

GCCCGTTGCAACGGAGGCCAATGAGCAGGTATGCATGTATATCCTCGGAGAAAGCA

TGAGCAGTATTAGGTCGAAATGCCCCGTCGAAGAGTCGGAAGCCTCCACACCACCT

AGCACGCTGCCTTGCTTGTGCATCCATGCCATGACTCCAGAAAGAGTACAGCGCCTA

AAAGCCTCACGTCCAGAACAAATTACTGTGTGCTCATCCTTTCCATTGCCGAAGTAT

AGAATCACTGGTGTGCAGAAGATCCAATGCTCCCAGCCTATATTGTTCTCACCGAAA

GTGCCTGCGTATATTCATCCAAGGAAGTATCTCGTGGAAACACCACCGGTAGACGA

GACTCCGGAGCCATCGGCAGAGAACCAATCCACAGAGGGGACACCTGAACAACCAC

CACTTATAACCGAGGATGAGACCAGGACTAGAACGCCTGAGCCGATCATCATCGAA

GAGGAAGAAGAGGATAGCATAAGTTTGCTGTCAGATGGCCCGACCCACCAGGTGCT

GCAAGTCGAGGCAGACATTCACGGGCCGCCCTCTGTATCTAGCTCATCCTGGTCCAT

TCCTCATGCATCCGACTTTGATGTGGACAGTTTATCCATACTTGACACCCTGGAGGG

AGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCG

AGAACCAGCCTAGTTTCCACCCCGCCAGGCGTGAATAGGGTGATCACTAGAGAGGA

GCTCGAGGCGCTTACCCCGTCACGCACTCCTAGCAGGTCGGTCTCGAGAACCAGCCT

GGTCTCCAACCCGCCAGGCGTAAATAGGGTGATTACAAGAGAGGAGTTTGAGGCGT

TCGTAGCACAACAACAATGACGGTTTGATGCGGGTGCATACATCTTTTCCTCCGACA

CCGGTCAAGGGCATTTACAACAAAAATCAGTAAGGCAAACGGTGCTATCCGAAGTG

GTGTTGGAGAGGACCGAATTGGAGATTTCGTATGCCCCGCGCCTCGACCAAGAAAA

AGAAGAATTACTACGCAAGAAATTACAGTTAAATCCCACACCTGCTAACAGAAGCA

GATACCAGTCCAGGAAGGTGGAGAACATGAAAGCCATAACAGCTAGACGTATTCTG

CAAGGCCTAGGGCATTATTTGAAGGCAGAAGGAAAAGTGGAGTGCTACCGAACCCT

GCATCCTGTTCCTTTGTATTCATCTAGTGTGAACCGTGCCTTTTCAAGCCCCAAGGTC

GCAGTGGAAGCCTGTAACGCCATGTTGAAAGAGAACTTTCCGACTGTGGCTTCTTAC

TGTATTATTCCAGAGTACGATGCCTATTTGGACATGGTTGACGGAGCTTCATGCTGC

TTAGACACTGCCAGTTTTTGCCCTGCAAAGCTGCGCAGCTTTCCAAAGAAACACTCC

TATTTGGAACCCACAATACGATCGGCAGTGCCTTCAGCGATCCAGAACACGCTCCAG

AACGTCCTGGCAGCTGCCACAAAAAGAAATTGCAATGTCACGCAAATGAGAGAATT

-continued

GCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACG

TGGTAAATTACATTACCAAATTAAAAGGACCAAAAGCTGCTGCTCTTTTTGCGAAGA

CACATAATTTGAATATGTTGCAGGACATACCAATGGACAGGTTTGTAATGGACTTAA

AGAGAGACGTGAAAGTGACTCCAGGAACAAAACATACTGAAGAACGGCCCAAGGT

ACAGGTGATCCAGGCTGCCGATCCGCTAGCAACAGCGTATCTGTGCGGAATCCACC

GAGAGCTGGTTAGGAGATTAAATGCGGTCCTGCTTCCGAACATTCATACACTGTTTG

ATATGTCGGCTGAAGACTTTGACGCTATTATAGCCGAGCACTTCCAGCCTGGGGATT

GTGTTCTGGAAACTGACATCGCGTCGTTTGATAAAAGTGAGGACGACGCCATGGCTC

TGACCGCGTTAATGATTCTGGAAGACTTAGGTGTGGACGCAGAGCTGTTGACGCTGA

TTGAGGCGGCTTTCGGCGAAATTTCATCAATACATTTGCCCACTAAAACTAAATTTA

AATTCGGAGCCATGATGAAATCTGGAATGTTCCTCACACTGTTTGTGAACACAGTCA

TTAACATTGTAATCGCAAGCAGAGTGTTGAGAGAACGGCTAACCGGATCACCATGT

GCAGCATTCATTGGAGATGACAATATCGTGAAAGGAGTCAAATCGGACAAATTAAT

GGCAGACAGGTGCGCCACCTGGTTGAATATGGAAGTCAAGATTATAGATGCTGTGG

TGGGCGAGAAAGCGCCTTATTTCTGTGGAGGGTTTATTTTGTGTGACTCCGTGACCG

GCACAGCGTGCCGTGTGGCAGACCCCCTAAAAAGGCTGTTTAAGCTTGGCAAACCT

CTGGCAGCAGACGATGAACATGATGATGACAGGAGAAGGGCATTGCATGAAGAGTC

AACACGCTGGAACCGAGTGGGTATTCTTTCAGAGCTGTGCAAGGCAGTAGAATCAA

GGTATGAAACCGTAGGAACTTCCATCATAGTTATGGCCATGACTACTCTAGCTAGCA

GTGTTAAATCATTCAGCTACCTGAGAGGGGCCCCTATAACTCTCTACGGCTAACCTG

AATGGACTACGACATAGTCTAGTCCGCCAAGTTCGAAGGCGCGCCTCTAGAgccaccAT

GGTGAGCAAGGGCGAGGAGCTGTTCACCGGGGTGGTGCCCATCCTGGTCGAGCTGG

ACGGCGACGTAAACGGCCACAAGTTCAGCGTGTCCGGCGAGGGCGAGGGCGATGCC

ACCTACGGCAAGCTGACCCTGAAGTTCATCTGCACCACCGGCAAGCTGCCCGTGCCC

TGGCCCACCCTCGTGACCACCCTGACCTACGGCGTGCAGTGCTTCAGCCGCTACCCC

GACCACATGAAGCAGCACGACTTCTTCAAGTCCGCCATGCCCGAAGGCTACGTCCA

GGAGCGCACCATCTTCTTCAAGGACGACGGCAACTACAAGACCCGCGCCGAGGTGA

AGTTCGAGGGCGACACCCTGGTGAACCGCATCGAGCTGAAGGGCATCGACTTCAAG

GAGGACGGCAACATCCTGGGGCACAAGCTGGAGTACAACTACAACAGCCACAACGT

CTATATCATGGCCGACAAGCAGAAGAACGGCATCAAGGTGAACTTCAAGATCCGCC

ACAACATCGAGGACGGCAGCGTGCAGCTCGCCGACCACTACCAGCAGAACACCCCC

ATCGGCGACGGCCCCGTGCTGCTGCCCGACAACCACTACCTGAGCACCCAGTCCGCC

CTGAGCAAAGACCCCAACGAGAAGCGCGATCACATGGTCCTGCTGGAGTTCGTGAC

CGCCGCCGGGATCACTCTCGGCATGGACGAGCTGTACAAGtagcATCGATGATATCGC

GGCCGCATACAGCAGCAATTGGCAAGCTGCTTACATAGAACTCGCGGCGATTGGCA

TGCCGCCTTAAAATTTTTATTTTATTTTTCTTTTCTTTTCCGAATCGGATTTTGTTTTTA

ATATTTCAAAAAAAAAAAAAAAA

SAM002

(SEQ ID NO: 21)

AAAAAAAAAACGCGTGATAACGCAGGAAAGAACATGTGAGCAAAAGGCCAGCAAA

AGGCCAGGAACCGTAAAAAGGCCGCGTTGCTGGCGTTTTTCCATAGGCTCCGCCCCC

-continued

CTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGT

AGCGGTTTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACTCACGTTA

AGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTA

CCAATGCTTAATCAGTGAGGCACCTATCTCAGCGATCTGTCTATTTCGTTCATCCATA

GTTGCCTGACTCCCCGTCGTGTAGATAACTACGATACGGGAGGGCTTACCATCTGGC

CCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGC

CTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTT

GGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAG

TTGGCCGCAGTGTTATCACTCATGGTTATGGCAGCACTGCATAATTCTCTTACTGTCA

TGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAA

AACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAG

GAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTT

CCCCGAAAAGTGCCACCTGAGCTCTAATACGACTCACTATAGgATaGGCGGCGCATG

AGAGAAGCCCAGACCAATTACCTACCCAAAATGGAGAAAGTTCACGTTGACATCGA

GGAAGACAGCCCATTCCTCAGAGCTTTGCAGCGGAGCTTCCCGCAGTTTGAGGTAGA

AGCCAAGCAGGTCACTGATAATGACCATGCTAATGCCAGAGCGTTTTCGCATCTGGC

TTCAAAACTGATCGAAACGGAGGTGGACCCATCCGACACGATCCTTGACATTGGAA

GTGCGCCCGCCCGCAGAATGTATTCTAAGCACAAGTATCATTGTATCTGTCCGATGA

GATGTGCGGAAGATCCGGACAGATTGTATAAGTATGCAACTAAGCTGAAGAAAAAC

TGTAAGGAAATAACTGATAAGGAATTGGACAAGAAAATGAAGGAGCTGGCCGCCGT

CATGAGCGACCCTGACCTGGAAACTGAGACTATGTGCCTCCACGACGACGAGTCGT

GTCGCTACGAAGGGCAAGTCGCTGTTTACCAGGATGTATACGCGGTTGACGGACCG

-continued

ACAAGTCTCTATCACCAAGCCAATAAGGGAGTTAGAGTCGCCTACTGGATAGGCTTT

GACACCACCCCTTTTATGTTTAAGAACTTGGCTGGAGCATATCCATCATACTCTACC

AACTGGGCCGACGAAACCGTGTTAACGGCTCGTAACATAGGCCTATGCAGCTCTGA

CGTTATGGAGCGGTCACGTAGAGGGATGTCCATTCTTAGAAAGAAGTATTTGAAACC

ATCCAACAATGTTCTATTCTCTGTTGGCTCGACCATCTACCACGAGAAGAGGGACTT

ACTGAGGAGCTGGCACCTGCCGTCTGTATTTCACTTACGTGGCAAGCAAAATTACAC

ATGTCGGTGTGAGACTATAGTTAGTTGCGACGGGTACGTCGTTAAAAGAATAGCTAT

CAGTCCAGGCCTGTATGGGAAGCCTTCAGGCTATGCTGCTACGATGCACCGCGAGG

GATTCTTGTGCTGCAAAGTGACAGACACATTGAACGGGGAGAGGGTCTCTTTTCCCG

TGTGCACGTATGTGCCAGCTACATTGTGTGACCAAATGACTGGCATACTGGCAACAG

ATGTCAGTGCGGACGACGCGCAAAAACTGCTGGTTGGGCTCAACCAGCGTATAGTC

GTCAACGGTCGCACCCAGAGAAACACCAATACCATGAAAAATTACCTTTTGCCCGT

AGTGGCCCAGGCATTTGCTAGGTGGGCAAAGGAATATAAGGAAGATCAAGAAGATG

AAAGGCCACTAGGACTACGAGATAGACAGTTAGTCATGGGGTGTTGTTGGGCTTTTA

GAAGGCACAAGATAACATCTATTTATAAGCGCCCGGATACCCAAACCATCATCAAA

GTGAACAGCGATTTCCACTCATTCGTGCTGCCCAGGATAGGCAGTAACACATTGGAG

ATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAG

GAGGTGCGTGAAGCCGAGGAGTTGCGCGCAGCTCTACCACCTTTGGCAGCTGATGTT

GAGGAGCCCACTCTGGAAGCCGATGTCGACTTGATGTTACAAGAGGCTGGGGCCGG

CTCAGTGGAGACACCTCGTGGCTTGATAAAGGTTACCAGCTACGATGGCGAGGACA

AGATCGGCTCTTACGCTGTGCTTTCTCCGCAGGCTGTACTCAAGAGTGAAAAATTAT

CTTGCATCCACCCTCTCGCTGAACAAGTCATAGTGATAACACACTCTGGCCGAAAAG

GGCGTTATGCCGTGGAACCATACCATGGTAAAGTAGTGGTGCCAGAGGGACATGCA

ATACCCGTCCAGGACTTTCAAGCTCTGAGTGAAAGTGCCACCATTGTGTACAACGAA

CGTGAGTTCGTAAACAGGTACCTGCACCATATTGCCACACATGGAGGAGCGCTGAA

CACTGATGAAGAATATTACAAAACTGTCAAGCCCAGCGAGCACGACGGCGAATACC

TGTACGACATCGACAGGAAACAGTGCGTCAAGAAAGAACTAGTCACTGGGCTAGGG

CTCACAGGCGAGCTGGTGGATCCTCCCTTCCATGAATTCGCCTACGAGAGTCTGAGA

ACACGACCAGCCGCTCCTTACCAAGTACCAACCATAGGGGTGTATGGCGTGCCAGG

ATCAGGCAAGTCTGGCATCATTAAAAGCGCAGTCACCAAAAAAGATCTAGTGGTGA

GCGCCAAGAAAGAAAACTGTGCAGAAATTATAAGGGACGTCAAGAAAATGAAAGG

GCTGGACGTCAATGCCAGAACTGTGGACTCAGTGCTCTTGAATGGATGCAAACACCC

CGTAGAGACCCTGTATATTGACGAAGCTTTTGCTTGTCATGCAGGTACTCTCAGAGC

GCTCATAGCCATTATAAGACCTAAAAAGGCAGTGCTCTGCGGGGATCCCAAACAGT

GCGGTTTTTTTAACATGATGTGCCTGAAAGTGCATTTTAACCACGAGATTTGCACAC

AAGTCTTCCACAAAAGCATCTCTCGCCGTTGCACTAAATCTGTGACTTCGGTCGTCTC

AACCTTGTTTTACGACAAAAAAATGAGAACGACGAATCCGAAAGAGACTAAGATTG

TGATTGACACTACCGGCAGTACCAAACCTAAGCAGGACGATCTCATTCTCACTTGTT

TCAGAGGGTGGGTGAAGCAGTTGCAAATAGATTACAAAGGCAACGAAATAATGACG

GCAGCTGCCTCTCAAGGGCTGACCCGTAAAGGTGTGTATGCCGTTCGGTACAAGGTG

-continued

AATGAAAATCCTCTGTACGCACCCACCTCAGAACATGTGAACGTCCTACTGACCCGC

ACGGAGGACCGCATCGTGTGGAAAACACTAGCCGGCGACCCATGGATAAAAACACT

GACTGCCAAGTACCCTGGGAATTTCACTGCCACGATAGAGGAGTGGCAAGCAGAGC

ATGATGCCATCATGAGGCACATCTTGGAGAGACCGGACCCTACCGACGTCTTCCAG

AATAAGGCAAACGTGTGTTGGGCCAAGGCTTTAGTGCCGGTGCTGAAGACCGCTGG

CATAGACATGACCACTGAACAATGGAACACTGTGGATTATTTTGAAACGGACAAAG

CTCACTCAGCAGAGATAGTATTGAACCAACTATGCGTGAGGTTCTTTGGACTCGATC

TGGACTCCGGTCTATTTTCTGCACCCACTGTTCCGTTATCCATTAGGAATAATCACTG

GGATAACTCCCCGTCGCCTAACATGTACGGGCTGAATAAAGAAGTGGTCCGTCAGCT

CTCTCGCAGGTACCCACAACTGCCTCGGGCAGTTGCCACTGGAAGAGTCTATGACAT

GAACACTGGTACACTGCGCAATTATGATCCGCGCATAAACCTAGTACCTGTAAACAG

AAGACTGCCTCATGCTTTAGTCCTCCACCATAATGAACACCCACAGAGTGACTTTTC

TTCATTCGTCAGCAAATTGAAGGGCAGAACTGTCCTGGTGGTCGGGGAAAAGTTGTC

CGTCCCAGGCAAAATGGTTGACTGGTTGTCAGACCGGCCTGAGGCTACCTTCAGAGC

TCGGCTGGATTTAGGCATCCCAGGTGATGTGCCCAAATATGACATAATATTTGTTAA

TGTGAGGACCCCATATAAATACCATCACTATCAGCAGTGTGAAGACCATGCCATTAA

GCTTAGCATGTTGACCAAGAAAGCTTGTCTGCATCTGAATCCCGGCGGAACCTGTGT

CAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGG

AAGTTCTGTTTGTATTCATTGGGTACGATCGCAAGGCCCGTACGCACAATtCTTACAA

GCTTTCATCAACCTTGACCAACATTTATACAGGTTCCAGACTCCACGAAGCCGGATG

TGCACCCTCATATCATGTGGTGCGAGGGGATATTGCCACGGCCACCGAAGGAGTGA

TTATAAATGCTGCTAACAGCAAAGGACAACCTGGCGGAGGGGTGTGCGGAGCGCTG

TATAAGAAATTCCCGGAAAGCTTCGATTTACAGCCGATCGAAGTAGGAAAAGCGCG

ACTGGTCAAAGGTGCAGCTAAACATATCATTCATGCCGTAGGACCAAACTTCAACA

AAGTTTCGGAGGTTGAAGGTGACAAACAGTTGGCAGAGGCTTATGAGTCCATCGCT

AAGATTGTCAACGATAACAATTACAAGTCAGTAGCGATTCCACTGTTGTCCACCGGC

ATCTTTTCCGGGAACAAAGATCGACTAACCCAATCATTGAACCATTTGCTGACAGCT

TTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCG

ACGACTCTTCAGTGACAGAACCTGATGCAGAGCTGGTGAGGGTGCATCCGAAGAGT

TCTTTGGCTGGAAGGAAGGGCTACAGCACAAGCGATGGCAAAACTTTCTCATATTTG

GAAGGGACCAAGTTTCACCAGGCGGCCAAGGATATAGCAGAAATTAATGCCATGTG

GCCCGTTGCAACGGAGGCCAATGAGCAGGTATGCATGTATATCCTCGGAGAAAGCA

TGAGCAGTATTAGGTCGAAATGCCCCGTCGAAGAGTCGGAAGCCTCCACACCACCT

AGCACGCTGCCTTGCTTGTGCATCCATGCCATGACTCCAGAAAGAGTACAGCGCCTA

AAAGCCTCACGTCCAGAACAAATTACTGTGTGCTCATCCTTTCCATTGCCGAAGTAT

AGAATCACTGGTGTGCAGAAGATCCAATGCTCCCAGCCTATATTGTTCTCACCGAAA

GTGCCTGCGTATATTCATCCAAGGAAGTATCTCGTGGAAACACCACCGGTAGACGA

GACTCCGGAGCCATCGGCAGAGAACCAATCCACAGAGGGGACACCTGAACAACCAC

-continued

CACTTATAACCGAGGATGAGACCAGGACTAGAACGCCTGAGCCGATCATCATCGAA

GAGGAAGAAGAGGATAGCATAAGTTTGCTGTCAGATGGCCCGACCCACCAGGTGCT

GCAAGTCGAGGCAGACATTCACGGGCCGCCCTCTGTATCTAGCTCATCCTGGTCCAT

TCCTCATGCATCCGACTTTGATGTGGACAGTTTATCCATACTTGACACCCTGGAGGG

AGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCG

AGAACCAGCCTAGTTTCCACCCCGCCAGGCGTGAATAGGGTGATCACTAGAGAGGA

GCTCGAGGCGCTTACCCCGTCACGCACTCCTAGCAGGTCGGTCTCGAGAACCAGCCT

GGTCTCCAACCCGCCAGGCGTAAATAGGGTGATTACAAGAGAGGAGTTTGAGGCGT

TCGTAGCACAACAACAATGACGGTTTGATGCGGGTGCATACATCTTTTCCTCCGACA

CCGGTCAAGGGCATTTACAACAAAAATCAGTAAGGCAAACGGTGCTATCCGAAGTG

GTGTTGGAGAGGACCGAATTGGAGATTTCGTATGCCCCGCGCCTCGACCAAGAAAA

AGAAGAATTACTACGCAAGAAATTACAGTTAAATCCCACACCTGCTAACAGAAGCA

GATACCAGTCCAGGAAGGTGGAGAACATGAAAGCCATAACAGCTAGACGTATTCTG

CAAGGCCTAGGGCATTATTTGAAGGCAGAAGGAAAAGTGGAGTGCTACCGAACCCT

GCATCCTGTTCCTTTGTATTCATCTAGTGTGAACCGTGCCTTTTCAAGCCCCAAGGTC

GCAGTGGAAGCCTGTAACGCCATGTTGAAAGAGAACTTTCCGACTGTGGCTTCTTAC

TGTATTATTCCAGAGTACGATGCCTATTTGGACATGGTTGACGGAGCTTCATGCTGC

TTAGACACTGCCAGTTTTTGCCCTGCAAAGCTGCGCAGCTTTCCAAAGAAACACTCC

TATTTGGAACCCACAATACGATCGGCAGTGCCTTCAGCGATCCAGAACACGCTCCAG

AACGTCCTGGCAGCTGCCACAAAAAGAAATTGCAATGTCACGCAAATGAGAGAATT

GCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACG

TGGTAAATTACATTACCAAATTAAAAGGACCAAAAGCTGCTGCTCTTTTTGCGAAGA

CACATAATTTGAATATGTTGCAGGACATACCAATGGACAGGTTTGTAATGGACTTAA

AGAGAGACGTGAAAGTGACTCCAGGAACAAAACATACTGAAGAACGGCCCAAGGT

ACAGGTGATCCAGGCTGCCGATCCGCTAGCAACAGCGTATCTGTGCGGAATCCACC

GAGAGCTGGTTAGGAGATTAAATGCGGTCCTGCTTCCGAACATTCATACACTGTTTG

ATATGTCGGCTGAAGACTTTGACGCTATTATAGCCGAGCACTTCCAGCCTGGGGATT

GTGTTCTGGAAACTGACATCGCGTCGTTTGATAAAAGTGAGGACGACGCCATGGCTC

TGACCGCGTTAATGATTCTGGAAGACTTAGGTGTGGACGCAGAGCTGTTGACGCTGA

TTGAGGCGGCTTTCGGCGAAATTTCATCAATACATTTGCCCACTAAAACTAAATTTA

AATTCGGAGCCATGATGAAATCTGGAATGTTCCTCACACTGTTTGTGAACACAGTCA

TTAACATTGTAATCGCAAGCAGAGTGTTGAGAGAACGGCTAACCGGATCACCATGT

GCAGCATTCATTGGAGATGACAATATCGTGAAAGGAGTCAAATCGGACAAATTAAT

GGCAGACAGGTGCGCCACCTGGTTGAATATGGAAGTCAAGATTATAGATGCTGTGG

TGGGCGAGAAAGCGCCTTATTTCTGTGGAGGGTTTATTTTGTGTGACTCCGTGACCG

GCACAGCGTGCCGTGTGGCAGACCCCCTAAAAAGGCTGTTTAAGCTTGGCAAACCT

CTGGCAGCAGACGATGAACATGATGATGACAGGAGAAGGGCATTGCATGAAGAGTC

AACACGCTGGAACCGAGTGGGTATTCTTTCAGAGCTGTGCAAGGCAGTAGAATCAA

-continued

GGTATGAAACCGTAGGAACTTCCATCATAGTTATGGCCATGACTACTCTAGCTAGCA

GTGTTAAATCATTCAGCTACCTGAGAGGGGCCCCTATAACTCTCTACGGCTAACCTG

AATGGACTACGACATAGTCTAGTCCGCCAAGTTCGAAGGCGCGCCTCTAGAGCCAC

CATGGTGAGCAAGGGCGAGGAGCTGTTCACCGGGGTGGTGCCCATCCTGGTCGAGC

TGGACGGCGACGTAAACGGCCACAAGTTCAGCGTGTCCGGCGAGGGCGAGGGCGAT

GCCACCTACGGCAAGCTGACCCTGAAGTTCATCTGCACCACCGGCAAGCTGCCCGTG

CCCTGGCCCACCCTCGTGACCACCCTGACCTACGGCGTGCAGTGCTTCAGCCGCTAC

CCCGACCACATGAAGCAGCACGACTTCTTCAAGTCCGCCATGCCCGAAGGCTACGTC

CAGGAGCGCACCATCTTCTTCAAGGACGACGGCAACTACAAGACCCGCGCCGAGGT

GAAGTTCGAGGGCGACACCCTGGTGAACCGCATCGAGCTGAAGGGCATCGACTTCA

AGGAGGACGGCAACATCCTGGGGCACAAGCTGGAGTACAACTACAACAGCCACAA

CGTCTATATCATGGCCGACAAGCAGAAGAACGGCATCAAGGTGAACTTCAAGATCC

GCCACAACATCGAGGACGGCAGCGTGCAGCTCGCCGACCACTACCAGCAGAACACC

CCCATCGGCGACGGCCCCGTGCTGCTGCCCGACAACCACTACCTGAGCACCCAGTCC

GCCCTGAGCAAAGACCCCAACGAGAAGCGCGATCACATGGTCCTGCTGGAGTTCGT

GACCGCCGCCGGGATCACTCTCGGCATGGACGAGCTGTACAAGTAGCATCGATGAT

ATCGCGGCCGCATACAGCAGCAATTGGCAAGCTGCTTACATAGAACTCGCGGCGAT

TGGCATGCCGCCTTAAAATTTTTATTTTATTTTTCTTTTCTTTTCCGAATCGGATTTTG

TTTTTAATATTTCAAAAAAAAAAAAAAAA

In sequences SVP242 and SVP201 the bolded, underlined and italicized sequence is the SGP (a T7 promoter).

SVP242

(SEQ ID NO: 22)

AAAAAAAAAACGCGTGATAACGCAGGAAAGAACATGTGAGCAAAAGGCCAGCAAA

AGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGT

AGCGGTTTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACTCACGTTA

AGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTA

CCAATGCTTAATCAGTGAGGCACCTATCTCAGCGATCTGTCTATTTCGTTCATCCATA

GTTGCCTGACTCCCCGTCGTGTAGATAACTACGATACGGGAGGGCTTACCATCTGGC

-continued

CCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGC

CTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTT

GGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAG

TTGGCCGCAGTGTTATCACTCATGGTTATGGCAGCACTGCATAATTCTCTTACTGTCA

TGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAA

AACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAG

GAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTT

CCCCGAAAAGTGCCACCTGAGCTC*TAATACGACTCACTATAGG*ATAGGCGGCGCATG

AGAGAAGCCCAGACCAATTACCTACCCAAAATGGAGAAAGTTCACGTTGACATCGA

GGAAGACAGCCCATTCCTCAGAGCTTTGCAGCGGAGCTTCCCGCAGTTTGAGGTAGA

AGCCAAGCAGGTCACTGATAATGACCATGCTAATGCCAGAGCGTTTTCGCATCTGGC

TTCAAAACTGATCGAAACGGAGGTGGACCCATCCGACACGATCCTTGACATTGGAA

GTGCGCCCGCCCGCAGAATGTATTCTAAGCACAAGTATCATTGTATCTGTCCGATGA

GATGTGCGGAAGATCCGGACAGATTGTATAAGTATGCAACTAAGCTGAAGAAAAAC

TGTAAGGAAATAACTGATAAGGAATTGGACAAGAAAATGAAGGAGCTGGCCGCCGT

CATGAGCGACCCTGACCTGGAAACTGAGACTATGTGCCTCCACGACGACGAGTCGT

GTCGCTACGAAGGGCAAGTCGCTGTTTACCAGGATGTATACGCGGTTGACGGACCG

ACAAGTCTCTATCACCAAGCCAATAAGGGAGTTAGAGTCGCCTACTGGATAGGCTTT

GACACCACCCCTTTTATGTTTAAGAACTTGGCTGGAGCATATCCATCATACTCTACC

AACTGGGCCGACGAAACCGTGTTAACGGCTCGTAACATAGGCCTATGCAGCTCTGA

CGTTATGGAGCGGTCACGTAGAGGGATGTCCATTCTTAGAAAGAAGTATTTGAAACC

ATCCAACAATGTTCTATTCTCTGTTGGCTCGACCATCTACCACGAGAAGAGGGACTT

ACTGAGGAGCTGGCACCTGCCGTCTGTATTTCACTTACGTGGCAAGCAAAATTACAC

ATGTCGGTGTGAGACTATAGTTAGTTGCGACGGGTACGTCGTTAAAAGAATAGCTAT

CAGTCCAGGCCTGTATGGGAAGCCTTCAGGCTATGCTGCTACGATGCACCGCGAGG

GATTCTTGTGCTGCAAAGTGACAGACACATTGAACGGGGAGAGGGTCTCTTTTCCCG

TGTGCACGTATGTGCCAGCTACATTGTGTGACCAAATGACTGGCATACTGGCAACAG

ATGTCAGTGCGGACGACGCGCAAAAACTGCTGGTTGGGCTCAACCAGCGTATAGTC

GTCAACGGTCGCACCCAGAGAAACACCAATACCATGAAAAATTACCTTTTGCCCGT

AGTGGCCCAGGCATTTGCTAGGTGGGCAAAGGAATATAAGGAAGATCAAGAAGATG

AAAGGCCACTAGGACTACGAGATAGACAGTTAGTCATGGGGTGTTGTTGGGCTTTTA

GAAGGCACAAGATAACATCTATTTATAAGCGCCCGGATACCCAAACCATCATCAAA

GTGAACAGCGATTTCCACTCATTCGTGCTGCCCAGGATAGGCAGTAACACATTGGAG

-continued

ATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAG

GAGGTGCGTGAAGCCGAGGAGTTGCGCGCAGCTCTACCACCTTTGGCAGCTGATGTT

GAGGAGCCCACTCTGGAAGCCGATGTCGACTTGATGTTACAAGAGGCTGGGGCCGG

CTCAGTGGAGACACCTCGTGGCTTGATAAAGGTTACCAGCTACGATGGCGAGGACA

AGATCGGCTCTTACGCTGTGCTTTCTCCGCAGGCTGTACTCAAGAGTGAAAAATTAT

CTTGCATCCACCCTCTCGCTGAACAAGTCATAGTGATAACACACTCTGGCCGAAAAG

GGCGTTATGCCGTGGAACCATACCATGGTAAAGTAGTGGTGCCAGAGGGACATGCA

ATACCCGTCCAGGACTTTCAAGCTCTGAGTGAAAGTGCCACCATTGTGTACAACGAA

CGTGAGTTCGTAAACAGGTACCTGCACCATATTGCCACACATGGAGGAGCGCTGAA

CACTGATGAAGAATATTACAAAACTGTCAAGCCCAGCGAGCACGACGGCGAATACC

TGTACGACATCGACAGGAAACAGTGCGTCAAGAAAGAACTAGTCACTGGGCTAGGG

CTCACAGGCGAGCTGGTGGATCCTCCCTTCCATGAATTCGCCTACGAGAGTCTGAGA

ACACGACCAGCCGCTCCTTACCAAGTACCAACCATAGGGGTGTATGGCGTGCCAGG

ATCAGGCAAGTCTGGCATCATTAAAAGCGCAGTCACCAAAAAAGATCTAGTGGTGA

GCGCCAAGAAAGAAAACTGTGCAGAAATTATAAGGGACGTCAAGAAAATGAAAGG

GCTGGACGTCAATGCCAGAACTGTGGACTCAGTGCTCTTGAATGGATGCAAACACCC

CGTAGAGACCCTGTATATTGACGAAGCTTTTGCTTGTCATGCAGGTACTCTCAGAGC

GCTCATAGCCATTATAAGACCTAAAAAGGCAGTGCTCTGCGGGGATCCCAAACAGT

GCGGTTTTTTTAACATGATGTGCCTGAAAGTGCATTTTAACCACGAGATTTGCACAC

AAGTCTTCCACAAAAGCATCTCTCGCCGTTGCACTAAATCTGTGACTTCGGTCGTCTC

AACCTTGTTTTACGACAAAAAAATGAGAACGACGAATCCGAAAGAGACTAAGATTG

TGATTGACACTACCGGCAGTACCAAACCTAAGCAGGACGATCTCATTCTCACTTGTT

TCAGAGGGTGGGTGAAGCAGTTGCAAATAGATTACAAAGGCAACGAAATAATGACG

GCAGCTGCCTCTCAAGGGCTGACCCGTAAAGGTGTGTATGCCGTTCGGTACAAGGTG

AATGAAAATCCTCTGTACGCACCCACCTCAGAACATGTGAACGTCCTACTGACCCGC

ACGGAGGACCGCATCGTGTGGAAAACACTAGCCGGCGACCCATGGATAAAAACACT

GACTGCCAAGTACCCTGGGAATTTCACTGCCACGATAGAGGAGTGGCAAGCAGAGC

ATGATGCCATCATGAGGCACATCTTGGAGAGACCGGACCCTACCGACGTCTTCCAG

AATAAGGCAAACGTGTGTTGGGCCAAGGCTTTAGTGCCGGTGCTGAAGACCGCTGG

CATAGACATGACCACTGAACAATGGAACACTGTGGATTATTTTGAAACGGACAAAG

CTCACTCAGCAGAGATAGTATTGAACCAACTATGCGTGAGGTTCTTTGGACTCGATC

TGGACTCCGGTCTATTTTCTGCACCCACTGTTCCGTTATCCATTAGGAATAATCACTG

GGATAACTCCCCGTCGCCTAACAcGTACGGGCTGAATAAAGAAGTGGTCCGTCAGCT

CTCTCGCAGGTACCCACAACTGCCTCGGGCAGTTGCCACTGGAAGAGTCTATGACAT

GAACACTGGTACACTGCGCAATTATGATCCGCGCATAAACCTAGTACCTGTAAACAG

AAGACTGCCTCATGCTTTAGTCCTCCACCATAATGAACACCCACAGAGTGACTTTTC

TTCATTCGTCAGCAAATTGAAGGGCAGAACTGTCCTGGTGGTCGGGGAAAAGTTGTC

CGTCCCAGGCAAAATGGTTGACTGGTTGTCAGACCGGCCTGAGGCTACCTTCAGAGC

TCGGCTGGATTTAGGCATCCCAGGTGATGTGCCCAAATATGACATAATATTTGTTAA

-continued

TGTGAGGACCCCATATAAATACCATCACTATCAGCAGTGTGAAGACCATGCCATTAA

GCTTAGCATGTTGACCAAGAAAGCTTGTCTGCATCTGAATCCCGGCGGAACCTGTGT

CAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGG

AAGTTCTGTTTGTATTCATTGGGTACGATCGCAAGGCCCGTACGCACAATICTTACAA

GCTTTCATCAACCTTGACCAACATTTATACAGGTTCCAGACTCCACGAAGCCGGATG

TGCACCCTCATATCATGTGGTGCGAGGGGATATTGCCACGGCCACCGAAGGAGTGA

TTATAAATGCTGCTAACAGCAAAGGACAACCTGGCGGAGGGGTGTGCGGAGCGCTG

TATAAGAAATTCCCGGAAAGCTTCGATTTACAGCCGATCGAAGTAGGAAAAGCGCG

ACTGGTCAAAGGTGCAGCTAAACATATCATTCATGCCGTAGGACCAAACTTCAACA

AAGTTTCGGAGGTTGAAGGTGACAAACAGTTGGCAGAGGCTTATGAGTCCATCGCT

AAGATTGTCAACGATAACAATTACAAGTCAGTAGCGATTCCACTGTTGTCCACCGGC

ATCTTTTCCGGGAACAAAGATCGACTAACCCAATCATTGAACCATTTGCTGACAGCT

TTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCG

ACGACTCTTCAGTGACAGAACCTGATGCAGAGCTGGTGAGGGTGCATCCGAAGAGT

TCTTTGGCTGGAAGGAAGGGCTACAGCACAAGCGATGGCAAAACTTTCTCATATTTG

GAAGGGACCAAGTTTCACCAGGCGGCCAAGGATATAGCAGAAATTAATGCCATGTG

GCCCGTTGCAACGGAGGCCAATGAGCAGGTATGCATGTATATCCTCGGAGAAAGCA

TGAGCAGTATTAGGTCGAAATGCCCCGTCGAAGAGTCGGAAGCCTCCACACCACCT

AGCACGCTGCCTTGCTTGTGCATCCATGCCATGACTCCAGAAAGAGTACAGCGCCTA

AAAGCCTCACGTCCAGAACAAATTACTGTGTGCTCATCCTTTCCATTGCCGAAGTAT

AGAATCACTGGTGTGCAGAAGATCCAATGCTCCCAGCCTATATTGTTCTCACCGAAA

GTGCCTGCGTATATTCATCCAAGGAAGTATCTCGTGGAAACACCACCGGTAGACGA

GACTCCGGAGCCATCGGCAGAGAACCAATCCACAGAGGGGACACCTGAACAACCAC

CACTTATAACCGAGGATGAGACCAGGACTAGAACGCCTGAGCCGATCATCATCGAA

GAGGAAGAAGAGGATAGCATAAGTTTGCTGTCAGATGGCCCGACCCACCAGGTGCT

GCAAGTCGAGGCAGACATTCACGGGCCGCCCTCTGTATCTAGCTCATCCTGGTCCAT

TCCTCATGCATCCGACTTTGATGTGGACAGTTTATCCATACTTGACACCCTGGAGGG

AGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCG

AGAACCAGCCTAGTTTCCACCCCGCCAGGCGTGAATAGGGTGATCACTAGAGAGGA

GCTCGAGGCGCTTACCCCGTCACGCACTCCTAGCAGGTCGGTCTCGAGAACCAGCCT

GGTCTCCAACCCGCCAGGCGTAAATAGGGTGATTACAAGAGAGGAGTTTGAGGCGT

TCGTAGCACAACAACAATGACGGTTTGATGCGGGTGCATACATCTTTTCCTCCGACA

CCGGTCAAGGGCATTTACAACAAAAATCAGTAAGGCAAACGGTGCTATCCGAAGTG

GTGTTGGAGAGGACCGAATTGGAGATTTCGTATGCCCCGCGCCTCGACCAAGAAAA

AGAAGAATTACTACGCAAGAAATTACAGTTAAATCCCACACCTGCTAACAGAAGCA

GATACCAGTCCAGGAAGGTGGAGAACATGAAAGCCATAACAGCTAGACGTATTCTG

CAAGGCCTAGGGCATTATTTGAAGGCAGAAGGAAAAGTGGAGTGCTACCGAACCCT

-continued

GCATCCTGTTCCTTTGTATTCATCTAGTGTGAACCGTGCCTTTTCAAGCCCCAAGGTC

GCAGTGGAAGCCTGTAACGCCATGTTGAAAGAGAACTTTCCGACTGTGGCTTCTTAC

TGTATTATTCCAGAGTACGATGCCTATTTGGACATGGTTGACGGAGCTTCATGCTGC

TTAGACACTGCCAGTTTTTGCCCTGCAAAGCTGCGCAGCTTTCCAAAGAAACACTCC

TATTTGGAACCCACAATACGATCGGCAGTGCCTTCAGCGATCCAGAACACGCTCCAG

AACGTCCTGGCAGCTGCCACAAAAAGAAATTGCAATGTCACGCAAATGAGAGAATT

GCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACG

TGGTAAATTACATTACCAAATTAAAAGGACCAAAAGCTGCTGCTCTTTTTGCGAAGA

CACATAATTTGAATATGTTGCAGGACATACCAATGGACAGGTTTGTAATGGACTTAA

AGAGAGACGTGAAAGTGACTCCAGGAACAAAACATACTGAAGAACGGCCCAAGGT

ACAGGTGATCCAGGCTGCCGATCCGCTAGCAACAGCGTATCTGTGCGGAATCCACC

GAGAGCTGGTTAGGAGATTAAATGCGGTCCTGCTTCCGAACATTCATACACTGTTTG

ATATGTCGGCTGAAGACTTTGACGCTATTATAGCCGAGCACTTCCAGCCTGGGGATT

GTGTTCTGGAAACTGACATCGCGTCGTTTGATAAAAGTGAGGACGACGCCATGGCTC

TGACCGCGTTAATGATTCTGGAAGACTTAGGTGTGGACGCAGAGCTGTTGACGCTGA

TTGAGGCGGCTTTCGGCGAAATTTCATCAATACATTTGCCCACTAAAACTAAATTTA

AATTCGGAGCCATGATGAAATCTGGAATGTTCCTCACACTGTTTGTGAACACAGTCA

TTAACATTGTAATCGCAAGCAGAGTGTTGAGAGAACGGCTAACCGGATCACCATGT

GCAGCATTCATTGGAGATGACAATATCGTGAAAGGAGTCAAATCGGACAAATTAAT

GGCAGACAGGTGCGCCACCTGGTTGAATATGGAAGTCAAGATTATAGATGCTGTGG

TGGGCGAGAAAGCGCCTTATTTCTGTGGAGGGTTTATTTTGTGTGACTCCGTGACCG

GCACAGCGTGCCGTGTGGCAGACCCCCTAAAAAGGCTGTTTAAGCTTGGCAAACCT

CTGGCAGCAGACGATGAACATGATGATGACAGGAGAAGGGCATTGCATGAAGAGTC

AACACGCTGGAACCGAGTGGGTATTCTTTCAGAGCTGTGCAAGGCAGTAGAATCAA

GGTATGAAACCGTAGGAACTTCCATCATAGTTATGGCCATGACTACTCTAGCTAGCA

GTGTTAAATCATTCAGCTACCTGAGAGGGGCCCCTATAACTCTCTACGGCTAACCTG

AATGGACTACGACATAGTCTAGTCCGCCAAGTTCGAAGGCGCGCCTCTAGAgccaccAT

GGTGAGCAAGGGCGAGGAGCTGTTCACCGGGGTGGTGCCCATCCTGGTCGAGCTGG

ACGGCGACGTAAACGGCCACAAGTTCAGCGTGTCCGGCGAGGGCGAGGGCGATGCC

ACCTACGGCAAGCTGACCCTGAAGTTCATCTGCACCACCGGCAAGCTGCCCGTGCCC

TGGCCCACCCTCGTGACCACCCTGACCTACGGCGTGCAGTGCTTCAGCCGCTACCCC

GACCACATGAAGCAGCACGACTTCTTCAAGTCCGCCATGCCCGAAGGCTACGTCCA

GGAGCGCACCATCTTCTTCAAGGACGACGGCAACTACAAGACCCGCGCCGAGGTGA

AGTTCGAGGGCGACACCCTGGTGAACCGCATCGAGCTGAAGGGCATCGACTTCAAG

GAGGACGGCAACATCCTGGGGCACAAGCTGGAGTACAACTACAACAGCCACAACGT

CTATATCATGGCCGACAAGCAGAAGAACGGCATCAAGGTGAACTTCAAGATCCGCC

ACAACATCGAGGACGGCAGCGTGCAGCTCGCCGACCACTACCAGCAGAACACCCCC

ATCGGCGACGGCCCCGTGCTGCTGCCCGACAACCACTACCTGAGCACCCAGTCCGCC

CTGAGCAAAGACCCCAACGAGAAGCGCGATCACATGGTCCTGCTGGAGTTCGTGAC

-continued

CGCCGCCGGGATCACTCTCGGCATGGACGAGCTGTACAAGtagcATCGATGATATCGC

GGCCGCATACAGCAGCAATTGGCAAGCTGCTTACATAGAACTCGCGGCGATTGGCA

TGCCGCCTTAAAATTTTTATTTTATTTTTCTTTTCTTTTCCGAATCGGATTTTGTTTTTA

ATATTTCAAAAAAAAAAAAAAAA

SVP201

(SEQ ID NO: 23)

AAAAAAAAAACGCGTGATAACGCAGGAAAGAACATGTGAGCAAAAGGCCAGCAAA

AGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGT

AGCGGTTTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACTCACGTTA

AGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTA

CCAATGCTTAATCAGTGAGGCACCTATCTCAGCGATCTGTCTATTTCGTTCATCCATA

GTTGCCTGACTCCCCGTCGTGTAGATAACTACGATACGGGAGGGCTTACCATCTGGC

CCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGC

CTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTT

GGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAG

TTGGCCGCAGTGTTATCACTCATGGTTATGGCAGCACTGCATAATTCTCTTACTGTCA

TGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAA

AACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAG

GAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTT

CCCCGAAAAGTGCCACCTGAGCTC*TAATACGACTCACTATAGGATAGG*CGGCGCATG

AGAGAAGCCCAGACCAATTACCTACCCAAAATGGAGAAAGTTCACGTTGACATCGA

GGAAGACAGCCCATTCCTCAGAGCTTTGCAGCGGAGCTTCCCGCAGTTTGAGGTAGA

AGCCAAGCAGGTCACTGATAATGACCATGCTAATGCCAGAGCGTTTTCGCATCTGGC

-continued

TTCAAAACTGATCGAAACGGAGGTGGACCCATCCGACACGATCCTTGACATTGGAA

GTGCGCCCGCCCGCAGAATGTATTCTAAGCACAAGTATCATTGTATCTGTCCGATGA

GATGTGCGGAAGATCCGGACAGATTGTATAAGTATGCAACTAAGCTGAAGAAAAAC

TGTAAGGAAATAACTGATAAGGAATTGGACAAGAAAATGAAGGAGCTGGCCGCCGT

CATGAGCGACCCTGACCTGGAAACTGAGACTATGTGCCTCCACGACGACGAGTCGT

GTCGCTACGAAGGGCAAGTCGCTGTTTACCAGGATGTATACGCGGTTGACGGACCG

ACAAGTCTCTATCACCAAGCCAATAAGGGAGTTAGAGTCGCCTACTGGATAGGCTTT

GACACCACCCCTTTTATGTTTAAGAACTTGGCTGGAGCATATCCATCATACTCTACC

AACTGGGCCGACGAAACCGTGTTAACGGCTCGTAACATAGGCCTATGCAGCTCTGA

CGTTATGGAGCGGTCACGTAGAGGGATGTCCATTCTTAGAAAGAAGTATTTGAAACC

ATCCAACAATGTTCTATTCTCTGTTGGCTCGACCATCTACCACGAGAAGAGGGACTT

ACTGAGGAGCTGGCACCTGCCGTCTGTATTTCACTTACGTGGCAAGCAAAATTACAC

ATGTCGGTGTGAGACTATAGTTAGTTGCGACGGGTACGTCGTTAAAAGAATAGCTAT

CAGTCCAGGCCTGTATGGGAAGCCTTCAGGCTATGCTGCTACGATGCACCGCGAGG

GATTCTTGTGCTGCAAAGTGACAGACACATTGAACGGGGAGAGGGTCTCTTTTCCCG

TGTGCACGTATGTGCCAGCTACATTGTGTGACCAAATGACTGGCATACTGGCAACAG

ATGTCAGTGCGGACGACGCGCAAAAACTGCTGGTTGGGCTCAACCAGCGTATAGTC

GTCAACGGTCGCACCCAGAGAAACACCAATACCATGAAAAATTACCTTTTGCCCGT

AGTGGCCCAGGCATTTGCTAGGTGGGCAAAGGAATATAAGGAAGATCAAGAAGATG

AAAGGCCACTAGGACTACGAGATAGACAGTTAGTCATGGGGTGTTGTTGGGCTTTTA

GAAGGCACAAGATAACATCTATTTATAAGCGCCCGGATACCCAAACCATCATCAAA

GTGAACAGCGATTTCCACTCATTCGTGCTGCCCAGGATAGGCAGTAACACATTGGAG

ATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAG

GAGGTGCGTGAAGCCGAGGAGTTGCGCGCAGCTCTACCACCTTTGGCAGCTGATGTT

GAGGAGCCCACTCTGGAAGCCGATGTCGACTTGATGTTACAAGAGGCTGGGGCCGG

CTCAGTGGAGACACCTCGTGGCTTGATAAAGGTTACCAGCTACGATGGCGAGGACA

AGATCGGCTCTTACGCTGTGCTTTCTCCGCAGGCTGTACTCAAGAGTGAAAAATTAT

CTTGCATCCACCCTCTCGCTGAACAAGTCATAGTGATAACACACTCTGGCCGAAAAG

GGCGTTATGCCGTGGAACCATACCATGGTAAAGTAGTGGTGCCAGAGGGACATGCA

ATACCCGTCCAGGACTTTCAAGCTCTGAGTGAAAGTGCCACCATTGTGTACAACGAA

CGTGAGTTCGTAAACAGGTACCTGCACCATATTGCCACACATGGAGGAGCGCTGAA

CACTGATGAAGAATATTACAAAACTGTCAAGCCCAGCGAGCACGACGGCGAATACC

TGTACGACATCGACAGGAAACAGTGCGTCAAGAAAGAACTAGTCACTGGGCTAGGG

CTCACAGGCGAGCTGGTGGATCCTCCCTTCCATGAATTCGCCTACGAGAGTCTGAGA

ACACGACCAGCCGCTCCTTACCAAGTACCAACCATAGGGGTGTATGGCGTGCCAGG

ATCAGGCAAGTCTGGCATCATTAAAAGCGCAGTCACCAAAAAAGATCTAGTGGTGA

GCGCCAAGAAAGAAAACTGTGCAGAAATTATAAGGGACGTCAAGAAAATGAAAGG

GCTGGACGTCAATGCCAGAACTGTGGACTCAGTGCTCTTGAATGGATGCAAACACCC

CGTAGAGACCCTGTATATTGACGAAGCTTTTGCTTGTCATGCAGGTACTCTCAGAGC

-continued

GCTCATAGCCATTATAAGACCTAAAAAGGCAGTGCTCTGCGGGGATCCCAAACAGT

GCGGTTTTTTTAACATGATGTGCCTGAAAGTGCATTTTAACCACGAGATTTGCACAC

AAGTCTTCCACAAAAGCATCTCTCGCCGTTGCACTAAATCTGTGACTTCGGTCGTCTC

AACCTTGTTTTACGACAAAAAAATGAGAACGACGAATCCGAAAGAGACTAAGATTG

TGATTGACACTACCGGCAGTACCAAACCTAAGCAGGACGATCTCATTCTCACTTGTT

TCAGAGGGTGGGTGAAGCAGTTGCAAATAGATTACAAAGGCAACGAAATAATGACG

GCAGCTGCCTCTCAAGGGCTGACCCGTAAAGGTGTGTATGCCGTTCGGTACAAGGTG

AATGAAAATCCTCTGTACGCACCCACCTCAGAACATGTGAACGTCCTACTGACCCGC

ACGGAGGACCGCATCGTGTGGAAAACACTAGCCGGCGACCCATGGATAAAAACACT

GACTGCCAAGTACCCTGGGAATTTCACTGCCACGATAGAGGAGTGGCAAGCAGAGC

ATGATGCCATCATGAGGCACATCTTGGAGAGACCGGACCCTACCGACGTCTTCCAG

AATAAGGCAAACGTGTGTTGGGCCAAGGCTTTAGTGCCGGTGCTGAAGACCGCTGG

CATAGACATGACCACTGAACAATGGAACACTGTGGATTATTTTGAAACGGACAAAG

CTCACTCAGCAGAGATAGTATTGAACCAACTATGCGTGAGGTTCTTTGGACTCGATC

TGGACTCCGGTCTATTTTCTGCACCCACTGTTCCGTTATCCATTAGGAATAATCACTG

GGATAACTCCCCGTCGCCTAACATGTACGGGCTGAATAAAGAAGTGGTCCGTCAGCT

CTCTCGCAGGTACCCACAACTGCCTCGGGCAGTTGCCACTGGAAGAGTCTATGACAT

GAACACTGGTACACTGCGCAATTATGATCCGCGCATAAACCTAGTACCTGTAAACAG

AAGACTGCCTCATGCTTTAGTCCTCCACCATAATGAACACCCACAGAGTGACTTTTC

TTCATTCGTCAGCAAATTGAAGGGCAGAACTGTCCTGGTGGTCGGGGAAAAGTTGTC

CGTCCCAGGCAAAATGGTTGACTGGTTGTCAGACCGGCCTGAGGCTACCTTCAGAGC

TCGGCTGGATTTAGGCATCCCAGGTGATGTGCCCAAATATGACATAATATTTGTTAA

TGTGAGGACCCCATATAAATACCATCACTATCAGCAGTGTGAAGACCATGCCATTAA

GCTTAGCATGTTGACCAAGAAAGCTTGTCTGCATCTGAATCCCGGCGGAACCTGTGT

CAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGG

AAGTTCTGTTTGTATTCATTGGGTACGATCGCAAGGCCCGTACGCACAATtCTTACAA

GCTTTCATCAACCTTGACCAACATTTATACAGGTTCCAGACTCCACGAAGCCGGATG

TGCACCCTCATATCATGTGGTGCGAGGGGATATTGCCACGGCCACCGAAGGAGTGA

TTATAAATGCTGCTAACAGCAAAGGACAACCTGGCGGAGGGGTGTGCGGAGCGCTG

TATAAGAAATTCCCGGAAAGCTTCGATTTACAGCCGATCGAAGTAGGAAAAGCGCG

ACTGGTCAAAGGTGCAGCTAAACATATCATTCATGCCGTAGGACCAAACTTCAACA

AAGTTTCGGAGGTTGAAGGTGACAAACAGTTGGCAGAGGCTTATGAGTCCATCGCT

AAGATTGTCAACGATAACAATTACAAGTCAGTAGCGATTCCACTGTTGTCCACCGGC

ATCTTTTCCGGGAACAAAGATCGACTAACCCAATCATTGAACCATTTGCTGACAGCT

TTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCG

ACGACTCTTCAGTGACAGAACCTGATGCAGAGCTGGTGAGGGTGCATCCGAAGAGT

TCTTTGGCTGGAAGGAAGGGCTACAGCACAAGCGATGGCAAAACTTTCTCATATTTG

GAAGGGACCAAGTTTCACCAGGCGGCCAAGGATATAGCAGAAATTAATGCCATGTG

GCCCGTTGCAACGGAGGCCAATGAGCAGGTATGCATGTATATCCTCGGAGAAAGCA

-continued

TGAGCAGTATTAGGTCGAAATGCCCCGTCGAAGAGTCGGAAGCCTCCACACCACCT

AGCACGCTGCCTTGCTTGTGCATCCATGCCATGACTCCAGAAAGAGTACAGCGCCTA

AAAGCCTCACGTCCAGAACAAATTACTGTGTGCTCATCCTTTCCATTGCCGAAGTAT

AGAATCACTGGTGTGCAGAAGATCCAATGCTCCCAGCCTATATTGTTCTCACCGAAA

GTGCCTGCGTATATTCATCCAAGGAAGTATCTCGTGGAAACACCACCGGTAGACGA

GACTCCGGAGCCATCGGCAGAGAACCAATCCACAGAGGGGACACCTGAACAACCAC

CACTTATAACCGAGGATGAGACCAGGACTAGAACGCCTGAGCCGATCATCATCGAA

GAGGAAGAAGAGGATAGCATAAGTTTGCTGTCAGATGGCCCGACCCACCAGGTGCT

GCAAGTCGAGGCAGACATTCACGGGCCGCCCTCTGTATCTAGCTCATCCTGGTCCAT

TCCTCATGCATCCGACTTTGATGTGGACAGTTTATCCATACTTGACACCCTGGAGGG

AGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCG

AGAACCAGCCTAGTTTCCACCCCGCCAGGCGTGAATAGGGTGATCACTAGAGAGGA

GCTCGAGGCGCTTACCCCGTCACGCACTCCTAGCAGGTCGGTCTCGAGAACCAGCCT

GGTCTCCAACCCGCCAGGCGTAAATAGGGTGATTACAAGAGAGGAGTTTGAGGCGT

TCGTAGCACAACAACAATGACGGTTTGATGCGGGTGCATACATCTTTTCCTCCGACA

CCGGTCAAGGGCATTTACAACAAAAATCAGTAAGGCAAACGGTGCTATCCGAAGTG

GTGTTGGAGAGGACCGAATTGaAGATTTCGTATGCCCCGCGCCTCGACCAAGAAAAA

GAAGAATTACTACGCAAGAAATTACAGTTAAATCCCACACCTGCTAACAGAAGCAG

ATACCAGTCCAGGAAGGTGGAGAACATGAAAGCCATAACAGCTAGACGTATTCTGC

AAGGCCTAGGGCATTATTTGAAGGCAGAAGGAAAAGTGGAGTGCTACCGAACCCTG

CATCCTGTTCCTTTGTATTCATCTAGTGTGAACCGTGCCTTTTCAAGCCCCAAGGTCG

CAGTGGAAGCCTGTAACGCCATGTTGAAAGAGAACTTTCCGACTGTGGCTTCTTACT

GTATTATTCCAGAGTACGATGCCTATTTGGACATGGTTGACGGAGCTTCATGCTGCT

TAGACACTGCCAGTTTTTGCCCTGCAAAGCTGCGCAGCTTTCCAAAGAAACACTCCT

ATTTGGAACCCACAATACGATCGGCAGTGCCTTCAGCGATCCAGAACACGCTCCAG

AACGTCCTGGCAGCTGCCACAAAAAGAAATTGCAATGTCACGCAAATGAGAGAATT

GCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACG

TGGTAAATTACATTACCAAATTAAAAGGACCAAAAGCTGCTGCTCTTTTTGCGAAGA

CACATAATTTGAATATGTTGCAGGACATACCAATGGACAGGTTTGTAATGGACTTAA

AGAGAGACGTGAAAGTGACTCCAGGAACAAAACATACTGAAGAACGGCCCAAGGT

ACAGGTGATCCAGGCTGCCGATCCGCTAGCAACAGCGTATCTGTGCGGAATCCACC

GAGAGCTGGTTAGGAGATTAAATGCGGTCCTGCTTCCGAACATTCATACACTGTTTG

ATATGTCGGCTGAAGACTTTGACGCTATTATAGCCGAGCACTTCCAGCCTGGGGATT

GTGTTCTGGAAACTGACATCGCGTCGTTTGATAAAAGTGAGGACGACGCCATGGCTC

TGACCGCGTTAATGATTCTGGAAGACTTAGGTGTGGACGCAGAGCTGTTGACGCTGA

TTGAGGCGGCTTTCGGCGAAATTTCATCAATACATTTGCCCACTAAAACTAAATTTA

AATTCGGAGCCATGATGAAATCTGGAATGTTCCTCACACTGTTTGTGAACACAGTCA

-continued

TTAACATTGTAATCGCAAGCAGAGTGTTGAGAGAACGGCTAACCGGATCACCATGT

GCAGCATTCATTGGAGATGACAATATCGTGAAAGGAGTCAAATCGGACAAATTAAT

GGCAGACAGGTGCGCCACCTGGTTGAATATGGAAGTCAAGATTATAGATGCTGTGG

TGGGCGAGAAAGCGCCTTATTTCTGTGGAGGGTTTATTTTGTGTGACTCCGTGACCG

GCACAGCGTGCCGTGTGGCAGACCCCCTAAAAAGGCTGTTTAAGCTTGGCAAACCT

CTGGCAGCAGACGATGAACATGATGATGACAGGAGAAGGGCATTGCATGAAGAGTC

AACACGCTGGAACCGAGTGGGTATTCTTTCAGAGCTGTGCAAGGCAGTAGAATCAA

GGTATGAAACCGTAGGAACTTCCATCATAGTTATGGCCATGACTACTCTAGCTAGCA

GTGTTAAATCATTCAGCTACCTGAGAGGGGCCCCTATAACTCTCTACGGCTAACCTG

AATGGACTACGACATAGTCTAGTCCGCCAAGTTCGAAGGCGCGCCTCTAGAgccaccAT

GGTGAGCAAGGGCGAGGAGCTGTTCACCGGGGTGGTGCCCATCCTGGTCGAGCTGG

ACGGCGACGTAAACGGCCACAAGTTCAGCGTGTCCGGCGAGGGCGAGGGCGATGCC

ACCTACGGCAAGCTGACCCTGAAGTTCATCTGCACCACCGGCAAGCTGCCCGTGCCC

TGGCCCACCCTCGTGACCACCCTGACCTACGGCGTGCAGTGCTTCAGCCGCTACCCC

GACCACATGAAGCAGCACGACTTCTTCAAGTCCGCCATGCCCGAAGGCTACGTCCA

GGAGCGCACCATCTTCTTCAAGGACGACGGCAACTACAAGACCCGCGCCGAGGTGA

AGTTCGAGGGCGACACCCTGGTGAACCGCATCGAGCTGAAGGGCATCGACTTCAAG

GAGGACGGCAACATCCTGGGGCACAAGCTGGAGTACAACTACAACAGCCACAACGT

CTATATCATGGCCGACAAGCAGAAGAACGGCATCAAGGTGAACTTCAAGATCCGCC

ACAACATCGAGGACGGCAGCGTGCAGCTCGCCGACCACTACCAGCAGAACACCCCC

ATCGGCGACGGCCCCGTGCTGCTGCCCGACAACCACTACCTGAGCACCCAGTCCGCC

CTGAGCAAAGACCCCAACGAGAAGCGCGATCACATGGTCCTGCTGGAGTTCGTGAC

CGCCGCCGGGATCACTCTCGGCATGGACGAGCTGTACAAGtagcATCGATGATATCGC

GGCCGCATACAGCAGCAATTGGCAAGCTGCTTACATAGAACTCGCGGCGATTGGCA

TGCCGCCTTAAAATTTTTATTTTATTTTTCTTTTCTTTTCCGAATCGGATTTTGTTTTTA

ATATTTCAAAAAAAAAAAAAAAA

Anti-CD19 scFv (SEQ ID NO: 25)

ATGGATTGGACATGGCGAATCCTCTTTTTGGTCGCAGCAGCGACGGGAACACACGC

AGACATTCAAATGACTCAGACTACGAGCTCCCTCTCCGCATCCCTCGGCGACCGGGT

GACTATTAGCTGCCGCGCCTCTCAAGATATTAGCAAATACCTTAATTGGTACCAACA

GAAGCCGGACGGAACAGTAAAGCTCCTGATTTACCACACGTCTCGACTTCATTCCGG

CGTACCTAGTAGGTTTTCTGGCTCTGGA

Human CAR backbone (SEQ ID NO: 26)

TCTGGTACCGACTACTCCCTCACAATTTCCAATTTGGAACAAGAAGACATTGCCACC

TACTTCTGTCAACAGGGCAATACGCTGCCATACACGTTCGGCGGGGGTACCAAACTG

GAGATTACCGGGTCCACATCTGGATCCGGGAAGCCGGGCTCCGGTGAGGGATCAAC

CAAAGGCGAAGTCAAGTTGCAGGAATCTGGACCGGGCCTCGTTGCACCGTCTCAGT

CTTTGTCCGTCACTTGCACAGTATCAGGAGTTTCCCTTCCTGACTACGGGGTATCTTG

GATCCGACAGCCGCCCAGAAAGGGGCTGGAGTGGCTCGGAGTGATATGGGGGTCTG

AAACCACCTACTATAATAGCGCCCTCAAGAGTAGACTGACTATTATTAAGGATAACT

CCAAGTCTCAGGTATTTCTCAAAATGAACAGTCTTCAGACTGACGACACAGCCATAT

-continued

ACTACTGTGCGAAACACTATTATTACGGTGGCAGTTACGCCATGGACTACTGGGGCC

AGGGGACAAGCGTAACCGTTTCAAGTGCAGCCGCAACAACGACTCCAGCTCCCAGG

CCGCCGACTCCTGCTCCGACGATAGCCTCCCAACCCTTGTCACTCCGCCCTGAAGCA

TGTAGGCCAGCCGCAGGAGGCGCTGTTCATACCCGAGGATTGGATTTCGCTTGCGAT

ATTTATATCTGGGCACCGTTGGCAGGGACATGCGGCGTGCTGTTGTTGAGCCTCGTA

ATAACGCTGTACAGGTCCAAGAGGTCCCGCCTTCTTCATTCCGATTACATGAACATG

ACCCCCAGACGCCCAGGTCCAACACGAAAACATTATCAACCATATGCTCCACCTAG

GGACTTTGCAGCATACCGATCtCGCGTGAAATTCAGCCGATCTGCCGACGCACCGGC

CTATCAGCAAGGCCAGAACCAACTTTACAACGAGCTTAACTTGGGGAGAAGAGAGG

AATATGATGTACTGGACAAGCGGCGAGGTCGGGATCCTGAGATGGGAGGTAAACCT

CAACGGAGAAAAAACCCACAAGAAGGTCTCTACAACGAGCTGCAAAAGGACAAGA

TGGCCGAGGCATATTCAGAAATTGGGATGAAGGGCGAACGACGCCGAGGCAAAGG

ACATGATGGATTGTACCAGGGCCTCTCTACCGCAACTAAAGATACCTACGATGCCCT

CCATATGCAGGCACTTCCCCCGCG

In sequences SVP410, SVP411, SVP412, SVP413, and the anti-CD19 scFV and human CAR construct: the bolded, underlined and italicized sequence is the SGP (a T7 promoter); the bolded sequence is the anti-CD-19 scFV (SEQ ID NO: 25); and the italicized sequence is a human CAR sequence. The sequence between the SGP and the bolded sequence is the 5'UTR sequence. Accordingly, the present disclosure includes delivery of a payload in which the nucleotides 5' to the 5'UTR sequence are not present. In some aspects, the present disclosure includes delivery of a payload in which the nucleotides before the 5'UTR sequence are present. In the following constructs, the poly A sequence starts after the C at position 20 and ends after the A at position 130 in SEQ ID NO: 24. In the following constructs, the 3'UTR sequence starts, for example, at the T at position 3812 in SEQ ID NO: 24. Accordingly, the present disclosure includes both self-amplifying mRNAs having the structure comprising (5'UTR-nsP1-4-SGP-GOI-3'UTR) or the modified mRNAs comprising (5'UTR-GOI-3'UTR), wherein one or more linkers may be resent. The GOI comprises a ScFv-CAR backbone as described herein.

SVP410

(SEQ ID NO: 24)

AGCCACACCCTGGAGCTAGCAAAAAAAAAAAAAAAAAAAAAAAAA

AAAAAGCATATGACTAAAAAAAAAAAAAAAAAAAAAAAAAAAAAA

AAAAAAAAAAAAAAAAAAAAAAAAAAAAAAAAAAAAAAAAcgcgt

ATCGATGATATCGCGGCCGCATACAGCAGCAATTGGCAAGCTGCT

TACATAGAACTCGCGGCGATTGGCATGCCGCCTTAAAATTTTTAT

TTTATTTTTCTTTTCTTTTCCGAATCGGATTTTGTTTTTAATATT

TCAAAAAAAAAAAAAAAAAAAAAAAAAACGCGTGATAACGCAGGA

AAGAACATGTGAGCAAAAGGCCAGCAAAAGGCCAGGAACCGTAAA

AAGGCCGCGTTGCTGGCGTTTTTCCATAGGCTCCGCCCCCCTGAC

GAGCATCACAAAAATCGACGCTCAAGTCAGAGGTGGCGAAACCCG

-continued

ACAGGACTATAAAGATACCAGGCGTTTCCCCCTGGAAGCTCCCTC

GTGCGCTCTCCTGTTCCGACCCTGCCGCTTACCGGATACCTGTCC

GCCTTTCTCCCTTCGGGAAGCGTGGCGCTTTCTCATAGCTCACGC

TGTAGGTATCTCAGTTCGGTGTAGGTCGTTCGCTCCAAGCTGGGC

TGTGTGCACGAACCCCCCGTTCAGCCCGACCGCTGCGCCTTATCC

GGTAACTATCGTCTTGAGTCCAACCCGGTAAGACACGACTTATCG

CCACTGGCAGCAGCCACTGGTAACAGGATTAGCAGAGCGAGGTAT

GTAGGCGGTGCTACAGAGTTCTTGAAGTGGTGGCCTAACTACGGC

TACACTAGAAGAACAGTATTTGGTATCTGCGCTCTGCTGAAGCCA

GTTACCTTCGGAAAAAGAGTTGGTAGCTCTTGATCCGGCAAACAA

ACCACCGCTGGTAGCGGTTTTTTTGTTTGCAAGCAGCAGATTACG

CGCAGAAAAAAAGGATCTCAAGAAGATCCTTTGATCTTTTCTACG

GGGTCTGACGCTCAGTGGAACGAAAACTCACGTTAAGGGATTTTG

GTCATGAGATTATCAAAAAGGATCTTCACCTAGATCCTTTTAAAT

TAAAAATGAAGTTTTAAATCAATCTAAAGTATATATGAGTAAACT

TGGTCTGACAGTTACCAATGCTTAATCAGTGAGGCACCTATCTCA

GCGATCTGTCTATTTCGTTCATCCATAGTTGCCTGACTCCCCGTC

GTGTAGATAACTACGATACGGGAGGGCTTACCATCTGGCCCCAGT

GCTGCAATGATACCGCGAGACCCACGCTCACCGGCTCCAGATTTA

TCAGCAATAAACCAGCCAGCCGGAAGGGCCGAGCGCAGAAGTGGT

CCTGCAACTTTATCCGCCTCCATCCAGTCTATTAATTGTTGCCGG

GAAGCTAGAGTAAGTAGTTCGCCAGTTAATAGTTTGCGCAACGTT

GTTGCCATTGCTACAGGCATCGTGGTGTCACGCTCGTCGTTTGGT

ATGGCTTCATTCAGCTCCGGTTCCCAACGATCAAGGCGAGTTACA

TGATCCCCCATGTTGTGCAAAAAAGCGGTTAGCTCCTTCGGTCCT

-continued

CCGATCGTTGTCAGAAGTAAGTTGGCCGCAGTGTTATCACTCATG
GTTATGGCAGCACTGCATAATTCTCTTACTGTCATGCCATCCGTA
AGATGCTTTTCTGTGACTGGTGAGTACTCAACCAAGTCATTCTGA
GAATAGTGTATGCGGCGACCGAGTTGCTCTTGCCCGGCGTCAATA
CGGGATAATACCGCGCCACATAGCAGAACTTTAAAAGTGCTCATC
ATTGGAAAACGTTCTTCGGGGCGAAAACTCTCAAGGATCTTACCG
CTGTTGAGATCCAGTTCGATGTAACCCACTCGTGCACCCAACTGA
TCTTCAGCATCTTTTACTTTCACCAGCGTTTCTGGGTGAGCAAAA
ACAGGAAGGCAAAATGCCGCAAAAAAGGGAATAAGGGCGACACGG
AAATGTTGAATACTCATACTCTTCCTTTTTCAATATTATTGAAGC
ATTTATCAGGGTTATTGTCTCATGAGCGGATACATATTTGAATGT
ATTTAGAAAAATAAACAAATAGGGGTTCCGCGCACATTTCCCCGA
AAAGTGCCACCTGAGCTC*TAATACGACTCACTATAGGATAGG*ACA
TTTGCTTCTGACACAACTGTGTTCACTAGCAACCTCAAACAGACA
CCATGGATTGGACATGGCGAATCCTCTTTTTGGTCGCAGCAGCGA
CGGGAACACACGCAGACATTCAAATGACTCAGACTACGAGCTCCC
TCTCCGCATCCCTCGGCGACCGGGTGACTATTAGCTGCCGCGCCT
CTCAAGATATTAGCAAATACCTTAATTGGTACCAACAGAAGCCGG
ACGGAACAGTAAAGCTCCTGATTTACCACACGTCTCGACTTCATT
CCGGCGTACCTAGTAGGTTTTCTGGCTCTGGA*TCTGGTACCGACT*
*ACTCCCTCACAATTTCCAATTTGGAACAAGAAGACATTGCCACCT*
*ACTTCTGTCAACAGGGCAATACGCTGCCATACACGTTCGGCGGGG*
*GTACCAAACTGGAGATTACCGGGTCCACATCTGGATCCGGGAAGC*
*CGGGCTCCGGTGAGGGATCAACCAAAGGCGAAGTCAAGTTGCAGG*
*AATCTGGACCGGGCCTCGTTGCACCGTCTCAGTCTTTGTCCGTCA*
*CTTGCACAGTATCAGGAGTTTCCCTTCCTGACTACGGGGTATCTT*
*GGATCCGACAGCCGCCCAGAAAGGGGCTGGAGTGGCTCGGAGTGA*
*TATGGGGGTCTGAAACCACCTACTATAATAGCGCCCTCAAGAGTA*
*GACTGACTATTATTAAGGATAACTCCAAGTCTCAGGTATTTCTCA*
AAATGAACAGTCTTCAGACTGACGACACAGCCATATACTACTGTG
*CGAAACACTATTATTACGGTGGCAGTTACGCCATGGACTACTGGG*
*GCCAGGGGACAAGCGTAACCGTTTCAAGTGCAGCCGCAACAACGA*
*CTCCAGCTCCCAGGCCGCCGACTCCTGCTCCGACGATAGCCTCCC*
*AACCCTTGTCACTCCGCCCTGAAGCATGTAGGCCAGCCGCAGGAG*
*GCGCTGTTCATACCCGAGGATTGGATTTCGCTTGCGATATTTATA*
*TCTGGGCACCGTTGGCAGGGACATGCGGCGTGCTGTTGTTGAGCC*
*TCGTAATAACGCTGTACAGGTCCAAGAGGTCCCGCCTTCTTCATT*
*CCGATTACATGAACATGACCCCCAGACGCCCAGGTCCAACACGAA*
*AACATTATCAACCATATGCTCCACCTAGGGACTTTGCAGCATACC*
*GATCtCGCGTGAAATTCAGCCGATCTGCCGACGCACCGGCCTATC*

-continued

*AGCAAGGCCAGAACCAACTTTACAACGAGCTTAACTTGGGGAGAA*
*GAGAGGAATATGATGTACTGGACAAGCGGCGAGGTCGGGATCCTG*
*AGATGGGAGGTAAACCTCAACGGAGAAAAAACCCACAAGAAGGTC*
*TCTACAACGAGCTGCAAAAGGACAAGATGGCCGAGGCATATTCAG*
*AAATTGGGATGAAGGGCGAACGACGCCGAGGCAAAGGACATGATG*
*GATTGTACCAGGGCCTCTCTACCGCAACTAAAGATACCTACGATG*
*CCCTCCATATGCAGGCACTTCCCCCGCGATAGGCTCGCTTTCTTG*
CTGTCCAATTTCTATTAAAGGTTCCTTTGTTCCCTAAGTCCAACT
ACTAAACTGGGGGATATTATGAAGGGCCTTGAGCATCTGGATTCT
GCCTAATAAAAAACATTTATTTTCATTGCAA

SVP411

(SEQ ID NO: 27)

AGCCACACCCTGGAGCTAGCAAAAAAAAAAAAAAAAAAAAAAAAAAAAAA
AAAAAGCATATGACTAAAAAAAAAAAAAAAAAAAAAAAAAAAAAAAAAAA
AAAAAAAAAAAAAAAAAAAAAAAAAAAAAAAAAAAAAAAAAAAAAcgcgt
ATCGATGATATCGCGGCCGCATACAGCAGCAATTGGCAAGCTGCT
TACATAGAACTCGCGGCGATTGGCATGCCGCCTTAAAATTTTTAT
TTTATTTTTCTTTTCTTTTCCGAATCGGATTTTGTTTTTAATATT
TCAAAAAAAAAAAAAAAAAAAAAAAAAAAAAAACGCGTGATAACGCAGGA
AAGAACATGTGAGCAAAAGGCCAGCAAAAGGCCAGGAACCGTAAA
AAGGCCGCGTTGCTGGCGTTTTTCCATAGGCTCCGCCCCCCTGAC
GAGCATCACAAAAATCGACGCTCAAGTCAGAGGTGGCGAAACCCG
ACAGGACTATAAAGATACCAGGCGTTTCCCCCTGGAAGCTCCCTC
GTGCGCTCTCCTGTTCCGACCCTGCCGCTTACCGGATACCTGTCC
GCCTTTCTCCCTTCGGGAAGCGTGGCGCTTTCTCATAGCTCACGC
TGTAGGTATCTCAGTTCGGTGTAGGTCGTTCGCTCCAAGCTGGGC
TGTGTGCACGAACCCCCCGTTCAGCCCGACCGCTGCGCCTTATCC
GGTAACTATCGTCTTGAGTCCAACCCGGTAAGACACGACTTATCG
CCACTGGCAGCAGCCACTGGTAACAGGATTAGCAGAGCGAGGTAT
GTAGGCGGTGCTACAGAGTTCTTGAAGTGGTGGCCTAACTACGGC
TACACTAGAAGAACAGTATTTGGTATCTGCGCTCTGCTGAAGCCA
GTTACCTTCGGAAAAAGAGTTGGTAGCTCTTGATCCGGCAAACAA
ACCACCGCTGGTAGCGGTTTTTTTGTTTGCAAGCAGCAGATTACG
CGCAGAAAAAAAGGATCTCAAGAAGATCCTTTGATCTTTTCTACG
GGGTCTGACGCTCAGTGGAACGAAAACTCACGTTAAGGGATTTTG
GTCATGAGATTATCAAAAAGGATCTTCACCTAGATCCTTTTAAAT
TAAAAATGAAGTTTTAAATCAATCTAAAGTATATATGAGTAAACT
TGGTCTGACAGTTACCAATGCTTAATCAGTGAGGCACCTATCTCA
GCGATCTGTCTATTTCGTTCATCCATAGTTGCCTGACTCCCCGTC
GTGTAGATAACTACGATACGGGAGGGCTTACCATCTGGCCCCAGT
GCTGCAATGATACCGCGAGACCCACGCTCACCGGCTCCAGATTTA
TCAGCAATAAACCAGCCAGCCGGAAGGGCCGAGCGCAGAAGTGGT -continued CCTGCAACTTTATCCGCCTCCATCCAGTCTATTAATTGTTGCCGG
GAAGCTAGAGTAAGTAGTTCGCCAGTTAATAGTTTGCGCAACGTT
GTTGCCATTGCTACAGGCATCGTGGTGTCACGCTCGTCGTTTGGT
ATGGCTTCATTCAGCTCCGGTTCCCAACGATCAAGGCGAGTTACA
TGATCCCCCATGTTGTGCAAAAAAGCGGTTAGCTCCTTCGGTCCT
CCGATCGTTGTCAGAAGTAAGTTGGCCGCAGTGTTATCACTCATG
GTTATGGCAGCACTGCATAATTCTCTTACTGTCATGCCATCCGTA
AGATGCTTTTCTGTGACTGGTGAGTACTCAACCAAGTCATTCTGA
GAATAGTGTATGCGGCGACCGAGTTGCTCTTGCCCGGCGTCAATA
CGGGATAATACCGCGCCACATAGCAGAACTTTAAAAGTGCTCATC
ATTGGAAAACGTTCTTCGGGGCGAAAACTCTCAAGGATCTTACCG
CTGTTGAGATCCAGTTCGATGTAACCCACTCGTGCACCCAACTGA
TCTTCAGCATCTTTTACTTTCACCAGCGTTTCTGGGTGAGCAAAA
ACAGGAAGGCAAAATGCCGCAAAAAAGGGAATAAGGGCGACACGG
AAATGTTGAATACTCATACTCTTCCTTTTTCAATATTATTGAAGC
ATTTATCAGGGTTATTGTCTCATGAGCGGATACATATTTGAATGT
ATTTAGAAAAATAAACAAATAGGGGTTCCGCGCACATTTCCCCGA
AAAGTGCCACCTGAGCTC*TAATACGACTCACTATAGGATAGG*ACA
TTTGCTTCTGACACAACTGTGTTCACTAGCAACCTCAAACAGACA
CCATGGATTGGACATGGCGAATCCTCTTTTTGGTCGCAGCAGCGA
CGGGAACACACGCAGACATTCAAATGACTCAGACTACGAGCTCCC
TCTCCGCATCCCTCGGCGACCGGGTGACTATTAGCTGCCGCGCCT
CTCAAGATATTAGCAAATACCTTAATTGGTACCAACAGAAGCCGG
ACGGAACAGTAAAGCTCCTGATTTACCACACGTCTCGACTTCATT
CCGGCGTACCTAGTAGGTTTTCTGGCTCTGGA*TCTGGTACCGACT*
*ACTCCCTCACAATTTCCAATTTGGAACAAGAAGACATTGCCACCT*
*ACTTCTGTCAACAGGGCAATACGCTGCCATACACGTTCGGCGGGG*
*GTACCAAACTGGAGATTACCGGGTCCACATCTGGATCCGGGAAGC*
*CGGGCTCCGGTGAGGGATCAACCAAAGGCGAAGTCAAGTTGCAGG*
*AATCTGGACCGGGCCTCGTTGCACCGTCTCAGTCTTTGTCCGTCA*
*CTTGCACAGTATCAGGAGTTTCCCTTCCTGACTACGGGGTATCTT*
*GGATCCGACAGCCGCCCAGAAAGGGGCTGGAGTGGCTCGGAGTGA*
*TATGGGGGTCTGAAACCACCTACTATAATAGCGCCCTCAAGAGTA*
*GACTGACTATTATTAAGGATAACTCCAAGTCTCAGGTATTTCTCA*
*AAATGAACAGTCTTCAGACTGACGACACAGCCATATACTACTGTG*
*CGAAACACTATTATTACGGTGGCAGTTACGCCATGGACTACTGGG*
*GCCAGGGGACAAGCGTAACCGTTTCAAGTGCAGCCGCAACAACGA*
*CTCCAGCTCCCCGGCCGCCCACCCCTGCACCTACAATTGCGTCTC*
*AACCCCTTAGTCTTCGACCTGAAGCTTGTCGCCCCGCAGCAGGCG*
*GGGCTGTCCACACGAGGGGATTGGACTTTGCTTGTGATATTTACA*

-continued

*TATGGGCACCTCTTGCAGGAACTTGTGGGGTGCTGCTCCTCAGTT*
*TGGTCATTACCCTGTATTGTAAGAGAGGAAGGAAAAAACTCTTGT*
*ACATTTTCAAACAACCGTTTATGCGACCAGTGCAAACGACACAAG*
*AGGAAGACGGGTGTAGTTGCCGCTTCCCTGAAGAGGAAGAGGGGG*
*GTTGTGAGCTGAGGGTTAAATTCTCCCGAAGTGCCGATGCTCCGG*
*CCTATCAACAGGGCCAGAACCAACTCTATAACGAACTTAATCTGG*
*GAAGAAGAGAGGAATACGATGTACTGGACAAGCGGCGAGGGAGAG*
*ATCCCGAGATGGGCGGCAAACCCCGAAGAAAAAATCCGCAGGAGG*
*GGCTTTATAACGAATTGCAAAAGGATAAAATGGCGGAAGCTTATA*
*GTGAGATTGGAATGAAGGGTGAAAGGCGACGAGGCAAGGGCCATG*
*ACGGGCTCTATCAGGGATTGTCTACCGCTACGAAAGACACTTACG*
*AtGCGTTGCACATGCAGGCTCTCCCACCCCG*ATAGGCTCGCTTTC
TTGCTGTCCAATTTCTATTAAAGGTTCCTTTGTTCCCTAAGTCCA
ACTACTAAACTGGGGGATATTATGAAGGGCCTTGAGCATCTGGAT
TCTGCCTAATAAAAAACATTTATTTTCATTGCAA

SVP412

(SEQ ID NO: 28)

AGCCACACCCTGGAGCTAGCAAAAAAAAAAAAAAAAAAAAAAAAA
AAAAAGCATATGACTAAAAAAAAAAAAAAAAAAAAAAAAAAAAAA
AAAAAAAAAAAAAAAAAAAAAAAAAAAAAAAAAAAAAAAAcgcgt
ATCGATGATATCGCGGCCGCATACAGCAGCAATTGGCAAGCTGCT
TACATAGAACTCGCGGCGATTGGCATGCCGCCTTAAAATTTTTAT
TTTATTTTTCTTTTCTTTTCCGAATCGGATTTTGTTTTTAATATT
TCAAAAAAAAAAAAAAAAAAAAAAAAAACGCGTGATAACGCAGGA
AAGAACATGTGAGCAAAAGGCCAGCAAAAGGCCAGGAACCGTAAA
AAGGCCGCGTTGCTGGCGTTTTTCCATAGGCTCCGCCCCCCTGAC
GAGCATCACAAAAATCGACGCTCAAGTCAGAGGTGGCGAAACCCG
ACAGGACTATAAAGATACCAGGCGTTTCCCCCTGGAAGCTCCCTC
GTGCGCTCTCCTGTTCCGACCCTGCCGCTTACCGGATACCTGTCC
GCCTTTCTCCCTTCGGGAAGCGTGGCGCTTTCTCATAGCTCACGC
TGTAGGTATCTCAGTTCGGTGTAGGTCGTTCGCTCCAAGCTGGGC
TGTGTGCACGAACCCCCCGTTCAGCCCGACCGCTGCGCCTTATCC
GGTAACTATCGTCTTGAGTCCAACCCGGTAAGACACGACTTATCG
CCACTGGCAGCAGCCACTGGTAACAGGATTAGCAGAGCGAGGTAT
GTAGGCGGTGCTACAGAGTTCTTGAAGTGGTGGCCTAACTACGGC
TACACTAGAAGAACAGTATTTGGTATCTGCGCTCTGCTGAAGCCA
GTTACCTTCGGAAAAAGAGTTGGTAGCTCTTGATCCGGCAAACAA
ACCACCGCTGGTAGCGGTTTTTTTGTTTGCAAGCAGCAGATTACG
CGCAGAAAAAAAGGATCTCAAGAAGATCCTTTGATCTTTTCTACG
GGGTCTGACGCTCAGTGGAACGAAAACTCACGTTAAGGGATTTTG
GTCATGAGATTATCAAAAAGGATCTTCACCTAGATCCTTTTAAAT
TAAAAATGAAGTTTTAAATCAATCTAAAGTATATATGAGTAAACT -continued

TGGTCTGACAGTTACCAATGCTTAATCAGTGAGGCACCTATCTCA

GCGATCTGTCTATTTCGTTCATCCATAGTTGCCTGACTCCCCGTC

GTGTAGATAACTACGATACGGGAGGGCTTACCATCTGGCCCCAGT

GCTGCAATGATACCGCGAGACCCACGCTCACCGGCTCCAGATTTA

TCAGCAATAAACCAGCCAGCCGGAAGGGCCGAGCGCAGAAGTGGT

CCTGCAACTTTATCCGCCTCCATCCAGTCTATTAATTGTTGCCGG

GAAGCTAGAGTAAGTAGTTCGCCAGTTAATAGTTTGCGCAACGTT

GTTGCCATTGCTACAGGCATCGTGGTGTCACGCTCGTCGTTTGGT

ATGGCTTCATTCAGCTCCGGTTCCCAACGATCAAGGCGAGTTACA

TGATCCCCCATGTTGTGCAAAAAAGCGGTTAGCTCCTTCGGTCCT

CCGATCGTTGTCAGAAGTAAGTTGGCCGCAGTGTTATCACTCATG

GTTATGGCAGCACTGCATAATTCTCTTACTGTCATGCCATCCGTA

AGATGCTTTTCTGTGACTGGTGAGTACTCAACCAAGTCATTCTGA

GAATAGTGTATGCGGCGACCGAGTTGCTCTTGCCCGGCGTCAATA

CGGGATAATACCGCGCCACATAGCAGAACTTTAAAAGTGCTCATC

ATTGGAAAACGTTCTTCGGGGCGAAAACTCTCAAGGATCTTACCG

CTGTTGAGATCCAGTTCGATGTAACCCACTCGTGCACCCAACTGA

TCTTCAGCATCTTTTACTTTCACCAGCGTTTCTGGGTGAGCAAAA

ACAGGAAGGCAAAATGCCGCAAAAAAGGGAATAAGGGCGACACGG

AAATGTTGAATACTCATACTCTTCCTTTTTCAATATTATTGAAGC

ATTTATCAGGGTTATTGTCTCATGAGCGGATACATATTTGAATGT

ATTTAGAAAAATAAACAAATAGGGGTTCCGCGCACATTTCCCCGA

AAAGTGCCACCTGAGCTC*TAATACGACTCACTATAGGATAGG*ACA

TTTGCTTCTGACACAACTGTGTTCACTAGCAACCTCAAACAGACA

CC*ATGGATTGGACATGGCGAATCCTCTTTTTGGTCGCAGCAGCGA*

*CGGGAACACACGCAGACATTCAAATGACTCAGACTACGAGCTCCC*

*TCTCCGCATCCCTCGGCGACCGGGTGACTATTAGCTGCCGCGCCT*

*CTCAAGATATTAGCAAATACCTTAATTGGTACCAACAGAAGCCGG*

*ACGGAACAGTAAAGCTCCTGATTTACCACACGTCTCGACTTCATT*

*CCGGCGTACCTAGTAGGTTTTCTGGCTCTGGATCTGGTACCGACT*

*ACTCCCTCACAATTTCCAATTTGGAACAAGAAGACATTGCCACCT*

*ACTTCTGTCAACAGGGCAATACGCTGCCATACACGTTCGGCGGGG*

*GTACCAAACTGGAGATTACCGGGTCCACATCTGGATCCGGGAAGC*

*CGGGCTCCGGTGAGGGATCAACCAAAGGCGAAGTCAAGTTGCAGG*

*AATCTGGACCGGGCCTCGTTGCACCGTCTCAGTCTTTGTCCGTCA*

*CTTGCACAGTATCAGGAGTTTCCCTTCCTGACTACGGGGTATCTT*

*GGATCCGACAGCCGCCCAGAAAGGGGCTGGAGTGGCTCGGAGTGA*

*TATGGGGGTCTGAAACCACCTACTATAATAGCGCCCTCAAGAGTA*

*GACTGACTATTATTAAGGATAACTCCAAGTCTCAGGTATTTCTCA*

*AAATGAACAGTCTTCAGACTGACGACACAGCCATATACTACTGTG*

-continued

*CGAAACACTATTATTACGGTGGCAGTTACGCCATGGACTACTGGG*

*GCCAGGGGACAAGCGTAACCGTTTCAAGTGCAGCCGCAACAACGA*

*CTCCAGCTCCCAGGCCACCCACCCCGGCGCCGACTATAGCATCTC*

*AGCCTCTTTCCTTGAGACCGGAAGCATGTCGACCAGCCGCCGGAG*

*GGGCGGTCCATACCCGCGGCCTTGACTTCGCATGTGATTTCTGGG*

*TTCTCGTAGTAGTCGGCGGAGTCCTCGCTTGTTACTCTCTGCTCG*

*TGACCGTGGCTTTCATCATCTTTTGGGTACGATCTAAAAGAAGTC*

*GCCTCTTGCATTCCGATTATATGAATATGACCCCTAGACGGCCTG*

*GGCCAACGCGCAAGCATTACCAGCCGTATGCTCCTCCTAGAGACT*

*TTGCAGCTTACCGCTCCCGGAAACGCGGTAGGAAAAAGCTCCTGT*

*ATATCTTCAAGCAGCCCTTTATGCGACCCGTGCAGACGACTCAGG*

*AGGAGGACGGATGCTCATGCCGCTTTCCCGAGGAAGAGGAAGGCG*

*GTTGCGAATTGAGGGTGAAGTTCAGTAGAAGCGCAGATGCCCCAG*

*CTTATCAGCAAGGTCAAAACCAACTGTATAATGAATTGAACCTGG*

*GACGGAGAGAAGAGTATGACGTCCTCGATAAACGGCGGGGCAGGG*

*ACCCTGAGATGGGGGGGAAGCCTCGAAGGAAGAACCCGCAGGAAG*

*GGTTGTATAATGAACTCCAGAAAGATAAAATGGCCGAGGCATATT*

*CCGAGATAGGGATGAAGGGCGAGCGGCGGCGAGGCAAGGGGCATG*

*ATGGACTCTATCAGGGATTGTCAACAGCGACTAAAGATACATATG*

*ACGCTTTGCACATGCAGGCTCTGCCACCTCGGTAGGCTCGCTTTC*

TTGCTGTCCAATTTCTATTAAAGGTTCCTTTGTTCCCTAAGTCCA

ACTACTAAACTGGGGGATATTATGAAGGGCCTTGAGCATCTGGAT

TCTGCCTAATAAAAAACATTTATTTTCATTGCAA

SVP413

(SEQ ID NO: 29)

AGCCACACCCTGGAGCTAGCAAAAAAAAAAAAAAAAAAAAAAAAAA

AAAAAGCATATGACTAAAAAAAAAAAAAAAAAAAAAAAAAAAAAAA

AAAAAAAAAAAAAAAAAAAAAAAAAAAAAAAAAAAAAAAAAcgcgt

ATCGATGATATCGCGGCCGCATACAGCAGCAATTGGCAAGCTGCT

TACATAGAACTCGCGGCGATTGGCATGCCGCCTTAAAATTTTTAT

TTTATTTTTCTTTTCTTTTCCGAATCGGATTTTGTTTTTAATATT

TCAAAAAAAAAAAAAAAAAAAAAAAAAACGCGTGATAACGCAGGA

AAGAACATGTGAGCAAAAGGCCAGCAAAAGGCCAGGAACCGTAAA

AAGGCCGCGTTGCTGGCGTTTTTCCATAGGCTCCGCCCCCCTGAC

GAGCATCACAAAAATCGACGCTCAAGTCAGAGGTGGCGAAACCCG

ACAGGACTATAAAGATACCAGGCGTTTCCCCCTGGAAGCTCCCTC

GTGCGCTCTCCTGTTCCGACCCTGCCGCTTACCGGATACCTGTCC

GCCTTTCTCCCTTCGGGAAGCGTGGCGCTTTCTCATAGCTCACGC

TGTAGGTATCTCAGTTCGGTGTAGGTCGTTCGCTCCAAGCTGGGC

TGTGTGCACGAACCCCCCGTTCAGCCCGACCGCTGCGCCTTATCC

GGTAACTATCGTCTTGAGTCCAACCCGGTAAGACACGACTTATCG

CCACTGGCAGCAGCCACTGGTAACAGGATTAGCAGAGCGAGGTAT

-continued

GTAGGCGGTGCTACAGAGTTCTTGAAGTGGTGGCCTAACTACGGC
TACACTAGAAGAACAGTATTTGGTATCTGCGCTCTGCTGAAGCCA
GTTACCTTCGGAAAAAGAGTTGGTAGCTCTTGATCCGGCAAACAA
ACCACCGCTGGTAGCGGTTTTTTTGTTTGCAAGCAGCAGATTACG
CGCAGAAAAAAAGGATCTCAAGAAGATCCTTTGATCTTTTCTACG
GGGTCTGACGCTCAGTGGAACGAAAACTCACGTTAAGGGATTTTG
GTCATGAGATTATCAAAAAGGATCTTCACCTAGATCCTTTTAAAT
TAAAAATGAAGTTTTAAATCAATCTAAAGTATATATGAGTAAACT
TGGTCTGACAGTTACCAATGCTTAATCAGTGAGGCACCTATCTCA
GCGATCTGTCTATTTCGTTCATCCATAGTTGCCTGACTCCCCGTC
GTGTAGATAACTACGATACGGGAGGGCTTACCATCTGGCCCCAGT
GCTGCAATGATACCGCGAGACCCACGCTCACCGGCTCCAGATTTA
TCAGCAATAAACCAGCCAGCCGGAAGGGCCGAGCGCAGAAGTGGT
CCTGCAACTTTATCCGCCTCCATCCAGTCTATTAATTGTTGCCGG
GAAGCTAGAGTAAGTAGTTCGCCAGTTAATAGTTTGCGCAACGTT
GTTGCCATTGCTACAGGCATCGTGGTGTCACGCTCGTCGTTTGGT
ATGGCTTCATTCAGCTCCGGTTCCCAACGATCAAGGCGAGTTACA
TGATCCCCCATGTTGTGCAAAAAAGCGGTTAGCTCCTTCGGTCCT
CCGATCGTTGTCAGAAGTAAGTTGGCCGCAGTGTTATCACTCATG
GTTATGGCAGCACTGCATAATTCTCTTACTGTCATGCCATCCGTA
AGATGCTTTTCTGTGACTGGTGAGTACTCAACCAAGTCATTCTGA
GAATAGTGTATGCGGCGACCGAGTTGCTCTTGCCCGGCGTCAATA
CGGGATAATACCGCGCCACATAGCAGAACTTTAAAAGTGCTCATC
ATTGGAAAACGTTCTTCGGGGCGAAAACTCTCAAGGATCTTACCG
CTGTTGAGATCCAGTTCGATGTAACCCACTCGTGCACCCAACTGA
TCTTCAGCATCTTTTACTTTCACCAGCGTTTCTGGGTGAGCAAAA
ACAGGAAGGCAAAATGCCGCAAAAAAGGGAATAAGGGCGACACGG
AAATGTTGAATACTCATACTCTTCCTTTTTCAATATTATTGAAGC
ATTTATCAGGGTTATTGTCTCATGAGCGGATACATATTTGAATGT
ATTTAGAAAAATAAACAAATAGGGGTTCCGCGCACATTTCCCCGA
AAAGTGCCACCTGAGCTC*TAATACGACTCACTATAGGATAGG*ACA
TTTGCTTCTGACACAACTGTGTTCACTAGCAACCTCAAACAGACA
CCATGGATTGGACATGGCGAATCCTCTTTTTGGTCGCAGCAGCGA
CGGGAACACACGCAGACATTCAAATGACTCAGACTACGAGCTCCC
TCTCCGCATCCCTCGGCGACCGGGTGACTATTAGCTGCCGCGCCT
CTCAAGATATTAGCAAATACCTTAATTGGTACCAACAGAAGCCGG
ACGGAACAGTAAAGCTCCTGATTTACCACACGTCTCGACTTCATT
CCGGCGTACCTAGTAGGTTTTCTGGCTCTGGA*TCTGGTACCGACT*
*ACTCCCTCACAATTTCCAATTTGGAACAAGAAGACATTGCCACCT*
*ACTTCTGTCAACAGGGCAATACGCTGCCATACACGTTCGGCGGGG*

-continued

*GTACCAAACTGGAGATTACCGGGTCCACATCTGGATCCGGGAAGC*
*CGGGCTCCGGTGAGGGATCAACCAAAGGCGAAGTCAAGTTGCAGG*
*AATCTGGACCGGGCCTCGTTGCACCGTCTCAGTCTTTGTCCGTCA*
*CTTGCACAGTATCAGGAGTTTCCCTTCCTGACTACGGGGTATCTT*
*GGATCCGACAGCCGCCCAGAAAGGGGCTGGAGTGGCTCGGAGTGA*
*TATGGGGGTCTGAAACCACCTACTATAATAGCGCCCTCAAGAGTA*
*GACTGACTATTATTAAGGATAACTCCAAGTCTCAGGTATTTCTCA*
*AAATGAACAGTCTTCAGACTGACGACACAGCCATATACTACTGTG*
CGAAACACTATTATTACGGTGGCAGTTACGCCATGGACTACTGGG
*GCCAGGGGACAAGCGTAACCGTTTCAAGTGCAGCCGCAACAACGA*
*CTCCAGCTCCCAGACCACCGACCCCAGCACCAACAATTGCGTCCC*
*AACCTCTCTCCCTTCGACCTGAAGCATGTCGACCGGCAGCGGGCG*
*GAGCCGTACACACCAGGGGGCTTGATTTCGCTTGTGACAGACGAC*
*CTCCATCTAAACCGTTCTGGGTGCTTGTCGTTGTGGGAGGGGTGC*
*TTGCCTGCTACAGCCTCTTGGTGACTGTGGCGTTTATTATCTTTT*
*GGGTGCGGGCGTCTCTCCGGGTAAAATTCTCCAGAAGTGCGGATG*
*CCCCTGCCTATCAGCAGGGACAAAATCAACTTTACAATGAACTGA*
*ACTTGGGCAGGAGGGAGGAGTATGATGTTCTCGACAAGAGGCGAG*
*GACGCGACCCGGAAATGGGAGGTAAACCTCAAAGGCGCAAGAATC*
*CCCAAGAGGGTCTTTATAATGAATTGCAGAAAGATAAGATGGCCG*
*AAGCCTACAGCGAGATCGGTATGAAGGGAGAGCGACGGCGAGGGA*
*AGGGTCACGACGGGTTGTACCAAGGACTGTCCACGGCGACTAAGG*
*ATACCTATGATGCGTTGCATATGCAAGCACTGCCCCCCCAGGGCAA*
*GTTAGGCTCGCTTTCTTGCTGTCCAATTTCTATTAAAGGTTCCTT*
TGTTCCCTAAGTCCAACTACTAAACTGGGGGATATTATGAAGGGC
CTTGAGCATCTGGATTCTGCCTAATAAAAAACATTTATTTTCATT
GCAA

Anti-CD19 scFv and CAR Construct
(SEQ ID NO: 30)

ATGGATTGGACATGGCGAATCCTCTTTTTGGTCGCAGCAGCGACG
GGAACACACGCAGACATTCAAATGACTCAGACTACGAGCTCCCTC
TCCGCATCCCTCGGCGACCGGGTGACTATTAGCTGCCGCGCCTCT
CAAGATATTAGCAAATACCTTAATTGGTACCAACAGAAGCCGGAC
GGAACAGTAAAGCTCCTGATTTACCACACGTCTCGACTTCATTCC
GGCGTACCTAGTAGGTTTTCTGGCTCTGGA*TCTGGTACCGACTAC*
*TCCCTCACAATTTCCAATTTGGAACAAGAAGACATTGCCACCTAC*
*TTCTGTCAACAGGGCAATACGCTGCCATACACGTTCGGCGGGGGT*
*ACCAAACTGGAGATTACCGGGTCCACATCTGGATCCGGGAAGCCG*
*GGCTCCGGTGAGGGATCAACCAAAGGCGAAGTCAAGTTGCAGGAA*
*TCTGGACCGGGCCTCGTTGCACCGTCTCAGTCTTTGTCCGTCACT*
*TGCACAGTATCAGGAGTTTCCCTTCCTGACTACGGGGTATCTTGG*
*ATCCGACAGCCGCCCAGAAAGGGGCTGGAGTGGCTCGGAGTGATA*

-continued

*TGGGGGTCTGAAACCACCTACTATAATAGCGCCCTCAAGAGTAGA*

*CTGACTATTATTAAGGATAACTCCAAGTCTCAGGTATTTCTCAAA*

*ATGAACAGTCTTCAGACTGACGACACAGCCATATACTACTGTGCG*

*AAACACTATTATTACGGTGGCAGTTACGCCATGGACTACTGGGGC*

*CAGGGGACAAGCGTAACCGTTTCAAGTGCAGCCGCAACAACGACT*

*CCAGCTCCCAGGCCGCCGACTCCTGCTCCGACGATAGCCTCCCAA*

*CCCTTGTCACTCCGCCCTGAAGCATGTAGGCCAGCCGCAGGAGGC*

*GCTGTTCATACCCGAGGATTGGATTTCGCTTGCGATATTTATATC*

*TGGGCACCGTTGGCAGGGACATGCGGCGTGCTGTTGTTGAGCCTC*

*GTAATAACGCTGTACAGGTCCAAGAGGTCCCGCCTTCTTCATTCC*

*GATTACATGAACATGACCCCCAGACGCCCAGGTCCAACACGAAAA*

*CATTATCAACCATATGCTCCACCTAGGGACTTTGCAGCATACCGA*

*TCtCGCGTGAAATTCAGCCGATCTGCCGACGCACCGGCCTATCAG*

*CAAGGCCAGAACCAACTTTACAACGAGCTTAACTTGGGGAGAAGA*

*GAGGAATATGATGTACTGGACAAGCGGCGAGGTCGGGATCCTGAG*

*ATGGGAGGTAAACCTCAACGGAGAAAAAACCCACAAGAAGGTCTC*

*TACAACGAGCTGCAAAAGGACAAGATGGCCGAGGCATATTCAGAA*

*ATTGGGATGAAGGGCGAACGACGCCGAGGCAAAGGACATGATGGA*

*TTGTACCAGGGCCTCTCTACCGCAACTAAAGATACCTACGATGCC*

*CTCCATATGCAGGCACTTCCCCCGCGA*

Anti-CD25 scFv (SEQ ID NO: 32)

MKKTAIAIAVALAGFATVAQADYKDDDDKLHHHHHHKLQVKLEES

GTVLARPGASVKMSCKASGYRFTNYWMHWVKQRPGQGLEWIGVIY

PGNSDTSYNQKFKGKAKLTAVTSASTAYMELSSLTNEDSAVYYCT

REGEGSDYWGQGTTVTVSSGGGGSGGGGSGGGGSDIQLTQSPTTM

AASPGEKITITCSASSSISSNYLHWYQQKPGFSPKLLIYRTSNLA

SGVPARFSGSGSGTSYSLTIGTMEAEDVATYYCQQGSSIPYTFGT

KLELKRLEHHHHHHLEGGSLAALTAHQACHLPLETFTRHRQPRGW

EQLEQCGYPVQRLVALYLAARLSWNQVDQVIRNALASPGSGGDLG

EAIREQPEQARLALTLAAAESERFVRQGTGNDEAGAANADVVSLT

CPVAAGECAGPADSGDALLERNYPTGAEFLGDGGDVSFSTRGTQN

WTVERLLQAHRQLEERGYVFVGYHGTFLEAAQSIVFGGVRARSQD

LDAIWRGFYIAGDPALAYAYAQDQEPDARGRIRNGALLRVYVPRS

SLPGFYRTSLTLAAPEAAGEVERLIGHPLPLRLDAITGPEEEGGR

LETILGWPLAERTVVIPSAIPTDPRNVGGDLDPSSIPDKEQAISA

LPDYASQPGKPPREDLK

3C10 scFv (SEQ ID NO: 33)

MEIQLQQSGAELVKPGASVKLSCTGPGFNIEDYYIHWVKQRTEQG

LEWIGRIDPENDETKYGPIFQGRATITADTSSNTVYLQLSSLTSE

DTAVYYCALRGGVYWGPGTTLTVSSGGGGSGGGGSGGGGSHMDVV

-continued

MTQSPLTLSVAIGQSASISCKSSQSLLDSDGKTYLNWLLQRPGQS

PKRLISLVSKLDSGVPDRFTGSGSGTDFTLRISRVEAEDLGIYYC

WQGTHFPGTFGGGTKLEIKRSGGGGSGGGGSIMRGSHHHHHHGMA

SMTGGQQMGRDLYDDDDKDPSSRSAAGTMEFEA

Anti-VEGF scFv (SEQ ID NO: 34)

MKYLLPTAAAGLLLLAAQPAMAEVQLVQSGGGLVKPGGSLRLSCA

ASGFTFSSYSMNWVRQAPGKGLEWVSSISSSSSYIYYADSVKGRF

TISRDNAKNSLYLQMNSLRAEDTAVYYCARVTDAFDIWGQGTMVT

VSSGLGGLGGGGSGGGGSGGSSGVGSDIQMTQSPSSVSASIGDRV

TITCRASQGIDNWLGWYQQKPGKAPKLLIYDASNLDTGVPSRFSG

SGSGTYFTLTISSLQAEDFAVYFCQQAKAFPPTFGGGTKVDIKRG

GASLVEFEQKLISEEDL

Anti-Mesothelin scFv (SEQ ID NO: 35)

MQVQLQQSGPELEKPGASVKISCKASGYSFTGYTMNWVKQSHGKS

LEWIGLITPYNGASSYNQKFRGKATLTVDKSSSTAYMDLLSLTSE

DSAVYFCARGGYDGRGFDYWGQGTTVTVSSGVGGSGGGGSGGGGS

DIELTQSPAIMSASPGEKVTMTCSASSSVSYMHWYQQKSGTSPKR

WIYDTSKLASGVPGRESGSGSGNSYSLTISSVEAEDDATYYCQQW

SGYPLTFGAGTKLEIK

Anti-Alpha-fetoprotein scFv (SEQ ID NO: 36)

QVKLQESGAELVRPGSSVKISCKASGYVFSNYWMNWVKQRPGQGL

EWIGQIFPGDGDSNYNGKFKDKATLTADKSSTTAYMHLSSLTSED

SAVYFCARLNWDSYAMDYWGQGTTGGGGSGGGGSGGGGSELTQSP

AIMSASPGEKVTMTCSASSSVVYIHWYQQKSGTSPKRWIYDTSKL

ASGVPARFSGSGSGTSYSLTISSMEAEDAATYYCQQWYSDPYTFG

GGTKLEINN

Anti-CD.K2 scFv (SEQ ID NO: 37)

DIQMTQSPSSLSASVGDRVTITCRASQSISSYLNWYQQKPGKAPK

LLIYAASSLQSGVPSRFSGSGSGTDFTLTISSLQPEDFATYYCQQ

SYSTPLTFGQGTKVEIKSGILGTTAASGSSGGSSSGAEVQLVQSG

AEVKKPGESLKISCKGSGYSFTSYWIGWVRQMPGKGLEWMGIIYP

GDSDTRYSPSFQGQVTISADKSISTAYLQWSSLKASDTAVYYCAR

FTYYYYDYDYAGFDYWGQGTLVTVSS

Anti-OX.F3 scFv (SEQ ID NO: 38)

QVQLQQSGPGLVKPWQTLSLTCGISGDSVSSNSVSWDWIRQSPSR

GLEWLGRTYYRSKWYNEYAVSVESRITINPDTSKNQFSLQLNSVT

PEDTAIYFCVRNNYFFDLWGRGTLVTVSSGILGSGGGGSGGGGSG

GGGSEIVLTQSPATLSLSPGERATLSCRASQSVSSYLAWYQQKPG

QAPRLLIYDASNRATGIPARFSGSGSGTDFTLTISSLEPEDFAVY

YCQQRSNWPPMYTFGQGTKLEIK

-continued

Anti-EGFR scFv (SEQ ID NO: 39)

QSVLTQPPASGTPGQRVTISCTGSSSNIGNNDVSWYQQLPGTAPK
LLIYDDNKRPSGVPDRFSGSKSGTSASLAISGLRSEDEADYYCGS
WDASLNAYVFGGGTKLTVLG

Anti-CD20 scFv (SEQ ID NO: 40)

MAADSQTPWLLTFSLLCLLWPQEAGALPLMDIQLTQSPAILSASP
GEKVTMTCRASSSLSFMHWYQQKPGSSPKPWIYATSNLASGVPAR
FSGSGSGTSYSLTISTVEAEDAASYFCHQWSSNPLTFGAGTKLEI
SSGGGGSGGGGSGDVMGVDSGGGLVQPGGSRKLSCAAPGFTFSSF
GMHWVRQAPEKGLEWVAYISSPSSTLHYADRVKGRFTISRDNPKN
TLFLQMKLPSLCYGLLGPRDHVHRLLKHHHHHHLEYPYDVPDYAT
TDAAHPGRSVVPALLPLLAGTLLLLETATAP

Anti-CD28 scFv (SEQ ID NO: 41)

MGWSWIFLFLLSGRDGVLSDIELTQSPASLAVSLGQRATISCRAS
ESVEYYVTSLMQWYQQKPGQPPKLLIFAASNVESGVPARFSGSGS
GTNFSLNIHPVDEDDVAMYFCQQSRKVPYTFGGGTKLEIKRGGGG
SGGGGSGGGGSQVKLQQSGPGLVTPSQSLSITCTVSGFSLSDYGV
HWVRQSPGQGLEWLGVIWAGGGTNYNSALMSRKSISKDNSKSQVF
LKMNSLQADDTAVYYCARDKGYSYYYSMDYWGQGTTVTVSSASTK
GPSVFPLAPSSSGSGQVKLQQSGPELVKPGASVKISCKASGYAFS
RSWMNWVKQRPGQGLEWIGRIYPGDGDTNYNGKFKGKATLTADKS
SSTAYMQVSSLTSVDSAVYFCARGNTVVVPYTMDYWGQGTTVTVS
SGGGGSGGGGSGGGGSDIELTQSPASLAVSLGQRATISCRASESV
DSYGNSFMHWYQQKPGQPPKLLIYLASNLESGVPARFSGSGSRTD
FTLTIDPVEADDAATYYCQQNNEDPLTFGGGTKLELKRAAAHHHH
HH

SV428-Amino acids sequence of VHH nanobody (SEQ ID NO: 42)

QVKLEESGGGLVQAGRSLRLSCAASEHTFSSHVMGWFRQAPGKER
ESVAVIGWRDISTSYADSVKGRFTISRDNAKKTLYLQMNSLKPED
TAVYYCAARRIDAADFDSWGQGTQVTVSSGGGGSEVQLVESGGGL
VQAGGSLRLSCAASGRTFTMGWFRQAPGKEREFVAAISLSPTLAY
YAESVKGRFTISRDNAKNTVVLQMNSLKPEDTALYYCAADRKSVM
SIRPDYWGQGTQVTVSS

SV429-Amino acid sequence of scFv (SEQ ID NO: 43)

QVQLVQSGAEVKKPGASVKVSCKASGYTFTNHIIHWVRQAPGQGL
EWMGYINPYPGYHAYNEKFQGRATMTSDTSTSTVYMELSSLRSED
TAVYYCARDGYYRDTDVLDYWGQGTLVTVSSGGGGSGGGGSGGGG
SDIQMTQSPSSLSASVGDRVTITCQASQDISNYLNWYQQKPGKAP
KLLIYYTSRLHTGVPSRFSGSGSGTDFTFTISSLEPEDIATYYCQ
QGNTLPWTFGQGTKVEIK

-continued

Mouse CAR backbone (SEQ ID NO: 44)

ACAACTACTAAACCTGTGCTTCGGACACCCTCCCCTGTTCACCCT
ACTGGGACATCACAGCCCCAAAGGCCAGAGGATTGTAGACCAAGG
GGCAGCGTCAAGGGGACCGGGCTGGATTTCGCTTGCGATATTTAC
ATATGGGCCCCATTGGCTGGCATATGCGTTGCTTTGCTTCTTAGT
CTCATAATTACCCTCATCAATTCCCGCCGAAACCGGTTGTTGCAA
AGCGACTATATGAACATGACTCCTAGGCGCCCAGGACTGACTAGG
AAACCCTACCAGCCATACGCACCCGCCAGAGACTTTGCTGCATAC
AGACCAAGAGCTAAATTCAGTAGGTCTGCCGAGACTGCCGCTAAC
CTTCAAGATCCCAACCAACTCTACAATGAGCTGAATTTGGGAAGG
CGCGAAGAGTACGATGTGCTGGAAAAGAAGCGAGCCCGCGACCCC
GAAATGGGTGGGAAGCAACAGCGACGCCGGAATCCCCAGGAGGGA
GTCTACAACGCCTTGCAAAAGGATAAAATGGCAGAAGCTTACTCT
GAAATTGGCACCAAGGGGGAACGAAGACGAGGAAAAGGGCATGAT
GGTTTGTACCAAGGTCTTAGCACAGCTACTAAGGATACCTATGAC
GCTTTGCATATGCAAACCCTGGCCCCACGA anti-mouse CD19 scFV, clone ID3

(SEQ ID NO: 45)

IQMTQSPASLSTSLGETVTIQCQASEDIYSGLAWYQQKPGKSPQL
LIYGASDLQDGVPSRFSGSGSGTQYSLKITSMQTEDEGVYFCQQG
LTYPRTFGGGTKLELKGGGGSGGGGSGGGGSEVQLQQSGAELVRP
GTSVKLSCKVSGDTITFYYMHFVKQRPGQGLEWIGRIDPEDESTK
YSEKFKNKATLTADTSSNTAYLKLSSLTSEDTATYFCIYGGYYFD
YWGQGVMVTVSS

The present disclosure includes the following items:

1. A lipid compound as depicted herein or in the claims below.
2. A method of delivering a payload to immune cells ex vivo comprising contacting immune cells with a lipid nanoparticle (LNP) encapsulating a payload encoding at least one polypeptide of interest, wherein the polypeptide of interest is an antigen receptor or an antibody.
3. A method of delivering a payload to immune cells in vivo comprising administering an LNP encapsulating a payload encoding at least one polypeptide of interest to a subject, wherein the polypeptide of interest is antigen receptor or antibody.
4. The method of any one of items 2-3, wherein the immune cells are T-cells, natural killer (NK) cells, or monocytes.
5. The method of any one of items 2-4, wherein the immune cells are human T-cells.
6. The method of one of items 2-5, wherein the antigen receptor is a chimeric antigen receptor (CAR), T-cell receptor (TCR), growth factor receptor (GFR), or hormone receptor (HR).
7. The method of any one of items 2-6, wherein the antibody is a natural antibody or a synthetic antibody.
8. The method of any one of items 2-7, wherein the synthetic antibody is a nanobody (Nb).
9. The method of any one of items 2-8, wherein the LNP comprises at least one lipid compound of item 1.

10. The method of any one of items 2-9, wherein the payload is an mRNA comprising a nucleic acid sequence encoding from 5' to 3':
   a. LP-Nb
   b. wherein, LP is a leading peptide; and Nb is a nanobody.
11. The method of any one of items 2-9, wherein the payload is an mRNA comprising a nucleic acid sequence encoding from 5' to 3':
   a. LP-AR or LP-scFv-AR
   b. wherein, LP is a leading peptide; scFv is a single-chain variable fragment and AR is an antigen receptor.
12. The method of any one of items 2-11, wherein the payload is an mRNA comprising a nucleic acid sequence encoding from 5' to 3':
   a. LP-VH-LK-VL-MyC-CD8-CD28-CD3z, wherein:
   b. LP is a leading peptide;
   c. VH is the variable region of an immunoglobulin heavy chain;
   d. LK is a linker;
   e. VL is the variable region of an immunoglobulin light chain;
   f. MyC is a Myc tag;
   g. CD8 is the hinge region of a CD8 alpha chain;
   h. CD28 is a CD28 activation domain; and
   i. CD3z is a CD3 zeta cytoplasmic domain.
13. The method of any one of items 2-12, wherein the payload is an mRNA comprising a nucleic acid sequence encoding from 5' to 3':
   a. LP-scFv-CAR
   b. wherein, LP is a leading peptide;
   c. scFv is a single-chain variable fragment; and
   d. CAR is a chimeric antigen receptor sequence,
   e. wherein scFv-CAR encodes from 5' to 3': VH-LK-VL-CD8-CD28-CD3z
      i. wherein, VH is the variable region of a immunoglobulin heavy chain,
      ii. LK is a linker,
      iii. VL is the variable region of an immunoglobulin light chain,
      iv. CD8 is the hinge region of a CD8 alpha chain,
      v. CD28 is a CD28 activation domain, and
      vi. CD3z is a CD3 zeta cytoplasmic domain.
14. The method of any one of items 10-13, wherein the LP encodes an amino acid sequence with at least about 85, 90, 95, 98, or 99% sequence identity to SEQ ID NO: 1.
15. The method of any one of items 12-14, wherein the LK encodes an amino acid sequence with at least about 85, 90, 95, 98, or 99% sequence identity to SEQ ID NO: 2.
16. The method of item 12, wherein the MyC encodes an amino acid sequence with at least about 85, 90, 95, 98, or 99% sequence identity to SEQ ID NO: 3.
17. The method of any one of items 12-16, wherein the CD8 encodes an amino acid sequence with at least about 85, 90, 95, 98, or 99% sequence identity to SEQ ID NO: 4 or SEQ ID NO: 7.
18. The method of any one of items 12-17, wherein the CD28 encodes an amino acid sequence with at least about 85, 90, 95, 98, or 99% sequence identity to SEQ ID NO: 5 or SEQ ID NO: 8.
19. The method of any one of items 12-18, wherein the CD3z encodes an amino acid sequence with at least about 85, 90, 95, 98, or 99% sequence identity to SEQ ID NO: 6 or SEQ ID NO: 9.
20. The method of any one of items 11-19, wherein the mRNA encodes from 5' to 3':
   a. (SEQ ID NO: 1)-VH-(SEQ ID NO: 2)-VL-(SEQ ID NO: 3)-(SEQ ID NO: 4)-(SEQ ID NO: 5)-(SEQ ID NO: 6).
21. The method of any one of items 11-19, wherein the mRNA encodes from 5' to 3':
22. (SEQ ID NO: 1)-VH-(SEQ ID NO: 2)-VL-(SEQ ID NO: 3)-(SEQ ID NO: 7)-(SEQ ID NO: 8)- (SEQ ID NO: 9).
23. The method of any one of items 10-21, wherein the mRNA is a modified mRNA, a self-amplifying mRNA or a circular RNA.
24. The method of item 22, wherein the modified mRNA is a modified self-amplifying mRNA or a modified circular RNA.
25. The method of any one of 2-7 and 9-23, wherein the mRNA comprises a nucleic acid sequence with at least about 85, 90, 95, 98, or 99% sequence identity to SEQ ID NO: 24, 25, 26, 27, 28, 29, or 44, or the mRNA comprises a nucleic acid sequence with at least about 85, 90, 95, 98, or 99% sequence identity to SEQ ID NO: 24, 27, 28, or 29, wherein nucleotides 5' to a 5'UTR sequence in SEQ ID NO: 24, 27, 28, or 29 are not present.
26. The method of any one of items 22-23, wherein the mRNA is a self-amplifying mRNA comprising a nucleic acid sequence from 5' to 3':
   a) 5'UTR-nsP-L-GOI-L-3'UTR-PolyA
   b) 5'UTR-nsP-GOI-L-3'UTR-PolyA;
   c) 5'UTR-nsP-L-GOI-3'UTR-PolyA; or
   d) 5'UTR-nsP-SGP-GOI-3'UTR-PolyA
   b. wherein
   c. 5'UTR is a 5' untranslated region,
   d. nsP is a plurality of non-structural replicase domain sequences,
   e. L is a linker,
   f. SGP is a subgenomic promoter,
   g. GOI is one or more genes of interest,
   h. 3'UTR is a 3' untranslated region, and
   i. poly-A is a 3' poly-adenylated tail (poly-A tail).
27. The method of item 25, wherein SGP is a nucleotide sequence selected from

```
                                         SEQ ID NO: 10
(TAACCTGAATGGACTACGACATAGTCTAGTCCGCCAAG);

                                         SEQ ID NO: 11
(GAACTTCCATCATAGTTATGGCCATGACTACTCTAGCTAGCAGTGTTA

AATCATTCAGCTACCTGAGAGGGGCCCCTATAACTCTCTACGGC); or

                                         SEQ ID NO: 31
(TAATACGACTCACTATAGGATAGG).
```

28. The method of any one of items 25-26, wherein L is a nucleotide sequence selected from

```
                                          SEQ ID NO: 12
(CGCGTGATAACGCAGGAAAGAACATGTGAGCAAAAGGCCAGCAAAAGG

CCAGGAACCGTAAAAAGGCCGCGTTGCTGGCGTT),

                                          SEQ ID NO: 13
(CACATTTCCCCGAAAAGTGCCACCTGAGCTC),
```

-continued

SEQ ID NO: 14
(TTCGAAGGCGCGCCTCTAGAGCCACC), or

SEQ ID NO: 15
(CATCGATGATATCGCGGCCGCATACAGCAGC).

29. The method of any one of items 25-27, wherein 5'UTR comprises nucleic acid sequence ATAGG.

30. The method of any one of items 25-28, wherein 3'UTR is a nucleotide sequence selected from

SEQ ID NO: 16
(GGATTTTGTTTTTAATATTTC),

SEQ ID NO: 17
(GGATTTTATTTTTAATATTTC),

SEQ ID NO: 18
(AAATTTTGTTTTTAATATTTC), or

SEQ ID NO: 19
(AAATTTTATTTTTAATATTTC).

31. The method of item 25, wherein at least one GOI is a reporter gene.

32. The method of item 30, wherein the reporter gene is green fluorescent protein (GFP) or an epitope tag.

33. The method of item 31, wherein the epitope tag is a Myc-tag.

34. The method of any one of items 25-32, wherein at least one GOI encodes a CAR, a TCR, a GFR, a HR, a Nb, a scFv a therapeutic peptide or protein, an antigen, or a reporter.

35. The method of any one of items 25-33, wherein the GOI encodes from 5' to 3: scFv-CAR.

36. The method of item 34, wherein the GOI comprises SEQ ID NO: 30.

37. The method of item 34, wherein the scFv encodes an amino acid sequence with at least about 85, 90, 95, 98, or 99% sequence identity to SEQ ID NO: 32, 33, 34, 35, 36, 37, 38, 39, 40, or 45 or comprises a nucleic acid sequence with at least about 85, 90, 95, 98, or 99% sequence identity to SEQ ID NO: 25.

38. The method of any one of items 34-36, wherein the CAR comprises a nucleic acid sequence with at least about 85, 90, 95, 98, or 99% sequence identity to SEQ ID NO: 26 or 44.

39. The method of any one of items 25-37, wherein the plurality of non-structural replicase domain sequences are obtained from a Group IV positive single strand RNA virus selected from the group comprising Picornaviridae, Togaviridae, Coronaviridae, Hepeviridae, Caliciviridae, Flaviviridae, and Astroviridae.

40. The method of any one of items 25-38, wherein the plurality of non-structural replicase domain sequences are obtained from an alphavirus selected from the group comprising Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

41. The method of any one of items 25-39, wherein the plurality of non-structural replicase domain sequences are alphavirus nonstructural proteins 1-4 (nsP1-4).

42. The method of any one of items 25-40, wherein the plurality of non-structural replicase domain sequences are obtained from the TC-83 strain of Venezuelan Equine Encephalitis virus (VEE).

43. The method of any one of items 25-41, wherein SGP is a viral promoter that is recognized by viral RNA dependent RNA polymerase.

44. A method of increasing transfection efficiency of mRNA, wherein the mRNA comprise at least one GOI encoding a CAR, a TCR, a GFR, a HR, a Nb, a scFv, or a reporter, said method comprising substituting uridine (U) nucleotide residues of a reference mRNA with nucleotide residues selected from the group consisting of 1-methylpseudouridine (m1ΨP) and pseudouridine (Ψ), thereby rendering modified mRNA, wherein the modified mRNA shows increased transfection efficiency than the reference mRNA.

45. The method of item 43, wherein the reference mRNA is a self-amplifying mRNA.

46. The method of item 43, wherein the reference mRNA is a circular RNA.

47. The method of any one of items 43-43, wherein the modified mRNA is a modified self-amplifying mRNA.

48. The method of item 43 or item 45, wherein the modified mRNA is a modified circular RNA.

49. The method of any one of items 43-47, wherein said modified mRNA exhibits enhanced ability to produce a a CAR, a TCR, a GFR, a HR, a Nb, or a reporter in an immune cell compared to the same quantity of a reference mRNA that exhibit same sequence but with uridine in place of said at least one modified nucleoside selected from the group consisting of 1-methylpseudouridine and pseudouridine, wherein said enhanced ability to produce said the CAR, TCR, GFR, HR, Nb, or reporter is determined by measuring a higher level of either the amount of the the CAR, TCR, GFR, HR, Nb, or reporter or other biological effect produced at one or more times after said contacting of said immune cell with said modified mRNA compared to the corresponding amount of the CAR, TCR, GFR, HR, Nb, or reporter or other biological effect produced in the same or equivalent immune cell at the same times after contacting with the same quantity of the reference mRNA.

50. The method of item 48, wherein the immune cell is a T-cell, a NK cells, or a monocyte.

51. The method of any one of items 48-49, wherein the immune cell is a human T-cell.

52. The method of any one of items 2-50, wherein the LNP further comprises a phospholipid selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesteryl-hemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

53. The method of any one of items 2-51, wherein the LNP further comprises a structural lipid selected from the group consisting of cholesterol, fecosterol, sitosterol, ergosterol, campesterol, stigmasterol, brassicasterol, tomatidine, ursolic acid, alpha-tocopherol, and mixtures thereof.
54. The method of item 52, wherein the structural lipid is cholesterol.
55. The method of any one of items 2-53, wherein the LNP further comprises a PEG lipid selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, a PEG-modified myristoyl diglyceride, and mixtures thereof.
56. A method of treating a subject in need of cell therapy, comprising modifying an immune cell by (i) delivering a mRNA encoding at least one polypeptide of interest, wherein the polypeptide of interest is an antigen receptor or antibody, (ii) maintaining the immune cell under conditions suitable for expression of the polypeptide of interest to produce a modified immune cell, and (iii) administering the modified immune cell to the subject.
57. A method of treating a subject in need of CAR-T therapy, comprising modifying a T-cell by (i) delivering a mRNA encoding CAR to the T-cell, (ii) maintaining the T-cell under conditions suitable for expression of CAR to produce a modified T-cell, and (iii) administering the modified T-cell to the subject.
58. The method of item 56, wherein the T-cell is isolated from the subject.
59. The method of any one of items 56-57, wherein the mRNA encoding CAR is delivered using an LNP comprising at least one lipid compound of item 1.
60. The method of any one of items 55-58, wherein the mRNA is a self-amplifying mRNA, a modified mRNA, or a circular RNA.
61. The method of item 59, wherein the modified mRNA is a modified mRNA or a modified circular RNA.
62. The method of any preceding method item, wherein the LNP comprises the lipid compound, the phospholipid, the cholesterol, and the PEG lipid in a mole ratio of 15 to 40:15 to 40:30 to 55:0.5 to 5.
63. The method of any preceding method item, wherein the LNP comprises the lipid compound, the phospholipid, the cholesterol, and the PEG lipid in a mole ratio of 20 to 35:20 to 35:35 to 50:1 to 4.
64. The method of any preceding method item, wherein the LNP comprises the lipid compound, the phospholipid, the cholesterol, and the PEG lipid in a mole ratio of 25 to 35:25 to 35:40 to 50:1.5 to 3.
65. A LNP comprising the lipid compound of item 1, a phospholipid, a cholesterol, and a PEG lipid in a mole ratio of 15 to 40:15 to 40:30 to 55:0.5 to 5.
66. A LNP comprising the lipid compound of item 1, a phospholipid, a cholesterol, and a PEG lipid in a mole ratio of 20 to 35:20 to 35:35 to 50:1 to 4.
67. A LNP comprising the lipid compound of item 1, a phospholipid, a cholesterol, and a PEG lipid in a mole ratio of 25 to 35:25 to 35:40 to 50:1.5 to 3.

EXAMPLES

Example 1: Novel Ionizable Lipid Characterization

One suitable system for delivering the sa-mRNA, modified mRNA or circRNA, of the disclosure is using a lipid nanoparticle (LNP) comprising a novel ionizable lipid of the disclosure. The ionizable lipid in an LNP formulation play a key role in the uptake of LNP by cells and the release of LNP from the endosome. A method of increasing transfection efficiency and decreasing cytotoxicity of a LNP delivery system is by formulating the LNP using a novel ionizable lipid of the disclosure.

The structures of the novel ionizable lipids of the present disclosure were confirmed using techniques known in the art, including nuclear magnetic resonance spectra of 1H and LC-Mass spectrometry.

The structure of E6 (1,1',1"-(1,3,5-triazinane-1,3,5-triyl) tris(3-(dinonylamino)propan-1-one) was confirmed by 1H NMR spectroscopy. Yield was 22%. 1H-NMR (400 MHz, CDCl3, δ) 5.26 (s, 6H), 2.81 (t, J=8 Hz, 6H), 2.67 (t, J=8 Hz, 6H), 2.43 (t, J=8 Hz, 12H), 1.44-1.23 (m, 132H), 0.88 (t, J=8 Hz, 18H The structure of E2 (1,1',1"-(1,3,5-triazinane-1,3,5-triyl) tris(3-(dinonylamino)propan-1-one)) was confirmed by 1H NMR spectroscopy. Yield was 25%. 1H-NMR (400 MHz, CDCl3, δ) 5.26 (s, 6H), 2.79 (t, J=8 Hz, 6H), 2.65 (t, J=8 Hz, 6H), 2.41 (t, J=8 Hz, 12H), 1.42-1.26 (m, 84H), 0.88 (t, J=8 Hz, 18H). MS (ESI) m/z 529.6 $[M+2H]^{2}+$.

The structure of P1C1 (ethyl (2-(1-ethylpiperidin-4-yl)-2-(N-(pentadecan-8-yl)tridecanamido)acetyl)glycinate) was confirmed by 1H NMR spectroscopy. Yield was 16%. 1H-NMR (400 MHz, Me-OD, δ) 4.34 (d, J=8 Hz, 1H), 4.21-4.14 (m, 4H), 3.41 (t, J=8 Hz, 1H), 3.01 (q, J=8 Hz, 2H), 2.47-2.40 (m, 5H), 2.01-1.83 (t, J=12 Hz, 2H), 1.65-1.56 (m, 6H), 1.29-1.17 (m, 42H), 1.17-1.10 (m, 6H), 0.93-0.89 (m, 9H). MS (APCI) m/z 678.7 [M+H]+.

The structure of P6A2 (N-(2-(cyclohex-1-en-1-ylamino)-1-(1-ethylpiperidin-4-yl)-2-oxoethyl)-N-(heptadecan-9-yl) palmitamide) was confirmed by 1H NMR spectroscopy. Yield was 45%. 1H-NMR (400 MHz, Me-OD, δ) 6.05 (t, J=8 Hz, 1H), 4.26 (s, 1H), 3.26-3.17 (m, 3H), 2.49-2.42 (m, 5H), 2.19-2.01 (m, 6H), 1.67-1.57 (m, 14H), 1.31-1.16 (m, 48H), 0.92-0.87 (m, 12H). MS (APCI) m/z 742.7 [M+H]+.

The structure of P30A1 (N-(2-(cyclohexylamino)-1-(1-ethylpiperidin-4-yl)-2-oxoethyl)-N-(pentadecan-8-yl)palmitamide) was confirmed by 1H NMR spectroscopy. Yield was 58%. 1H-NMR (400 MHz, CDCl3, δ) 8.41 (d, J=8 Hz, 1H), 3.70-3.63 (m, 1H), 3.57 (t, J=8 Hz, 1H), 3.18-3.09 (m, 3H), 2.80-2.24 (m, 3H), 2.44-2.24 (m, 4H), 1.79-1.20 (m, 67H), 0.89-0.85 (m, 9H). MS (APCI) m/z 716.8 [M+H]+.

The structure of P54B6 (N-(2-(((1s,3s)-adamantan-1-yl) amino)-1-(1-ethylpiperidin-4-yl)-2-oxoethyl)-N-(2-decyltetradecyl)undecanamide) was confirmed by mass spectrometry. Yield was 48%. MS (APCI) m/z 824.8 [M+H]+.

The structure of P38D1 (N-(2-(cycloheptylamino)-1-(1-ethylpiperidin-4-yl)-2-oxoethyl)-N-(pentadecan-8-yl)tetradecanamide) was confirmed by mass spectrometry. Yield was 56%. MS (APCI) m/z 702.7 [M+H]+.

The structure of P56A1 (N-(2-(((1s,3s)-adamantan-1-yl) amino)-1-(1-ethylpiperidin-4-yl)-2-oxoethyl)-N-(pentadecan-8-yl)palmitamide) was confirmed by mass spectrometry. Yield was 53%. MS (APCI) m/z 768.7 [M+H]+.

The structure of P56B1 (N-(2-(((1s,3s)-adamantan-1-yl) amino)-1-(1-ethylpiperidin-4-yl)-2-oxoethyl)-N-(pentadecan-8-yl)heptadecanamide) was confirmed by mass spectrometry. Yield was 59%. MS (APCI) m/z 782.8 [M+H]+.

The structure of P14A2 (N-(2-(butylamino)-1-(1-ethylpiperidin-4-yl)-2-oxoethyl)-N-(heptadecan-9-yl)octanamide) was confirmed by mass spectrometry. Yield was 40%. MS (APCI) m/z 606.6 [M+H]+.

The structure of P16B1 (N-(2-(butylamino)-1-(1-ethylpiperidin-4-yl)-2-oxoethyl)-N-(pentadecan-8-yl)undecanamide) was confirmed by mass spectrometry. Yield was 43%. MS (APCI) m/z 620.6 [M+H]+.

The structure of P26D4 (N-(2-(cyclohexylamino)-1-(1-ethylpiperidin-4-yl)-2-oxoethyl)-N-(2-octyldodecyl) tetradecanamide) was confirmed by mass spectrometry. Yield was 23%. MS (APCI) m/z 758.8 [M+H]+.

The structure of P1D4 (Ethyl (2-(1-ethylpiperidin-4-yl)-2-(N-(2-octyldodecyl)tetradecanamido)acetyl)glycinate) was confirmed by mass spectrometry. Yield was 30%. MS (APCI) m/z 762.8 [M+H]+.

The structure of P30B7 N-(1-(cyclohexylamino)-3-(1-methylpiperidin-4-yl)-1-oxopropan-2-yl)-N-(pentadecan-8-yl)heptadecanamide) was confirmed by mass spectrometry. Yield was 56%. MS (APCI) m/z 730.8 [M+H]+.

The structure of P30C7 (N-(1-(cyclohexylamino)-3-(1-methylpiperidin-4-yl)-1-oxopropan-2-yl)-N-(pentadecan-8-yl)stearamide) was confirmed by mass spectrometry. Yield was 53%. MS (APCI) m/z 744.8 [M+H]+.

The structure of P38D7 (N-(1-(cycloheptylamino)-3-(1-methylpiperidin-4-yl)-1-oxopropan-2-yl)-N-(pentadecan-8-yl)tetradecanamide) was confirmed by mass spectrometry. Yield was 45%. MS (APCI) m/z 702.7 [M+H]+.

The structure of P38D8 (N-(1-(cycloheptylamino)-3-(1-methylpiperidin-4-yl)-1-oxopropan-2-yl)-N-(heptadecan-9-yl)tetradecanamide) was confirmed by mass spectrometry. Yield was 52%. MS (APCI) m/z 730.7 [M+H]+.

The structure of P40B10 (N-(1-(cycloheptylamino)-3-(1-methylpiperidin-4-yl)-1-oxopropan-2-yl)-N-(2-octyldodecyl)undecanamide) was confirmed by mass spectrometry. Yield was 42%. MS (APCI) m/z 730.7 [M+H]+.

The structure of P40C11 (N-(1-(cycloheptylamino)-3-(1-methylpiperidin-4-yl)-1-oxopropan-2-yl)-N-(tricosan-12-yl)dodecanamide) was confirmed by 1H NMR spectroscopy and mass spectrometry. Yield was 57%. MS (APCI) m/z 786.8 [M+H]+.

The structure of P40C10 (N-(1-(cycloheptylamino)-3-(1-methylpiperidin-4-yl)-1-oxopropan-2-yl)-N-(2-octyldodecyl)dodecanamide) was confirmed by mass spectrometry. Yield was 70%. MS (APCI) m/z 744.8 [M+H]+.

The structure of P51C12 (N-(1-(tert-butylamino)-3-(1-methylpiperidin-4-yl)-1-oxopropan-2-yl)-N-(2-decyltetradecyl)tridecanamide) was confirmed by mass spectrometry. Yield was 70%. MS (APCI) m/z 774.8 [M+H]+.

The structure of P40D7 (N-(1-(cycloheptylamino)-3-(1-methylpiperidin-4-yl)-1-oxopropan-2-yl)-N-(pentadecan-8-yl)pentadecanamide) was confirmed by mass spectrometry. Yield was 61%. MS (APCI) m/z 716.7 [M+H]+.

The structure of P53A5 (N-(2-(tert-butylamino)-1-(1-ethylpiperidin-4-yl)-2-oxoethyl)-N-(tricosan-12-yl)decanamide) was confirmed by 1H NMR spectroscopy and mass spectrometry. Yield was 61%. MS (APCI) m/z 718.7 [M+H]+.

The structure of P53A6 (N-(2-(tert-butylamino)-1-(1-ethylpiperidin-4-yl)-2-oxoethyl)-N-(2-decyltetradecyl)decanamide) was confirmed by mass spectrometry. Yield was 61%. MS (APCI) m/z 732.7 [M+H]+.

The structure of P38D4 (N-(2-(cycloheptylamino)-1-(1-ethylpiperidin-4-yl)-2-oxoethyl)-N-(2-decyltetradecyl)tetradecanamide) was confirmed by mass spectrometry. Yield was 51%. MS (APCI) m/z 828.7 [M+H]+.

The structure of P56A2 (N-(2-(((1s,3s)-adamantan-1-yl) amino)-1-(1-ethylpiperidin-4-yl)-2-oxoethyl)-N-(heptadecan-9-yl)palmitamide) was confirmed by mass spectrometry. Yield was 46%. MS (APCI) m/z 796.7 [M+H]+.

The structure of P149A2 (N-(2-(cycloheptylamino)-1-(1-ethylpiperidin-4-yl)-2-oxoethyl)-N-(heptadecan-9-yl)oleamide) was confirmed by mass spectrometry. Yield was 42%. MS (APCI) m/z 784.8 [M+H]+.

The structure of P159C10 (dodecyl 4-((2-(cycloheptylamino)-1-(1-ethylpiperidin-3-yl)-2-oxoethyl)(2-octyldodecyl)amino)-4-oxobutanoate) was confirmed by mass spectrometry. Yield was 43%. MS (APCI) m/z 830.8 [M+H]+.

The structure of P161F10 (N-(1-(((1s,3s)-adamantan-1-yl)amino)-3-(1-methylpiperidin-4-yl)-1-oxopropan-2-yl)-4-(3,6-dihydroxy-10,13-dimethylhexadecahydro-1H-cyclopenta[a]phenanthren-17-yl)-N-(2-octyldodecyl) pentanamide) was confirmed by mass spectrometry. Yield was 53%. MS (APCI) m/z 974.9 [M+H]+.

The structure of P149A2 (N-(2-(cycloheptylamino)-2-oxo-1-(piperidin-4-yl)ethyl)-N-(heptadecan-9-yl)oleamide) was confirmed by mass spectrometry. Yield was 53%. MS (APCI) m/z 784.8 [M+H]+.

The structure of P153C3 (dodecyl 4-((2-(cycloheptylamino)-1-(1-ethylpiperidin-4-yl)-2-oxoethyl)(nonadecan-10-yl)amino)-4-oxobutanoate) was confirmed by mass spectrometry. Yield was 42%. MS (APCI) m/z 816.8 [M+H]+.

The structure of P153C5 (dodecyl 4-((2-(cycloheptylamino)-1-(1-ethylpiperidin-4-yl)-2-oxoethyl)(tricosan-12-yl)amino)-4-oxobutanoate) was confirmed by mass spectrometry. Yield was 53%. MS (APCI) m/z 872.8 [M+H]+.

The structure of P159C10 (dodecyl 4-((2-(cycloheptylamino)-1-(1-ethylpiperidin-3-yl)-2-oxoethyl)(2-octyldodecyl)amino)-4-oxobutanoate) was confirmed by mass spectrometry. Yield was 53%. MS (APCI) m/z 830.8 [M+H]+.

The structure of P149A1 (N-(2-(cycloheptylamino)-1-(1-ethylpiperidin-4-yl)-2-oxoethyl)-N-(pentadecan-8-yl)oleamide) was confirmed by mass spectrometry. Yield was 53%. MS (APCI) m/z 756.7 [M+H]+.

The structure of P153C1 (dodecyl 4-((2-(cycloheptylamino)-1-(1-ethylpiperidin-4-yl)-2-oxoethyl)(pentadecan-8-yl)amino)-4-oxobutanoate) was confirmed by mass spectrometry. Yield was 53%. MS (APCI) m/z 760.7 [M+H]+.

The structure of P161F6 (N-(2-(((1s,3s)-adamantan-1-yl) amino)-1-(1-ethylpiperidin-4-yl)-2-oxoethyl)-N-(2-decyltetradecyl)-4-(3,6-dihydroxy-10,13-dimethylhexadecahydro-1H-cyclopenta[a]phenanthren-17-yl) pentanamide) was confirmed by mass spectrometry. Yield was 53%. MS (APCI) m/z 1031.0 [M+H]+.

The structure of P149C2 ((Z)-N-(2-(cycloheptylamino)-1-(1-ethylpiperidin-4-yl)-2-oxoethyl)-N-(heptadecan-9-yl) hexadec-9-enamide) was confirmed by mass spectrometry. Yield was 53%. MS (APCI) m/z 756.7 [M+H]+.

Example 2: LNP Synthesis

LNPs formulated using the novel ionizable lipids of the disclosure or control ionizable lipids MC3 and SM-102 were synthesized by mixing the lipid components of the LNP in ethanol at a predetermined molar ratio (ionizable lipid/DOPE/Cholesterol/DMG-PEG2000=30/15/50/1.5) to prepare an organic phase. Sa-mRNA encoding firefly luciferase (LUC) or green fluorescent protein (GFP) was diluted in 50 mM citrate buffer (pH 4.5, Fisher) to prepare an aqueous phase. The sa-mRNA was stored at −80° C. and was thawed on ice prior to use. The ethanol and aqueous phases were mixed at a 1:3 ratio by pipette with the N/P=4.2/1. The resultant LNPs were purified by ultrafiltration (100,000 cut-off, MilliporeSigma™ Amicon™ Ultra-15 Centrifugal Filter Units) at 4° C. prior to transfection into a cell, such as a T-cell.

Example 3: Human T-Cell Isolation, Activation, and Transfection

LNPs formulated using novel ionizable lipids of the disclosure were synthesized using the procedure described in Example 2 and characterized. Table 4 below show the properties of each LNP formulated using a novel ionizable lipid of the disclosure.

TABLE 4

| LNP Characteristics | | | | | | | |
|---|---|---|---|---|---|---|---|
| Novel Ionizable Lipid | Avg. Size (nm) | Avg. PDI (RLU) | Avg. Encapsulation Efficiency (EE) % | Mole Ratio of Lipid Components: Ionizable Lipid | DOPE | Cholesterol | DMG-PEG2000 |
| E6 | 217 | 0.13 | 97.5 | 20 | 30 | 40 | 1.5 |
| E2 | 200 | 0.1 | 95.1 | 20 | 40 | 40 | 1.5 |
| P6A2 | 190.7 | 0.12 | 90.4 | 30 | 15 | 50 | 1.5 |
| P38D7 | 236.3 | 0.21 | 94.8 | 30 | 15 | 50 | 1.5 |
| P38D8 | 186.9 | 0.18 | 95.4 | 30 | 15 | 50 | 1.5 |
| P40B10 | 189.9 | 0.14 | 95.8 | 30 | 15 | 50 | 1.5 |
| P40C11 | 189.3 | 0.14 | 96.6 | 30 | 15 | 50 | 1.5 |
| P56A1 | 186.3 | 0.12 | 89.1 | 30 | 15 | 50 | 1.5 |
| P56B1 | 173.2 | 0.10 | 90.6 | 30 | 15 | 50 | 1.5 |
| P28D10 | 188.0 | 0.10 | 95.5 | 30 | 15 | 50 | 1.5 |
| P1D4 | 170.4 | 0.17 | 92.7 | 30 | 15 | 50 | 1.5 |
| P30B7 | 151.6 | 0.10 | 91.0 | 30 | 15 | 50 | 1.5 |
| P30C7 | 166.8 | 0.11 | 93.9 | 30 | 15 | 50 | 1.5 |
| P30A1 | 176.6 | 0.11 | 97.8 | 30 | 15 | 50 | 1.5 |
| P54B6 | 181.2 | 0.10 | 93.4 | 30 | 15 | 50 | 1.5 |
| P38D1 | 179.1 | 0.12 | 97.4 | 30 | 15 | 50 | 1.5 |
| P40C10 | 192.9 | 0.25 | 99.1 | 30 | 15 | 50 | 1.5 |
| P40D7 | 149.2 | 0.18 | 98.2 | 30 | 15 | 50 | 1.5 |
| P53A5 | 173.8 | 0.10 | 97.9 | 30 | 15 | 50 | 1.5 |
| P53A6 | 175.6 | 0.16 | 98.3 | 30 | 15 | 50 | 1.5 |
| P51C12 | 186.5 | 0.26 | 98.1 | 30 | 15 | 50 | 1.5 |
| P56A2 | 154.4 | 0.15 | 81.5 | 30 | 15 | 50 | 1.5 |
| P38D4 | 178 | 0.13 | 93.9 | 30 | 15 | 50 | 1.5 |
| P161F10 | 225 | 0.19 | 87.9 | 30 | 15 | 50 | 1.5 |
| P149A2 | 218 | 0.10 | 92.0 | 30 | 15 | 50 | 1.5 |
| P153C3 | 86.8 | 0.07 | 86.8 | 30 | 15 | 50 | 1.5 |
| P153C5 | 169 | 0.14 | 62.0 | 30 | 15 | 50 | 1.5 |
| P159C10 | 174 | 0.13 | 95.8 | 30 | 15 | 50 | 1.5 |
| P149A1 | 219 | 0.10 | 92.9 | 30 | 15 | 50 | 1.5 |
| P153C1 | 148 | 0.12 | 90.1 | 30 | 15 | 50 | 1.5 |
| P161F6 | 215 | 0.18 | 87.1 | 30 | 15 | 50 | 1.5 |
| P149C2 | 176 | 0.15 | 90.1 | 30 | 15 | 50 | 1.5 |

LNP encapsulating sa-mRNA or modified mRNA of the disclosure were then transfected into human T-cells. Human T cells were isolated from human leukopac using a commercially available T-cell isolation kit (StemCell) and activated by 20 μl anti-CD3/CD28/CD2 (StemCell) per milliliter at 1 million cells/milliliter. At day 4 after activation, the cells were transfected using LNP encapsulated sa-mRNA or modified mRNA encoding GFP at 1 μg sa-mRNA or modified mRNA for 0.5 million activated human primary T cells in 1 milliliter media.

Example 4: Decay Rate of mRNA in Human Primary T-Cells

Figure 8:
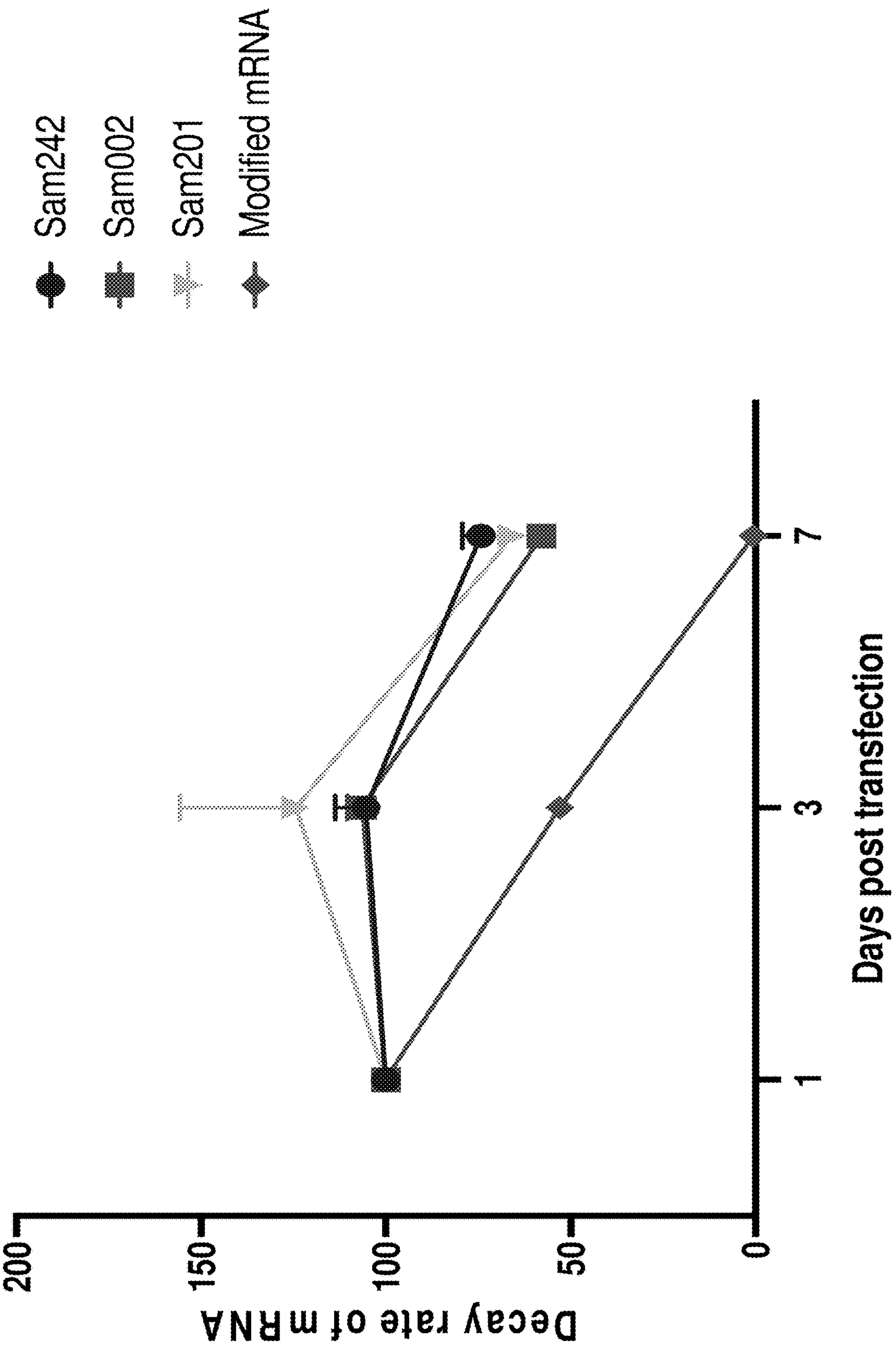
FIG. 8 shows the decay rate of 3 sa-mRNA variants and one modified mRNA encoding eGFP in activated human primary T cells. The activated human primary T cells were isolated from leukopac and transfected with mRNA using an LNP formulated with novel ionizable lipid P1D4. The data points for the sa-mRNA are derived from an average of measurements performed in replicate.

Human primary T-cells were isolated and activated using the procedure described in Example 3. The activated T-cells were transfected with LNP comprising novel ionizable lipid P1D4-LNP and encapsulated one of 66 sa-mRNA variants or a modified mRNA encoding eGFP. FIG. 8 shows the decay rate of GFP positive T-cells transfected with sa-mRNA variants comprising SEQ ID NOs: 10-12, compared to modified mRNA. The data points for the sa-mRNA were derived from an average of measurements performed in replicate.

Table 5 details the mRNA decay rate of replicates of sa-mRNAs SAM001 (SEQ ID NO: 20) and SAM002 (SEQ ID NO: 21) (1-66) compared to modified mRNA 67. The mRNA ID indicates each genetic allele, e.g., A means wild-type at the A allele, al means mutation at the A allele.

TABLE 5

| ID | | mRNA decay rate | | | | | | | | |
|---|---|---|---|---|---|---|---|---|---|---|
| Serial No. | mRNA ID | Day 1 | | | Day 3 | | | Day 7 | | |
| 1 | a1BCD-SAM002 | 100 | 100 | 100 | 97.62 | 94.89 | 90.38 | 55.95 | 57.95 | 56.73 |
| 2 | a1BCD-SAM001 | 100 | 100 | 100 | 25.69 | 29.02 | 23.70 | 7.25 | 5.13 | 5.21 |
| 3 | Ab1CD-SAM002 | 100 | 100 | 100 | 113.98 | 97.35 | 105.26 | 78.49 | 68.78 | 75.79 |
| 4 | Ab1CD-SAM001 | 100 | 100 | 100 | 32.37 | 18.53 | 17.27 | 5.04 | 3.44 | 4.42 |
| 5 | Ab2CD-SAM002 | 100 | 100 | 100 | 103.79 | 97.85 | 94.44 | 68.94 | 59.23 | 66.67 |
| 6 | Ab2CD-SAM001 | 100 | 100 | 100 | 37.27 | 24.70 | 26.29 | 6.55 | 4.45 | 5.15 |
| 7 | Ab3CD-SAM002 | 100 | 100 | 100 | 60.95 | 62.41 | 60.90 | 28.99 | 26.60 | 26.87 |
| 8 | Ab3CD-SAM001 | 100 | 100 | 100 | 20.71 | 20.81 | 26.52 | 2.43 | 2.54 | 3.48 |
| 9 | ABc1D-SAM002 | 100 | 100 | 100 | 79.81 | 85.40 | 88.31 | 43.19 | 41.61 | 45.97 |
| 10 | ABc1D-SAM001 | 100 | 100 | 100 | 16.10 | 15.15 | 22.08 | 3.02 | 2.79 | 3.46 |
| 11 | ABCd1-SAM002 | 100 | 100 | 100 | 104.70 | 95.04 | 86.56 | 65.77 | 56.74 | 56.13 |
| 12 | ABCd1-SAM001 | 100 | 100 | 100 | 22.10 | 18.07 | 18.26 | 7.73 | 6.30 | 5.65 |
| 13 | a1b1CD-SAM002 | 100 | 100 | 100 | 93.01 | 92.39 | 90.57 | 60.14 | 63.96 | 60.25 |
| 14 | a1b1CD-SAM001 | 100 | 100 | 100 | 30.53 | 27.61 | 25.49 | 4.20 | 4.42 | 5.49 |
| 15 | a1b2CD-SAM002 | 100 | 100 | 100 | 94.44 | 98.73 | 98.31 | 60.65 | 66.10 | 62.36 |
| 16 | a1b2CD-SAM001 | 100 | 100 | 100 | 29.02 | 29.34 | 33.33 | 5.94 | 5.79 | 3.85 |
| 17 | a1b3CD-SAM002 | 100 | 100 | 100 | 62.39 | 65.97 | 69.90 | 27.06 | 29.84 | 30.10 |
| 18 | a1b3CD-SAM001 | 100 | 100 | 100 | 19.89 | 17.62 | 21.48 | 4.14 | 4.14 | 4.03 |
| 19 | a1Bc1D-SAM002 | 100 | 100 | 100 | 72.27 | 70.14 | 76.95 | 44.92 | 43.06 | 46.48 |
| 20 | a1Bc1D-SAM001 | 100 | 100 | 100 | 23.86 | 18.23 | 18.60 | 5.00 | 4.84 | 3.31 |
| 21 | a1BCd1-SAM002 | 100 | 100 | 100 | 88.00 | 87.77 | 90.16 | 54.86 | 54.26 | 48.63 |
| 22 | a1BCd1-SAM001 | 100 | 100 | 100 | 19.26 | 24.43 | 17.50 | 4.51 | 4.98 | 4.10 |
| 23 | Ab1c1D-SAM002 | 100 | 100 | 100 | 71.01 | 68.86 | 74.29 | 31.52 | 37.00 | 34.69 |
| 24 | Ab1c1D-SAM001 | 100 | 100 | 100 | 24.86 | 19.90 | 20.10 | 2.77 | 4.23 | 3.19 |
| 25 | Ab2c1D-SAM002 | 100 | 100 | 100 | 78.06 | 80.60 | 77.12 | 45.58 | 38.25 | 41.07 |
| 26 | Ab2c1D-SAM001 | 100 | 100 | 100 | 27.23 | 20.42 | 19.57 | 4.50 | 5.00 | 4.68 |
| 27 | Ab3c1D-SAM002 | 100 | 100 | 100 | 31.53 | 29.82 | 34.88 | 5.86 | 7.37 | 7.47 |
| 28 | Ab3c1D-SAM001 | 100 | 100 | 100 | 30.16 | 16.67 | 18.07 | 5.08 | 2.74 | 3.45 |
| 29 | Ab1Cd1-SAM002 | 100 | 100 | 100 | 98.05 | 95.74 | 99.25 | 60.98 | 54.96 | 58.21 |
| 30 | Ab1Cd1-SAM001 | 100 | 100 | 100 | 17.01 | 18.38 | 19.34 | 5.15 | 4.04 | 4.12 |
| 31 | Ab2Cd1-SAM002 | 100 | 100 | 100 | 117.95 | 107.07 | 98.60 | 68.59 | 60.42 | 55.09 |
| 32 | Ab2Cd1-SAM001 | 100 | 100 | 100 | 18.99 | 20.92 | 20.51 | 5.53 | 5.29 | 5.36 |
| 33 | Ab3Cd1-SAM002 | 100 | 100 | 100 | 58.95 | 52.16 | 62.39 | 33.68 | 29.39 | 39.91 |
| 34 | Ab3Cd1-SAM001 | 100 | 100 | 100 | 44.29 | 16.90 | 12.42 | 0.65 | 2.86 | 2.86 |
| 35 | ABc1d1-SAM002 | 100 | 100 | 100 | 70.71 | 76.45 | 70.07 | 42.60 | 44.34 | 42.76 |
| 36 | ABc1d1-SAM001 | 100 | 100 | 100 | 21.59 | 19.74 | 17.52 | 3.07 | 5.20 | 5.84 |
| 37 | a1b1c1D-SAM002 | 100 | 100 | 100 | 77.48 | 64.26 | 66.27 | 34.73 | 34.75 | 34.51 |

TABLE 5-continued

| ID | | mRNA decay rate | | | | | | | | |
|---|---|---|---|---|---|---|---|---|---|---|
| Serial No. | mRNA ID | Day 1 | | | Day 3 | | | Day 7 | | |
| 38 | a1b1c1D-SAM001 | 100 | 100 | 100 | 28.21 | 18.28 | 19.44 | 3.08 | 3.49 | 2.22 |
| 39 | a1b2c1D-SAM002 | 100 | 100 | 100 | 87.13 | 74.07 | 75.47 | 40.81 | 39.75 | 41.82 |
| 40 | a1b2c1D-SAM001 | 100 | 100 | 100 | 22.03 | 19.18 | 20.72 | 3.83 | 2.24 | 2.07 |
| 41 | a1b3c1D-SAM002 | 100 | 100 | 100 | 30.73 | 26.92 | 34.40 | 4.22 | 8.33 | 7.34 |
| 42 | a1b3c1D-SAM001 | 100 | 100 | 100 | 22.83 | 16.88 | 16.43 | 5.22 | 3.90 | 3.33 |
| 43 | a1b1Cd1-SAM002 | 100 | 100 | 100 | 93.51 | 94.97 | 100.58 | 46.75 | 50.28 | 53.22 |
| 44 | a1b1Cd1-SAM001 | 100 | 100 | 100 | 40.85 | 29.00 | 64.61 | 7.46 | 6.30 | 36.58 |
| 45 | a1b2Cd1-SAM002 | 100 | 100 | 100 | 92.00 | 91.00 | 99.16 | 49.71 | 47.06 | 60.76 |
| 46 | a1b2Cd1-SAM001 | 100 | 100 | 100 | 24.50 | 16.05 | 22.22 | 6.42 | 4.35 | 5.29 |
| 47 | a1b3Cd1-SAM002 | 100 | 100 | 100 | 49.84 | 48.82 | 55.37 | 28.34 | 26.18 | 29.66 |
| 48 | a1b3Cd1-SAM001 | 100 | 100 | 100 | 16.98 | 10.73 | 18.14 | 1.82 | 2.20 | 3.07 |
| 49 | Ab1c1d1-SAM002 | 100 | 100 | 100 | 46.07 | 71.64 | 67.16 | 24.86 | 41.45 | 45.02 |
| 50 | Ab1c1d1-SAM001 | 100 | 100 | 100 | 14.65 | 15.52 | 13.13 | 2.68 | 5.00 | 3.38 |
| 51 | Ab2c1d1-SAM002 | 100 | 100 | 100 | 68.87 | 70.94 | 67.73 | 40.57 | 44.83 | 43.77 |
| 52 | Ab2c1d1-SAM001 | 100 | 100 | 100 | 18.92 | 18.52 | 15.88 | 2.25 | 2.78 | 3.41 |
| 53 | Ab3c1d1-SAM002 | 100 | 100 | 100 | 24.18 | 21.12 | 19.29 | 7.14 | 6.37 | 7.12 |
| 54 | Ab3c1d1-SAM001 | 100 | 100 | 100 | 24.00 | 15.60 | 14.81 | 3.20 | 1.99 | 2.22 |
| 55 | a1Bc1d1-SAM002 | 100 | 100 | 100 | 80.63 | 72.24 | 72.11 | 45.95 | 47.15 | 45.58 |
| 56 | a1Bc1d1-SAM001 | 100 | 100 | 100 | 18.72 | 14.00 | 15.79 | 3.35 | 2.00 | 2.84 |
| 57 | a1b1c1d1-SAM002 | 100 | 100 | 100 | 74.81 | 64.20 | 74.79 | 45.93 | 35.41 | 45.30 |
| 58 | a1b1c1d1-SAM001 | 100 | 100 | 100 | 16.52 | 18.31 | 20.80 | 4.70 | 7.04 | 7.28 |
| 59 | a1b2c1d1-SAM002 | 100 | 100 | 100 | 72.85 | 68.69 | 77.35 | 45.25 | 39.82 | 46.28 |
| 60 | a1b2c1d1-SAM001 | 100 | 100 | 100 | 25.35 | 17.52 | 21.13 | 2.54 | 4.27 | 2.99 |
| 61 | a1b3c1d1-SAM002 | 100 | 100 | 100 | 23.53 | 24.51 | 27.72 | 8.50 | 9.31 | 8.91 |
| 62 | a1b3c1d1-SAM001 | 100 | 100 | 100 | 12.84 | 14.59 | 17.37 | 1.38 | 2.49 | 2.04 |
| 63 | ABCD-SAM001 | 100 | 100 | 100 | 25.09 | 24.14 | 29.05 | 3.32 | 5.02 | 4.52 |
| 64 | ABCD-SAM002 | 100 | 100 | 100 | 103.56 | 104.62 | 111.21 | 57.71 | 55.12 | 61.37 |
| 65 | ABCd2-SAM002 | 100 | 100 | 100 | 158.33 | 96.49 | 118.60 | 80.56 | 54.39 | 62.79 |
| 66 | ABCd2-SAM001 | 100 | 100 | 100 | 32.37 | 26.52 | 33.77 | 11.51 | 6.63 | 9.74 |
| 67 | modified sa-mRNA | 100 | 100 | 100 | 49.65 | 56.07 | 53.47 | 0.37 | 0.83 | 0.73 |

Example 5: Delivery and In Vivo Expression of Modified mRNA to T and NK Cells LNP formulated using the ionizable lipids of the disclosure were used to deliver modified RNA encoding reporter genes to determine the transfection efficiency of exemplary ionizable lipids of the disclosure in immune cells and organs. Injections of mice with LNP-encapsulated modified mRNA encoding either Luciferases or eGFP were performed. In experiments with payloads encoding Luciferase mRNA, spleen expression was detected, which is an important organ with abundant pan T cells. In experiments with payloads encoding eGFP mRNA, transfection of primary T cells in vivo by FACS analysis was performed.

Figure 9:
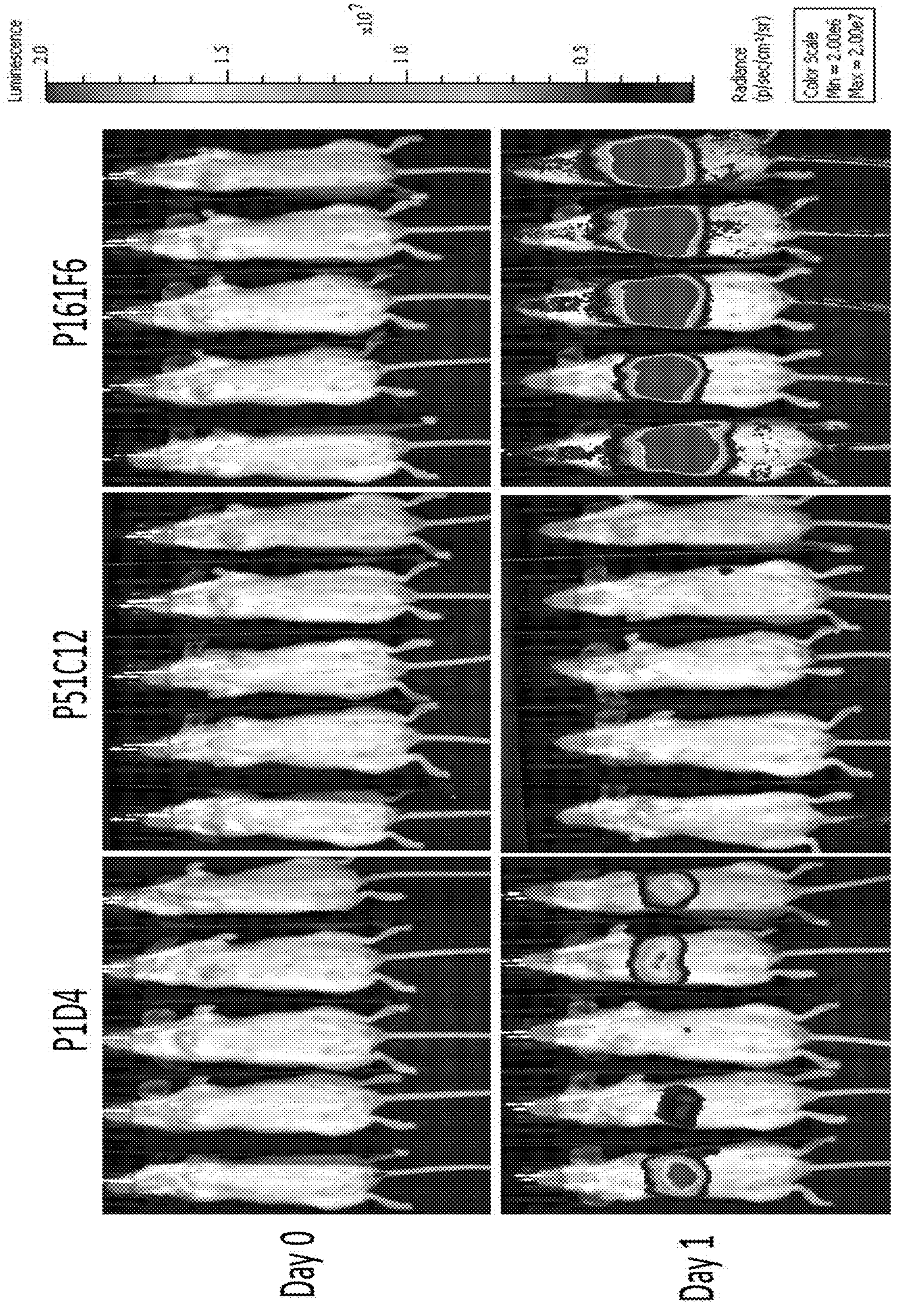
FIG. 9 shows in vivo Luciferase expression at 0 ("Day 0") and 18 hours ("Day 1") post injection. 10 μg modified mRNA encoding Luciferase were encapsulated by LNPs formulated with P1D4, P51C12, or P161F6 ionizable lipids. To detect luminescence, the mice were subsequently intraperitoneally injected with 6 mg Luciferin, a substrate of Luciferase, and imaged using IVIS (In Vivo Imaging System, Perkin Elmer) five minutes later.
Figure 10:
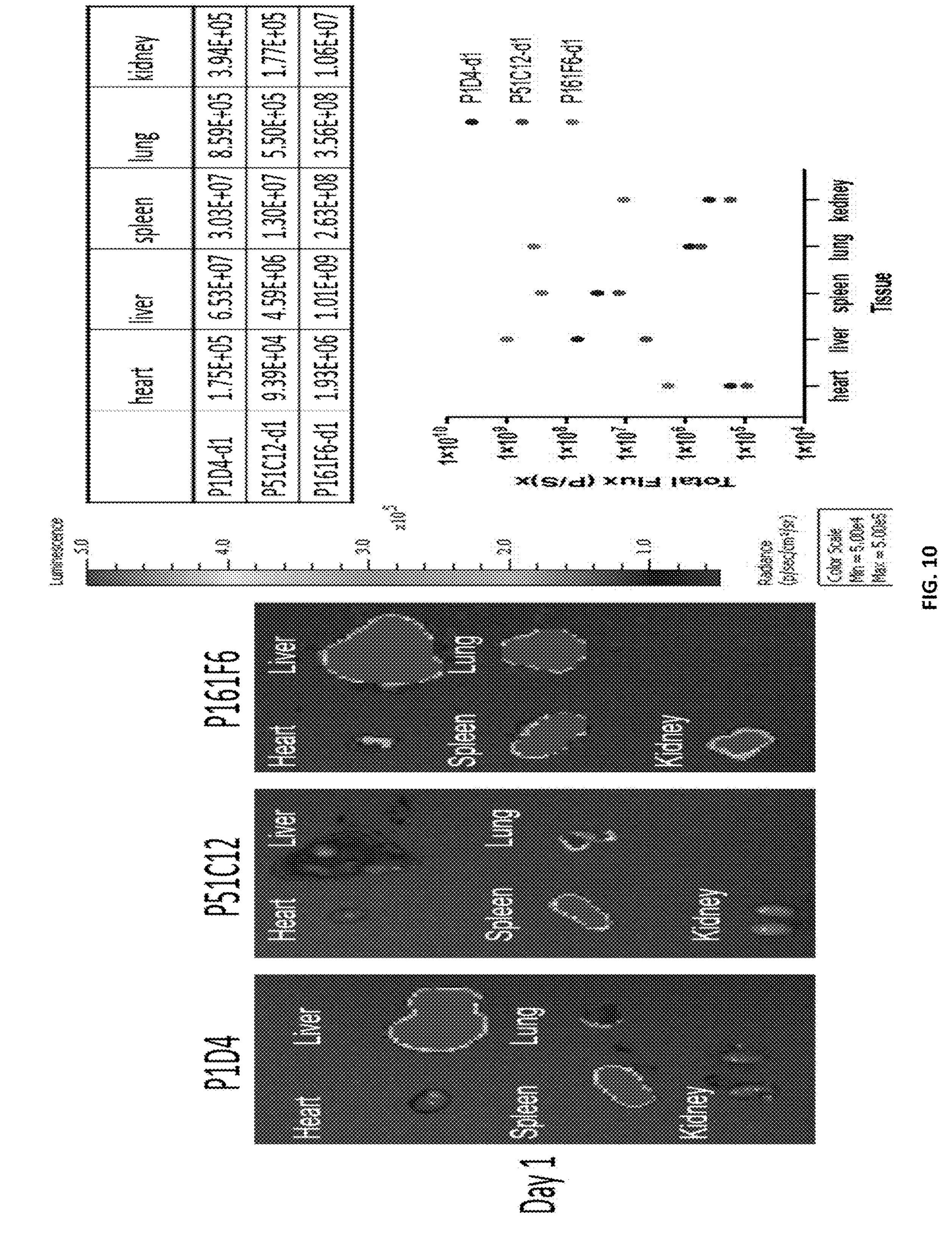
FIG. 10 shows in vivo Luciferase expression in the heart, liver, spleen, lung, and kidney of Balb/c mice at 18 hours ("Day 1") post injection of 10 μg modified mRNA encoding Luciferase, encapsulated by LNPs formulated with P1D4, P51C12, or P161F6 ionizable lipids. To detect luminescence, the mice were subsequently intraperitoneally injected with 6 mg Luciferin and imaged by IVIS five minutes later.

Balb/c mice were intraperitoneally injected with 10 mg modified mRNA encoding Luciferase, encapsulated by LNPs formulated with P1D4, P51C12, P161F6 ionizable lipids. To detect luminescence, the mice were subsequently injected with 6 mg Luciferin, a substrate of Luciferase and imaged by IVIS five minutes later. FIG. 9 shows in vivo Luciferase expression at 0 and 18 hours post injection ("1 Day"). FIG. 10 shows in vivo Luciferase expression in the heart, liver, spleen, lung, and kidney of Balb/c mice at 18 hours ("1 Day") post injection.

Figure 11A:
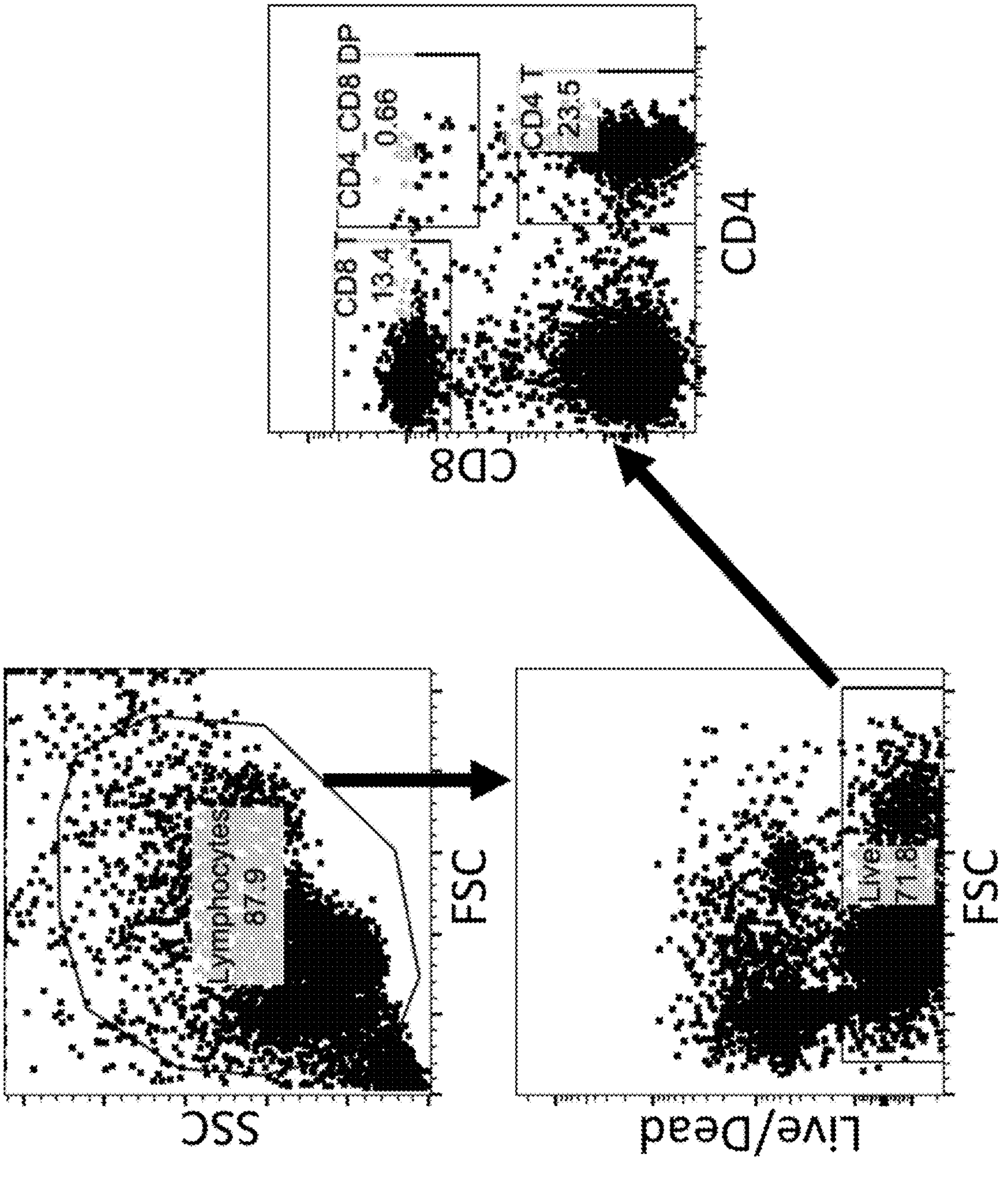
FIGS. 11A-11B show FACS of 10 μg modified mRNA encoding eGFP (enhanced green fluorescence protein) transfected in CD8, CD4, and CD4/CD8 double positive T cells (DP) of Balb/c mice. The modified mRNA encoding eGFP were delivered using LNPs formulated with P1D4 or P161F6 ionizable lipids (5 mice per group). A control group of 5 mice were injected with PBS. Balb/c mice were injected intravenously. All mice were sacrificed 18 hours after injection. Single cell splenocytes were prepared for FACS staining.
Figure 11B:
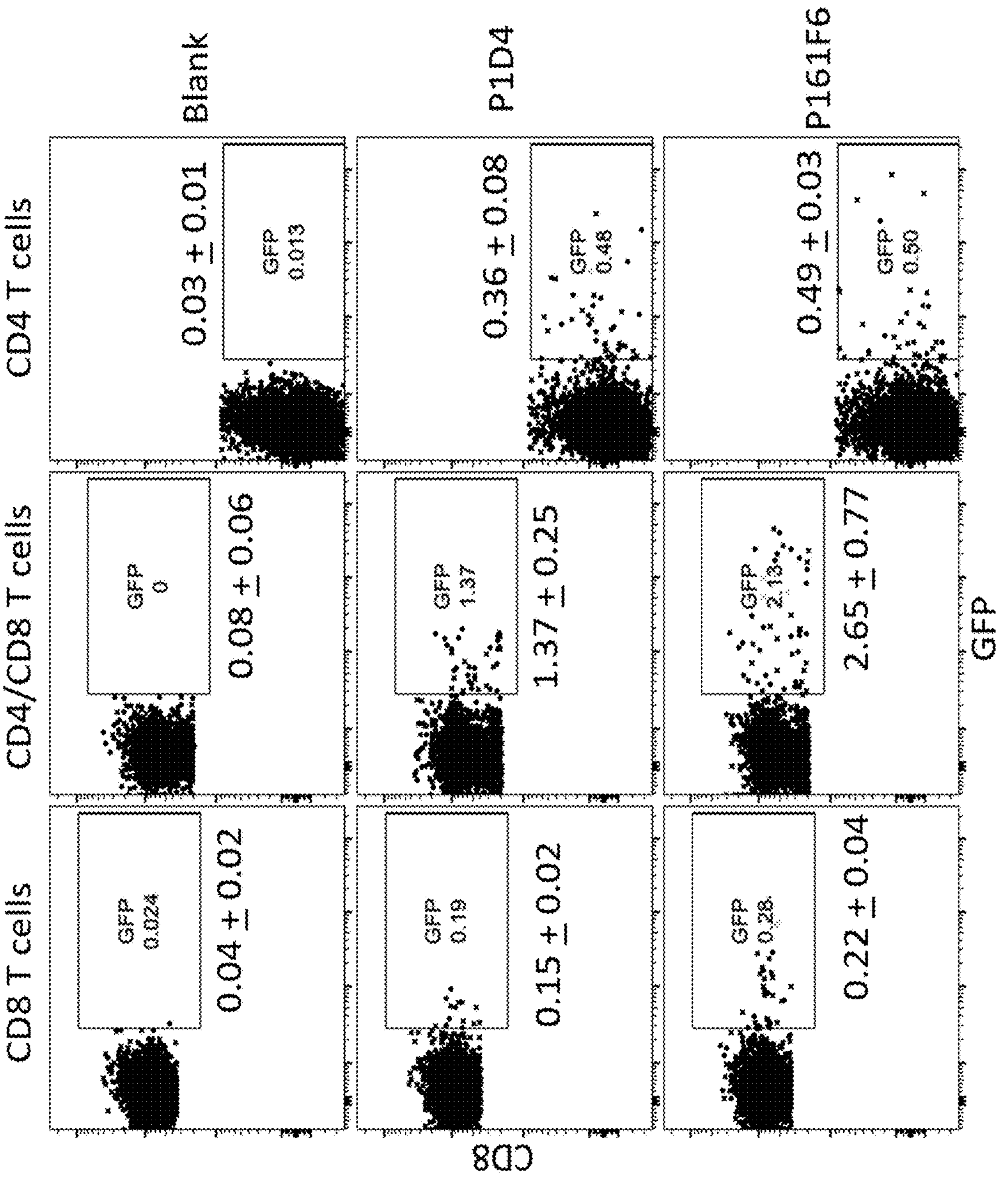
Figure 12:
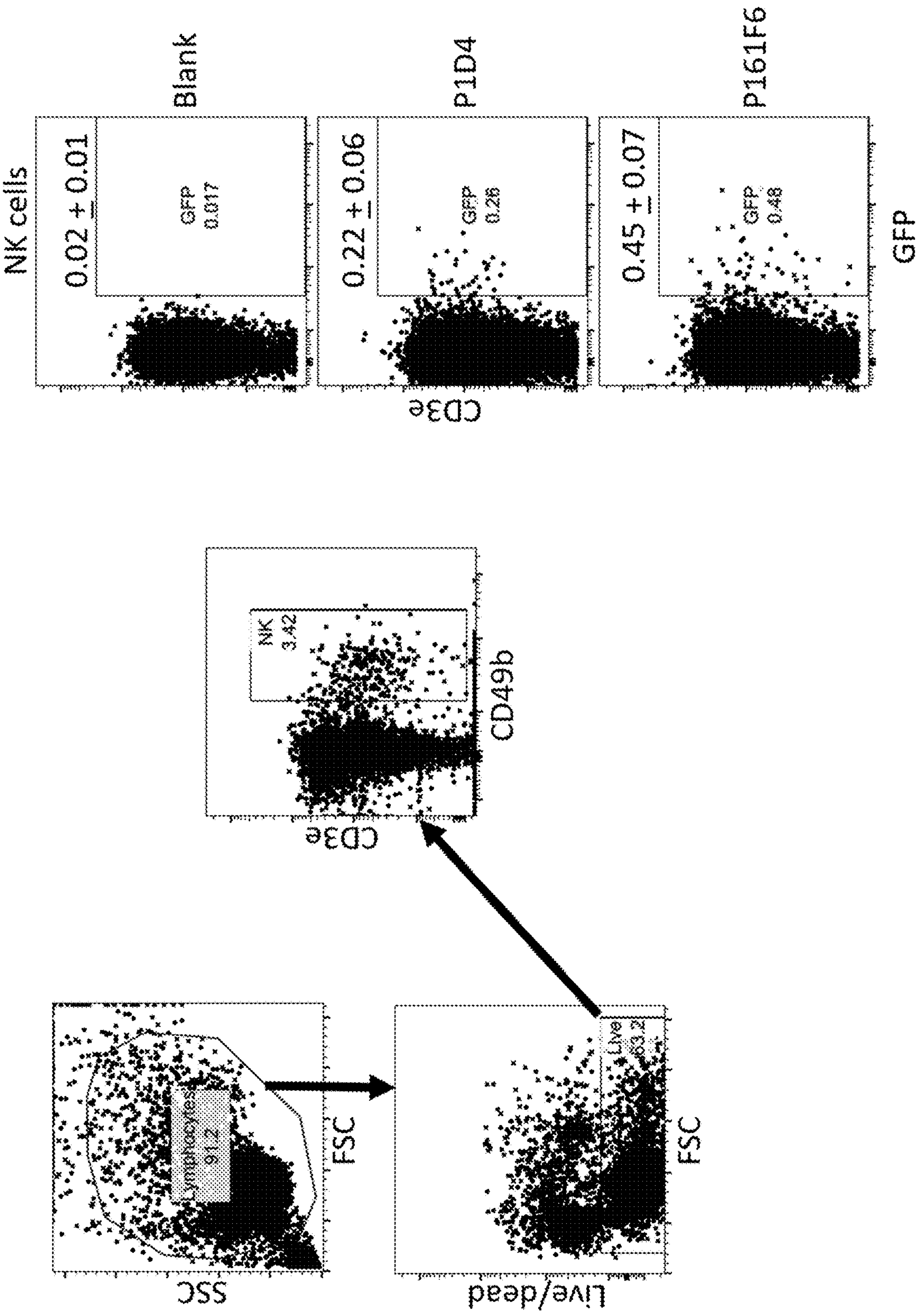
FIG. 12 shows FACS of 10 μg modified mRNA encoding eGFP (enhanced green fluorescence protein) transfected in NK cells of Balb/c mice. The modified mRNA encoding eGFP were delivered using LNPs formulated with P1D4 or P161F6 ionizable lipids (5 mice per group). A control group of 5 mice were injected with PBS. Balb/c mice were injected intravenously. All mice were sacrificed 18 hours after injection. Single cell splenocytes were prepared for FACS staining. The FACS gating strategies used are shown on the left, and percentages of transfected NK cells are shown on the right.
Figure 13:
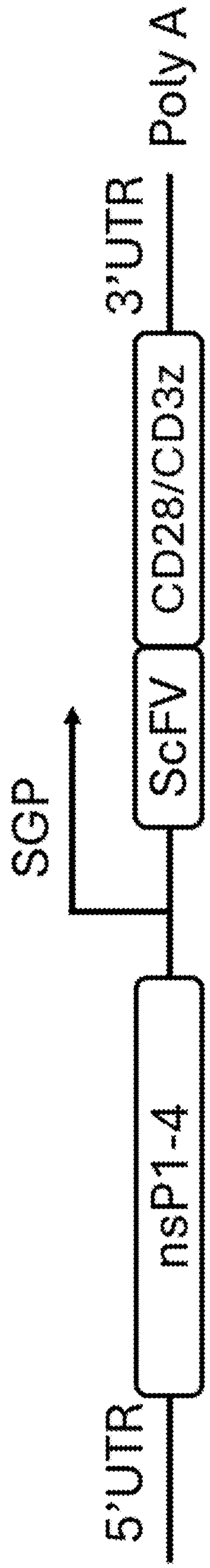
FIG. 13 shows a schematic of a sa-mRNA (top) wherein 5'UTR is a 5' untranslated region, nsP1-4 is a plurality of non-structural replicase domain sequences, SGP is a subgenomic promoter, CD8 is the hinge region of a CD8 alpha chain; CD28 is a CD28 activation domain; CD3z is a CD3 zeta cytoplasmic domain; scFv is a single-chain variable fragment, 3'UTR is a 3' untranslated region and poly-A is a a poly A tail.

Balb/c mice were intravenously injected with of 10 mg modified mRNA encoding eGFP. The modified mRNA encoding eGFP were delivered using LNPs formulated with P1D4 and P161F6 ionizable lipids in groups of 5 mice. A control group of 5 mice were injected with PBS. Balb/c mice were injected intravenously. The mice were sacrificed 18 hours after injection. Single cell splenocytes were prepared for FACS staining. FIG. 11A shows the FACS gating strategies used to detect transfection efficiency in CD8, CD4, and CD4/CD8 double positive T cells, and FIG. 11B shows percentages of transfected CD8, CD4, and CD4/CD8 double positive T cells (DP). FIG. 12 shows FACS gating strategies used on the left, and percentages of transfected NK cells are shown on the right.

The imaging and FACs results show that LNP formulated with ionizable lipids of the disclosure can efficiently transfect the spleen; endogenous CD4, CD8, and CD4/CD8 T cells; and NK cells in vivo. As the data show, each of P1D4 and P161F6 LNPs effectively transfected the spleen, making very strong signals while delivering Luciferase mRNA. P1D4 and P161F6 LNP could transfect endogenous CD4, CD8, CD4/CD8 T cells as well as NK cell.

Example 6: Delivery and In Vivo Expression of Modified mRNA to T and NK Cells LNP formulated using the ionizable lipids of the disclosure were used to deliver modified RNA encoding reporter genes to determine the transfection efficiency of exemplary ionizable lipids of the disclosure in immune cells and organs. Injections of mice with LNP-encapsulated modified mRNA encoding either Luciferases or eGFP were performed. In experiments with payloads encoding Luciferase mRNA, spleen expression was detected, which is an important organ with abundant pan T cells. In experiments with payloads encoding eGFP mRNA, transfection of primary T cells in vivo by FACS analysis was performed.

Example 7: Delivery and In Vitro Expression of Modified mRNA Encoding CAR and scFv LNP formulated using P6A2 (an ionizable lipid of the disclosure) was used to deliver modified RNA comprising a GOI encoding scFv and CAR to determine the level of GOI expression in human cells, specifically Human Embryonic Kidney (HEK) 293 cells (which are a human anti-CD19 stable cell line).

HEK293 cells were transfected with SV1-LNP encapsulating SVP410, SVP411, SVP412, and SVP413 mRNA (all encoding CAR recognizing CD19). One day post transfection, the HEK293 cells were stained with DAPI (Live/dead) and Human CD19 conjugated with phycoerythrin (PE). In experiments with payloads encoding scFv and CAR, transfection of HEK293 cells in vitro by FACS analysis was performed and compared to untransfected cells stained with DAPI (Live/dead) and Human CD19 conjugated with phycoerythrin (PE) (Neg-st) and unstained, unconjugated and untransfected cells (Neg) as shown in FIG. 15.

Figure 17:
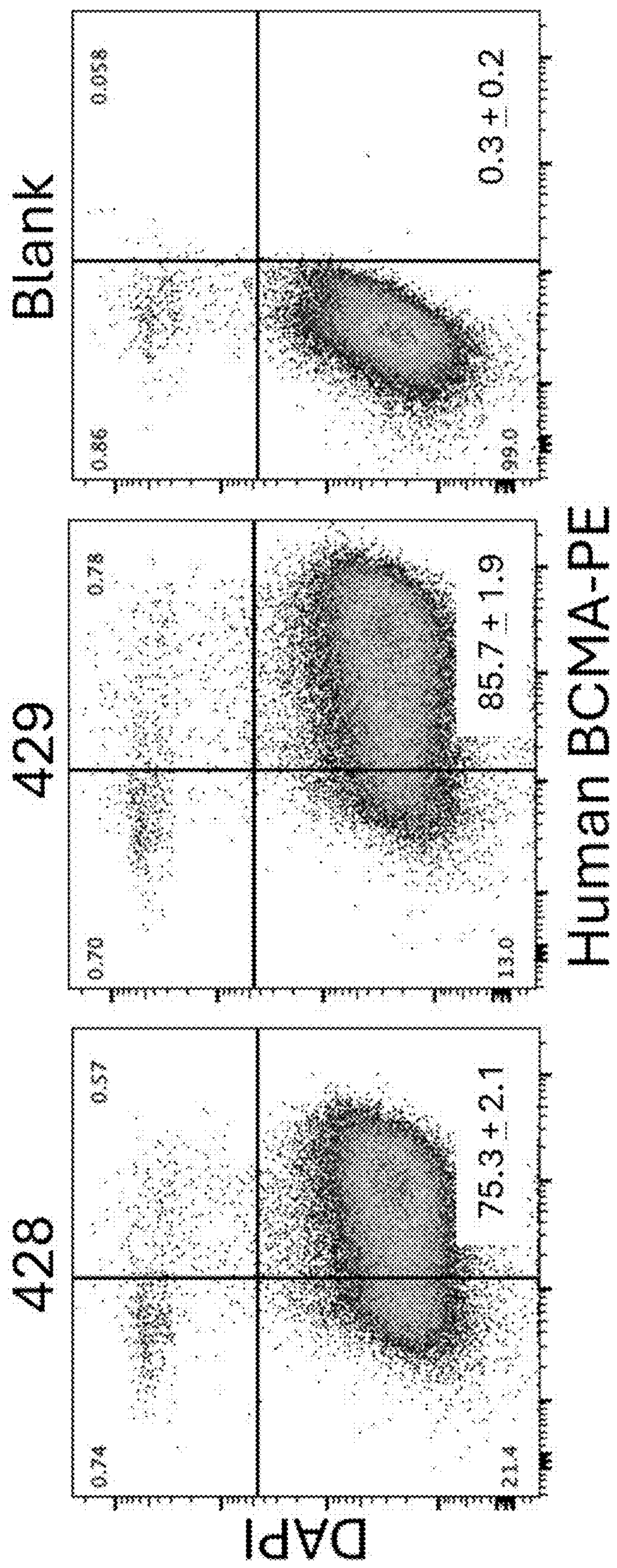
FIG. 17 shows FACS of HEK 293 cells transfected with modified mRNA encoding a nanobody and human CAR (SV428) or an scFv and human CAR (SV429), delivered using a LNP of the disclosure and stained with DAPI (Live/dead dye) and Human BCMA conjugated with PE. Human BCMA-PE is shown on the X-axis and DAPI is shown on the Y-axis.

HEK293 cells were transfected with SV1-LNP encapsulating modified mRNA SV428 (encoding SEQ ID NO: 42 and a SV-human CAR backbone) or SV429 (encoding SEQ ID NO: 43 and a SV-human CAR backbone). One day post transfection, the HEK293 cells were stained with DAPI (Live/dead) and Human CD19 conjugated with phycoerythrin (PE). In experiments with payloads encoding scFv and CAR, transfection of HEK293 cells in vitro by FACS analysis was performed and compared to a blank sample. FIG. 17 shows human BCMA-PE on the X-axis and DAPI on the Y-axis.

Example 8: In Vitro Efficacy of Modified mRNA Encoding CAR and ScFv

LNP formulated using PD14 (SV2 LNP) was used to deliver modified RNA comprising a GOI encoding scFv and CAR to determine the efficacy of the CAR and ScFv payload of the disclosure (mRNA-CD19-CAR) in tumor cells.

Figure 16:
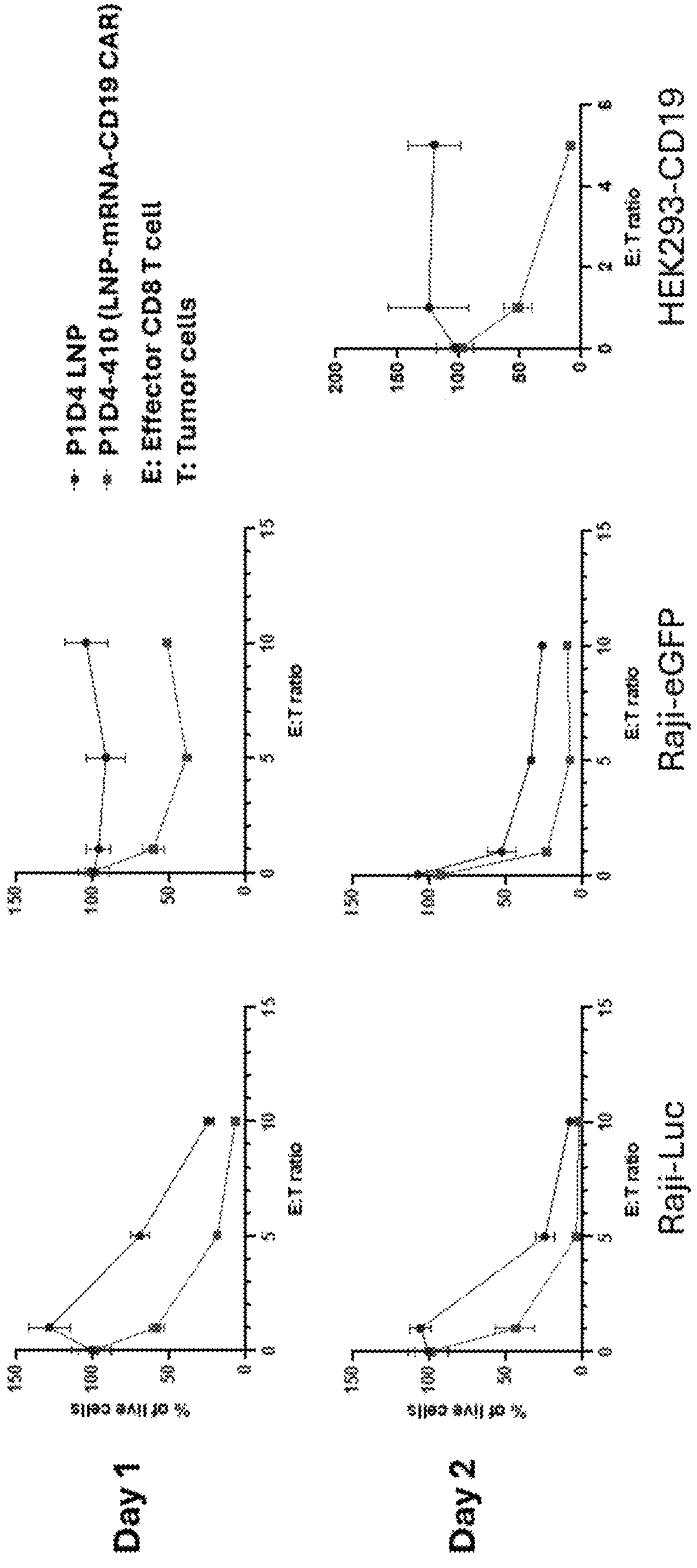
FIG. 16 shows the ratio of human primary T cells and tumor cells on day 1 (top row) and on day 2 (bottom row), wherein the human primary T cells were activated and transfected with no payload or a mRNA comprising a GOI encoding scFv and CAR and the activated and transfected human primary T cells were incubated with a tumor cell line (Raji-Luc, Raji-eGFP or HEK293-CD19).

Human primary T cells (effector CD8 T cells) were activated and transfected with SV2 LNP with no payload or SV2 LNP encapsulating modified mRNA comprising a GOI encoding scFv and CAR. At day 1 post transfection, the transfected cells were incubated with three cancer cell lines: Firefly Luciferase Raji Cells (Raji-Luc), enhanced GFP Raji Cells (Raji-eGFP), and HEK293. At day 1 and 2 post incubation, the cells were analyzed using flow cytometry. FIG. 16 shows the ratio of human primary T cells and tumor cells (Raji-Luc and Raji-eGFP) on day 1 in the top row and the ratio of human primary T cells and tumor cells (Raji-Luc, Raji-eGFP and HEK293) on day 2 on the bottom row.

Example 9: In Vivo Transfection Efficacy of Splenic Tropic LNP

Figure 18:
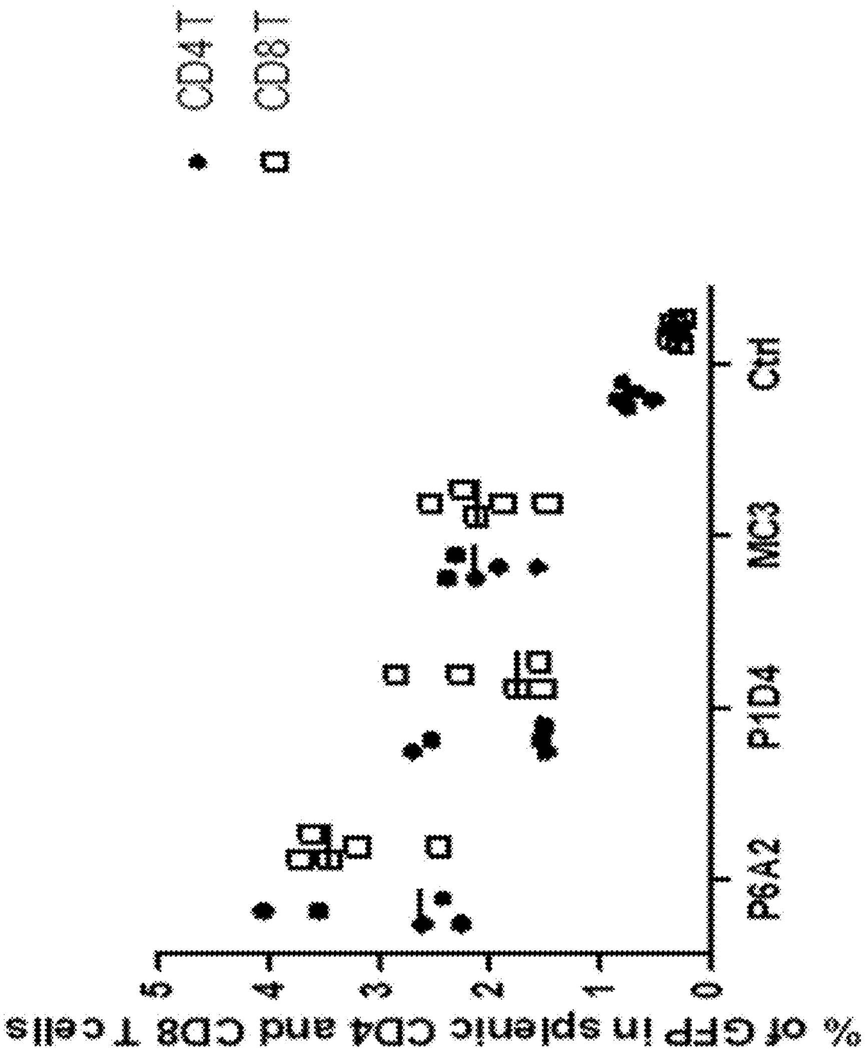
FIG. 18 shows a graph of GFP expression (Y-axis) in CD4 and CD8 expressing T cells transfected with LNPs comprising P6A2, P1D4 or MC3 (X-axis) compared to a negative control.

Balb/c mice (5 mice/group) were intravenously administered 10 μg of LNP comprising P6A2, P1D4 or MC3 LNP encapsulating modified RNA encoding eGFP. One day post injection, the mice were sacrificed and spleens were isolated. Single cell suspensions of splenocytes were stained with 7-AAD (live/dead) and gated for CD3F, CD4 and CD8 to determine the percent of GFP expression in CD4 and CD8 T cells. FIG. 18 shows a graph of GFP expression (Y-axis) in CD4 and CD8 expressing T cells transfected with LNPs comprising P6A2, P1D4 or MC3 (X-axis) compared to a negative control.

In addition, it is to be understood that any particular aspect of the present disclosure that falls within the prior art may be explicitly excluded from any one or more of the claims. Since such aspects are deemed to be part of the whole of the present disclosure, any part of the whole disclosure may be excluded even if the exclusion is not set forth explicitly herein.

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A method of delivering a payload to immune cells in vivo comprising administering an LNP encapsulating a payload encoding at least one polypeptide of interest to a subject, wherein the polypeptide of interest is an antigen receptor or an antibody, wherein the payload is a self-amplifying mRNA comprising a nucleic acid sequence from 5' to 3':

a) 5'UTR-nsP-L-SGP-LP-GOI-L-3'UTR-PolyA,
b) 5'UTR-nsP-SGP-LP-GOI-L-3'UTR-PolyA,
c) 5'UTR-nsP-L-SGP-LP-GOI-3'UTR-PolyA, or
d) 5'UTR-nsP-SGP-LP-GOI-3'UTR-PolyA wherein
5'UTR is a 5' untranslated region,
nsP is a plurality of non-structural replicase domain sequences,
L is a linker,
SGP is a subgenomic promoter,
3'UTR is a 3' untranslated region,
poly-A is a 3' poly-adenylated tail (poly-A tail),
LP is a leading peptide, and
wherein the GOI is one or more genes of interest encoding the polypeptide of interest;
wherein the 5'UTR comprises nucleic acid sequence ATAGG and/or the SGP is SEQ ID NO: 10, 11, or 31 and/or the L is SEQ ID NO: 12, 13, 14, or 15 and/or the 3'UTR is SEQ ID NO: 16, 17, 18, or 19; and
wherein the polypeptide of interest is:
a) a nanobody (Nb); or
b) an antigen receptor (AR); or
c) scFv-AR, wherein, scFv is a single-chain variable fragment; or
d) an scFv-CAR having the structure VH-LK-VL-MyC-CD8-CD28-CD3z, wherein:
VH is an immunoglobulin heavy chain variable region,
LK is a linker,
VL is an immunoglobulin light chain variable region,
MyC is a Myc tag,
CD8 is a CD8 alpha chain hinge region,
CD28 is a CD28 activation domain, and
CD3z is a CD3 zeta cytoplasmic domain; or
e) an scFv-CAR having the structure VH-LK-VL-CD8-CD28-CD3z, wherein:
VH is the immunoglobulin heavy chain variable region,
LK is the linker,
VL is the immunoglobulin light chain variable region,
CD8 is the CD8 alpha chain hinge region,
CD28 is the CD28 activation domain, and
CD3z is the CD3 zeta cytoplasmic domain.

2. The method of claim 1, wherein the antigen receptor is a chimeric antigen receptor (CAR), T-cell receptor (TCR), growth factor receptor (GFR), or hormone receptor (HR).

3. The method of claim 1, wherein the LNP comprises at least one lipid compound selected from:

(I)

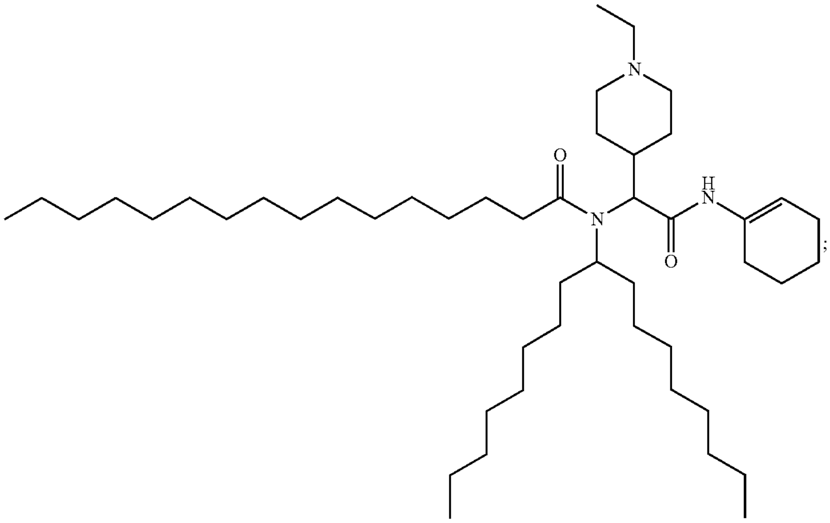

;

-continued
(II)
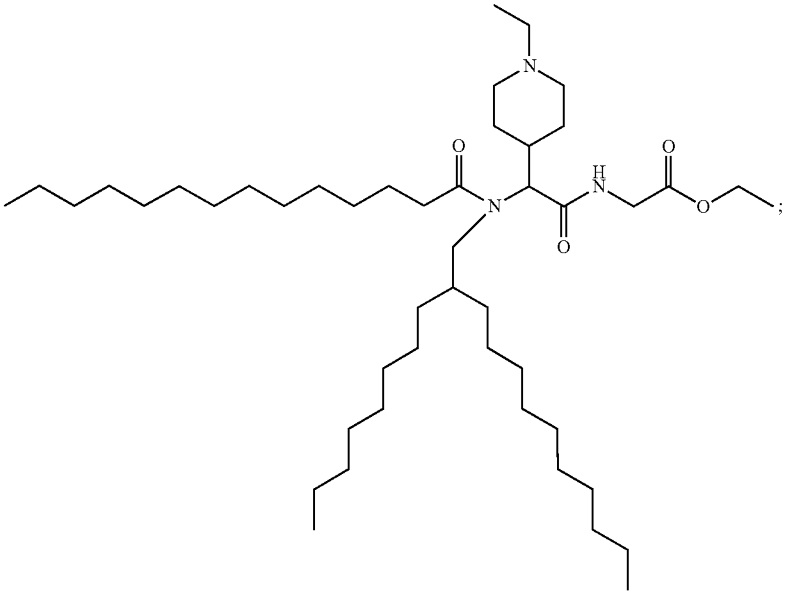
(III)
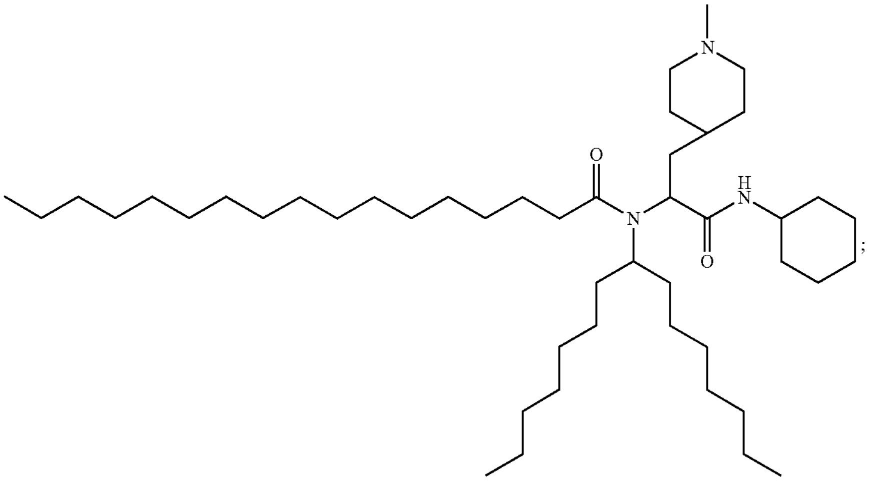
(IV)
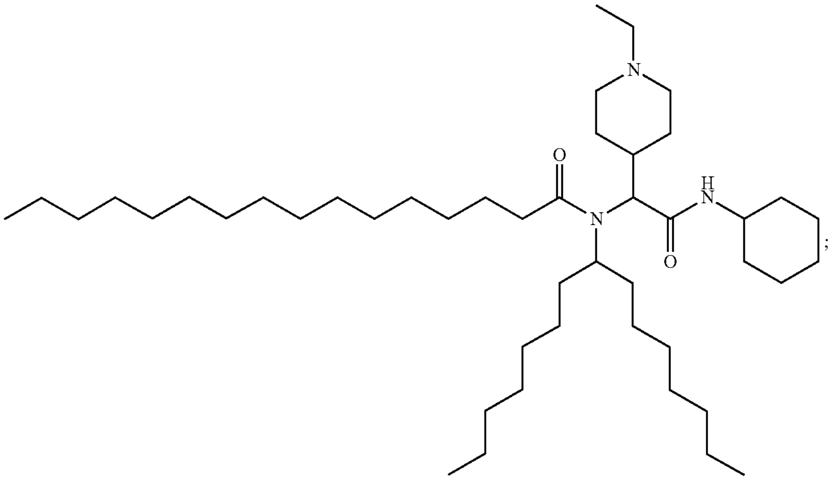

-continued
(V)
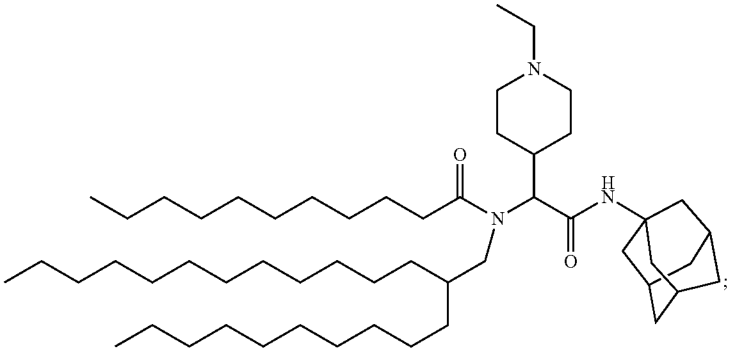
(VI)
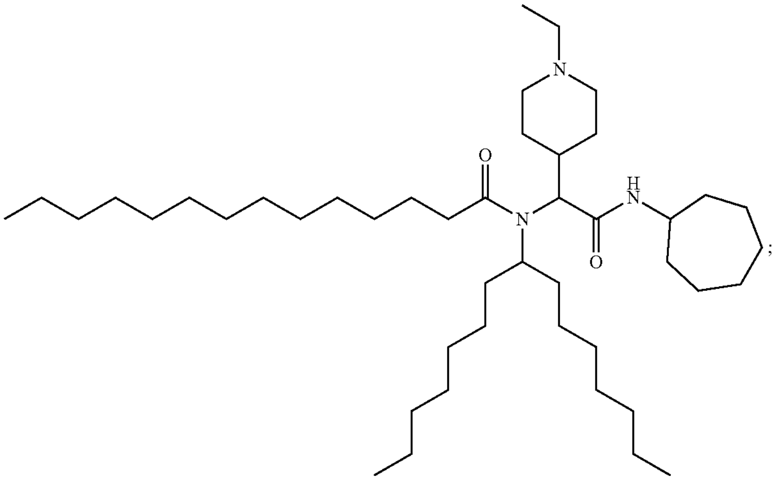
(VII)
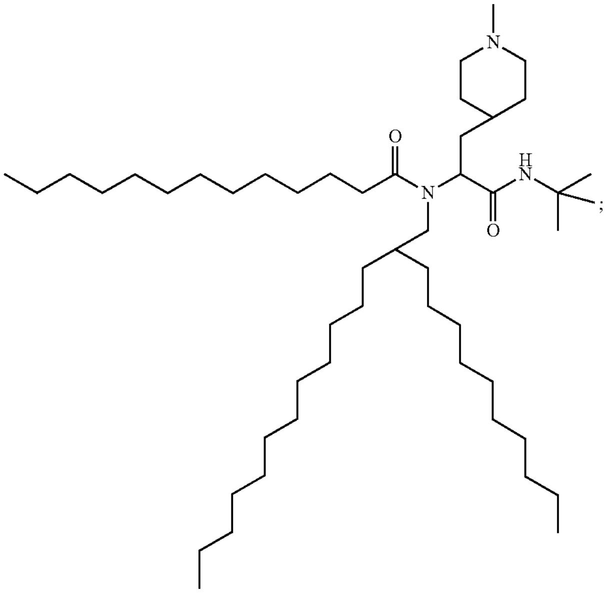

-continued
(VIII)
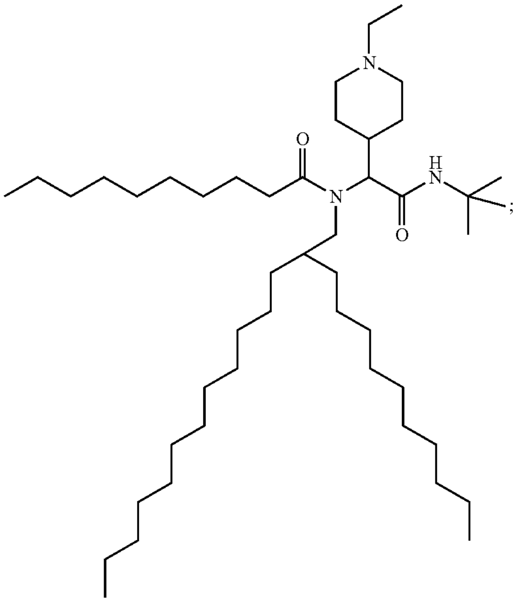
(IX)
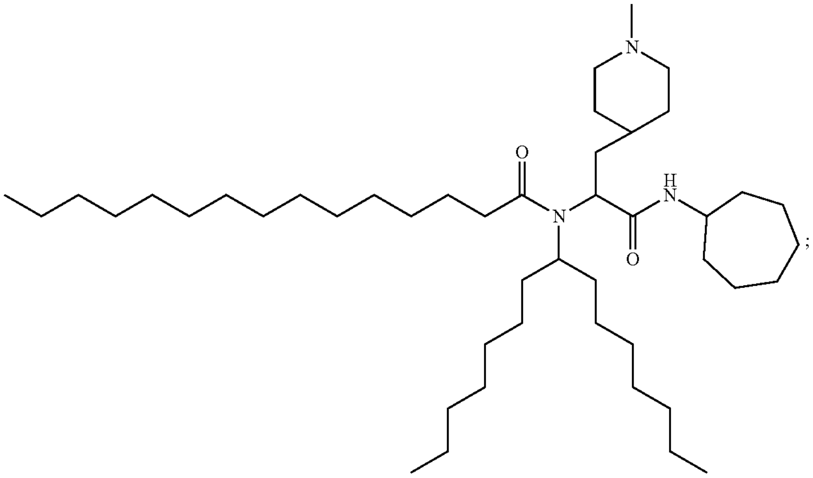
(X)
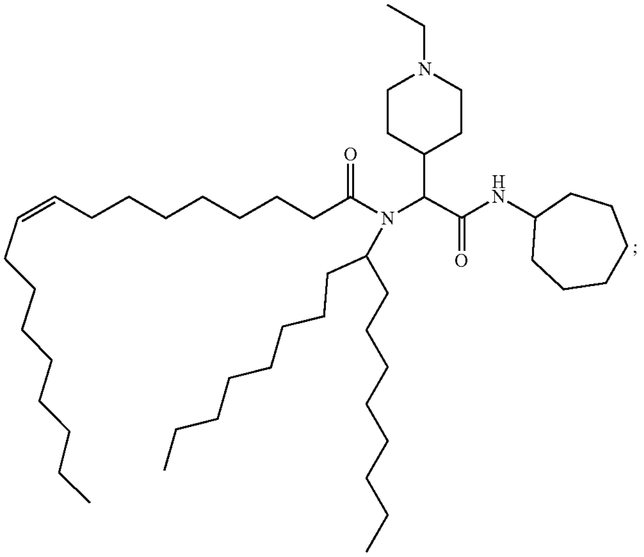

-continued
(XI)
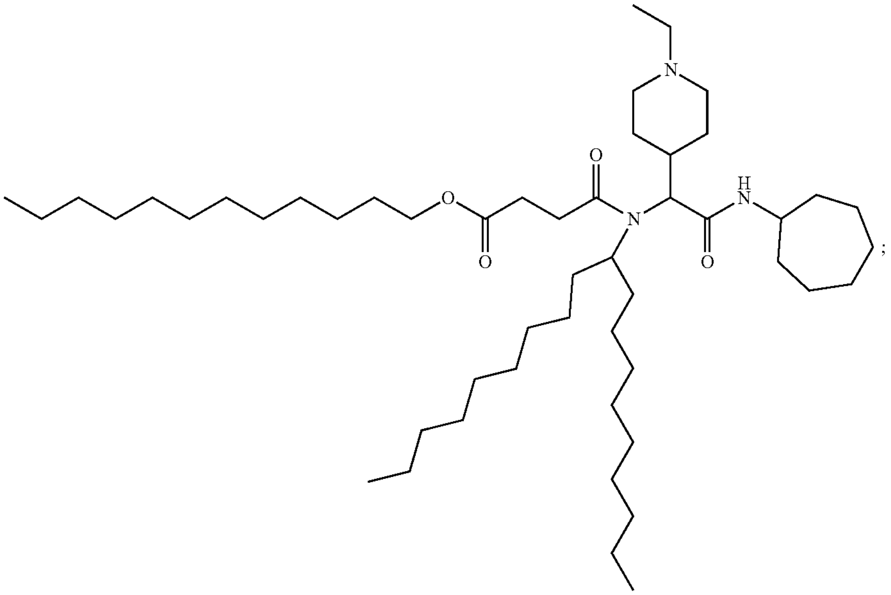
(XII)
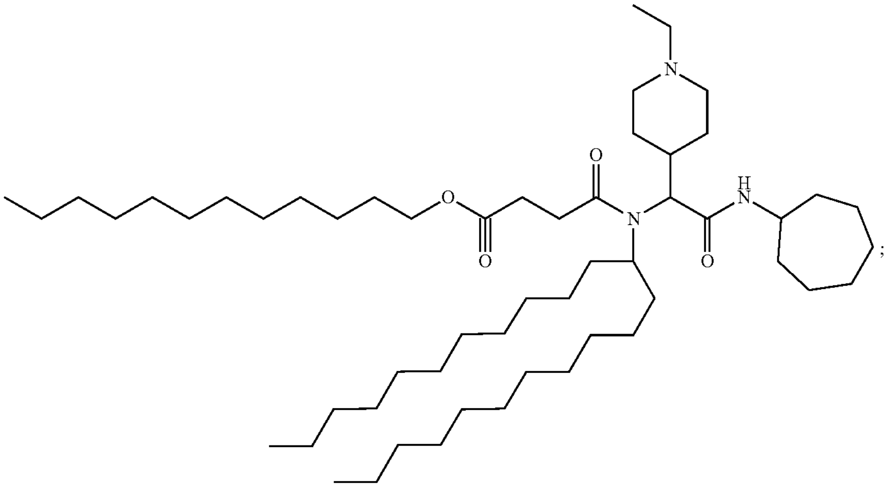
(XIII)
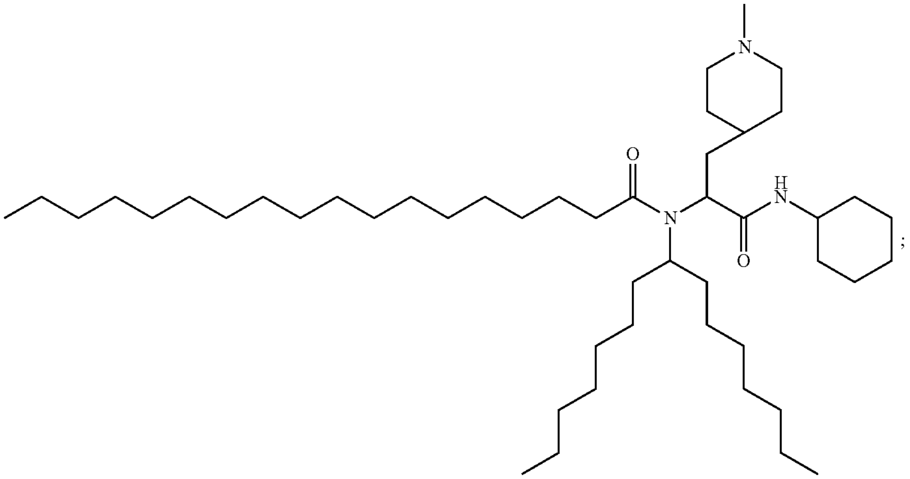

-continued
(XIV)
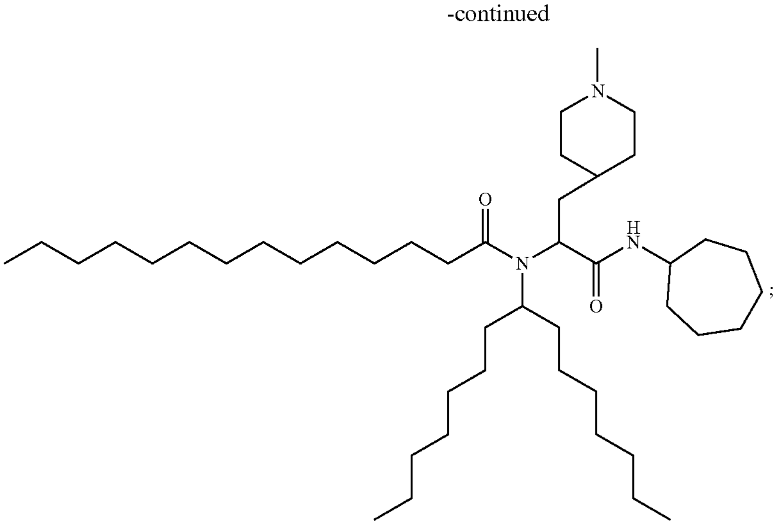
(XV)
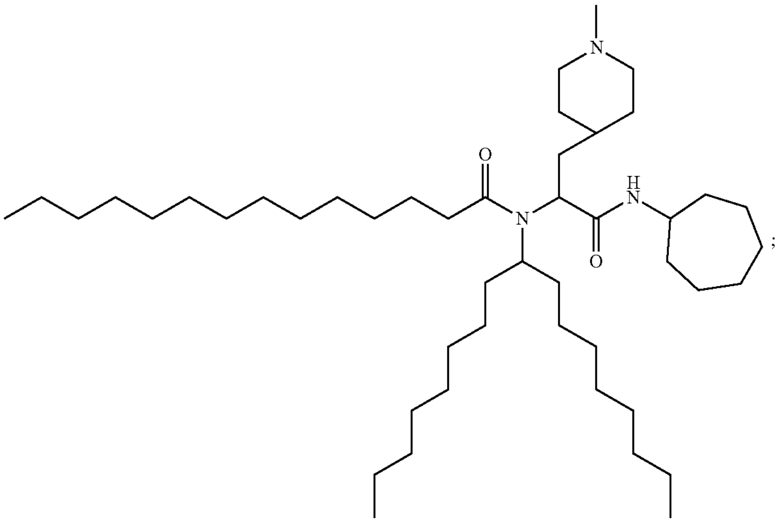
(XVI)
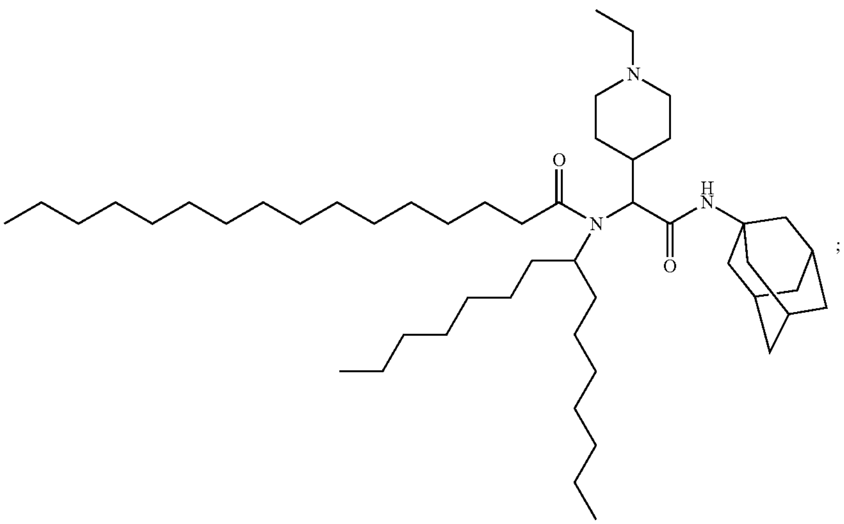

-continued
(XVII)
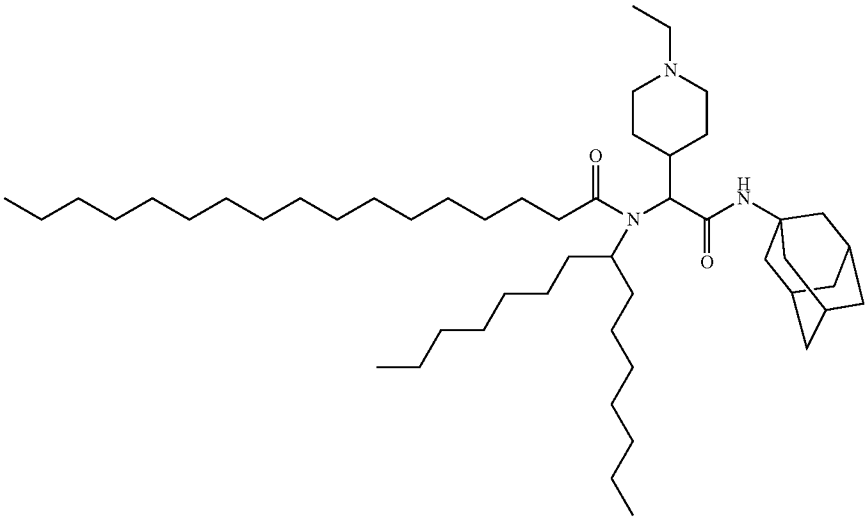
;
(XVIII)
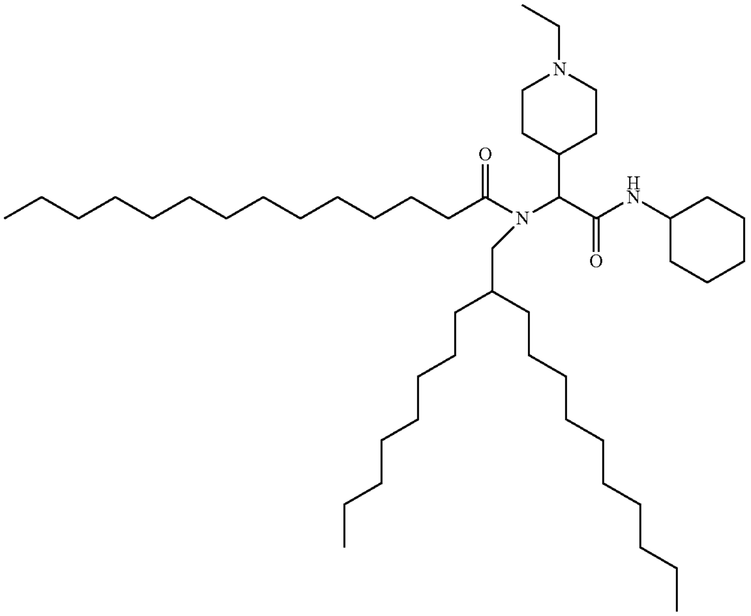
;

-continued
(XIX)
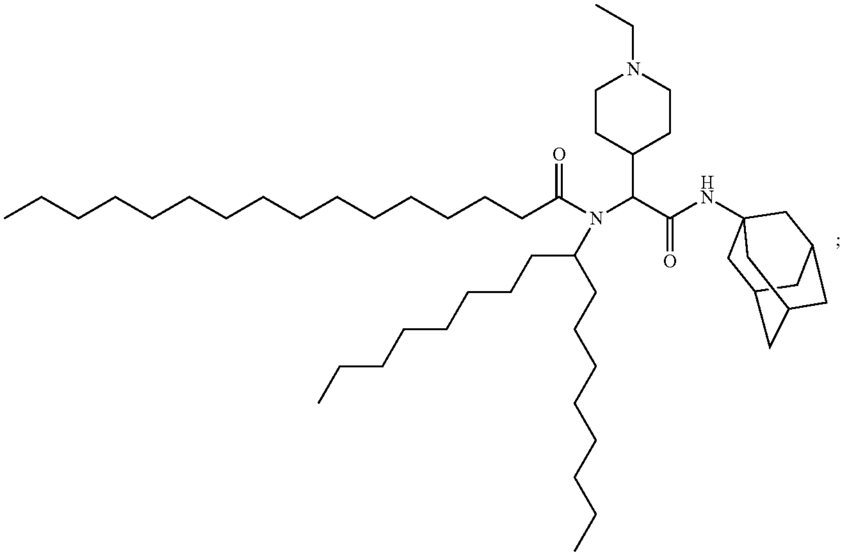
(XX)
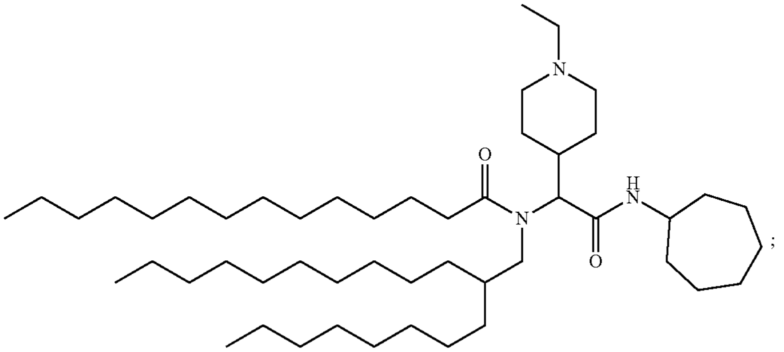
(XXI0
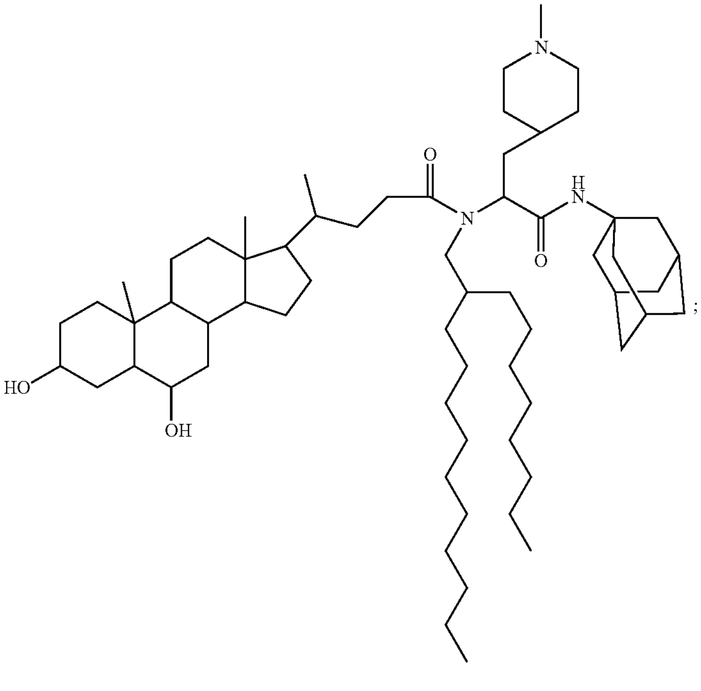

-continued
(XXII)
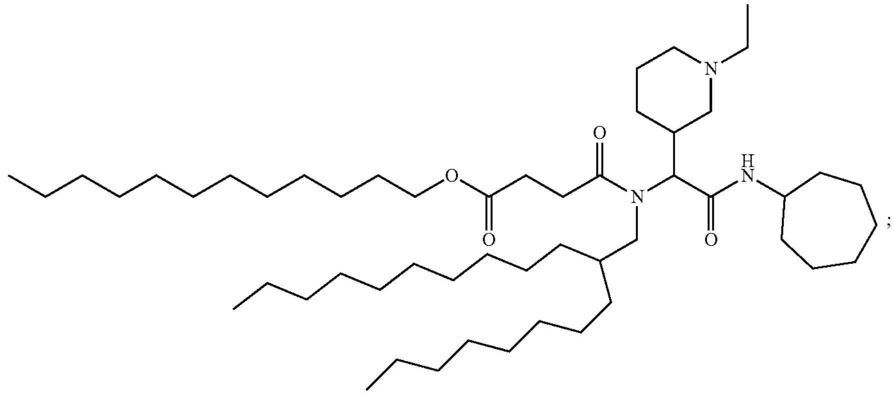
;
(XXIII)
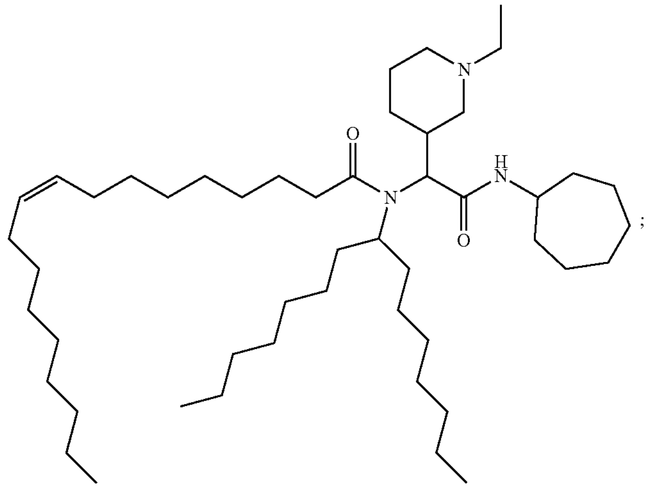
;
(XXIV)
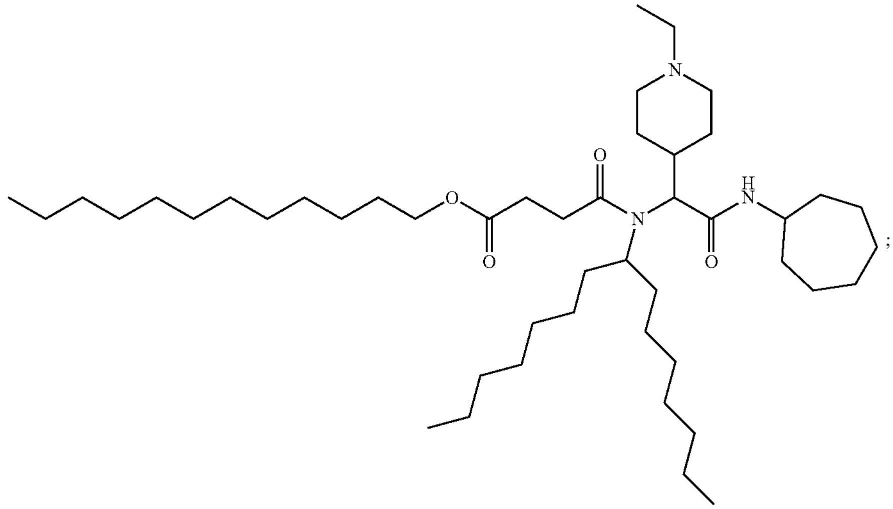
;

-continued
(XXV)
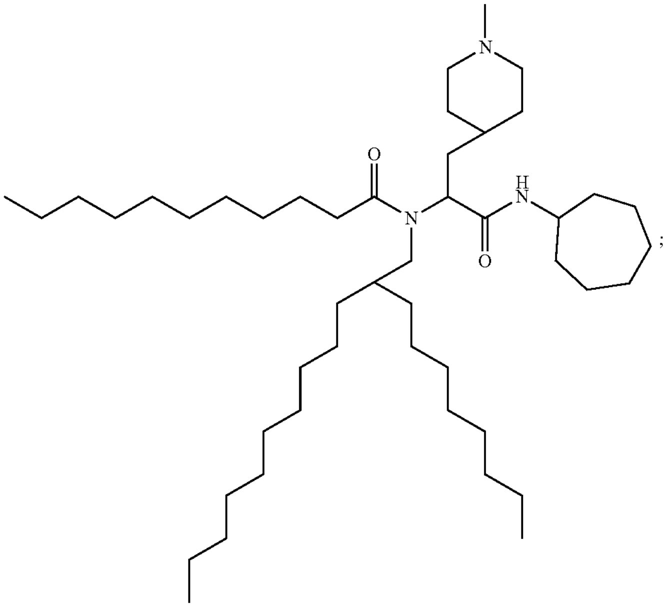
(XXVI)
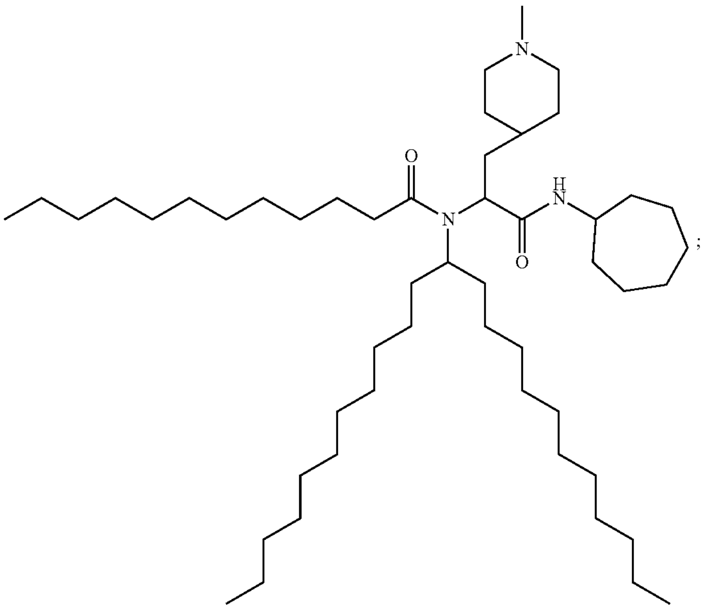

(XXVII)
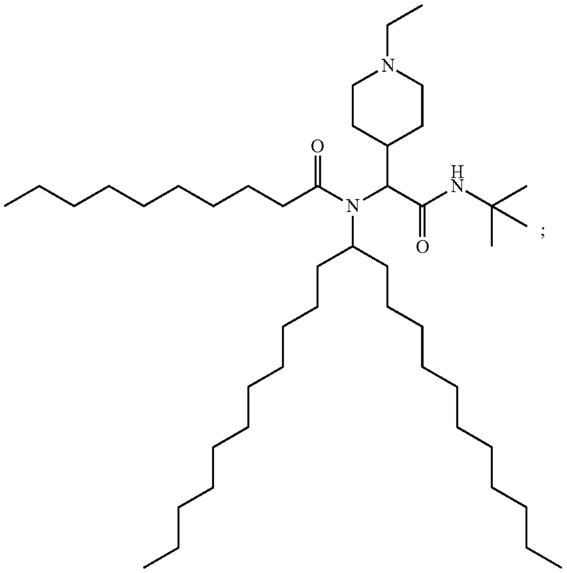
;
(XXVIII)
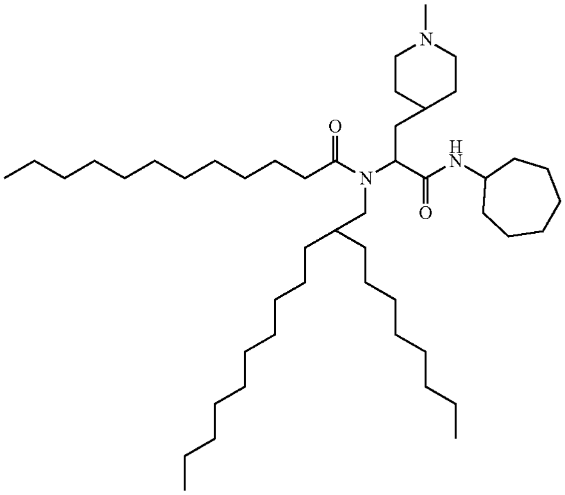
;
(XXIX)
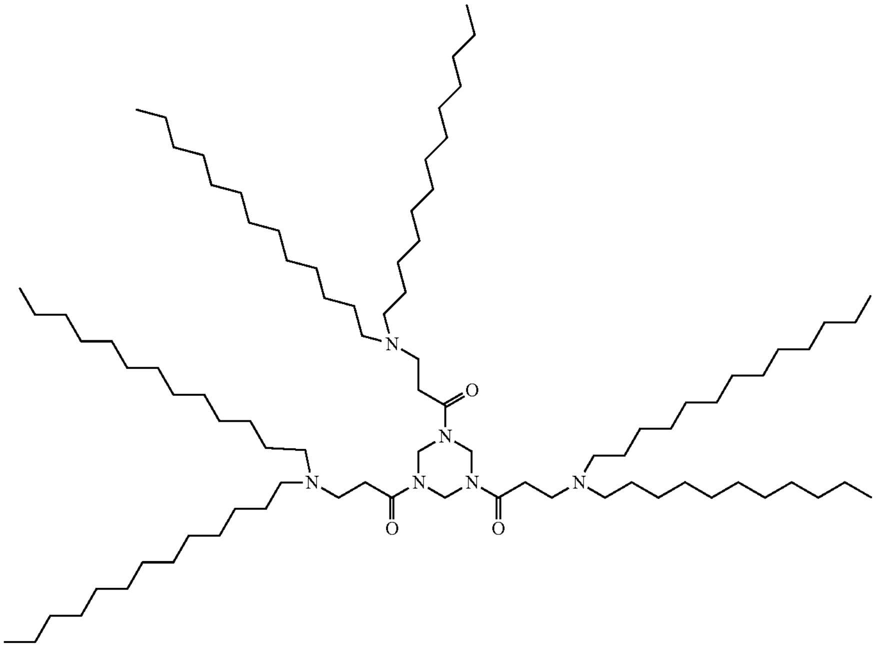
;

-continued
(XXX)
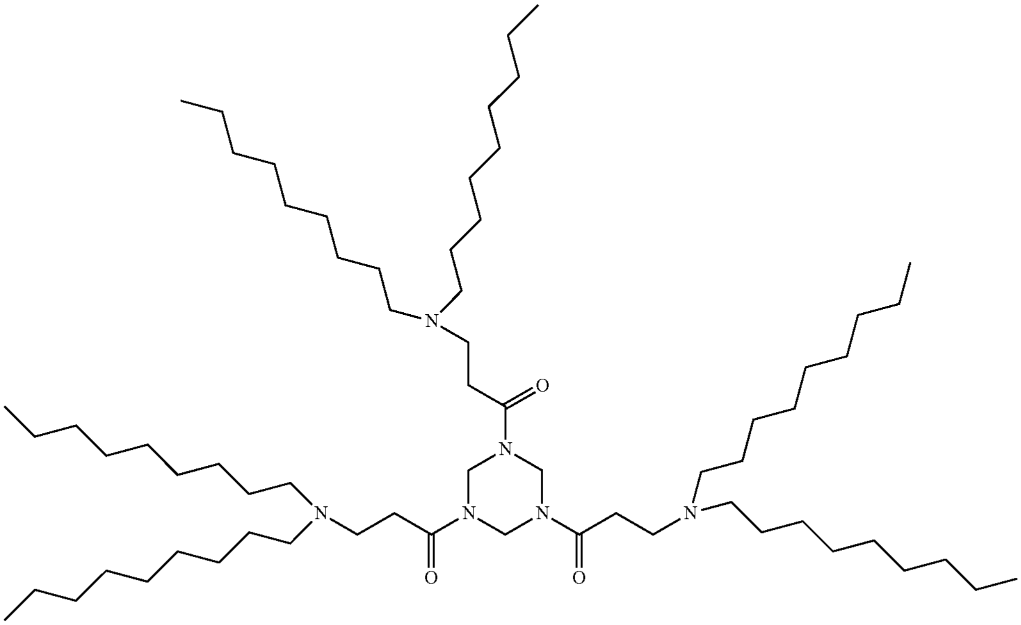
;
(XXXI)
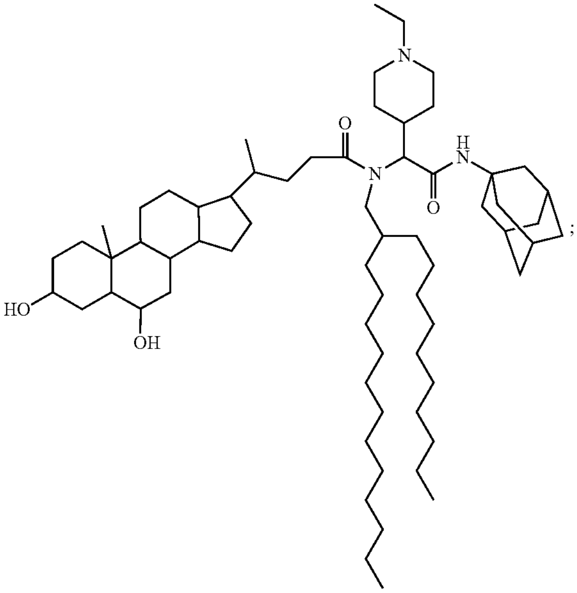
;
(XXXII)
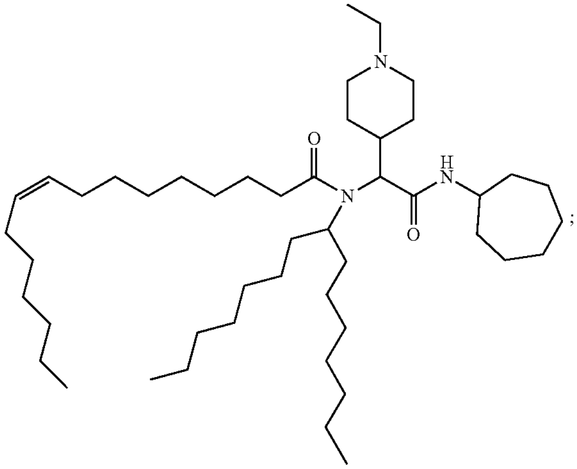
;

-continued
(XXXIII)
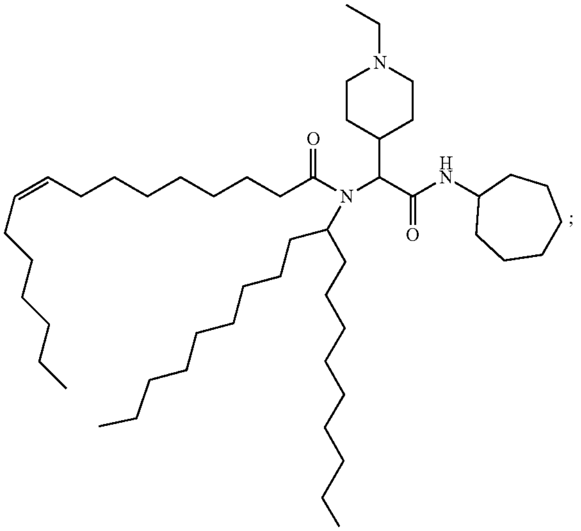
(XXXIV)
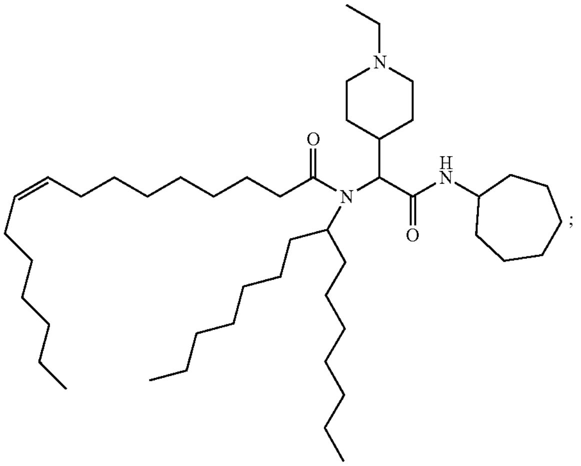
(XXXV)
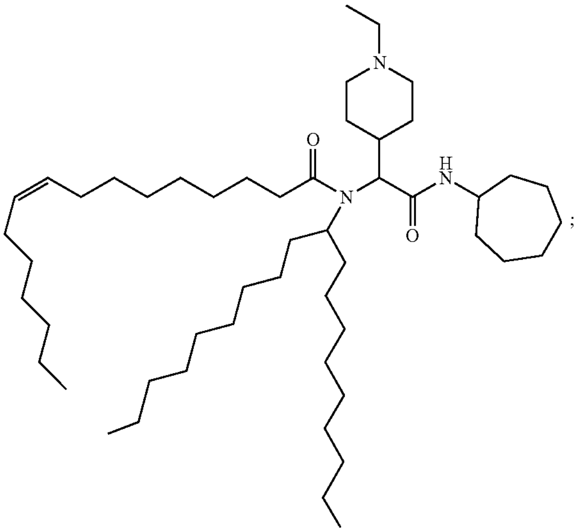
(XXXVI)
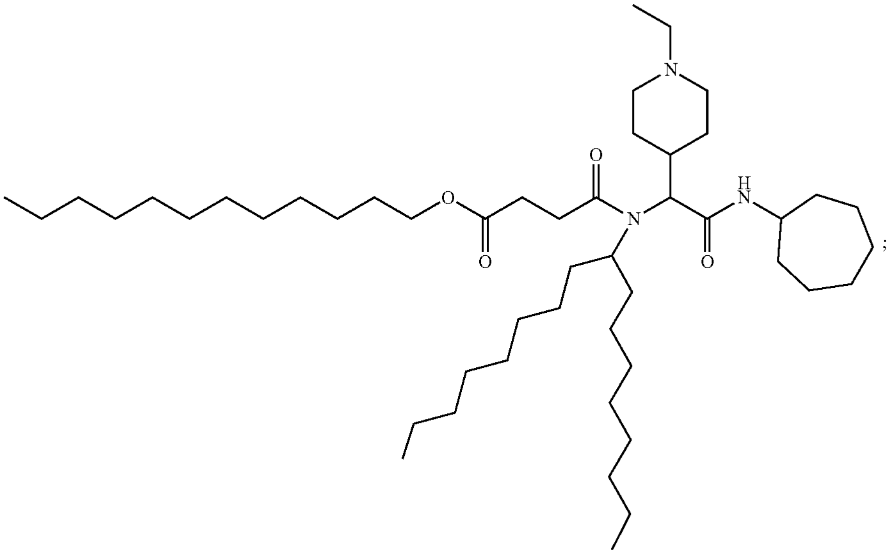

-continued
(XXXVII)
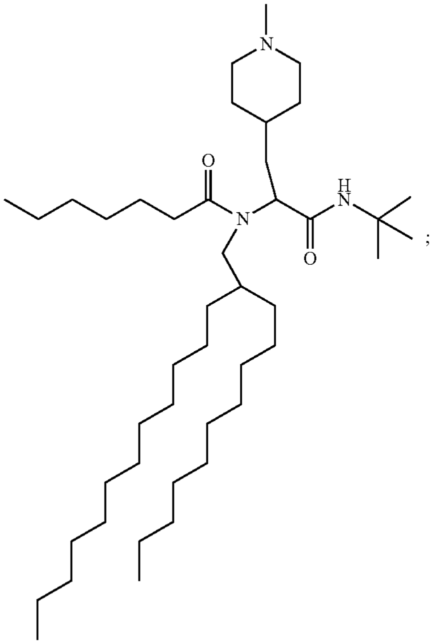
(XXXVIII)
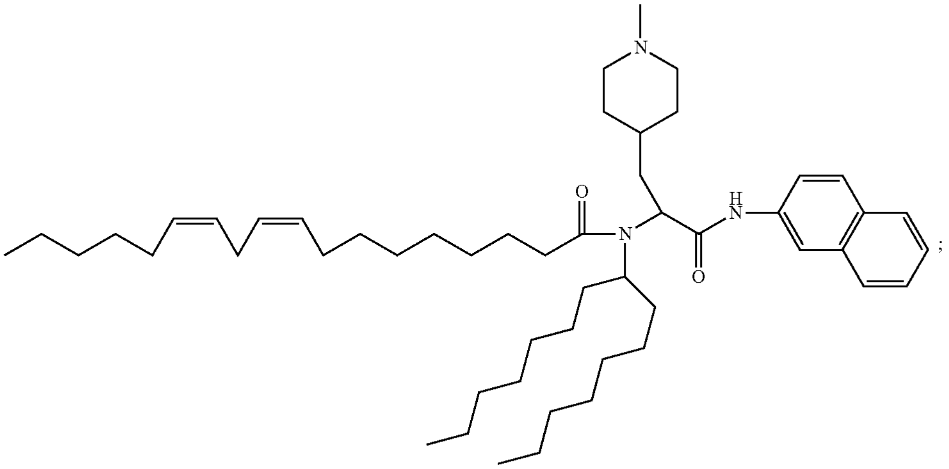
(XXXIX)
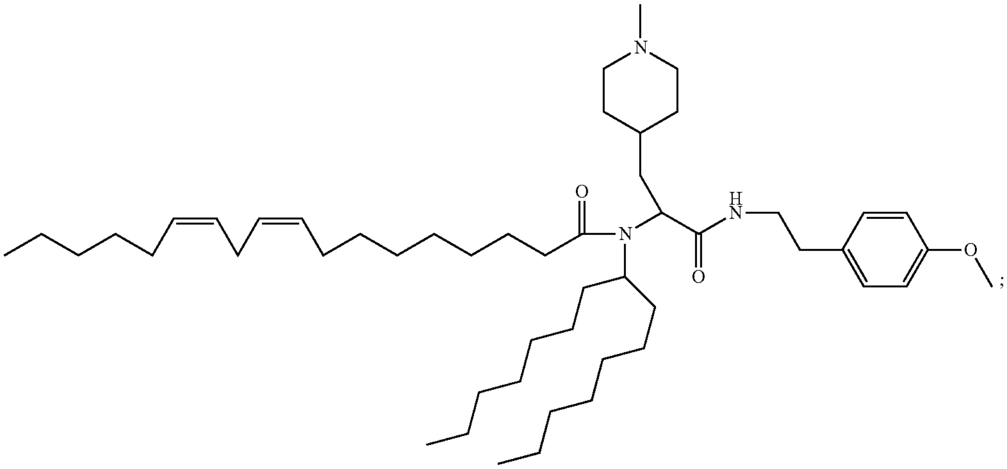

-continued
(XL)
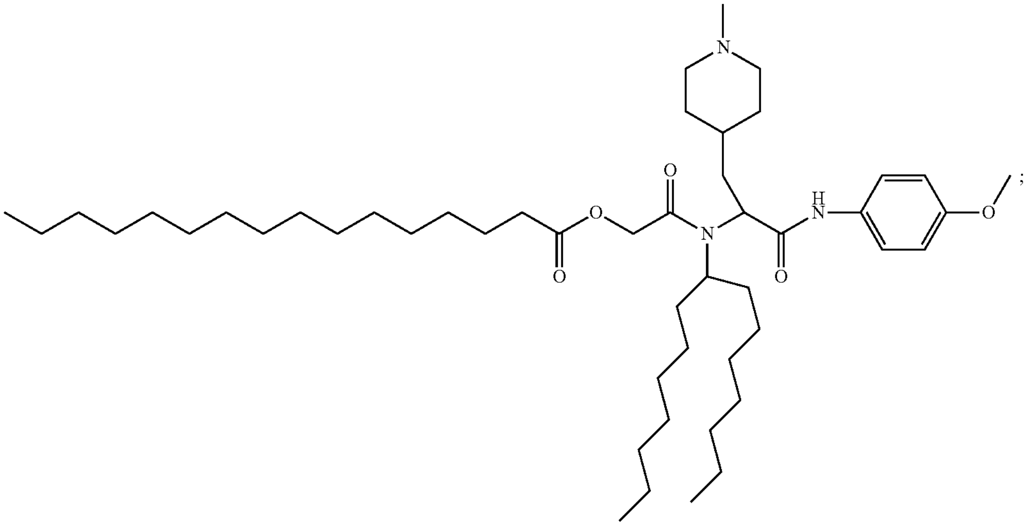
(XLI)
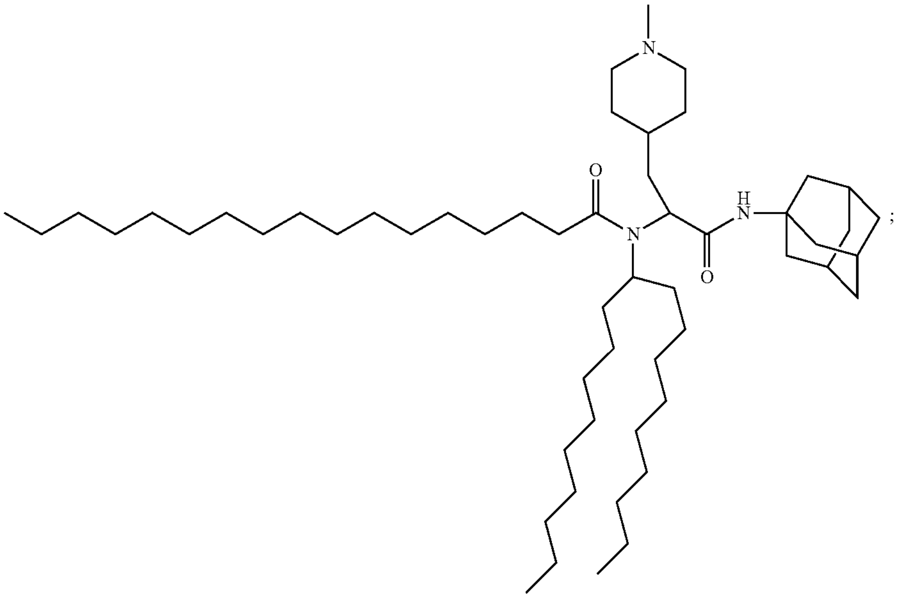
(XLII)
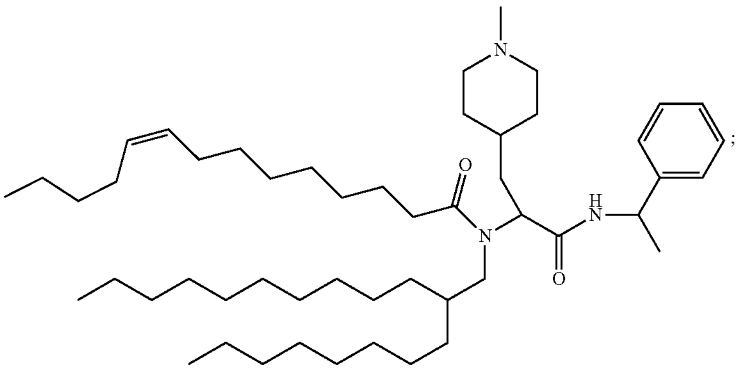

-continued
(XLIII)
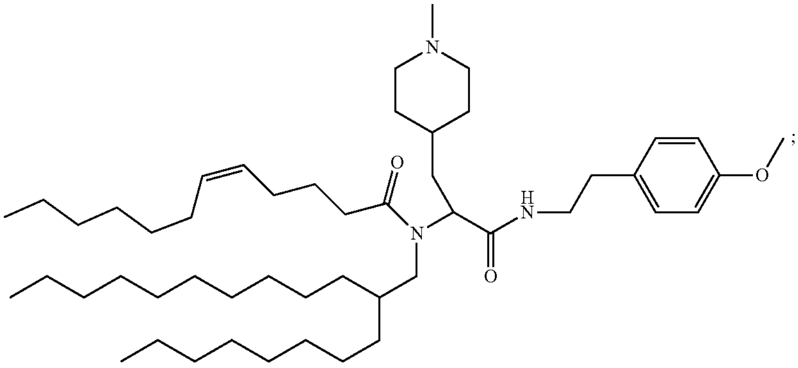
;
(XLIV)
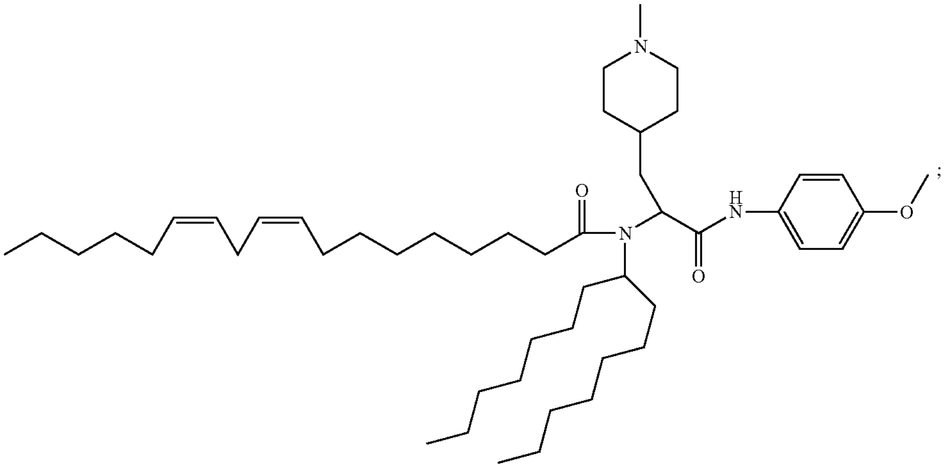
;
(XLV)
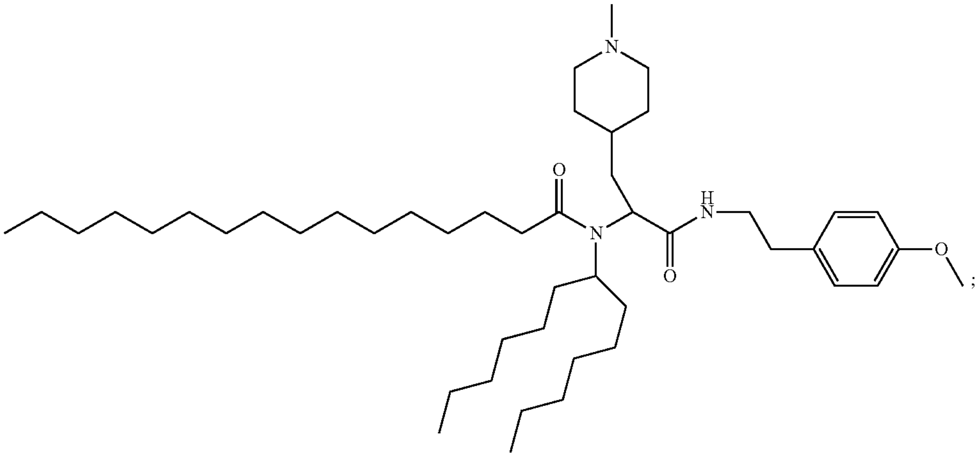
;

-continued
(XLVI)
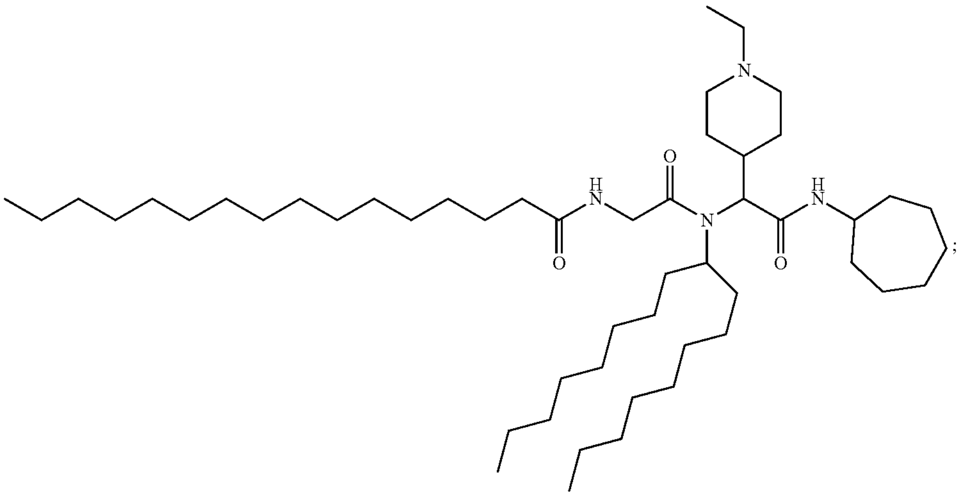
(XLVII)
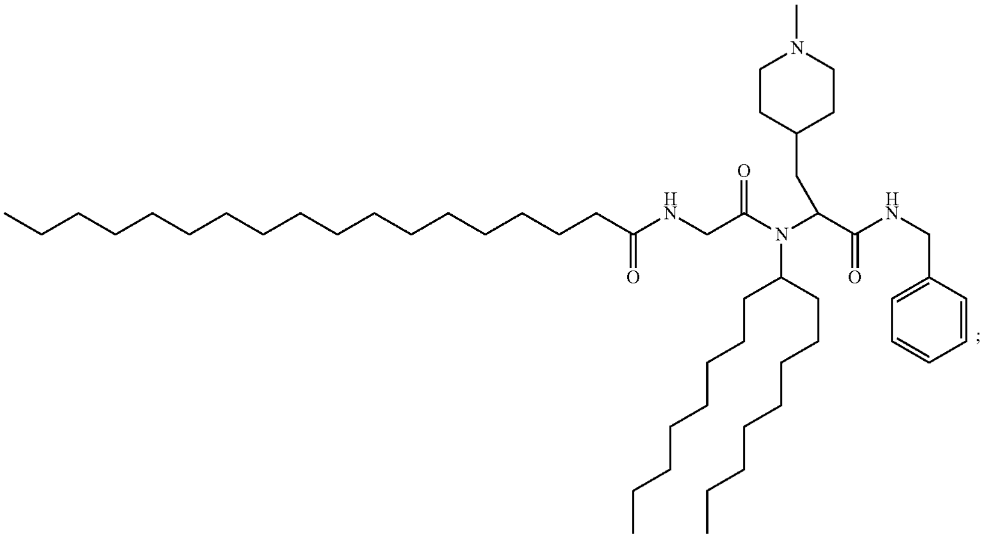
(XLVIII)
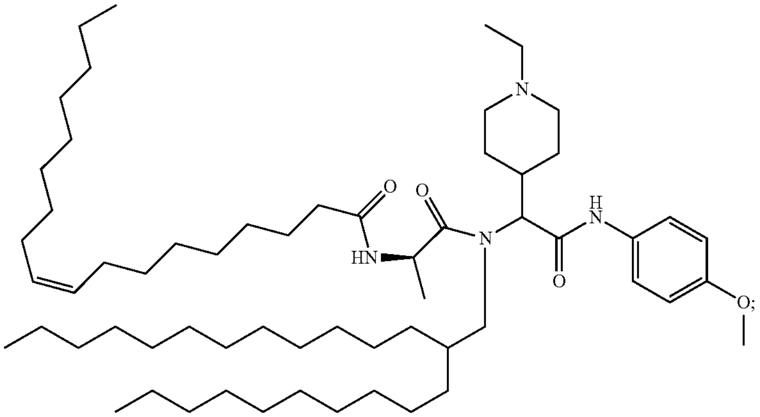

-continued
(XLIX)
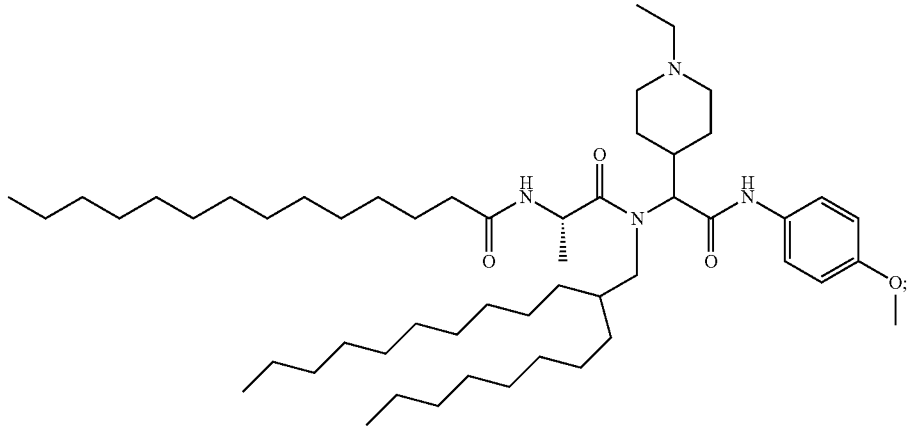
(L)
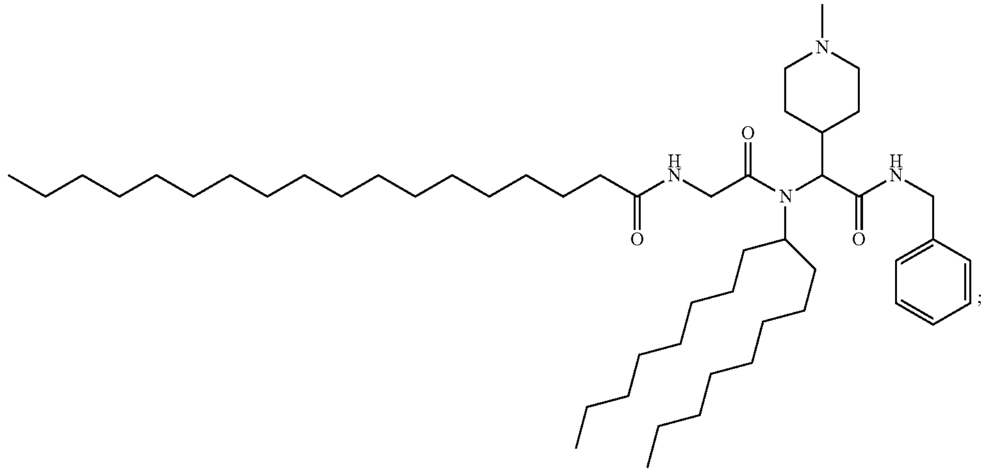
(LI)
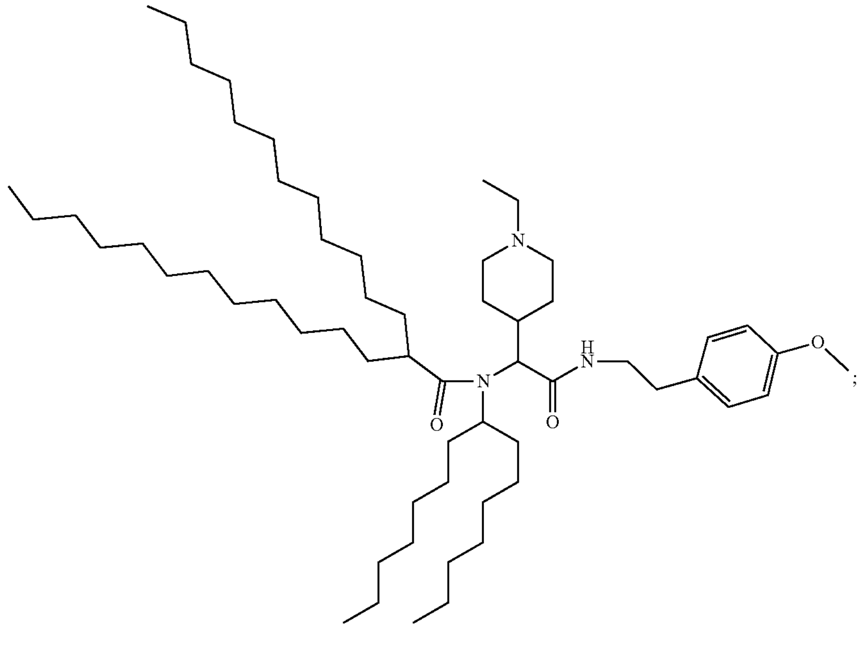

-continued
(LII)
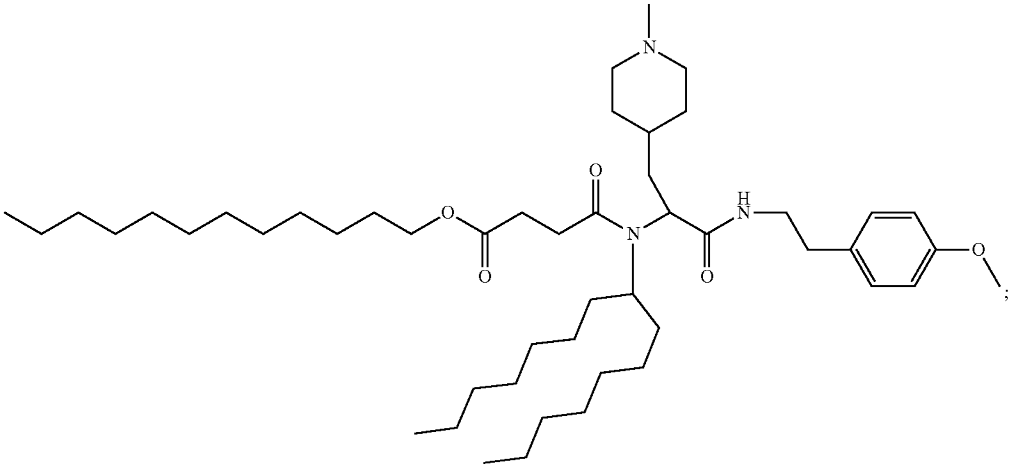
(LIII)
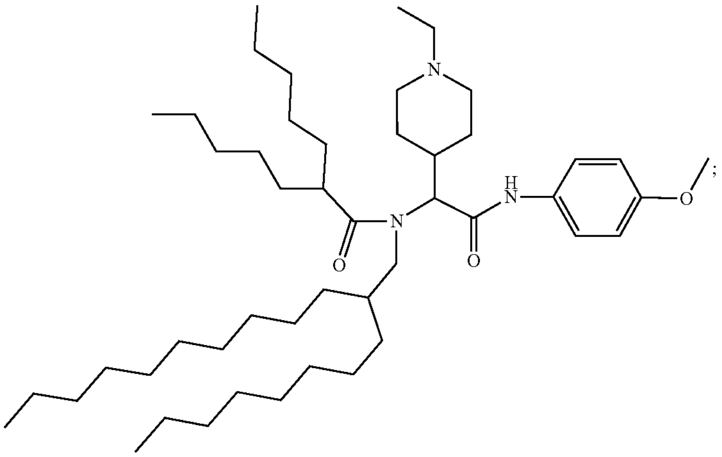
(LIV)
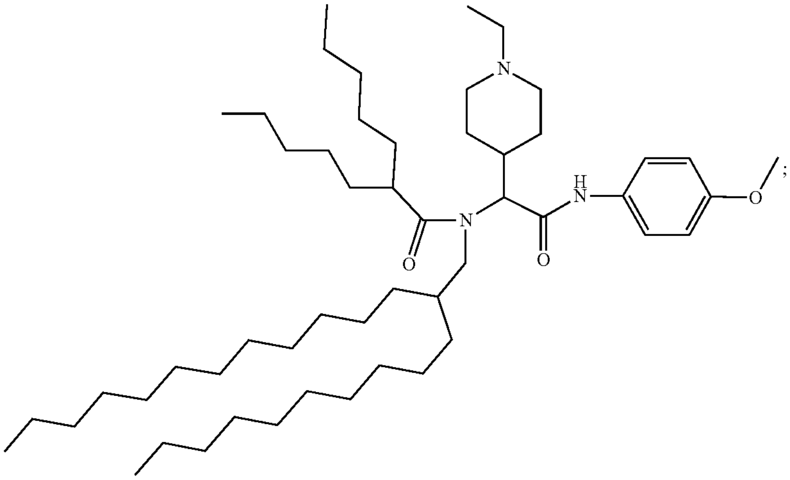

-continued
(LV)
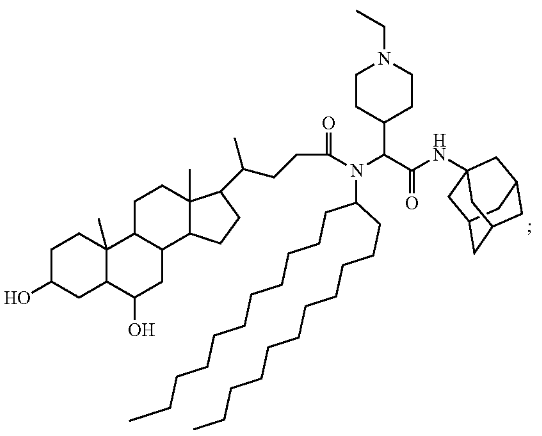
(LVI)
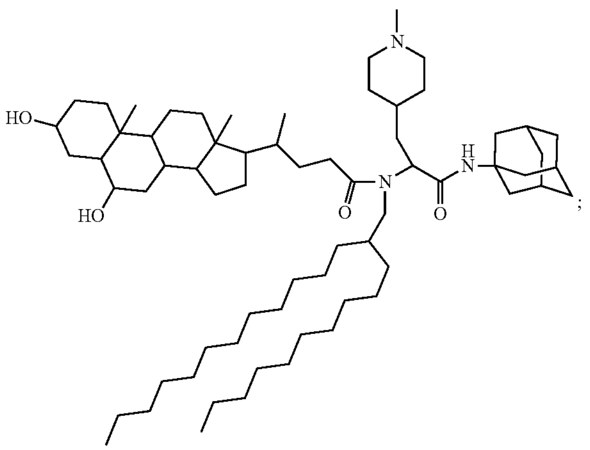
(LVII)
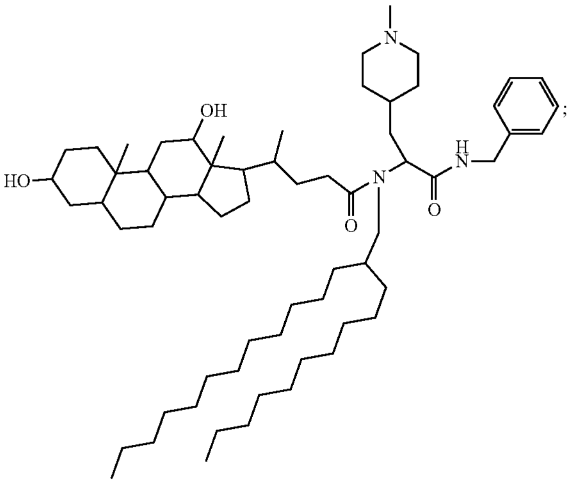
(LVIII)
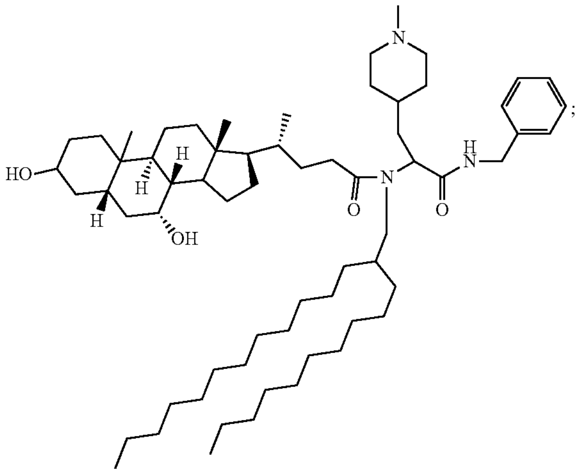
(LIX)
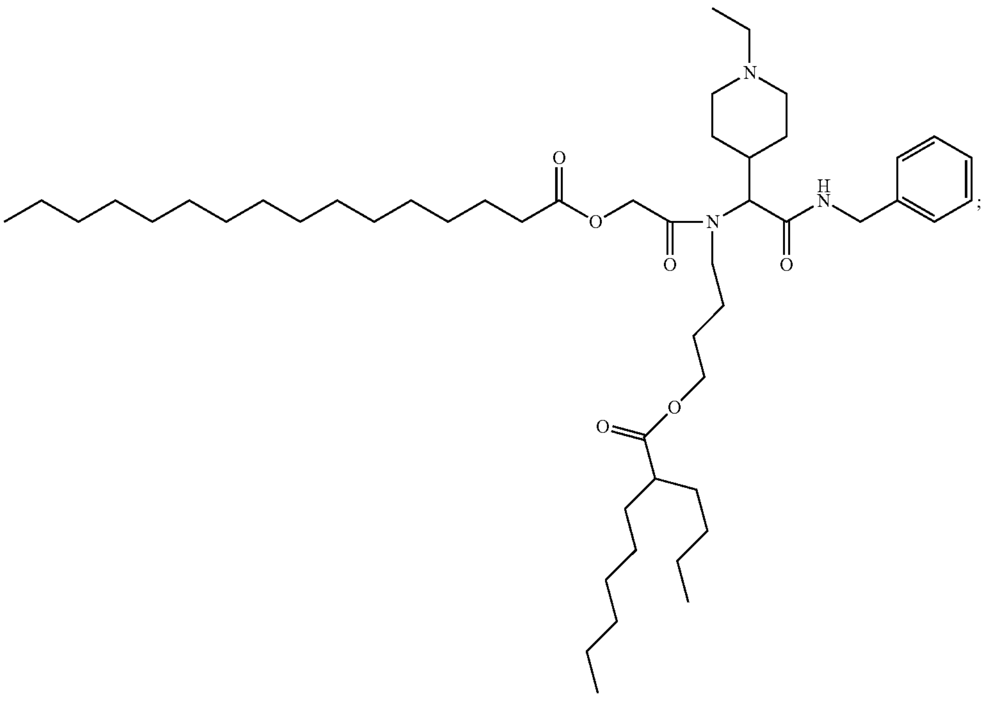

-continued (LX)

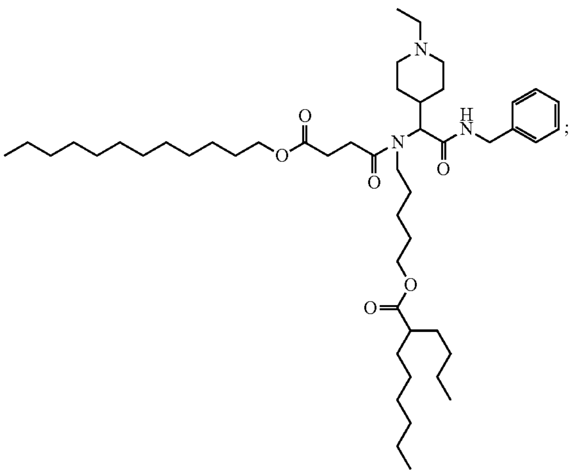

(LXI)

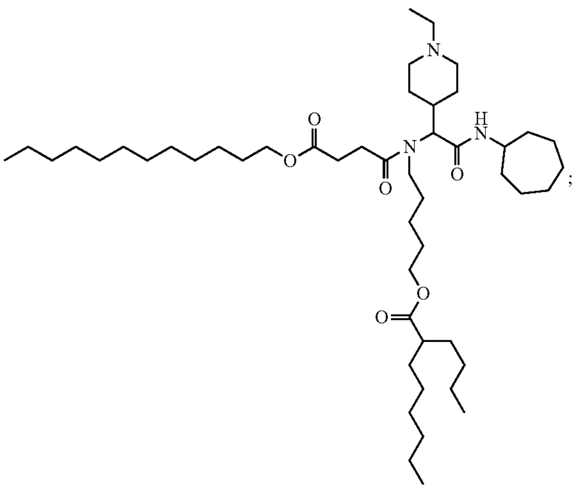

(LXII)

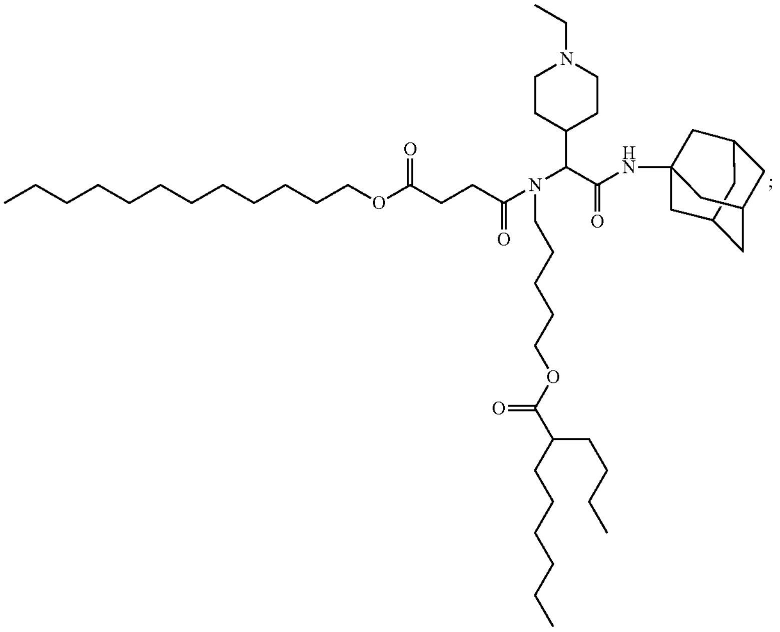

or a salt thereof.

4. The method of claim 3, wherein the LNP further comprises a phospholipid, a cholesterol, and a PEG lipid in a mole ratio of:

a) 15 to 40:15 to 40:30 to 55:0.5 to 5;

b) 20 to 35:20 to 35:35 to 50:1 to 4; or c) 25 to 35:25 to 35:40 to 50:1.5 to 3.

5. The method of claim 1, wherein the GOI encodes from 5' to 3': (SEQ ID NO: 1)-VH-(SEQ ID NO: 2)-VL-(SEQ ID NO: 3)-(SEQ ID NO: 4)-(SEQ ID NO: 5)-(SEQ ID NO: 6).

6. The method of claim 1, wherein the GOI encodes from 5' to 3': (SEQ ID NO: 1)-VH-(SEQ ID NO: 2)-VL-(SEQ ID NO: 3)-(SEQ ID NO: 7)-(SEQ ID NO: 8)-(SEQ ID NO: 9).

7. The method of claim 1, wherein the mRNA comprises a nucleic acid sequence with at least about 98% sequence identity to SEQ ID NO: 24, 25, 26, 27, 28, 29, or 44.

8. The method of claim 1, wherein the SGP is a nucleotide sequence selected from SEQ ID NOs: 10, 11, and 31.

9. The method of claim 1, wherein the L is a nucleotide sequence selected from SEQ ID NOs: 12, 13, 14, and 15.

10. The method of claim 1, wherein the 5'UTR comprises nucleic acid sequence ATAGG.

11. The method of claim 1, wherein the 3'UTR is a nucleotide sequence selected from SEQ ID NOs: 16, 17, 18, and 19.

12. The method of claim 1, wherein the GOI further encodes a reporter protein, wherein the reporter protein is green fluorescent protein (GFP) or an epitope tag.

13. The method of claim 12, wherein the epitope tag is a Myc-tag.

14. The method of claim 1, wherein the GOI comprises SEQ ID NO: 30.

15. The method of claim 1, wherein the scFv comprises an amino acid sequence with at least about 85% sequence identity to SEQ ID NO: 32, 33, 34, 35, 36, 37, 38, 39, 40, or 45.

16. The method of claim 1, wherein the nucleotide sequence encoding the CAR comprises a nucleic acid sequence with at least about 98% sequence identity to SEQ ID NO: 26 or 44.

17. The method of claim 1, wherein the plurality of non-structural replicase domain sequences are obtained from a Group IV positive single strand RNA virus selected from the group comprising Picornaviridae, Togaviridae, Coronaviridae, Hepeviridae, Caliciviridae, Flaviviridae, and Astroviridae, and/or wherein the plurality of non-structural replicase domain sequences are obtained from an alphavirus selected from the group comprising Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus, and/or wherein the plurality of non-structural replicase domain sequences are alphavirus nonstructural proteins 1-4 (nsP1-4), and/or wherein the plurality of non-structural replicase domain sequences are obtained from the TC-83 strain of Venezuelan Equine Encephalitis virus (VEE).

18. The method of claim 1, wherein the SGP is a viral promoter that is recognized by viral RNA dependent RNA polymerase.

19. The method of claim 1, wherein the self-amplifying mRNA comprises one or more nucleotide substitutions compared to a reference mRNA, wherein the one or more nucleotide substitutions comprise substituting uridine (U) nucleotide residues of the reference mRNA with nucleotide residues selected from the group consisting of 1-methylpseudouridine (m1ψ) and pseudouridine (ψ), thereby rendering modified mRNA, wherein the modified mRNA shows increased transfection efficiency compared to the reference mRNA.

20. The method of claim 19, wherein said modified mRNA exhibits enhanced ability to produce a CAR, a TCR, a GFR, a HR, a Nb, or a reporter in an immune cell compared to the same quantity of a reference mRNA that exhibit same sequence but with uridine in place of said at least one modified nucleoside selected from the group consisting of 1-methylpseudouridine and pseudouridine, wherein said enhanced ability to produce the CAR, TCR, GFR, HR, a Nb, or a reporter is determined by measuring a higher level of either the amount of the CAR, TCR, GFR, HR,a Nb, or a reporter or other biological effect produced at one or more times after said contacting of said immune cell with said modified mRNA compared to the corresponding amount of the CAR, TCR, GFR, HR, a Nb, or a reporter or other biological effect produced in the same or equivalent immune cell at the same times after contacting with the same quantity of the reference mRNA.

21. The method of claim 1, wherein the self-amplifying mRNA comprises from 5' to 3':

a) 1869 to 9441 of SEQ ID NO: 21, the GOI, nucleotides 10162 to 10325 of SEQ ID NO: 21 and nucleotides 1 to 10 of SEQ ID NO: 21; or b) 1869 to 9441 of SEQ ID NO: 22, the GOI, nucleotides 10162 to 10325 of SEQ ID NO: 22 and nucleotides 1 to 10 of SEQ ID NO: 22; or c) 1869 to 9441 of SEQ ID NO: 23, the GOI, nucleotides 10162 to 10325 of SEQ ID NO: 23 and nucleotides 1 to 10 of SEQ ID NO: 23.

22. A method of delivering a payload to immune cells in vivo comprising administering an LNP encapsulating a payload encoding at least one polypeptide of interest to a subject, wherein the polypeptide of interest is an antigen receptor, an antibody, or a reporter protein; and wherein the payload is a modified mRNA, a self-amplifying mRNA or a circular RNA comprising a nucleic acid sequence from 5' to 3':

a) 5'UTR-nsP-L-SGP-LP-GOI-L-3'UTR-PolyA, b) 5'UTR-nsP-SGP-LP-GOI-L-3'UTR-PolyA, c) 5'UTR-nsP-L-SGP-LP-GOI-3'UTR-PolyA, or d) 5'UTR-nsP-SGP-LP-GOI-3'UTR-PolyA wherein 5'UTR is a 5' untranslated region, nsP is a plurality of non-structural replicase domain sequences, L is a linker, SGP is a subgenomic promoter, 3'UTR is a 3' untranslated region, poly-A is a 3' poly-adenylated tail (poly-A tail), LP is a leading peptide, and wherein the GOI is one or more genes of interest;

wherein the 3'UTR comprises a nucleotide sequence selected from SEQ ID NOs: 16, 17, 18, and 19, and wherein the GOI encodes:

a) an Nb; or b) an AR; or c) scFv-AR, wherein, scFv is a single-chain variable fragment; or d) an scFv-CAR having the structure VH-LK-VL-MyC-CD8-CD28-CD3z, wherein:

VH is an immunoglobulin heavy chain variable region,

LK is a linker,

VL is an immunoglobulin light chain variable region,

MyC is a Myc tag,

CD8 is a CD8 alpha chain hinge region,

CD28 is a CD28 activation domain, and

CD3z is a CD3 zeta cytoplasmic domain; or e) an scFv-CAR having the structure VH-LK-VL-CD8-CD28-CD3z wherein, VH is the immunoglobulin heavy chain variable region, LK is the linker, VL is the immunoglobulin light chain variable region, CD8 is the CD8 alpha chain hinge region, CD28 is the CD28 activation domain, and CD3z is the CD3 zeta cytoplasmic domain; or f) a reporter protein.

23. The method of claim 22, wherein the reporter protein is GFP or an epitope tag.

24. The method of claim 23, wherein the epitope tag is a Myc-tag.

25. The method of claim 22, wherein the LNP comprises at least one lipid compound selected from:

(I)
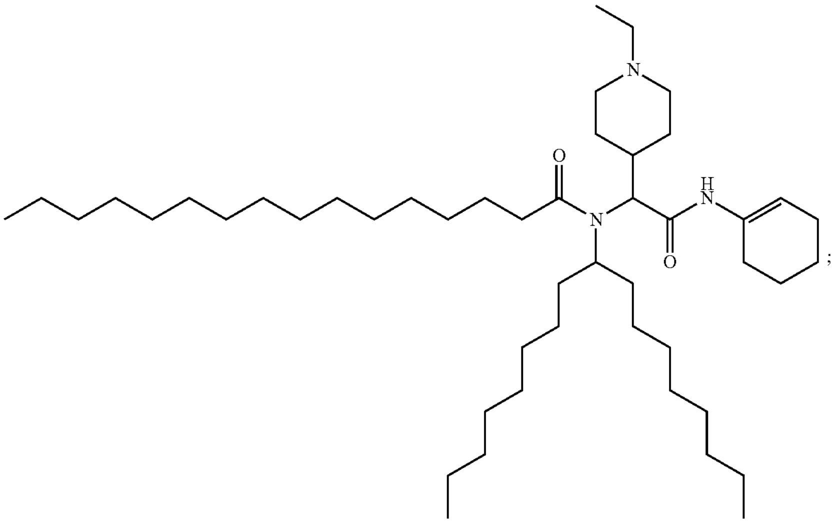
;
(II)
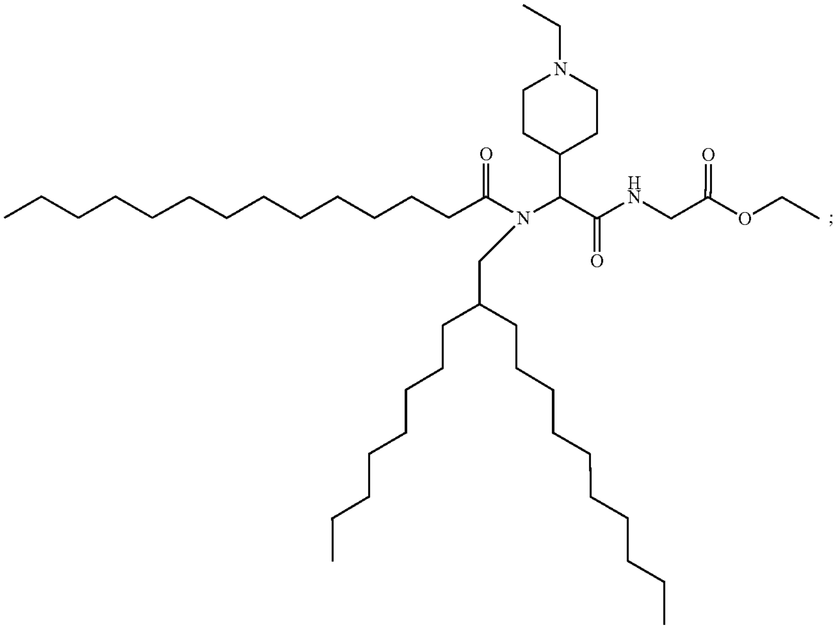
;
(III)
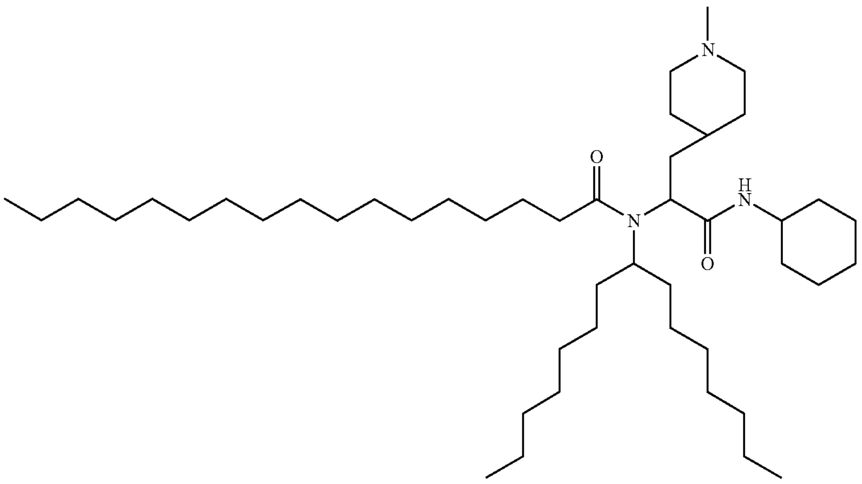
;

-continued
(IV)
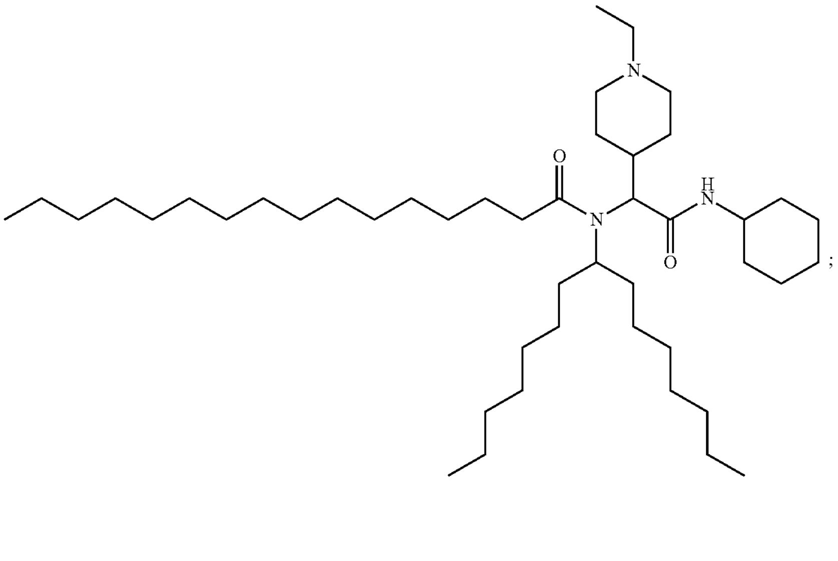
(V)
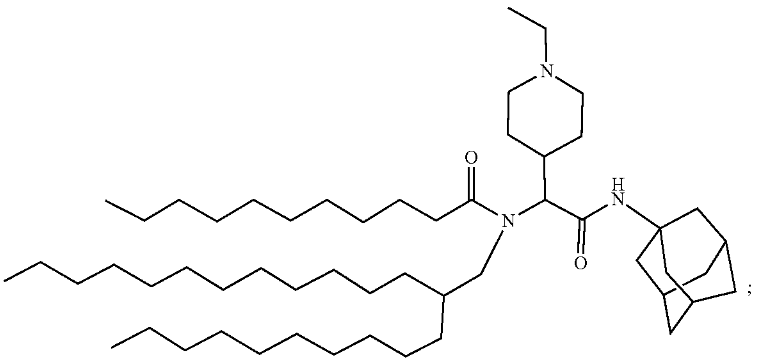
(VI)
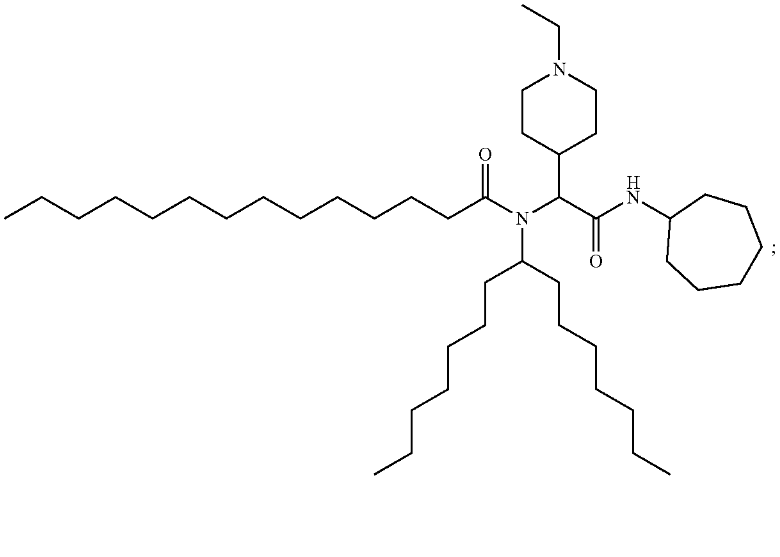

-continued
(VII)
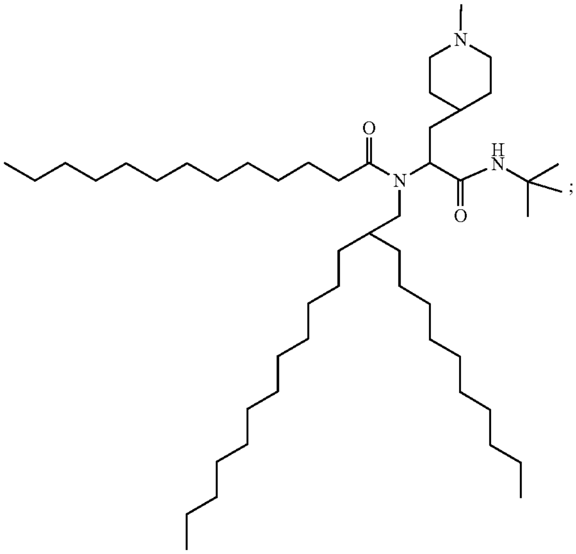
;
(VIII)
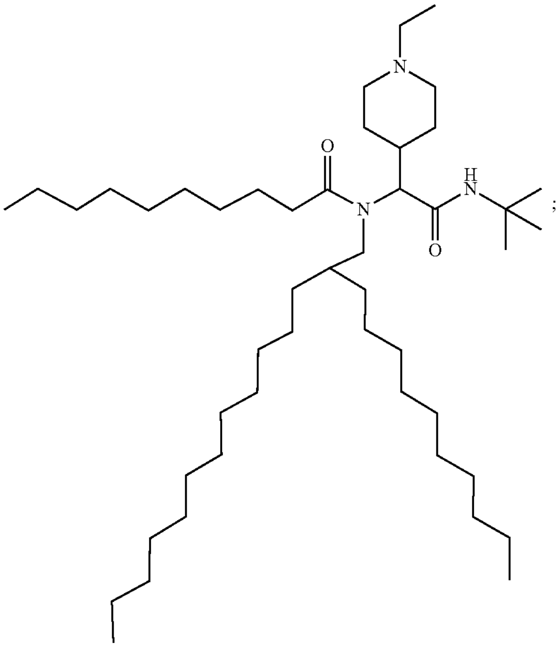
;
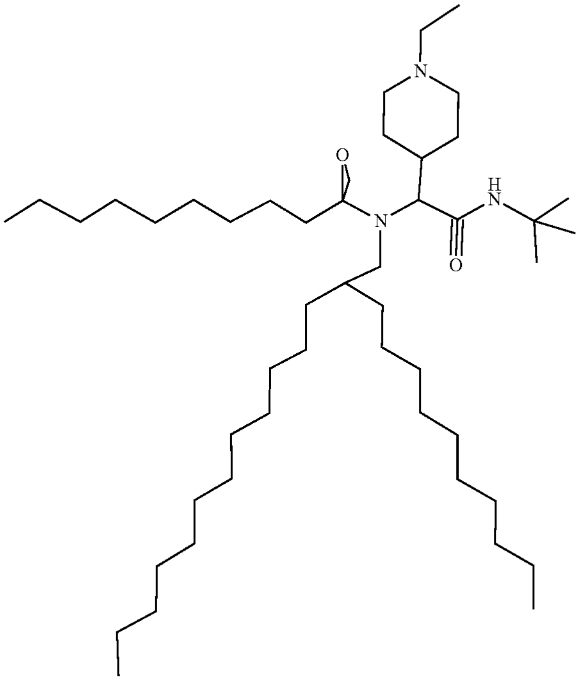

-continued
(IX)
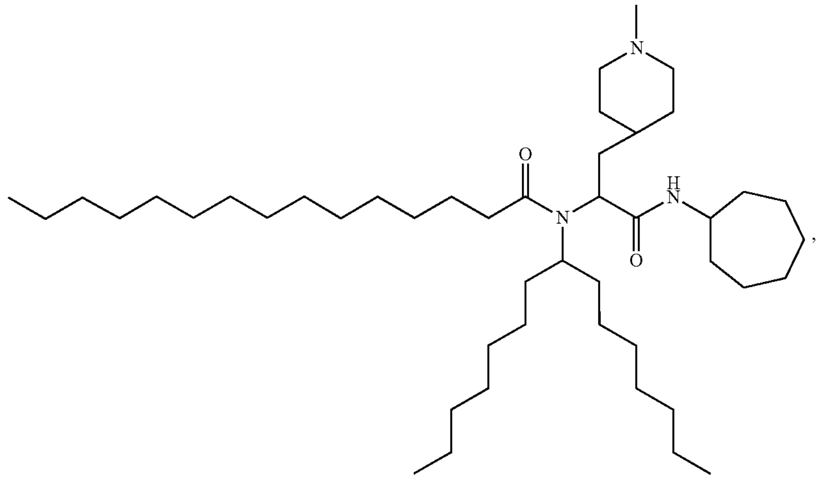
(X)
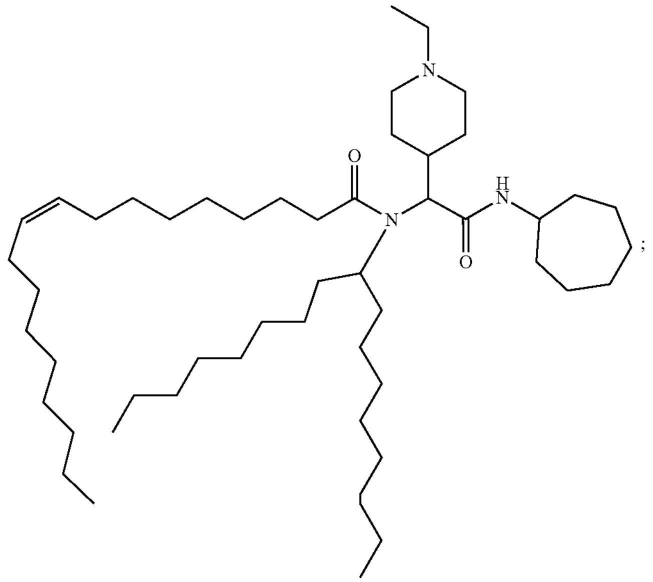

-continued
(XI)
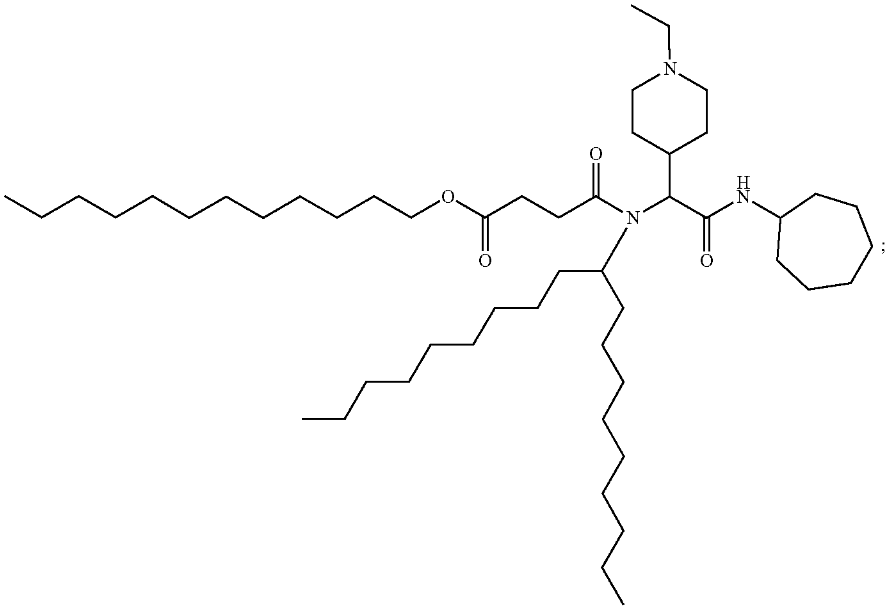
(XII)
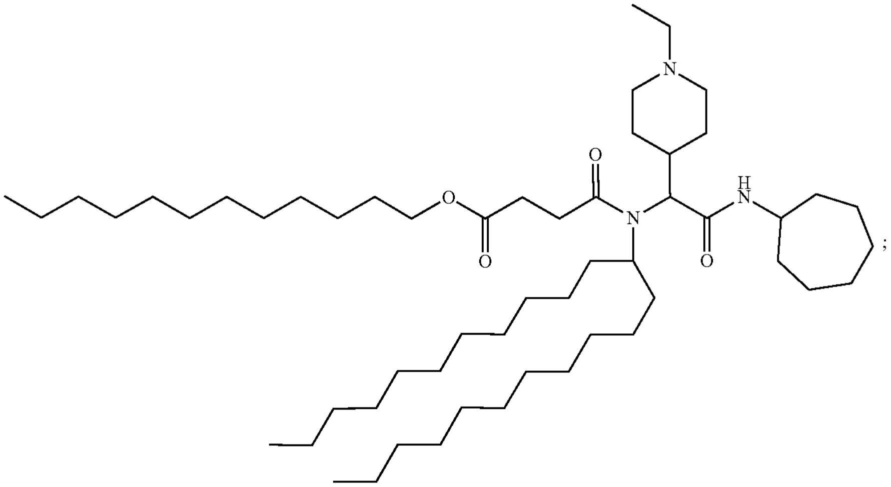
(XIII)
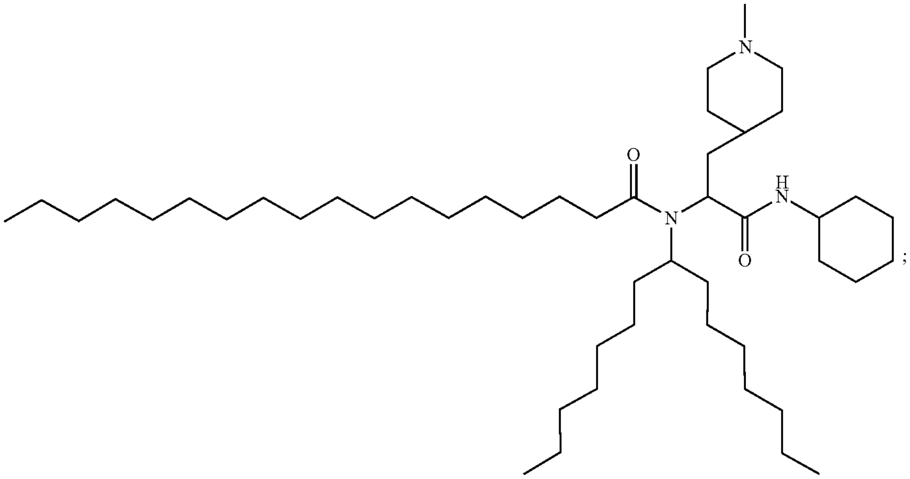

-continued
(XIV)
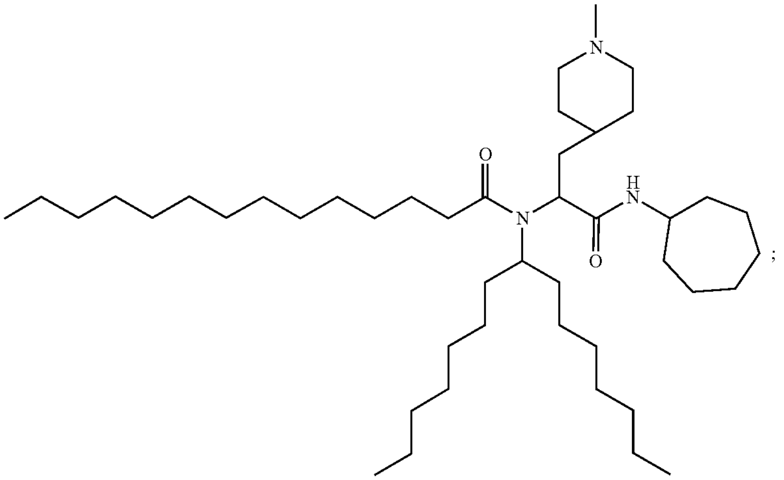
(XV)
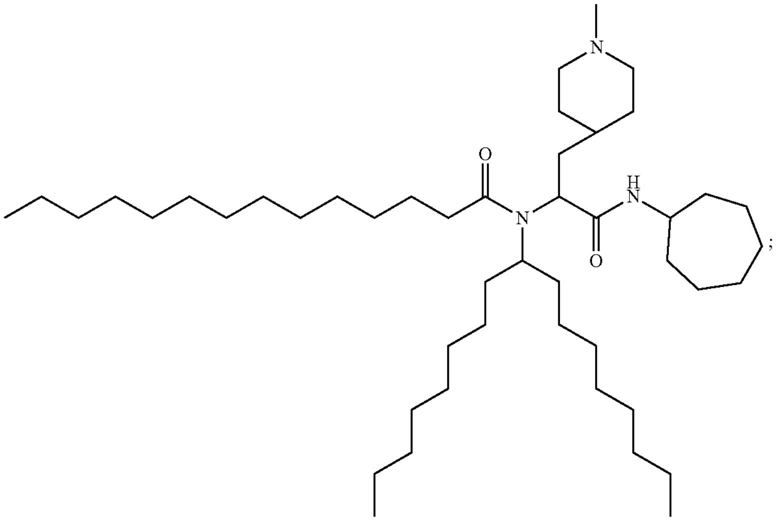
(XVI)
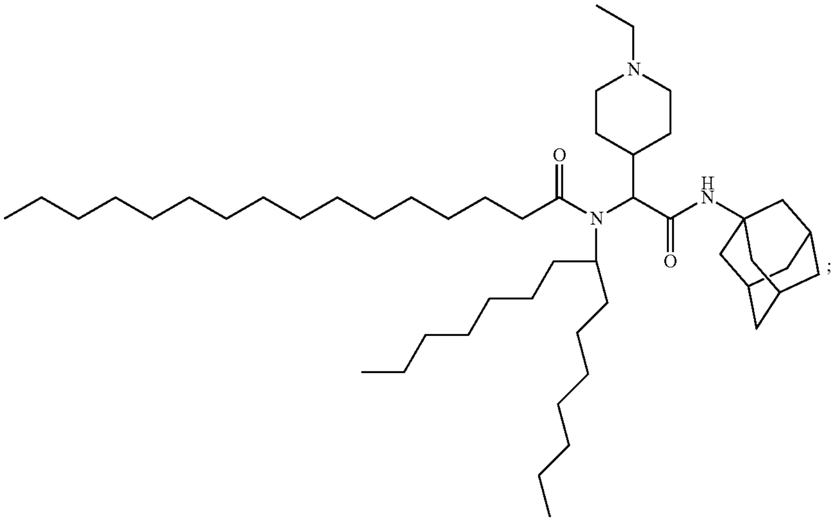

-continued
(XVII)
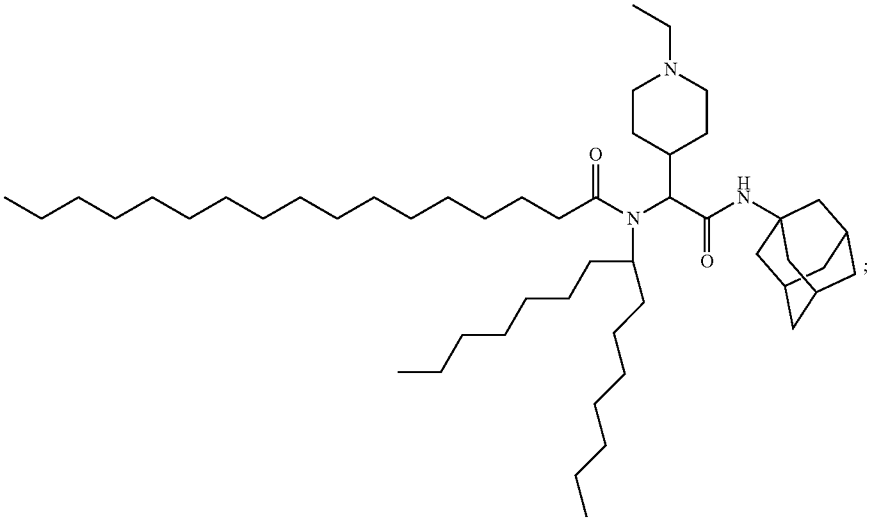
(XVIII)
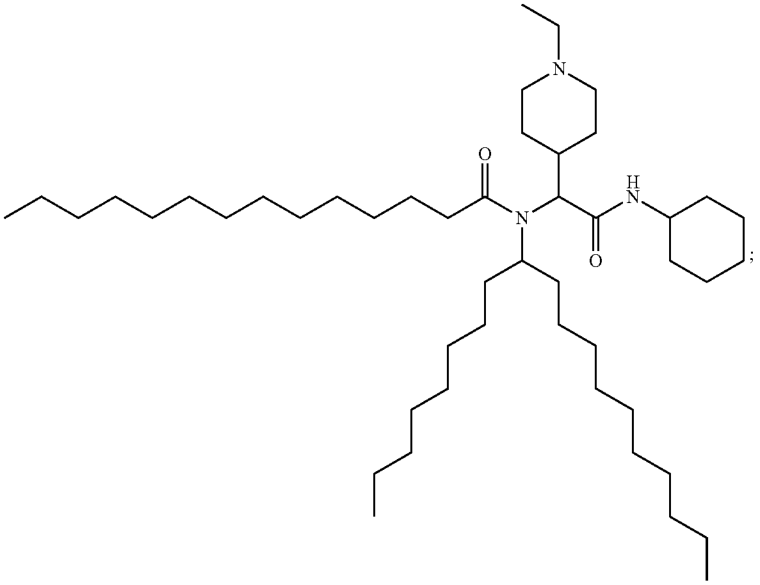
(XIX)
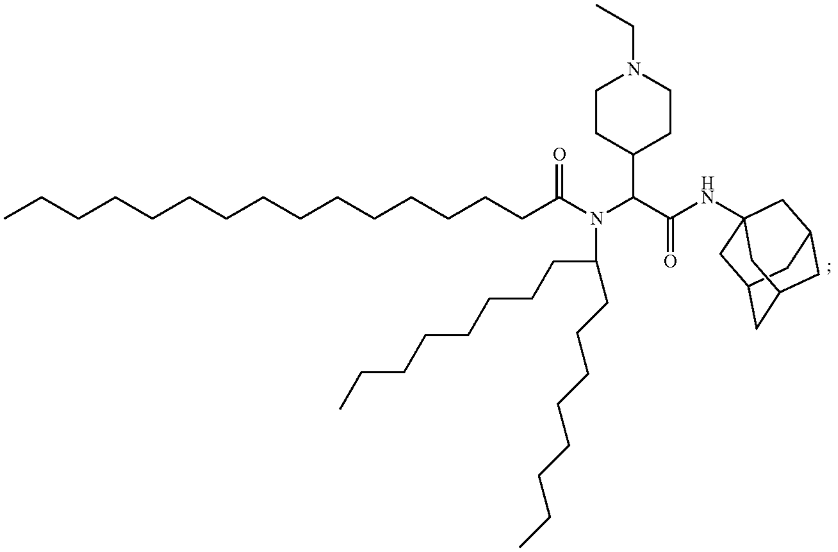

-continued
(XX)
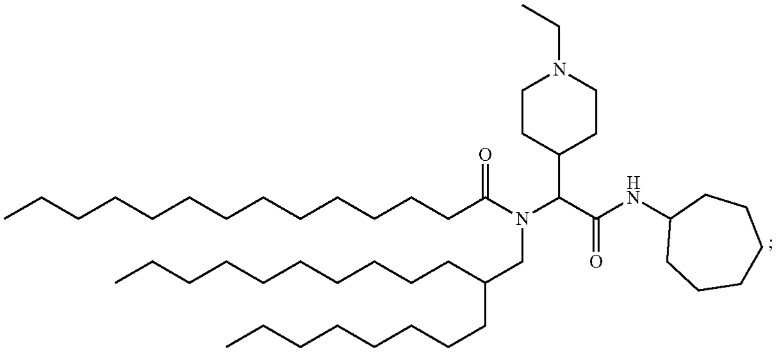
(XXI)
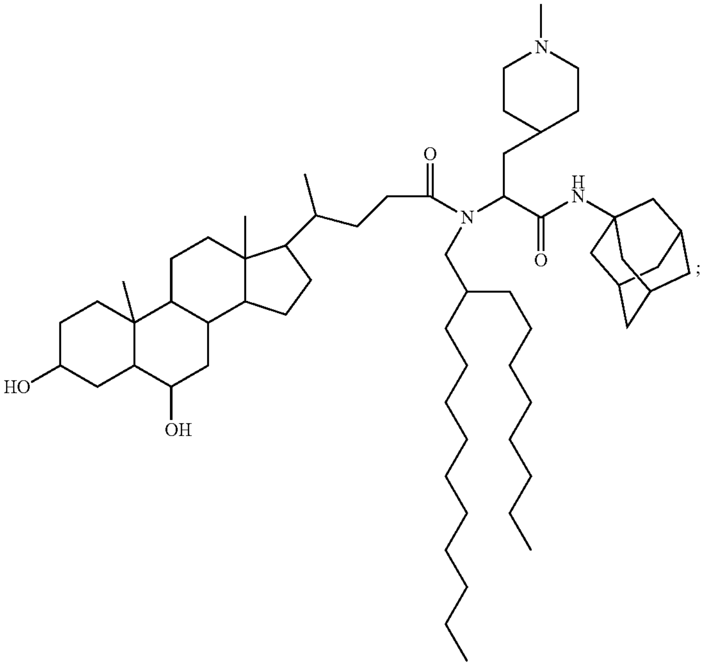
(XXII)
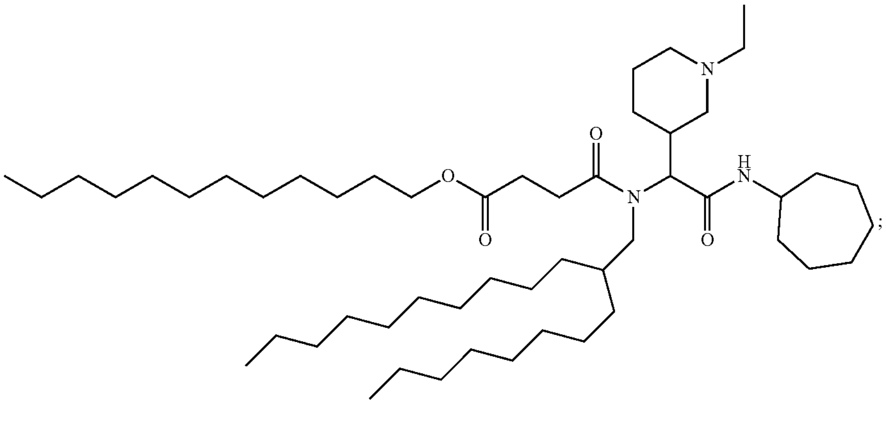

-continued
(XXIII)
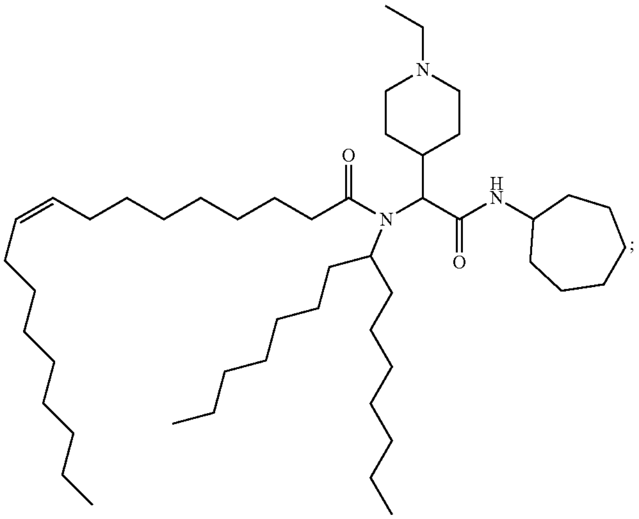
(XXIV)
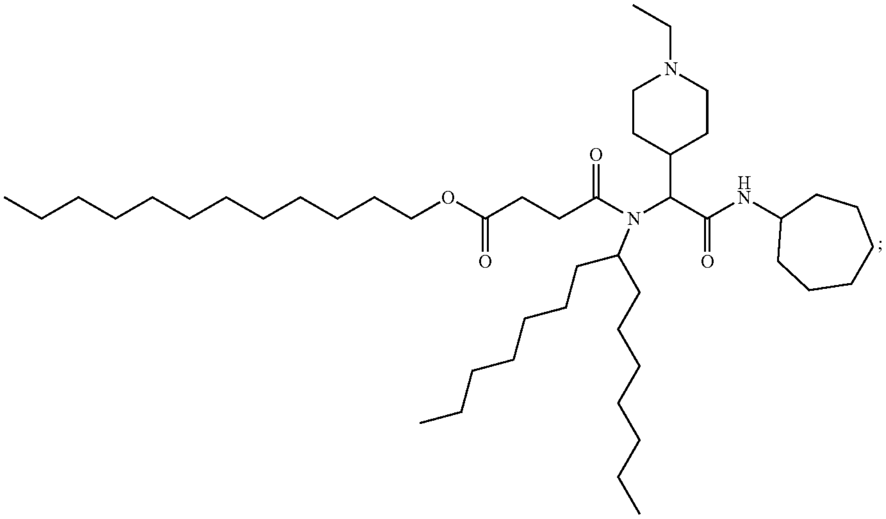
(XXV)
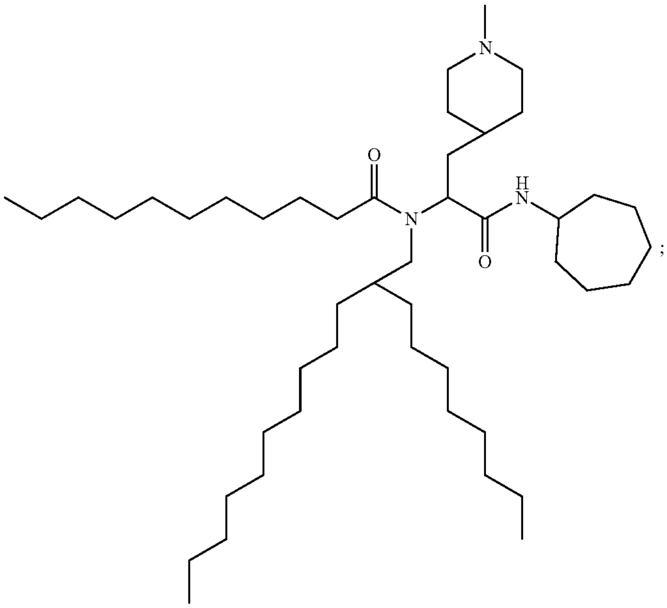

-continued
(XXVI)
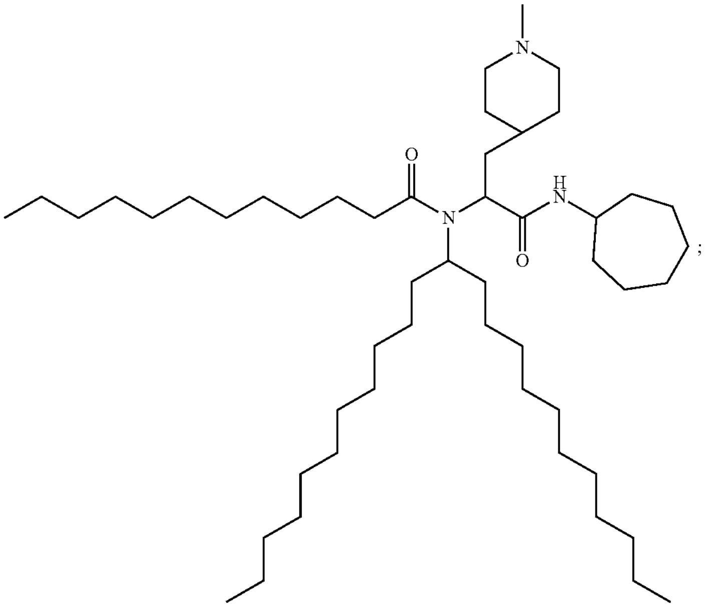
(XXVII)
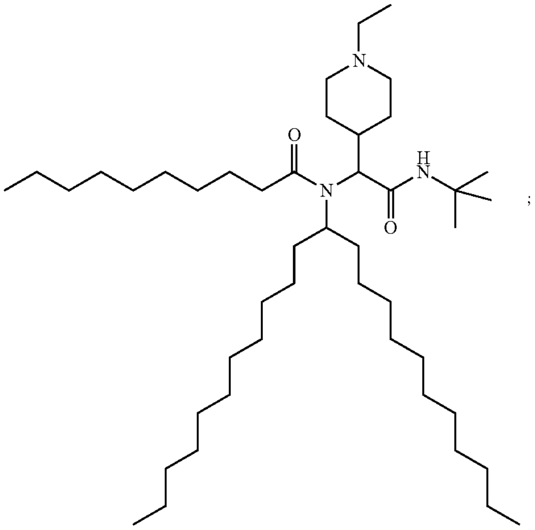
(XXVIII)
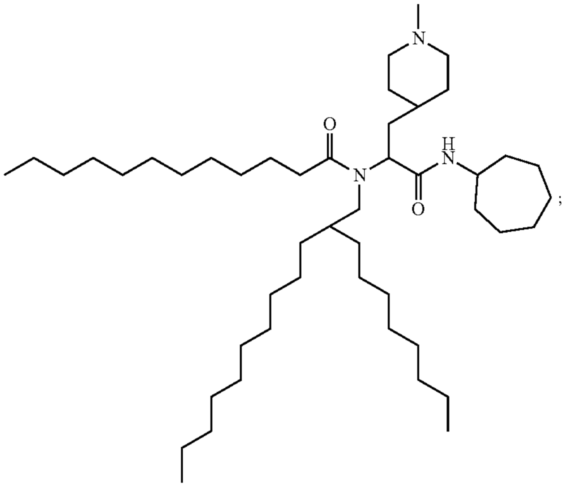

-continued
(XXIX)
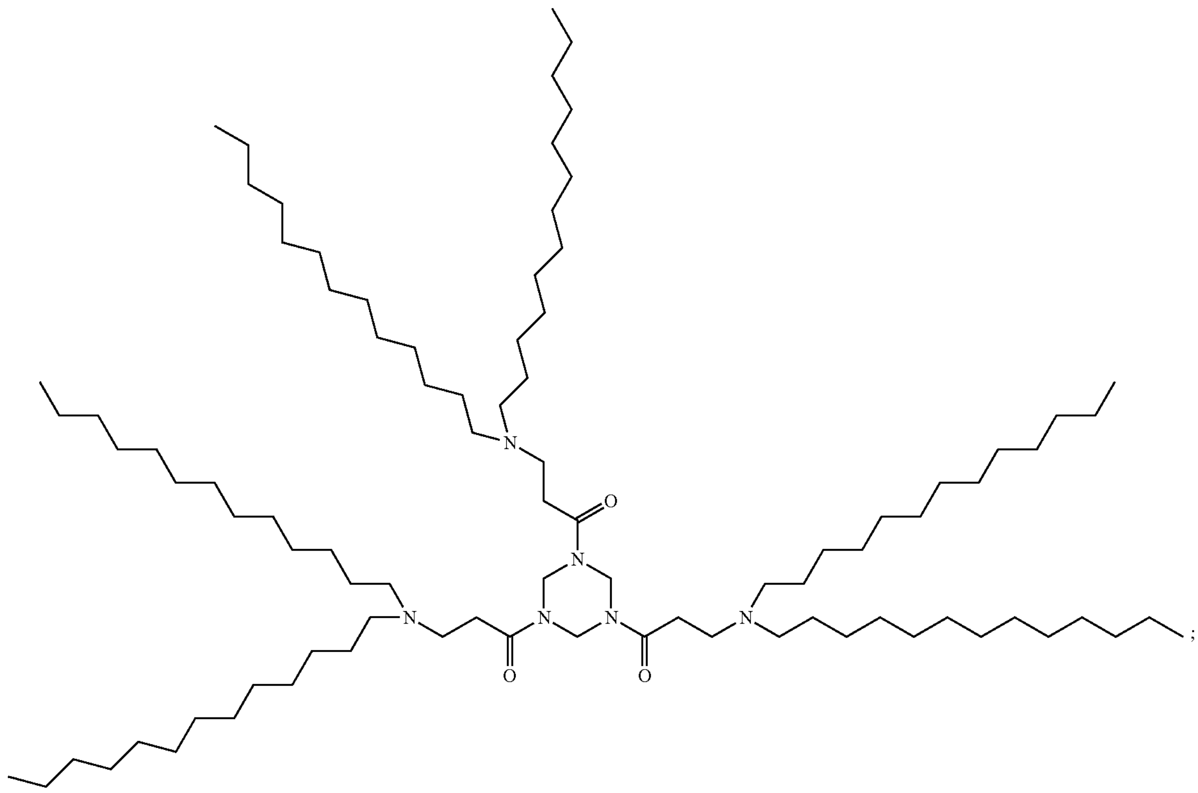
;
(XXX)
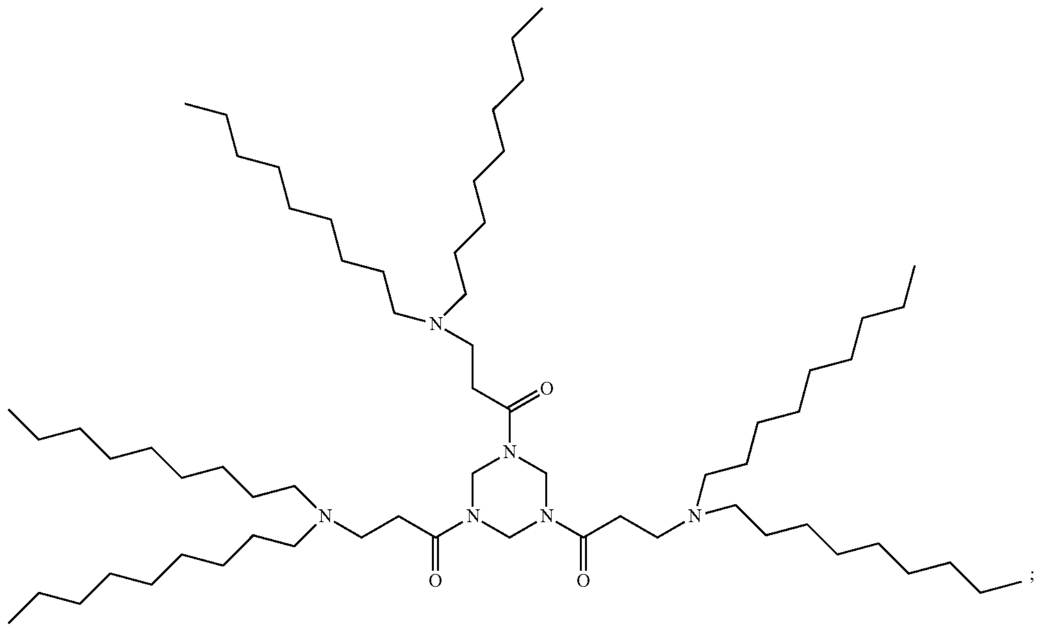
;

-continued
(XXXI)
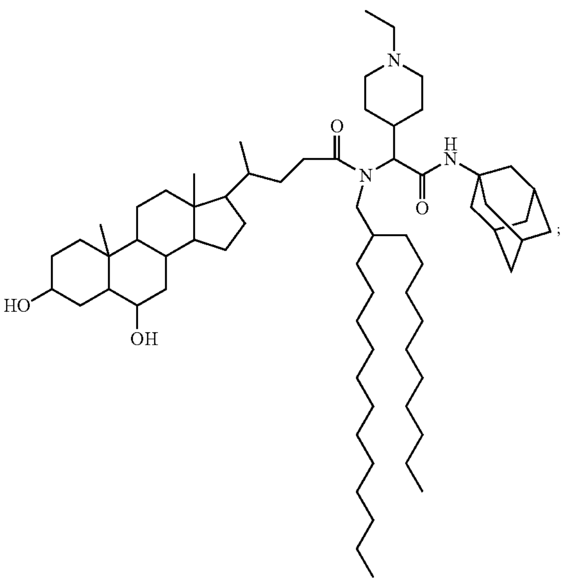
(XXXII)
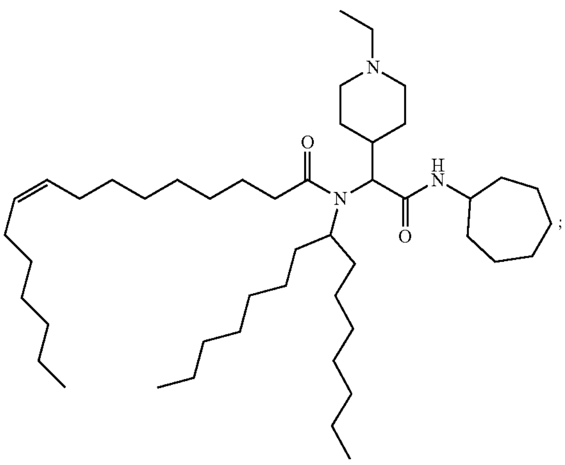
(XXXIII)
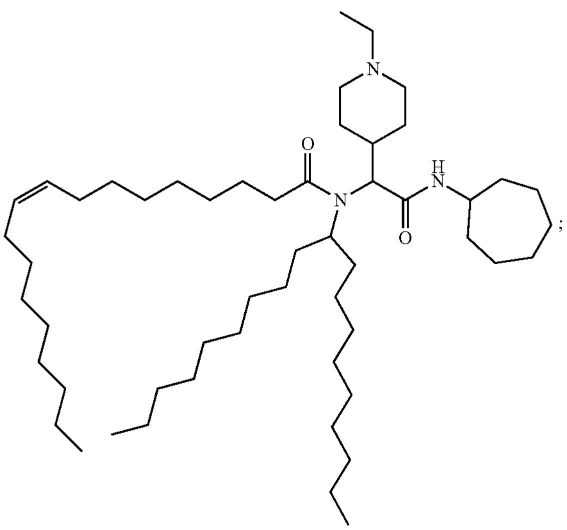
(XXXIV)
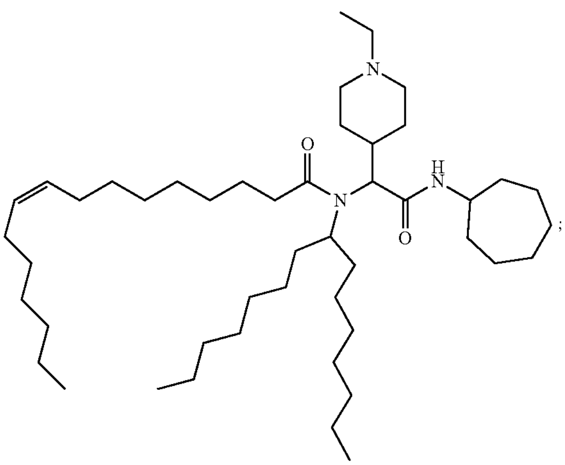

-continued
(XXXV)
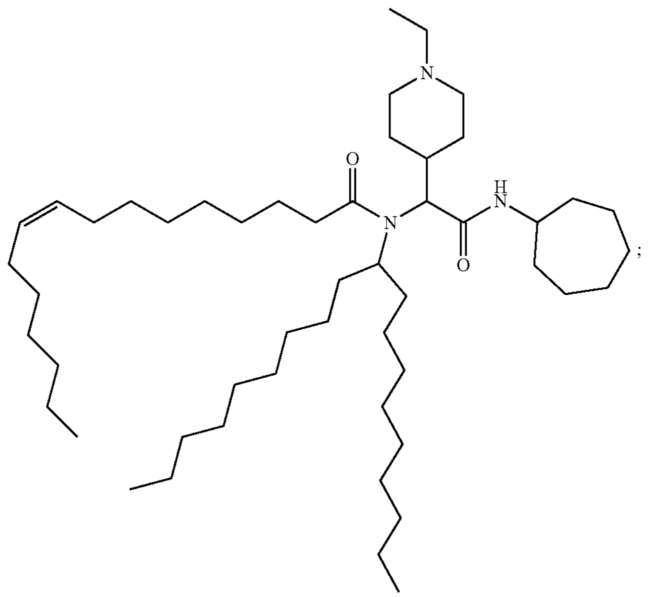
(XXXVI)
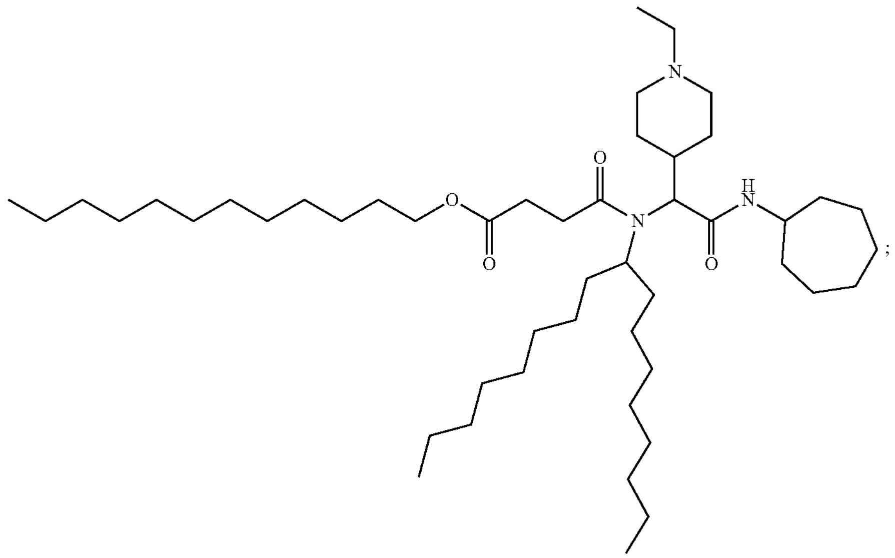

-continued
(XXXVII)
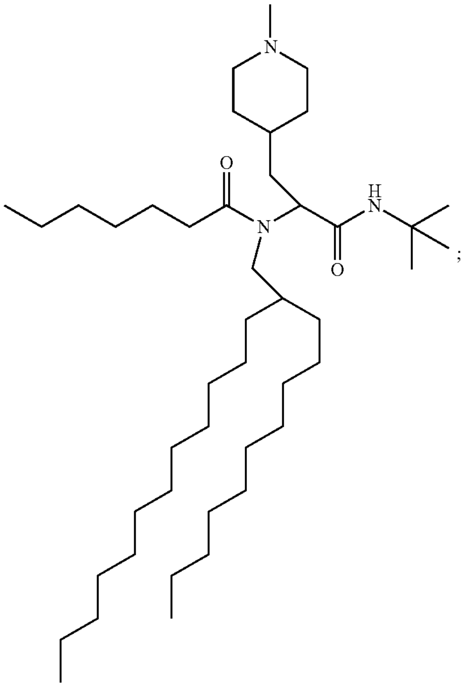
;
(XXXVIII)
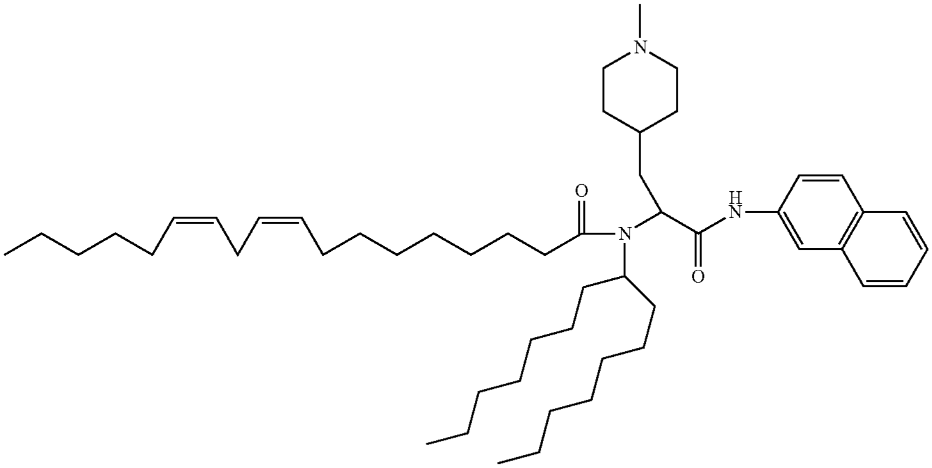
;

-continued
(XXXIX)
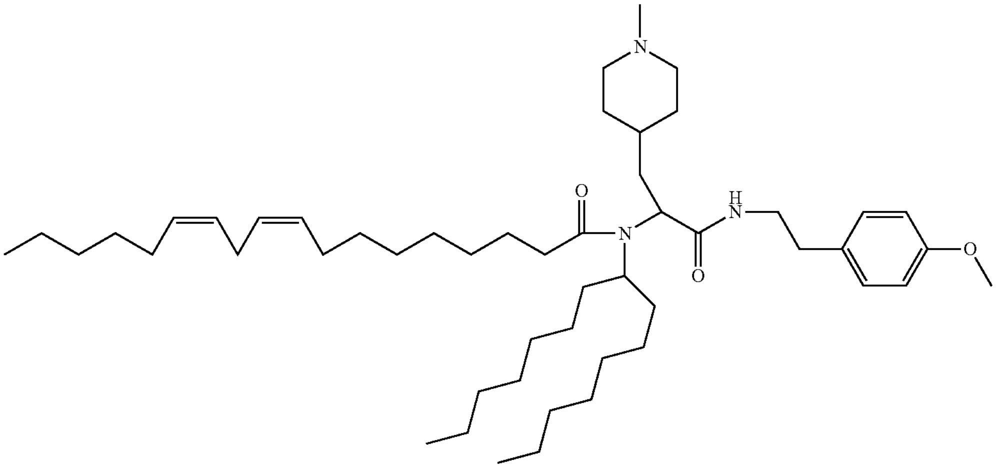
;
(XL)
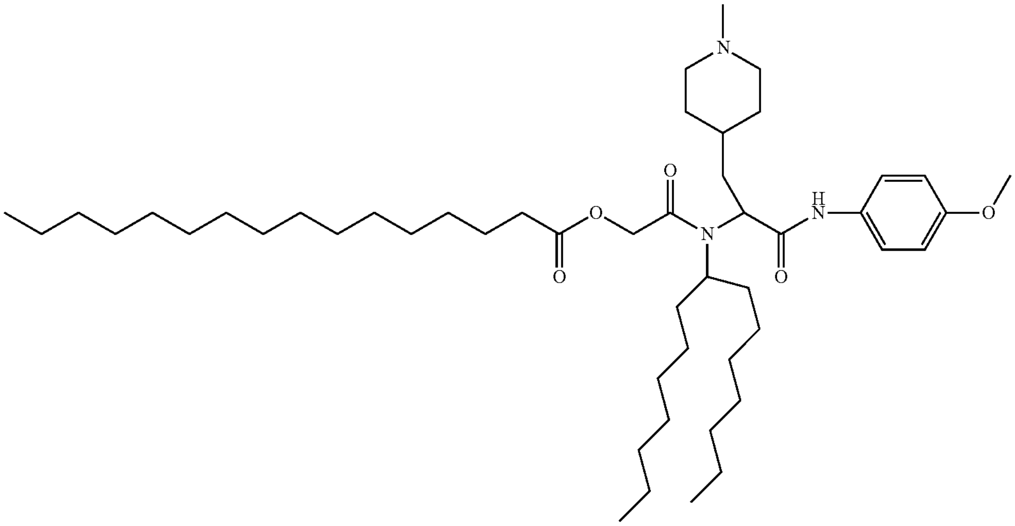
;
(XLI)
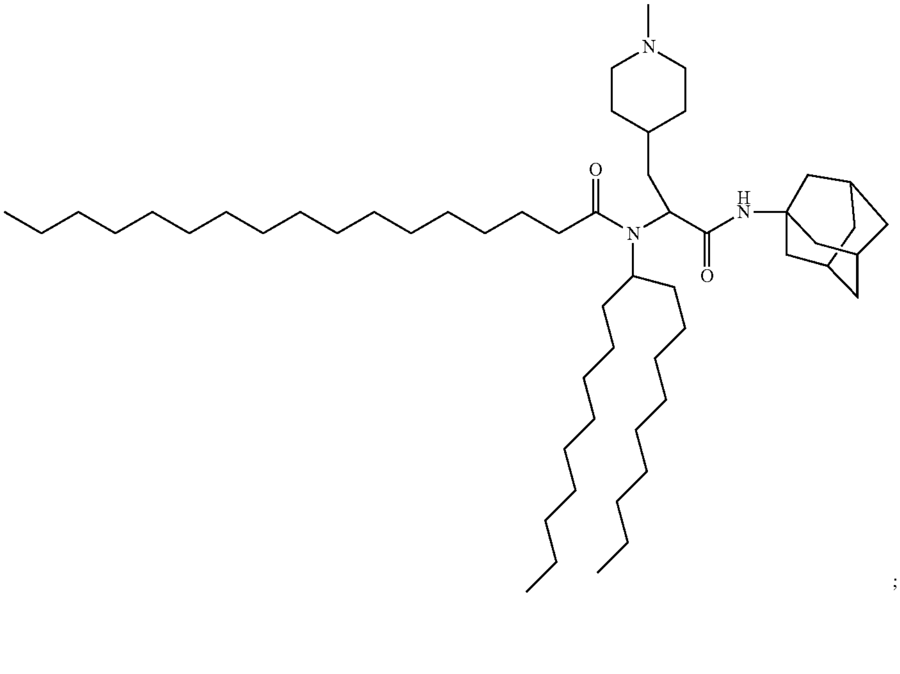
;

-continued
(XLII)
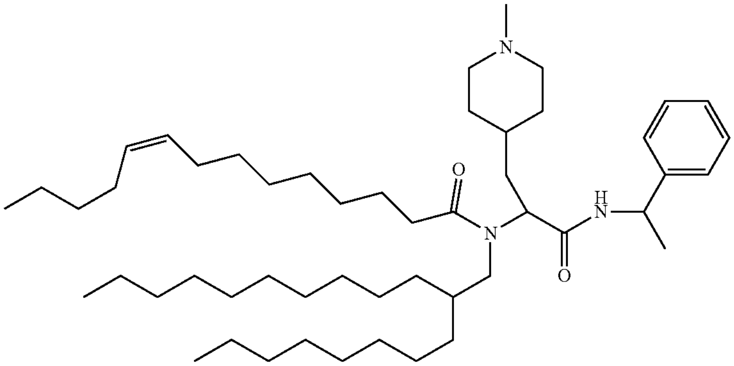
;
(XLIII)
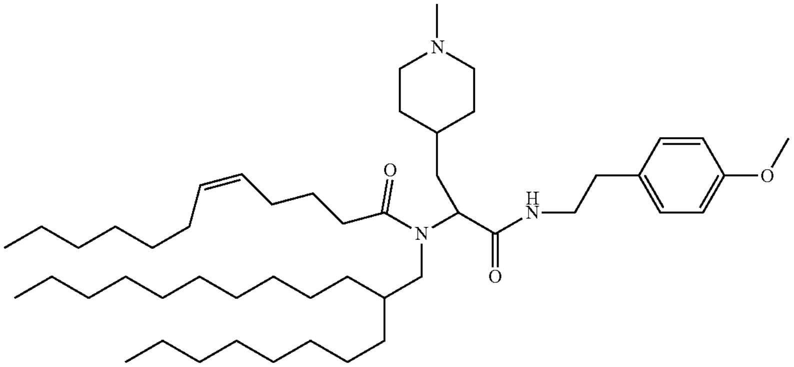
;
(XLIV)
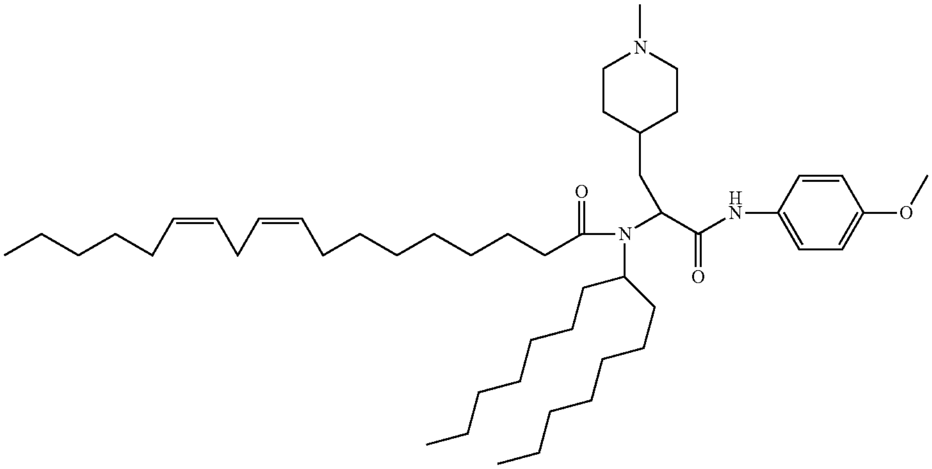
;

-continued
(XLV)
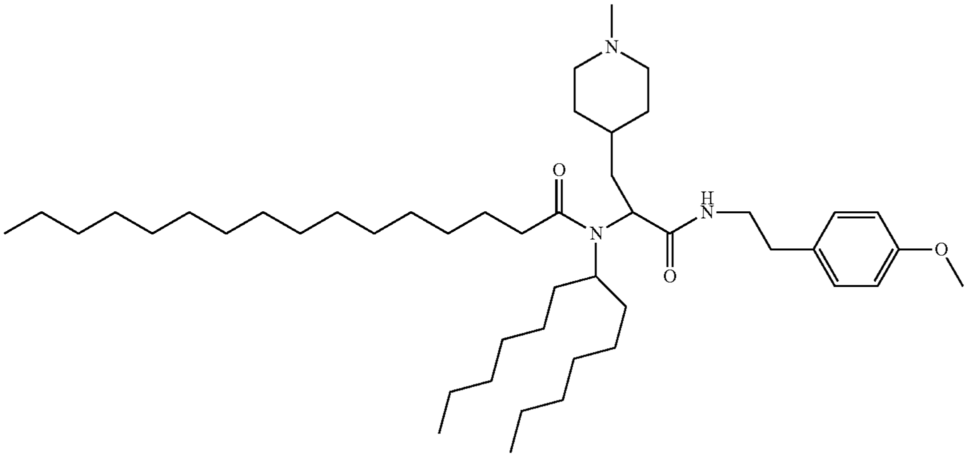
;
(XLVI)
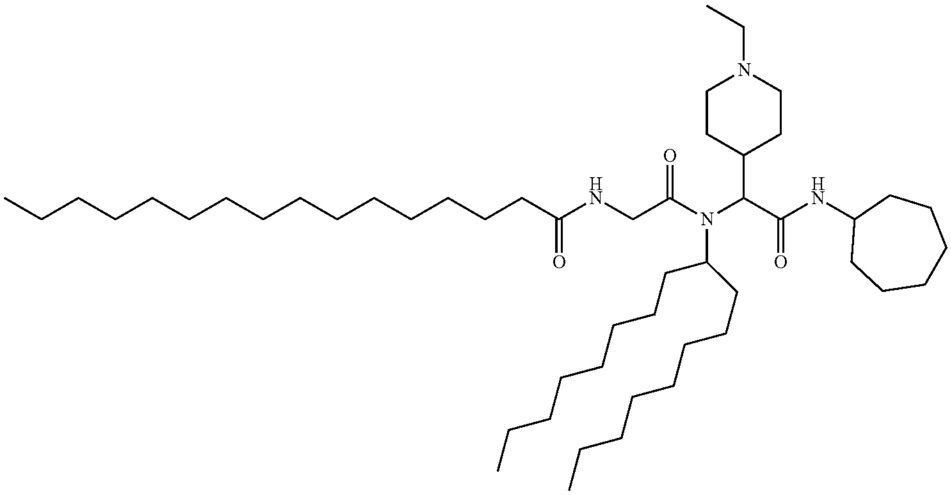
;
(XLVII)
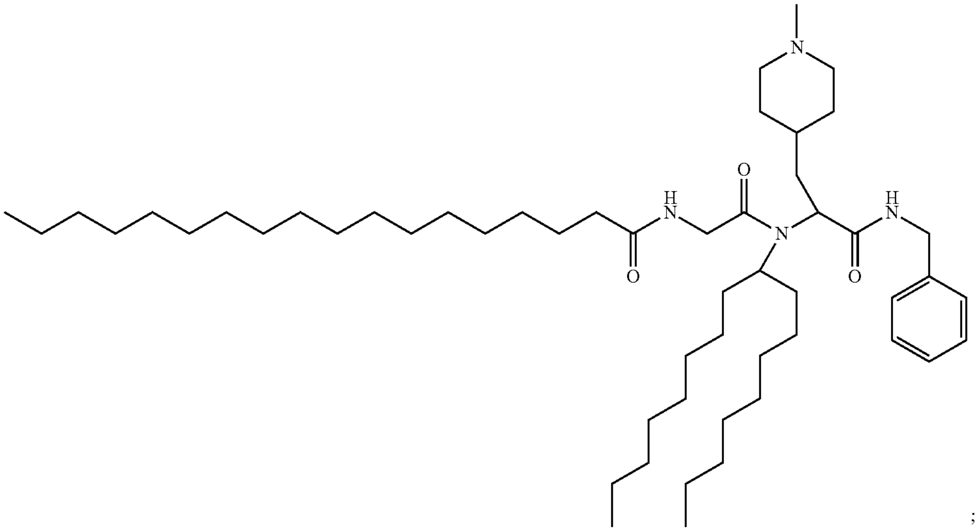
;

-continued
(XLVIII)
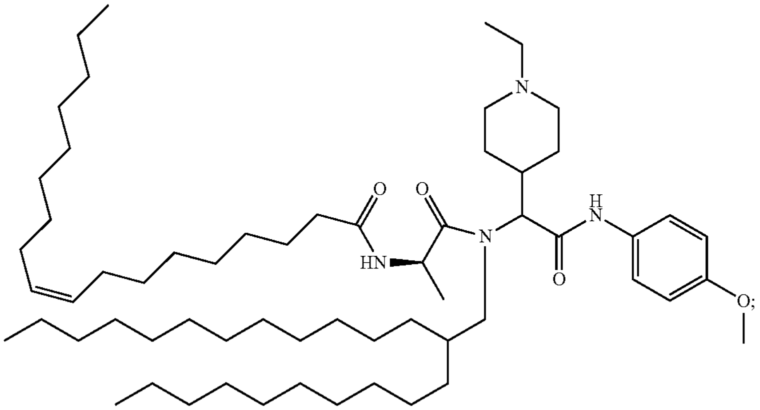
(XLIX)
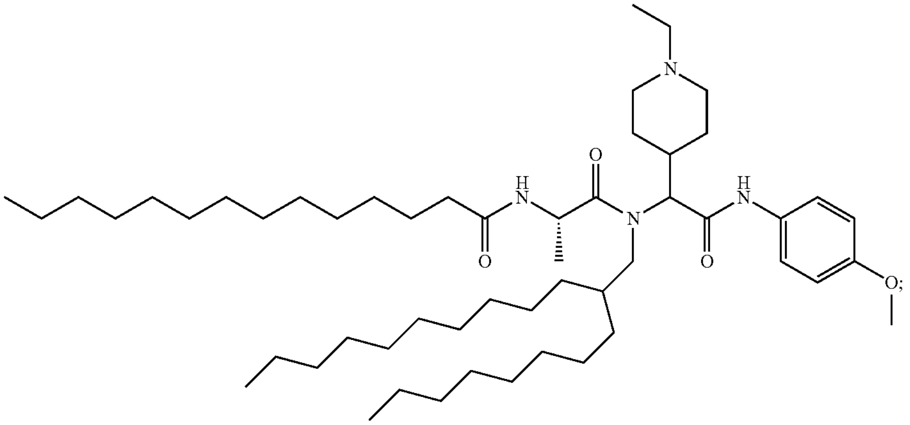
(L)
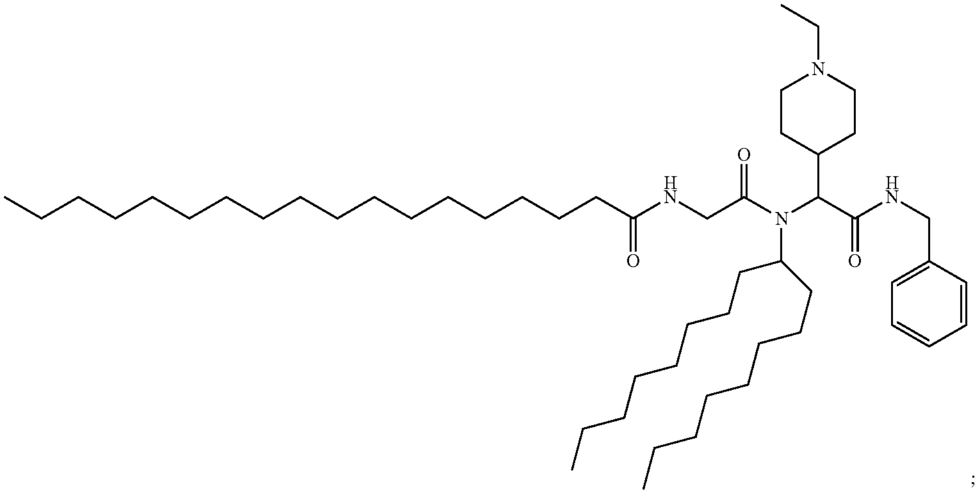
;

-continued
(LI)
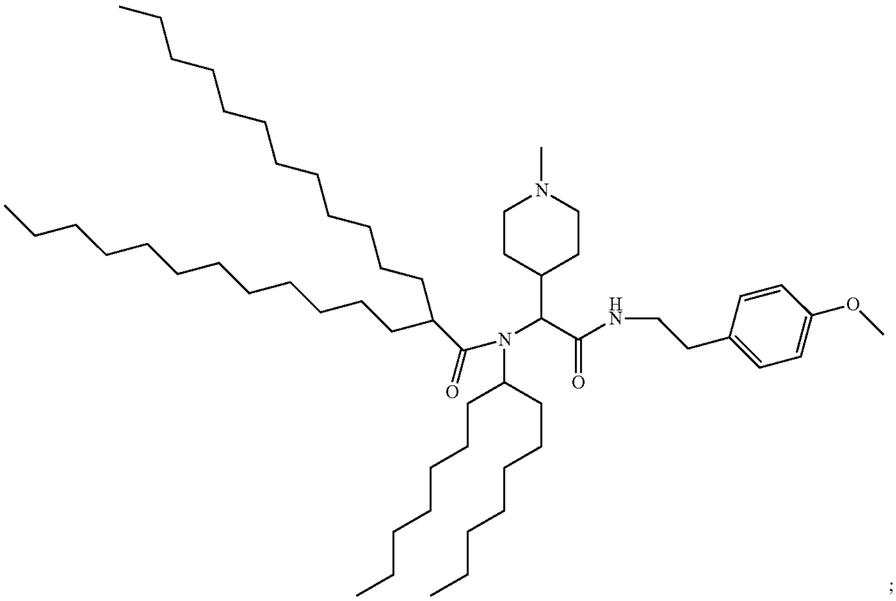
;
(LII)
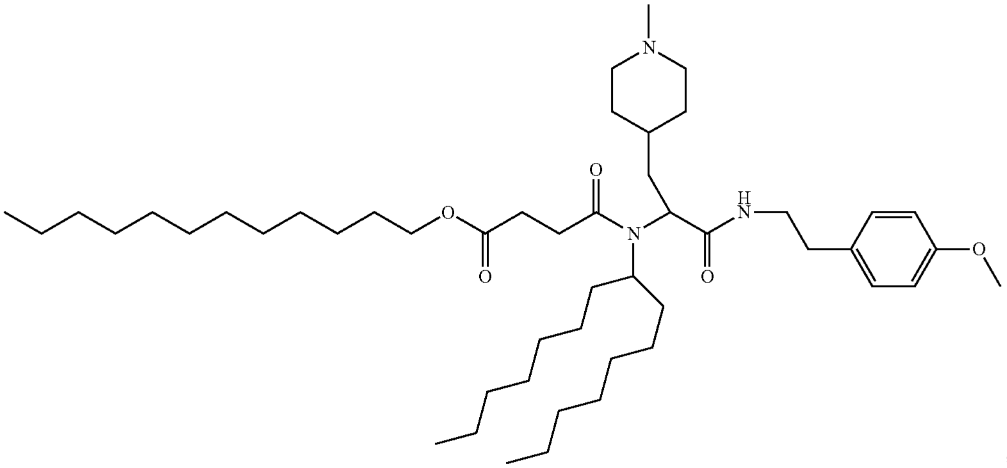
;
(LIII)
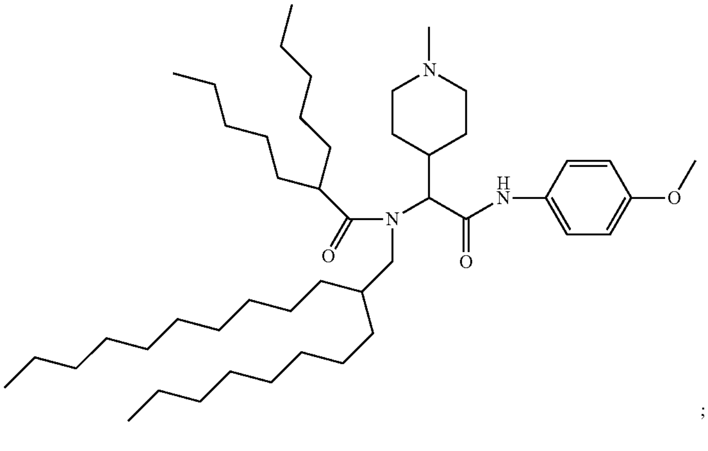
;

(LIV)
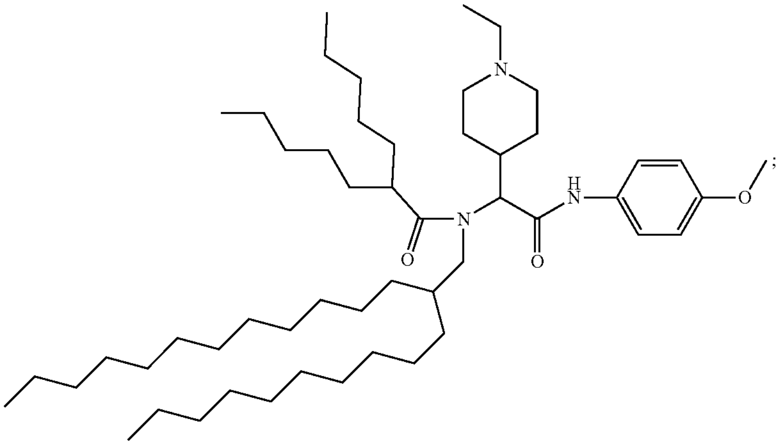
(LV)
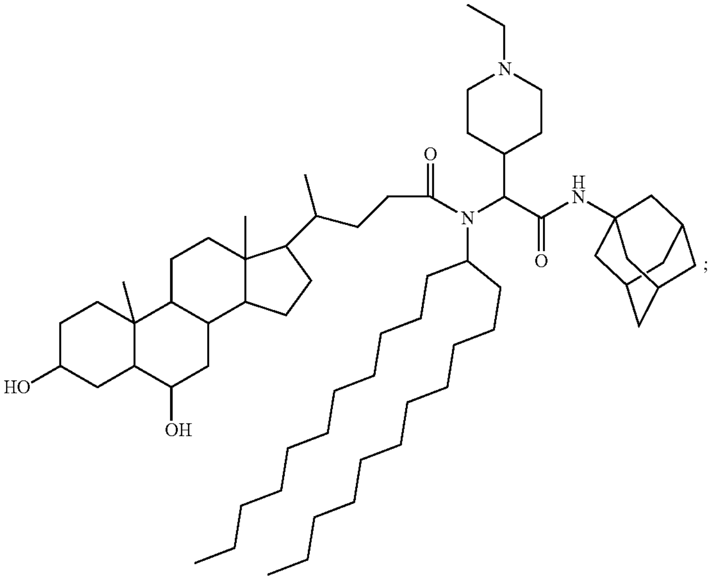
(LVI)
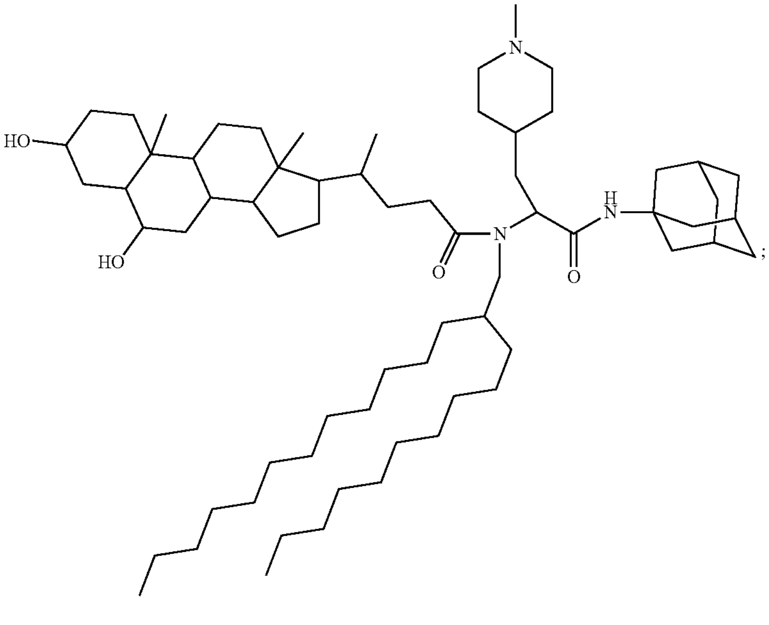

-continued
(LVII)
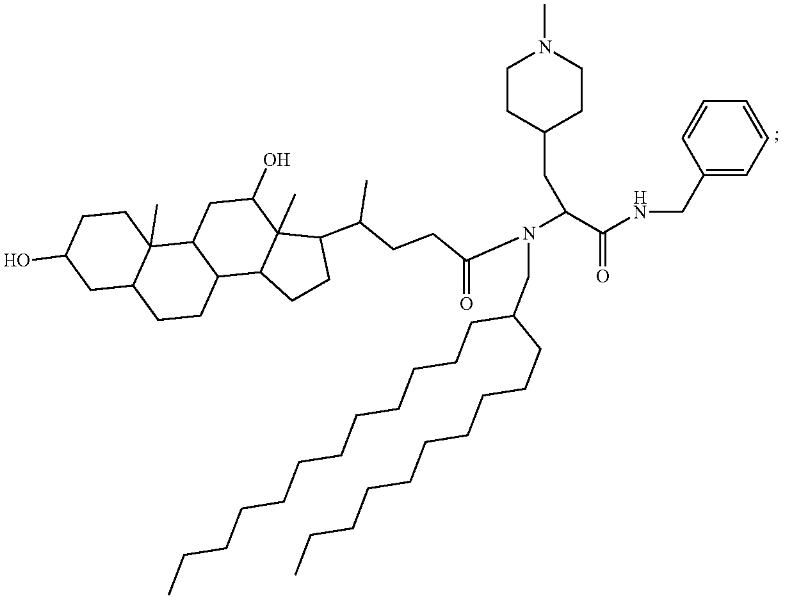
(LVIII)
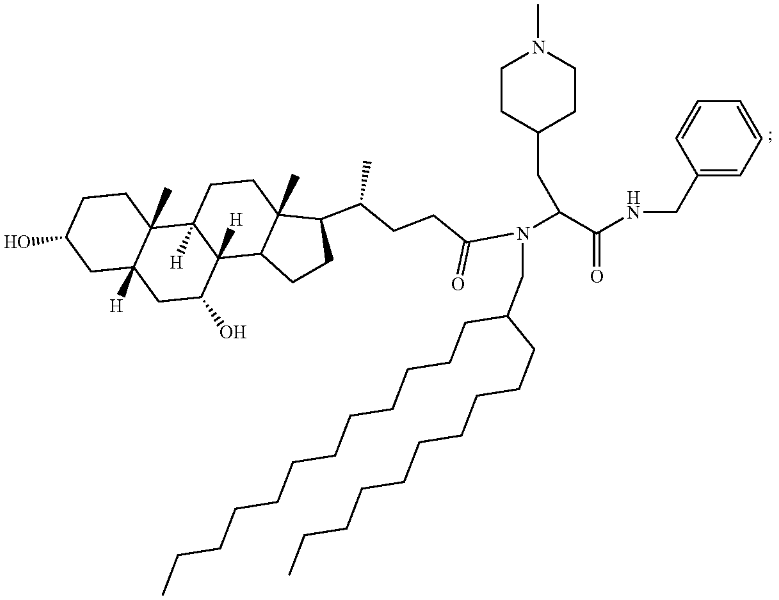

-continued
(LIX)
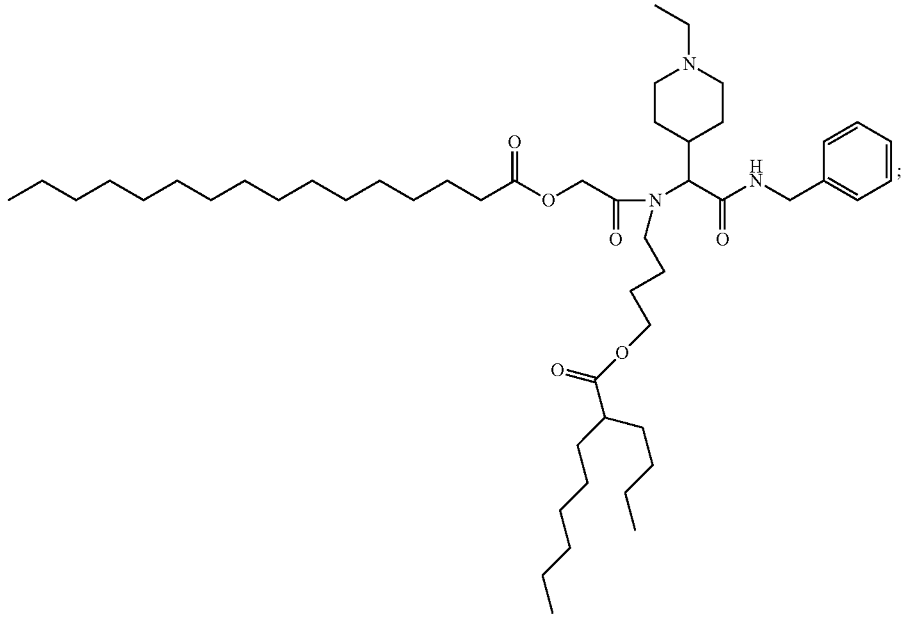
(LX)
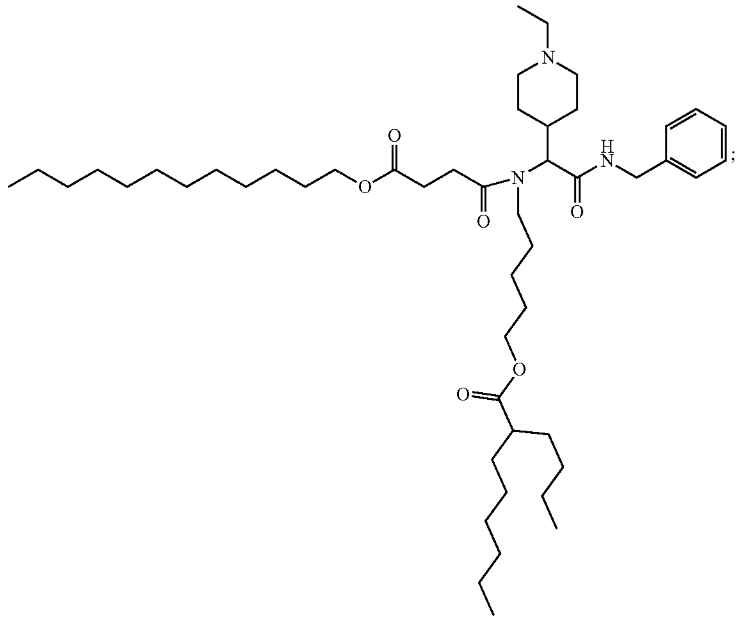

-continued (LXI)

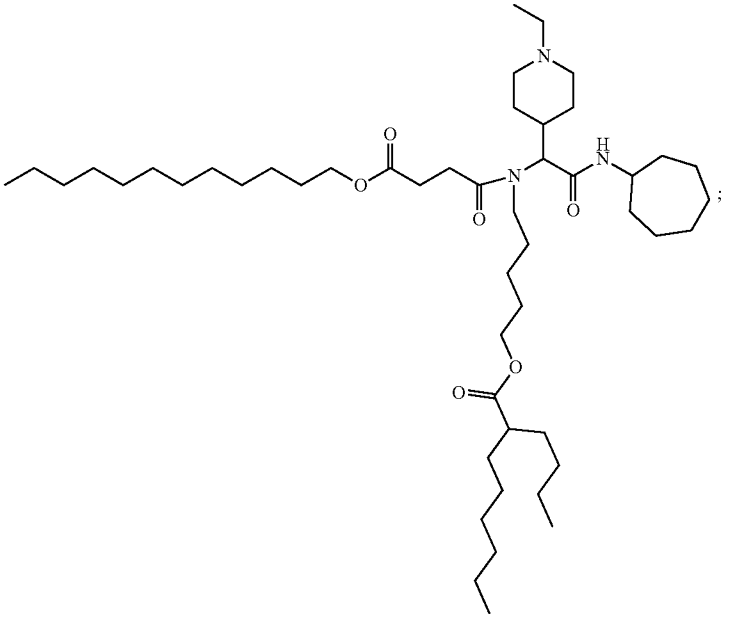

(LXII)

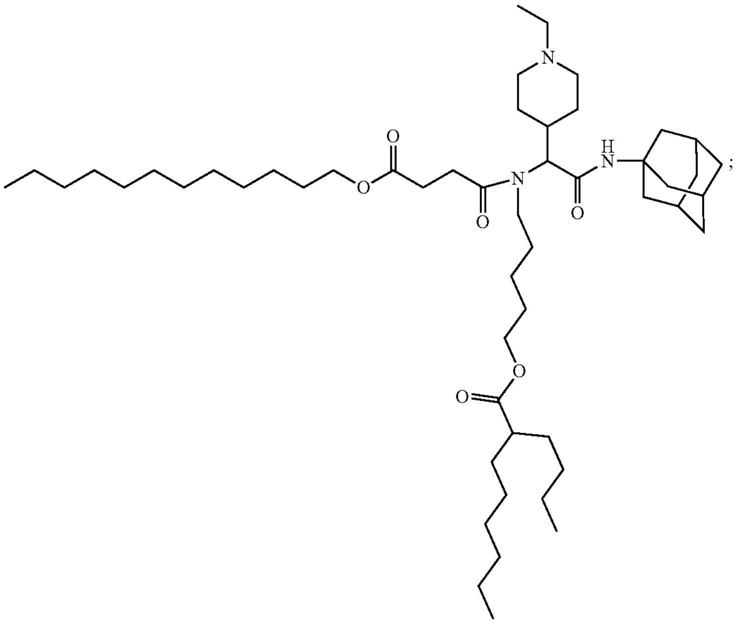

or a salt thereof.

26. The method of claim 22, wherein the self-amplifying mRNA comprises from 5' to 3':

a) 1869 to 9441 of SEQ ID NO: 21, the GOI, nucleotides 10162 to 10325 of SEQ ID NO: 21 and nucleotides 1 to 10 of SEQ ID NO: 21; or b) 1869 to 9441 of SEQ ID NO: 22, the GOI, nucleotides 10162 to 10325 of SEQ ID NO: 22 and nucleotides 1 to 10 of SEQ ID NO: 22; or c) 1869 to 9441 of SEQ ID NO: 23, the GOI, nucleotides 10162 to 10325 of SEQ ID NO: 23 and nucleotides 1 to 10 of SEQ ID NO: 23.

27. A method of delivering a payload to immune cells ex vivo comprising contacting immune cells with a lipid nanoparticle (LNP) encapsulating a payload encoding at least one polypeptide of interest, wherein the polypeptide of interest is an antigen receptor or an antibody, wherein the payload is a modified mRNA, a self-amplifying mRNA or a circular RNA comprising a nucleic acid sequence from 5' to 3':

a) 5'UTR-nsP-L-SGP-LP-GOI-L-3'UTR-PolyA, b) 5'UTR-nsP-SGP-LP-GOI-L-3'UTR-PolyA, c) 5'UTR-nsP-L-SGP-LP-GOI-3'UTR-PolyA, or d) 5'UTR-nsP-SGP-LP-GOI-3'UTR-PolyA wherein 5'UTR is a 5' untranslated region, nsP is a plurality of non-structural replicase domain sequences, L is a linker, SGP is a subgenomic promoter, 3'UTR is a 3' untranslated region, poly-A is a 3' poly-adenylated tail (poly-A tail), and wherein the GOI is one or more genes of interest; and wherein the GOI encodes:

a) an Nb; or b) an AR; or c) scFv-AR, wherein, scFv is a single-chain variable fragment; or d) an scFv-CAR having the structure VH-LK-VL-MyC-CD8-CD28-CD3z, wherein:

VH is an immunoglobulin heavy chain variable region,

LK is a linker,

VL is an immunoglobulin light chain variable region,

MyC is a Myc tag,

CD8 is a CD8 alpha chain hinge region,

CD28 is a CD28 activation domain, and

CD3z is a CD3 zeta cytoplasmic domain; or e) an scFv-CAR having the structure VH-LK-VL-CD8-CD28-CD3z wherein, VH is the immunoglobulin heavy chain variable region, LK is the linker, VL is the immunoglobulin light chain variable region, CD8 is the CD8 alpha chain hinge region, CD28 is the CD28 activation domain, and CD3z is the CD3 zeta cytoplasmic domain; or f) a reporter protein; and wherein the 5'UTR comprises nucleic acid sequence ATAGG and/or wherein the 3'UTR comprise a nucleotide sequence selected from SEQ ID NOs: 16, 17, 18, and 19;

wherein SGP is a nucleotide sequence selected from SEQ ID NOs: 10, 11, and 31;

wherein L is a nucleotide sequence selected from SEQ ID NOs: 12, 13, 14, and 15;

wherein the scFv encodes an amino acid sequence with at least about 85% sequence identity to SEQ ID NO: 32, 33, 34, 35, 36, 37, 38, 39, 40, or 45; and wherein the nucleotide sequence encoding the CAR comprises a nucleic acid sequence with at least about 98% sequence identity to SEQ ID NO: 26 or 44.

* * * * *

SEQUENCE LISTING

```
Sequence total quantity: 45
SEQ ID NO: 1            moltype = AA  length = 19
FEATURE                 Location/Qualifiers
source                  1..19
                        mol_type = protein
                        organism = synthetic construct
SEQUENCE: 1
MDWTWRILFL VAAATGTHA                                               19

SEQ ID NO: 2            moltype = AA  length = 17
FEATURE                 Location/Qualifiers
source                  1..17
                        mol_type = protein
                        organism = synthetic construct
SEQUENCE: 2
SSGGGGSGGG GSGGGGS                                                 17

SEQ ID NO: 3            moltype = AA  length = 10
FEATURE                 Location/Qualifiers
source                  1..10
                        mol_type = protein
                        organism = synthetic construct
SEQUENCE: 3
EQKLISEEDL                                                         10

SEQ ID NO: 4            moltype = AA  length = 66
FEATURE                 Location/Qualifiers
source                  1..66
                        mol_type = protein
                        organism = Mus musculus
SEQUENCE: 4
TTTKPVLRTP SPVHPTGTSQ PQRPEDCRPR GSVKGTGLDF ACDIYIWAPL AGICVALLLS  60
LIITLI                                                             66

SEQ ID NO: 5            moltype = AA  length = 41
FEATURE                 Location/Qualifiers
source                  1..41
                        mol_type = protein
                        organism = Mus musculus
SEQUENCE: 5
NSRRNRLLQS DYMNMTPRRP GLTRKPYQPY APARDFAAYR P                      41

SEQ ID NO: 6            moltype = AA  length = 113
FEATURE                 Location/Qualifiers
source                  1..113
                        mol_type = protein
                        organism = Mus musculus
SEQUENCE: 6
RAKFSRSAET AANLQDPNQL YNELNLGRRE EYDVLEKKRA RDPEMGGKQQ RRRNPQEGVY  60
NALQKDKMAE AYSEIGTKGE RRRGKGHDGL YQGLSTATKD TYDALHMQTL APR         113

SEQ ID NO: 7            moltype = AA  length = 68
FEATURE                 Location/Qualifiers
source                  1..68
                        mol_type = protein
                        organism = Homo sapiens
SEQUENCE: 7
TTTPAPRPPT PAPTIASQPL SLRPEACRPA AGGAVHTRGL DFACDIYIWA PLAGTCGVLL  60
LSLVITLY                                                           68

SEQ ID NO: 8            moltype = AA  length = 41
FEATURE                 Location/Qualifiers
source                  1..41
                        mol_type = protein
                        organism = Homo sapiens
SEQUENCE: 8
RSKRSRLLHS DYMNMTPRRP GPTRKHYQPY APPRDFAAYR S                      41

SEQ ID NO: 9            moltype = AA  length = 113
FEATURE                 Location/Qualifiers
source                  1..113
                        mol_type = protein
                        organism = Homo sapiens
SEQUENCE: 9
RVKFSRSADA PAYQQGQNQL YNELNLGRRE EYDVLDKRRG RDPEMGGKPQ RRKNPQEGLY  60
NELQKDKMAE AYSEIGMKGE RRRGKGHDGL YQGLSTATKD TYDALHMQAL PPR         113

SEQ ID NO: 10           moltype = RNA  length = 38
```

-continued

```
FEATURE                 Location/Qualifiers
source                  1..38
                        mol_type = other RNA
                        organism = synthetic construct
SEQUENCE: 10
taacctgaat ggactacgac atagtctagt ccgccaag                          38

SEQ ID NO: 11           moltype = RNA  length = 91
FEATURE                 Location/Qualifiers
source                  1..91
                        mol_type = other RNA
                        organism = synthetic construct
SEQUENCE: 11
gaacttccat catagttatg gccatgacta ctctagctag cagtgttaaa tcattcagct  60
acctgagagg ggcccctata actctctacg g                                 91

SEQ ID NO: 12           moltype = RNA  length = 82
FEATURE                 Location/Qualifiers
source                  1..82
                        mol_type = other RNA
                        organism = synthetic construct
SEQUENCE: 12
cgcgtgataa cgcaggaaag aacatgtgag caaaaggcca gcaaaaggcc aggaaccgta  60
aaaaggccgc gttgctggcg tt                                           82

SEQ ID NO: 13           moltype = RNA  length = 31
FEATURE                 Location/Qualifiers
source                  1..31
                        mol_type = other RNA
                        organism = synthetic construct
SEQUENCE: 13
cacatttccc cgaaaagtgc cacctgagct c                                 31

SEQ ID NO: 14           moltype = RNA  length = 26
FEATURE                 Location/Qualifiers
source                  1..26
                        mol_type = other RNA
                        organism = synthetic construct
SEQUENCE: 14
ttcgaaggcg cgcctctaga gccacc                                       26

SEQ ID NO: 15           moltype = RNA  length = 31
FEATURE                 Location/Qualifiers
source                  1..31
                        mol_type = other RNA
                        organism = synthetic construct
SEQUENCE: 15
catcgatgat atcgcggccg catacagcag c                                 31

SEQ ID NO: 16           moltype =   length =
SEQUENCE: 16
000

SEQ ID NO: 17           moltype = RNA  length = 21
FEATURE                 Location/Qualifiers
source                  1..21
                        mol_type = other RNA
                        organism = synthetic construct
SEQUENCE: 17
ggattttgtt tttaatattt c                                            21

SEQ ID NO: 18           moltype = RNA  length = 21
FEATURE                 Location/Qualifiers
source                  1..21
                        mol_type = other RNA
                        organism = synthetic construct
SEQUENCE: 18
ggattttatt tttaatattt c                                            21

SEQ ID NO: 19           moltype = RNA  length = 21
FEATURE                 Location/Qualifiers
source                  1..21
                        mol_type = other RNA
                        organism = synthetic construct
SEQUENCE: 19
aaattttatt tttaatattt c                                            21

SEQ ID NO: 20           moltype = RNA  length = 10325
FEATURE                 Location/Qualifiers
```

```
source                  1..10325
                        mol_type = other RNA
                        organism = synthetic construct
SEQUENCE: 20
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac cccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttaccttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aataccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag ggtgtatggg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacacccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
```

-continued

```
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cgggctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatc cttacaagct ttcatcaacc ttgaccaaca tttatacagg ttccagactc  5880
cacgaagccg gatgtgcacc ctcatatcat gtggtgcgag gggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
```

-continued

```
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttgtttt taatatttca aaaaaaaaaa  10320
aaaaa                                                              10325

SEQ ID NO: 21          moltype = RNA  length = 10325
FEATURE                Location/Qualifiers
source                 1..10325
                       mol_type = other RNA
                       organism = synthetic construct
SEQUENCE: 21
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac cccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttaccttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
```

-continued

```
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aataccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag ggtgtatgg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacatgta cgggctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatt cttacaagct ttcatcaacc ttgaccaaca tttatacagg ttccagactc  5880
cacgaagccg gatgtgcacc ctcatatcat tggtggcgag ggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
```

-continued

```
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagaccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agagggggcc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttgtttt taatatttca aaaaaaaaaa  10320
aaaaa                                                              10325
```

```
SEQ ID NO: 22          moltype = RNA  length = 10325
FEATURE                Location/Qualifiers
source                 1..10325
                       mol_type = other RNA
                       organism = synthetic construct
SEQUENCE: 22
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
```

-continued

```
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac ccccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttaccttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag ggtgtatggg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat tttctgcacc cactgttccg ttatccatta ggaataatca ctgggataac  5160
tccccgtcgc ctaacacgta cggctgaat aaagaagtgg tccgtcagct ctctcgcagg  5220
tacccacaac tgcctcgggc agttgccact ggaagagtct atgacatgaa cactggtaca  5280
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatt cttacaagct ttcatcaacc ttgaccaaca tttatacagg ttccagactc  5880
cacgaagccg gatgtgcacc ctcatatcat gtggtgcgag ggggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
```

-continued

```
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tggagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctatttg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttgtttt taatatttca aaaaaaaaaa  10320
aaaaa                                                              10325
```

```
SEQ ID NO: 23          moltype = RNA  length = 10325
FEATURE                Location/Qualifiers
source                 1..10325
                       mol_type = other RNA
                       organism = synthetic construct
SEQUENCE: 23
aaaaaaaaaa cgcgtgataa cgcaggaaag aacatgtgag caaaaggcca gcaaaaggcc  60
aggaaccgta aaaaggccgc gttgctggcg tttttccata ggctccgccc ccctgacgag  120
catcacaaaa atcgacgctc aagtcagagg tggcgaaacc cgacaggact ataaagatac  180
caggcgtttc cccctggaag ctccctcgtg cgctctcctg ttccgaccct gccgcttacc  240
ggatacctgt ccgcctttct cccttcggga agcgtggcgc tttctcatag ctcacgctgt  300
aggtatctca gttcggtgta ggtcgttcgc tccaagctgg gctgtgtgca cgaacccccc  360
gttcagcccg accgctgcgc cttatccggt aactatcgtc ttgagtccaa cccggtaaga  420
cacgacttat cgccactggc agcagccact ggtaacagga ttagcagagc gaggtatgta  480
ggcggtgcta cagagttctt gaagtggtgg cctaactacg gctacactag aagaacagta  540
```

-continued

```
tttggtatct gcgctctgct gaagccagtt accttcggaa aaagagttgg tagctcttga  600
tccggcaaac aaaccaccgc tggtagcggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg agctctaata cgactcacta  1860
taggataggc ggcgcatgag agaagcccag accaattacc tacccaaaat ggagaaagtt  1920
cacgttgaca tcgaggaaga cagcccattc ctcagagctt tgcagcggag cttcccgcag  1980
tttgaggtag aagccaagca ggtcactgat aatgaccatg ctaatgccag agcgttttcg  2040
catctggctt caaaactgat cgaaacggag gtggacccat ccgacacgat ccttgacatt  2100
ggaagtgcgc ccgcccgcag aatgtattct aagcacaagt atcattgtat ctgtccgatg  2160
agatgtgcgg aagatccgga cagattgtat aagtatgcaa ctaagctgaa gaaaaactgt  2220
aaggaaataa ctgataagga attggacaag aaaatgaagg agctggccgc cgtcatgagc  2280
gaccctgacc tggaaactga gactatgtgc ctccacgacg acgagtcgtg tcgctacgaa  2340
gggcaagtcg ctgtttacca ggatgtatac gcggttgacg gaccgacaag tctctatcac  2400
caagccaata agggagttag agtcgcctac tggataggct ttgacaccac ccccttttatg  2460
tttaagaact tggctggagc atatccatca tactctacca actgggccga cgaaaccgtg  2520
ttaacggctc gtaacatagg cctatgcagc tctgacgtta tggagcggtc acgtagaggg  2580
atgtccattc ttagaaagaa gtatttgaaa ccatccaaca atgttctatt ctctgttggc  2640
tcgaccatct accacgagaa gagggactta ctgaggagct ggcacctgcc gtctgtattt  2700
cacttacgtg gcaagcaaaa ttacacatgt cggtgtgaga ctatagttag ttgcgacggg  2760
tacgtcgtta aaagaatagc tatcagtcca ggcctgtatg ggaagccttc aggctatgct  2820
gctacgatgc accgcgaggg attcttgtgc tgcaaagtga cagacacatt gaacggggag  2880
agggtctctt ttcccgtgtg cacgtatgtg ccagctacat tgtgtgacca aatgactggc  2940
atactggcaa cagatgtcag tgcggacgac gcgcaaaaac tgctggttgg gctcaaccag  3000
cgtatagtcg tcaacggtcg cacccagaga aacaccaata ccatgaaaaa ttacctttttg  3060
cccgtagtgg cccaggcatt tgctaggtgg gcaaaggaat ataaggaaga tcaagaagat  3120
gaaaggccac taggactacg agatagacag ttagtcatgg ggtgttgttg ggcttttaga  3180
aggcacaaga taacatctat ttataagcgc ccggataccc aaaccatcat caaagtgaac  3240
agcgatttcc actcattcgt gctgcccagg ataggcagta acacattgga gatcgggctg  3300
agaacaagaa tcaggaaaat gttagaggag cacaaggagc cgtcacctct cattaccgcc  3360
gaggacgtac aagaagctaa gtgcgcagcc gatgaggcta aggaggtgcg tgaagccgag  3420
gagttgcgcg cagctctacc acctttggca gctgatgttg aggagcccac tctggaagcc  3480
gatgtcgact tgatgttaca agaggctggg gccggctcag tggagacacc tcgtggcttg  3540
ataaaggtta ccagctacga tggcgaggac aagatcggct cttacgctgt gctttctccg  3600
caggctgtac tcaagagtga aaaattatct tgcatccacc ctctcgctga acaagtcata  3660
gtgataacac actctggccg aaaagggcgt tatgccgtgg aaccatacca tggtaaagta  3720
gtggtgccag agggacatgc aatacccgtc caggactttc aagctctgag tgaaagtgcc  3780
accattgtgt acaacgaacg tgagttcgta aacaggtacc tgcaccatat tgccacacat  3840
ggaggagcgc tgaacactga tgaagaatat tacaaaactg tcaagcccag cgagcacgac  3900
ggcgaatacc tgtacgacat cgacaggaaa cagtgcgtca agaaagaact agtcactggg  3960
ctagggctca caggcgagct ggtggatcct cccttccatg aattcgccta cgagagtctg  4020
agaacacgac cagccgctcc ttaccaagta ccaaccatag gggtgtatgg cgtgccagga  4080
tcaggcaagt ctggcatcat taaaagcgca gtcaccaaaa aagatctagt ggtgagcgcc  4140
aagaaagaaa actgtgcaga aattataagg gacgtcaaga aaatgaaagg gctggacgtc  4200
aatgccagaa ctgtggactc agtgctcttg aatggatgca aacaccccgt agagaccctg  4260
tatattgacg aagcttttgc ttgtcatgca ggtactctca gagcgctcat agccattata  4320
agacctaaaa aggcagtgct ctgcggggat cccaaacagt gcggtttttt taacatgatg  4380
tgcctgaaag tgcattttaa ccacgagatt tgcacacaag tcttccacaa aagcatctct  4440
cgccgttgca ctaaatctgt gacttcggtc gtctcaacct tgttttacga caaaaaaatg  4500
agaacgacga atccgaaaga gactaagatt gtgattgaca ctaccggcag taccaaacct  4560
aagcaggacg atctcattct cacttgtttc agagggtggg tgaagcagtt gcaaatagat  4620
tacaaaggca acgaaataat gacggcagct gcctctcaag ggctgacccg taaaggtgtg  4680
tatgccgttc ggtacaaggt gaatgaaaat cctctgtacg cacccacctc agaacatgtg  4740
aacgtcctac tgacccgcac ggaggaccgc atcgtgtgga aaacactagc cggcgaccca  4800
tggataaaaa cactgactgc caagtaccct gggaatttca ctgccacgat agaggagtgg  4860
caagcagagc atgatgccat catgaggcac atcttggaga gaccggaccc taccgacgtc  4920
ttccagaata aggcaaacgt gtgttgggcc aaggctttag tgccggtgct gaagaccgct  4980
ggcatagaca tgaccactga acaatggaac actgtggatt attttgaaac ggacaaagct  5040
cactcagcag agatagtatt gaaccaacta tgcgtgaggt tctttggact cgatctggac  5100
tccggtctat ttttctgcacc cactgttccg ttatccatta ggaataatca ctgggataac  5160
tccccgtcgc ctaacatgta cgggctgaat aaagaagtgg tccgtcagct ctctcgcagg  5220
tacccacaac tgcctcgggc agttgccact ggaagagtct atgacatgaa cactggtaca  5280
```

-continued

```
ctgcgcaatt atgatccgcg cataaaccta gtacctgtaa acagaagact gcctcatgct  5340
ttagtcctcc accataatga acacccacag agtgactttt cttcattcgt cagcaaattg  5400
aagggcagaa ctgtcctggt ggtcggggaa aagttgtccg tcccaggcaa aatggttgac  5460
tggttgtcag accggcctga ggctaccttc agagctcggc tggatttagg catcccaggt  5520
gatgtgccca aatatgacat aatatttgtt aatgtgagga ccccatataa ataccatcac  5580
tatcagcagt gtgaagacca tgccattaag cttagcatgt tgaccaagaa agcttgtctg  5640
catctgaatc ccggcggaac ctgtgtcagc ataggttatg gttacgctga cagggccagc  5700
gaaagcatca ttggtgctat agcgcggcag ttcaagtttt cccgggtatg caaaccgaaa  5760
tcctcacttg aagagacgga agttctgttt gtattcattg ggtacgatcg caaggcccgt  5820
acgcacaatt cttacaagct ttcatcaacc ttgaccaaca tttatacagg ttccagactc  5880
cacgaagccg gatgtgcacc ctcatatcat gtggtgcgag ggggatattgc cacggccacc  5940
gaaggagtga ttataaatgc tgctaacagc aaaggacaac ctggcggagg ggtgtgcgga  6000
gcgctgtata agaaattccc ggaaagcttc gatttacagc cgatcgaagt aggaaaagcg  6060
cgactggtca aaggtgcagc taaacatatc attcatgccg taggaccaaa cttcaacaaa  6120
gtttcggagg ttgaaggtga caaacagttg gcagaggctt atgagtccat cgctaagatt  6180
gtcaacgata acaattacaa gtcagtagcg attccactgt tgtccaccgg catcttttcc  6240
gggaacaaag atcgactaac ccaatcattg aaccatttgc tgacagcttt agacaccact  6300
gatgcagatg tagccatata ctgcagggac aagaaatggg aaatgactct caaggaagca  6360
gtggctagga gagaagcagt ggaggagata tgcatatccg acgactcttc agtgacagaa  6420
cctgatgcag agctggtgag ggtgcatccg aagagttctt tggctggaag gaagggctac  6480
agcacaagcg atggcaaaac tttctcatat ttggaaggga ccaagtttca ccaggcggcc  6540
aaggatatag cagaaattaa tgccatgtgg cccgttgcaa cggaggccaa tgagcaggta  6600
tgcatgtata tcctcggaga aagcatgagc agtattaggt cgaaatgccc cgtcgaagag  6660
tcggaagcct ccacaccacc tagcacgctg ccttgcttgt gcatccatgc catgactcca  6720
gaaagagtac agcgcctaaa agcctcacgt ccagaacaaa ttactgtgtg ctcatccttt  6780
ccattgccga agtatagaat cactggtgtg cagaagatcc aatgctccca gcctatattg  6840
ttctcaccga aagtgcctgc gtatattcat ccaaggaagt atctcgtgga aacaccaccg  6900
gtagacgaga ctccggagcc atcggcagag aaccaatcca cagaggggac acctgaacaa  6960
ccaccactta taaccgagga tgagaccagg actagaacgc ctgagccgat catcatcgaa  7020
gaggaagaag aggatagcat aagtttgctg tcagatggcc cgacccacca ggtgctgcaa  7080
gtcgaggcag acattcacgg gccgccctct gtatctagct catcctggtc cattcctcat  7140
gcatccgact ttgatgtgga cagtttatcc atacttgaca ccctggaggg agctagcgtg  7200
accagcgggg caacgtcagc cgagactaac tcttacttcg caaagagtat ggagtttctg  7260
gcgcgaccgg tgcctgcgcc tcgaacagta ttcaggaacc ctccacatcc cgctccgcgc  7320
acaagaacac cgtcacttgc acccagcagg gcctgctcga gaaccagcct agtttccacc  7380
ccgccaggcg tgaatagggt gatcactaga gaggagctcg aggcgcttac cccgtcacgc  7440
actcctagca ggtcggtctc gagaaccagc ctggtctcca acccgccagg cgtaaatagg  7500
gtgattacaa gagaggagtt tgaggcgttc gtagcacaac aacaatgacg gtttgatgcg  7560
ggtgcataca tcttttcctc cgacaccggt caagggcatt tacaacaaaa atcagtaagg  7620
caaacggtgc tatccgaagt ggtgttggag aggaccgaat tgaagatttc gtatgccccg  7680
cgcctcgacc aagaaaaaga agaattacta cgcaagaaat tacagttaaa tcccacacct  7740
gctaacagaa gcagatacca gtccaggaag gtggagaaca tgaaagccat aacagctaga  7800
cgtattctgc aaggcctagg gcattatttg aaggcagaag gaaaagtgga gtgctaccga  7860
accctgcatc ctgttccttt gtattcatct agtgtgaacc gtgccttttc aagcccccaag  7920
gtcgcagtgg aagcctgtaa cgccatgttg aaagagaact ttccgactgt ggcttcttac  7980
tgtattattc cagagtacga tgcctatttg gacatggttg acggagcttc atgctgctta  8040
gacactgcca gtttttgccc tgcaaagctg cgcagctttc caaagaaaca ctcctattg  8100
gaacccacaa tacgatcggc agtgccttca gcgatccaga acacgctcca gaacgtcctg  8160
gcagctgcca caaaaagaaa ttgcaatgtc acgcaaatga gagaattgcc cgtattggat  8220
tcggcggcct ttaatgtgga atgcttcaag aaatatgcgt gtaataatga atattgggaa  8280
acgtttaaag aaaaccccat caggcttact gaagaaaacg tggtaaatta cattaccaaa  8340
ttaaaaggac caaaagctgc tgctcttttt gcgaagacac ataatttgaa tatgttgcag  8400
gacataccaa tggacaggtt tgtaatggac ttaaagagag acgtgaaagt gactccagga  8460
acaaaacata ctgaagaacg gcccaaggta caggtgatcc aggctgccga tccgctagca  8520
acagcgtatc tgtgcggaat ccaccgagag ctggttagga gattaaatgc ggtcctgctt  8580
ccgaacattc atacactgtt tgatatgtcg gctgaagact ttgacgctat tatagccgag  8640
cacttccagc ctggggattg tgttctggaa actgacatcg cgtcgtttga taaaagtgag  8700
gacgacgcca tggctctgac cgcgttaatg attctggaag acttaggtgt ggacgcagag  8760
ctgttgacgc tgattgaggc ggctttcggc gaaatttcat caatacattt gcccactaaa  8820
actaaattta aattcggagc catgatgaaa tctggaatgt tcctcacact gtttgtgaac  8880
acagtcatta acattgtaat cgcaagcaga gtgttgagag aacggctaac cggatcacca  8940
tgtgcagcat tcattggaga tgacaatatc gtgaaaggag tcaaatcgga caaattaatg  9000
gcagacaggt gcgccacctg gttgaatatg gaagtcaaga ttatagatgc tgtggtgggc  9060
gagaaagcgc cttatttctg tggagggttt attttgtgtg actccgtgac cggcacagcg  9120
tgccgtgtgg cagacccccct aaaaaggctg tttaagcttg gcaaacctct ggcagcagac  9180
gatgaacatg atgatgacag gagaagggca ttgcatgaag agtcaacacg ctggaaccga  9240
gtgggtattc tttcagagct gtgcaaggca gtagaatcaa ggtatgaaac cgtaggaact  9300
tccatcatag ttatggccat gactactcta gctagcagtg ttaaatcatt cagctacctg  9360
agaggggccc ctataactct ctacggctaa cctgaatgga ctacgacata gtctagtccg  9420
ccaagttcga aggcgcgcct ctagagccac catggtgagc aagggcgagg agctgttcac  9480
cggggtggtg cccatcctgg tcgagctgga cggcgacgta aacggccaca agttcagcgt  9540
gtccggcgag ggcgagggcg atgccaccta cggcaagctg accctgaagt tcatctgcac  9600
caccggcaag ctgcccgtgc cctggcccac cctcgtgacc accctgacct acggcgtgca  9660
gtgcttcagc cgctaccccg accacatgaa gcagcacgac ttcttcaagt ccgccatgcc  9720
cgaaggctac gtccaggagc gcaccatctt cttcaaggac gacggcaact acaagacccg  9780
cgccgaggtg aagttcgagg gcgacaccct ggtgaaccgc atcgagctga agggcatcga  9840
cttcaaggag gacggcaaca tcctggggca caagctggag tacaactaca acagccacaa  9900
cgtctatatc atggccgaca agcagaagaa cggcatcaag gtgaacttca agatccgcca  9960
caacatcgag gacggcagcg tgcagctcgc cgaccactac cagcagaaca cccccatcgg  10020
```

```
cgacggcccc gtgctgctgc ccgacaacca ctacctgagc acccagtccg ccctgagcaa  10080
agaccccaac gagaagcgcg atcacatggt cctgctggag ttcgtgaccg ccgccgggat  10140
cactctcggc atggacgagc tgtacaagta gcatcgatga tatcgcggcc gcatacagca  10200
gcaattggca agctgcttac atagaactcg cggcgattgg catgccgcct taaaattttt  10260
attttatttt tcttttcttt tccgaatcgg attttgtttt taatatttca aaaaaaaaaa  10320
aaaaa                                                              10325

SEQ ID NO: 24          moltype = RNA  length = 3811
FEATURE                Location/Qualifiers
source                 1..3811
                       mol_type = other RNA
                       organism = synthetic construct
SEQUENCE: 24
agccacaccc tggagctagc aaaaaaaaaa aaaaaaaaaa aaaaaaaaaa gcatatgact  60
aaaaaaaaaa aaaaaaaaaa aaaaaaaaaa aaaaaaaaaa aaaaaaaaaa aaaaaaaaaa  120
aaaaaaaaaa cgcgtatcga tgatatcgcg gccgcataca gcagcaattg gcaagctgct  180
tacatagaac tcgcggcgat tggcatgccg ccttaaaatt tttattttat tttctttttc  240
ttttccgaat cggattttgt ttttaatatt tcaaaaaaaa aaaaaaaaaa aaaaaaaacg  300
cgtgataacg caggaaagaa catgtgagca aaaggccagc aaaaggccag gaaccgtaaa  360
aaggccgcgt tgctggcgtt tttccatagg ctccgccccc ctgacgagca tcacaaaaat  420
cgacgctcaa gtcagaggtg gcgaaacccg acaggactat aaagatacca ggcgtttccc  480
cctggaagct ccctcgtgcg ctctcctgtt ccgaccctgc cgcttaccgg atacctgtcc  540
gcctttctcc cttcgggaag cgtggcgctt tctcatagct cacgctgtag gtatctcagt  600
tcggtgtagg tcgttcgctc caagctgggc tgtgtgcacg aaccccccgt tcagcccgac  660
cgctgcgcct tatccggtaa ctatcgtctt gagtccaacc cggtaagaca cgacttatcg  720
ccactggcag cagccactgg taacaggatt agcagagcga ggtatgtagg cggtgctaca  780
gagttcttga agtggtggcc taactacggc tacactagaa gaacagtatt tggtatctgc  840
gctctgctga agccagttac cttcggaaaa agagttggta gctcttgatc cggcaaacaa  900
accaccgctg gtagcggttt ttttgtttgc aagcagcaga ttacgcgcag aaaaaaagga  960
tctcaagaag atcctttgat cttttctacg gggtctgacg ctcagtggaa cgaaaactca  1020
cgttaaggga ttttggtcat gagattatca aaaaggatct tcacctagat ccttttaaat  1080
taaaaatgaa gttttaaatc aatctaaagt atatatgagt aaacttggtc tgacagttac  1140
caatgcttaa tcagtgaggc acctatctca gcgatctgtc tatttcgttc atccatagtt  1200
gcctgactcc ccgtcgtgta gataactacg atacgggagg gcttaccatc tggccccagt  1260
gctgcaatga taccgcgaga cccacgctca ccggctccag atttatcagc aataaaccag  1320
ccagccggaa gggccgagcg cagaagtggt cctgcaactt tatccgcctc catccagtct  1380
attaattgtt gccgggaagc tagagtaagt agttcgccag ttaatagttt gcgcaacgtt  1440
gttgccattg ctacaggcat cgtggtgtca cgctcgtcgt ttggtatggc ttcattcagc  1500
tccggttccc aacgatcaag gcgagttaca tgatccccca tgttgtgcaa aaaagcggtt  1560
agctccttcg gtcctccgat cgttgtcaga agtaagttgg ccgcagtgtt atcactcatg  1620
gttatggcag cactgcataa ttctcttact gtcatgccat ccgtaagatg cttttctgtg  1680
actggtgagt actcaaccaa gtcattctga gaatagtgta tgcggcgacc gagttgctct  1740
tgcccggcgt caatacggga taataccgcg ccacatagca gaactttaaa agtgctcatc  1800
attggaaaac gttcttcggg gcgaaaactc tcaaggatct taccgctgtt gagatccagt  1860
tcgatgtaac ccactcgtgc acccaactga tcttcagcat cttttacttt caccagcgtt  1920
tctgggtgag caaaaacagg aaggcaaaat gccgcaaaaa agggaataag ggcgacacgg  1980
aaatgttgaa tactcatact cttccttttt caatattatt gaagcattta tcagggttat  2040
tgtctcatga gcggatacat atttgaatgt atttagaaaa ataaacaaat aggggttccg  2100
cgcacatttc cccgaaaagt gccacctgag ctctaatacg actcactata ggataggaca  2160
tttgcttctg acacaactgt gttcactagc aacctcaaac agacaccatg gattggacat  2220
ggcgaatcct ctttttggtc gcagcagcga cgggaacaca cgcagacatt caaatgactc  2280
agactacgag ctccctctcc gcatccctcg gcgaccgggt gactattagc tgccgcgcct  2340
ctcaagatat tagcaaatac cttaattggt accaacagaa gccggacgga acagtaaagc  2400
tcctgattta ccacacgtct cgacttcatt ccggcgtacc tagtaggttt tctggctctg  2460
gatctggtac cgactactcc ctcacaattt ccaatttgga acaagaagac attgccacct  2520
acttctgtca acagggcaat acgctgccat acacgttcgg cgggggtacc aaactggaga  2580
ttaccgggtc cacatctgga tccgggaagc cgggctccgg tgagggatca accaaaggcg  2640
aagtcaagtt gcaggaatct ggaccgggcc tcgttgcacc gtctcagtct ttgtccgtca  2700
cttgcacagt atcaggagtt tcccttcctg actacggggt atcttggatc cgacagccgc  2760
ccagaaaggg gctggagtgg ctcggagtga tatgggggtc tgaaaccacc tactataata  2820
gcgccctcaa gagtagactg actattatta aggataactc caagtctcag gtatttctca  2880
aaatgaacag tcttcagact gacgacacag ccatatacta ctgtgcgaaa cactattatt  2940
acggtggcag ttacgccatg gactactggg gccaggggac aagcgtaacc gtttcaagtg  3000
cagccgcaac aacgactcca gctcccaggc cgccgactcc tgctccgacg atagcctccc  3060
aaccccttgtc actccgccct gaagcatgta ggccagccgc aggaggcgct gttcataccc  3120
gaggattgga tttcgcttgc gatatttata tctgggcacc gttggcaggg acatgcggcg  3180
tgctgttgtt gagcctcgta ataacgctgt acaggtccaa gaggtcccgc cttcttcatt  3240
ccgattacat gaacatgacc cccagacgcc caggtccaac acgaaaacat tatcaaccat  3300
atgctccacc tagggacttt gcagcatacc gatctcgcgt gaaattcagc cgatctgccg  3360
acgcaccggc ctatcagcaa ggccagaacc aactttacaa cgagcttaac ttggggagaa  3420
gagaggaata tgatgtactg gacaagcggc gaggtcggga tcctgagatg ggaggtaaac  3480
ctcaacggag aaaaaaccca caagaaggtc tctacaacga gctgcaaaag gacaagatgg  3540
ccgaggcata ttcagaaatt gggatgaagg gcgaacgacg ccgaggcaaa ggacatgatg  3600
gattgtacca gggcctctct accgcaacta aagataccta cgatgccctc catatgcagg  3660
cacttccccc gcgataggct cgctttcttg ctgtccaatt tctattaaag gttcctttgt  3720
tccctaagtc caactactaa actgggggat attatgaagg gccttgagca tctggattct  3780
gcctaataaa aaacatttat tttcattgca a                                 3811

SEQ ID NO: 25          moltype = RNA  length = 255
```

-continued

```
FEATURE                 Location/Qualifiers
source                  1..255
                        mol_type = other RNA
                        organism = synthetic construct
SEQUENCE: 25
atggattgga catggcgaat cctctttttg gtcgcagcag cgacgggaac acacgcagac  60
attcaaatga ctcagactac gagctccctc tccgcatccc tcggcgaccg ggtgactatt  120
agctgccgcg cctctcaaga tattagcaaa taccttaatt ggtaccaaca gaagccggac  180
ggaacagtaa agctcctgat ttaccacacg tctcgacttc attccggcgt acctagtagg  240
ttttctggct ctgga                                                   255

SEQ ID NO: 26           moltype = RNA  length = 1211
FEATURE                 Location/Qualifiers
source                  1..1211
                        mol_type = other RNA
                        organism = synthetic construct
SEQUENCE: 26
tctggtaccg actactccct cacaatttcc aatttggaac aagaagacat tgccacctac  60
ttctgtcaac agggcaatac gctgccatac acgttcggcg ggggtaccaa actggagatt  120
accgggtcca catctggatc cgggaagccg ggctccggtg agggatcaac caaaggcgaa  180
gtcaagttgc aggaatctgg accgggcctc gttgcaccgt ctcagtcttt gtccgtcact  240
tgcacagtat caggagtttc ccttcctgac tacggggtat cttggatccg acagccgccc  300
agaaaggggc tggagtggct cggagtgata tgggggtctg aaaccaccta ctataatagc  360
gccctcaaga gtagactgac tattattaag gataactcca agtctcaggt atttctcaaa  420
atgaacagtc ttcagactga cgacacagcc atatactact gtgcgaaaca ctattattac  480
ggtggcagtt acgccatgga ctactggggc caggggacaa gcgtaaccgt ttcaagtgca  540
gccgcaacaa cgactccagc tcccaggccg ccgactcctg ctccgacgat agcctcccaa  600
cccttgtcac tccgccctga agcatgtagg ccagccgcag gaggcgctgt tcatacccga  660
ggattggatt tcgcttgcga tatttatatc tgggcaccgt tggcagggac atgcggcgtg  720
ctgttgttga gcctcgtaat aacgctgtac aggtccaaga ggtcccgcct tcttcattcc  780
gattacatga acatgacccc cagacgccca ggtccaacac gaaaacatta tcaaccatat  840
gctccaccta gggactttgc agcataccga tctcgcgtga aattcagccg atctgccgac  900
gcaccggcct atcagcaagg ccagaaccaa ctttacaacg agcttaactt ggggagaaga  960
gaggaatatg atgtactgga caagcggcga ggtcgggatc ctgagatggg aggtaaacct  1020
caacggagaa aaaacccaca agaaggtctc tacaacgagc tgcaaaagga caagatggcc  1080
gaggcatatt cagaaattgg gatgaagggc gaacgacgcc gaggcaaggg acatgatgga  1140
ttgtaccagg gcctctctac cgcaactaaa gatacctacg atgccctcca tatgcaggca  1200
cttcccccgc g                                                       1211

SEQ ID NO: 27           moltype = RNA  length = 3814
FEATURE                 Location/Qualifiers
source                  1..3814
                        mol_type = other RNA
                        organism = synthetic construct
SEQUENCE: 27
agccacaccc tggagctagc aaaaaaaaaa aaaaaaaaaa aaaaaaaaaa gcatatgact  60
aaaaaaaaaa aaaaaaaaaa aaaaaaaaaa aaaaaaaaaa aaaaaaaaaa aaaaaaaaaa  120
aaaaaaaaaa cgcgtatcga tgatatcgcg gccgcataca gcagcaattg gcaagctgct  180
tacatagaac tcgcggcgat tggcatgccg ccttaaaatt tttattttat ttttcttttc  240
ttttccgaat cggattttgt ttttaatatt tcaaaaaaaa aaaaaaaaaa aaaaaaaacg  300
cgtgataacg caggaaagaa catgtgagca aaaggccagc aaaaggccag gaaccgtaaa  360
aaggccgcgt tgctggcgtt tttccatagg ctccgccccc ctgacgagca tcacaaaaat  420
cgacgctcaa gtcagaggtg gcgaaacccg acaggactat aaagatacca ggcgtttccc  480
cctggaagct ccctcgtgcg ctctcctgtt ccgaccctgc cgcttaccgg atacctgtcc  540
gcctttctcc cttcgggaag cgtggcgctt tctcatagct cacgctgtag gtatctcagt  600
tcggtgtagg tcgttcgctc caagctgggc tgtgtgcacg aaccccccgt tcagcccgac  660
cgctgcgcct tatccggtaa ctatcgtctt gagtccaacc cggtaagaca cgacttatcg  720
ccactggcag cagccactgg taacaggatt agcagagcga ggtatgtagg cggtgctaca  780
gagttcttga agtggtggcc taactacggc tacactagaa gaacagtatt tggtatctgc  840
gctctgctga agccagttac cttcggaaaa agagttggta gctcttgatc cggcaaacaa  900
accaccgctg gtagcggttt ttttgtttgc aagcagcaga ttacgcgcag aaaaaaagga  960
tctcaagaag atcctttgat cttttctacg gggtctgacg ctcagtggaa cgaaaactca  1020
cgttaaggga ttttggtcat gagattatca aaaaggatct tcacctagat ccttttaaat  1080
taaaaatgaa gttttaaatc aatctaaagt atatatgagt aaacttggtc tgacagttac  1140
caatgcttaa tcagtgaggc acctatctca gcgatctgtc tatttcgttc atccatagtt  1200
gcctgactcc ccgtcgtgta gataactacg atacgggagg gcttaccatc tggccccagt  1260
gctgcaatga taccgcgaga cccacgctca ccggctccag atttatcagc aataaaccag  1320
ccagccggaa gggccgagcg cagaagtggt cctgcaactt tatccgcctc catccagtct  1380
attaattgtt gccgggaagc tagagtaagt agttcgccag ttaatagttt gcgcaacgtt  1440
gttgccattg ctacaggcat cgtggtgtca cgctcgtcgt ttggtatggc ttcattcagc  1500
tccggttccc aacgatcaag gcgagttaca tgatccccca tgttgtgcaa aaaagcggtt  1560
agctccttcg gtcctccgat cgttgtcaga agtaagttgg ccgcagtgtt atcactcatg  1620
gttatggcag cactgcataa ttctcttact gtcatgccat ccgtaagatg cttttctgtg  1680
actggtgagt actcaaccaa gtcattctga gaatagtgta tgcggcgacc gagttgctct  1740
tgcccggcgt caatacggga taataccgcg ccacatagca gaactttaaa agtgctcatc  1800
attggaaaac gttcttcggg gcgaaaactc tcaaggatct taccgctgtt gagatccagt  1860
tcgatgtaac ccactcgtgc acccaactga tcttcagcat cttttacttt caccagcgtt  1920
tctgggtgag caaaaacagg aaggcaaaat gccgcaaaaa agggaataag ggcgacacgg  1980
aaatgttgaa tactcatact cttccttttt caatattatt gaagcattta tcagggttat  2040
```

```
tgtctcatga gcggatacat atttgaatgt atttagaaaa ataaacaaat aggggttccg  2100
cgcacatttc cccgaaaagt gccacctgag ctctaatacg actcactata ggataggaca  2160
tttgcttctg acacaactgt gttcactagc aacctcaaac agacaccatg gattggacat  2220
ggcgaatcct ctttttggtc gcagcagcga cgggaacaca cgcagacatt caaatgactc  2280
agactacgag ctccctctcc gcatccctcg gcgaccgggt gactattagc tgccgcgcct  2340
ctcaagatat tagcaaatac cttaattggt accaacagaa gccggacgga acagtaaagc  2400
tcctgattta ccacacgtct cgacttcatt ccggcgtacc tagtaggttt tctggctctg  2460
gatctggtac cgactactcc ctcacaattt ccaatttgga acaagaagac attgccacct  2520
acttctgtca acagggcaat acgctgccat acacgttcgg cgggggtacc aaactggaga  2580
ttaccgggtc cacatctgga tccgggaagc cgggctccgg tgagggatca accaaaggcg  2640
aagtcaagtt gcaggaatct ggaccgggcc tcgttgcacc gtctcagtct ttgtccgtca  2700
cttgcacagt atcaggagtt tcccttcctg actacggggt atcttggatc cgacagccgc  2760
ccagaaaggg gctggagtgg ctcggagtga tatgggggtc tgaaaccacc tactataata  2820
gcgccctcaa gagtagactg actattatta aggataactc caagtctcag gtatttctca  2880
aaatgaacag tcttcagact gacgacacag ccatatacta ctgtgcgaaa cactattatt  2940
acggtggcag ttacgccatg gactactggg gccaggggac aagcgtaacc gtttcaagtg  3000
cagccgcaac aacgactcca gctccccggc cgcccaccccc tgcacctaca attgcgtctc  3060
aacccccttag tcttcgacct gaagcttgtc gccccgcagc aggcggggct gtccacacga  3120
ggggattgga ctttgcttgt gatatttaca tatgggcacc tcttgcagga acttgtgggg  3180
tgctgctcct cagtttggtc attaccctgt attgtaagag aggaaggaaa aaactcttgt  3240
acattttcaa acaaccgttt atgcgaccag tgcaaacgac acaagaggaa gacgggtgta  3300
gttgccgctt ccctgaagag gaagaggggg gttgtgagct gagggttaaa ttctccccgaa  3360
gtgccgatgc tccggcctat caacagggcc agaaccaact ctataacgaa cttaatctgg  3420
gaagaagaga ggaatacgat gtactggaca agcggcgagg gagagatccc gagatgggcg  3480
gcaaaccccg aagaaaaaat ccgcaggagg ggctttataa cgaattgcaa aaggataaaa  3540
tggcggaagc ttatagtgag attggaatga agggtgaaag gcgacgaggc aagggccatg  3600
acgggctcta tcagggattg tctaccgcta cgaaagacac ttacgatgcg ttgcacatgc  3660
aggctctccc accccgatag gctcgctttc ttgctgtcca atttctatta aaggttcctt  3720
tgttccctaa gtccaactac taaactgggg gatattatga agggccttga gcatctggat  3780
tctgcctaat aaaaaacatt tattttcatt gcaa                              3814
```

```
SEQ ID NO: 28          moltype = RNA  length = 3949
FEATURE                Location/Qualifiers
source                 1..3949
                       mol_type = other RNA
                       organism = synthetic construct
SEQUENCE: 28
agccacaccc tggagctagc aaaaaaaaaa aaaaaaaaaa aaaaaaaaaa gcatatgact  60
aaaaaaaaaa aaaaaaaaaa aaaaaaaaaa aaaaaaaaaa aaaaaaaaaa aaaaaaaaaa  120
aaaaaaaaaa cgcgtatcga tgatatcgcg gccgcataca gcagcaattg gcaagctgct  180
tacatagaac tcgcggcgat tggcatgccg ccttaaaatt tttattttat ttttcttttc  240
ttttccgaat cggattttgt ttttaatatt tcaaaaaaaa aaaaaaaaaa aaaaaaaacg  300
cgtgataacg caggaaagaa catgtgagca aaaggccagc aaaaggccag gaaccgtaaa  360
aaggccgcgt tgctggcgtt tttccatagg ctccgccccc ctgacgagca tcacaaaaat  420
cgacgctcaa gtcagaggtg gcgaaacccg acaggactat aaagatacca ggcgtttccc  480
cctggaagct ccctcgtgcg ctctcctgtt ccgaccctgc cgcttaccgg atacctgtcc  540
gcctttctcc cttcgggaag cgtggcgctt tctcatagct cacgctgtag gtatctcagt  600
tcggtgtagg tcgttcgctc caagctgggc tgtgtgcacg aaccccccgt tcagcccgac  660
cgctgcgcct tatccggtaa ctatcgtctt gagtccaacc cggtaagaca cgacttatcg  720
ccactggcag cagccactgg taacaggatt agcagagcga ggtatgtagg cggtgctaca  780
gagttcttga agtggtggcc taactacggc tacactagaa gaacagtatt tggtatctgc  840
gctctgctga agccagttac cttcggaaaa agagttggta gctcttgatc cggcaaacaa  900
accaccgctg gtagcggttt ttttgtttgc aagcagcaga ttacgcgcag aaaaaaagga  960
tctcaagaag atcctttgat cttttctacg gggtctgacg ctcagtggaa cgaaaactca  1020
cgttaaggga ttttggtcat gagattatca aaaaggatct tcacctagat ccttttaaat  1080
taaaaatgaa gttttaaatc aatctaaagt atatatgagt aaacttggtc tgacagttac  1140
caatgcttaa tcagtgaggc acctatctca gcgatctgtc tatttcgttc atccatagtt  1200
gcctgactcc ccgtcgtgta gataactacg atacgggagg gcttaccatc tggccccagt  1260
gctgcaatga taccgcgaga cccacgctca ccggctccag atttatcagc aataaaccag  1320
ccagccggaa gggccgagcg cagaagtggt cctgcaactt tatccgcctc catccagtct  1380
attaattgtt gccgggaagc tagagtaagt agttcgccag ttaatagttt gcgcaacgtt  1440
gttgccattg ctacaggcat cgtggtgtca cgctcgtcgt ttggtatggc ttcattcagc  1500
tccggttccc aacgatcaag gcgagttaca tgatccccca tgttgtgcaa aaaagcggtt  1560
agctccttcg gtcctccgat cgttgtcaga agtaagttgg ccgcagtgtt atcactcatg  1620
gttatggcag cactgcataa ttctcttact gtcatgccat ccgtaagatg cttttctgtg  1680
actggtgagt actcaaccaa gtcattctga gaatagtgta tgcggcgacc gagttgctct  1740
tgcccggcgt caatacggga taataccgcg ccacatagca gaactttaaa agtgctcatc  1800
attggaaaac gttcttcggg gcgaaaactc tcaaggatct taccgctgtt gagatccagt  1860
tcgatgtaac ccactcgtgc acccaactga tcttcagcat cttttacttt caccagcgtt  1920
tctgggtgag caaaaacagg aaggcaaaat gccgcaaaaa agggaataag ggcgacacgg  1980
aaatgttgaa tactcatact cttccttttt caatattatt gaagcattta tcagggttat  2040
tgtctcatga gcggatacat atttgaatgt atttagaaaa ataaacaaat aggggttccg  2100
cgcacatttc cccgaaaagt gccacctgag ctctaatacg actcactata ggataggaca  2160
tttgcttctg acacaactgt gttcactagc aacctcaaac agacaccatg gattggacat  2220
ggcgaatcct ctttttggtc gcagcagcga cgggaacaca cgcagacatt caaatgactc  2280
agactacgag ctccctctcc gcatccctcg gcgaccgggt gactattagc tgccgcgcct  2340
ctcaagatat tagcaaatac cttaattggt accaacagaa gccggacgga acagtaaagc  2400
tcctgattta ccacacgtct cgacttcatt ccggcgtacc tagtaggttt tctggctctg  2460
gatctggtac cgactactcc ctcacaattt ccaatttgga acaagaagac attgccacct  2520
```

-continued

```
acttctgtca acagggcaat acgctgccat acacgttcgg cgggggtacc aaactggaga  2580
ttaccgggtc cacatctgga tccgggaagc cgggctccgg tgagggatca accaaaggcg  2640
aagtcaagtt gcaggaatct ggaccgggcc tcgttgcacc gtctcagtct ttgtccgtca  2700
cttgcacagt atcaggagtt tcccttcctg actacggggt atcttggatc cgacagccgc  2760
ccagaaaggg gctggagtgg ctcggagtga tatgggggtc tgaaaccacc tactataata  2820
gcgccctcaa gagtagactg actattatta aggataactc caagtctcag gtatttctca  2880
aaatgaacag tcttcagact gacgacacag ccatatacta ctgtgcgaaa cactattatt  2940
acggtggcag ttacgccatg gactactggg gccaggggac aagcgtaacc gtttcaagtg  3000
cagccgcaac aacgactcca gctcccaggc cacccacccc ggcgccgact atagcatctc  3060
agcctctttc cttgagaccg gaagcatgtc gaccagccgc cggaggggcg gtccataccc  3120
gcggccttga cttcgcatgt gatttctggg ttctcgtagt agtcggcgga gtcctcgctt  3180
gttactctct gctcgtgacc gtggctttca tcatcttttg ggtacgatct aaaagaagtc  3240
gcctcttgca ttccgattat atgaatatga cccctagacg gcctgggcca acgcgcaagc  3300
attaccagcc gtatgctcct cctagagact ttgcagctta ccgctcccgg aaacgcggta  3360
ggaaaaagct cctgtatatc ttcaagcagc cctttatgcg acccgtgcag acgactcagg  3420
aggaggacgg atgctcatgc cgctttcccg aggaagagga aggcggttgc gaattgaggg  3480
tgaagttcag tagaagcgca gatgccccag cttatcagca aggtcaaaac caactgtata  3540
atgaattgaa cctgggacgg agagaagagt atgacgtcct cgataaacgg cggggcaggg  3600
accctgagat ggggggggaag cctcgaagga agaacccgca ggaagggttg tataatgaac  3660
tccagaaaga taaaatggcc gaggcatatt ccgagatagg gatgaagggc gagcggcggc  3720
gaggcaaggg gcatgatgga ctctatcagg gattgtcaac agcgactaaa gatacatatg  3780
acgctttgca catgcaggct ctgccacctc ggtaggctcg ctttcttgct gtccaatttc  3840
tattaaaggt tcctttgttc cctaagtcca actactaaac tgggggatat tatgaagggc  3900
cttgagcatc tggattctgc ctaataaaaa acatttattt tcattgcaa             3949

SEQ ID NO: 29           moltype = RNA  length = 3739
FEATURE                 Location/Qualifiers
source                  1..3739
                        mol_type = other RNA
                        organism = synthetic construct
SEQUENCE: 29
agccacaccc tggagctagc aaaaaaaaaa aaaaaaaaaa aaaaaaaaaa gcatatgact  60
aaaaaaaaaa aaaaaaaaaa aaaaaaaaaa aaaaaaaaaa aaaaaaaaaa aaaaaaaaaa  120
aaaaaaaaaa cgcgtatcga tgatatcgcg gccgcataca gcagcaattg gcaagctgct  180
tacatagaac tcgcggcgat tggcatgccg ccttaaaatt tttattttat ttttcttttc  240
ttttccgaat cggattttgt ttttaatatt tcaaaaaaaa aaaaaaaaaa aaaaaaaacg  300
cgtgataacg caggaaagaa catgtgagca aaaggccagc aaaaggccag gaaccgtaaa  360
aaggccgcgt tgctggcgtt tttccatagg ctccgccccc ctgacgagca tcacaaaaat  420
cgacgctcaa gtcagaggtg gcgaaacccg acaggactat aaagatacca ggcgtttccc  480
cctggaagct ccctcgtgcg ctctcctgtt ccgaccctgc cgcttaccgg atacctgtcc  540
gcctttctcc cttcgggaag cgtggcgctt tctcatagct cacgctgtag gtatctcagt  600
tcggtgtagg tcgttcgctc caagctgggc tgtgtgcacg aaccccccgt tcagcccgac  660
cgctgcgcct tatccggtaa ctatcgtctt gagtccaacc cggtaagaca cgacttatcg  720
ccactggcag cagccactgg taacaggatt agcagagcga ggtatgtagg cggtgctaca  780
gagttcttga agtggtggcc taactacggc tacactagaa gaacagtatt tggtatctgc  840
gctctgctga agccagttac cttcggaaaa agagttggta gctcttgatc cggcaaacaa  900
accaccgctg gtagcggttt ttttgtttgc aagcagcaga ttacgcgcag aaaaaaagga  960
tctcaagaag atcctttgat cttttctacg gggtctgacg ctcagtggaa cgaaaactca  1020
cgttaaggga ttttggtcat gagattatca aaaaggatct tcacctagat ccttttaaat  1080
taaaaatgaa gttttaaatc aatctaaagt atatatgagt aaacttggtc tgacagttac  1140
caatgcttaa tcagtgaggc acctatctca gcgatctgtc tatttcgttc atccatagtt  1200
gcctgactcc ccgtcgtgta gataactacg atacgggagg gcttaccatc tggccccagt  1260
gctgcaatga taccgcgaga cccacgctca ccggctccag atttatcagc aataaaccag  1320
ccagccggaa gggccgagcg cagaagtggt cctgcaactt tatccgcctc catccagtct  1380
attaattgtt gccgggaagc tagagtaagt agttcgccag ttaatagttt gcgcaacgtt  1440
gttgccattg ctacaggcat cgtggtgtca cgctcgtcgt ttggtatggc ttcattcagc  1500
tccggttccc aacgatcaag gcgagttaca tgatccccca tgttgtgcaa aaaagcggtt  1560
agctccttcg gtcctccgat cgttgtcaga agtaagttgg ccgcagtgtt atcactcatg  1620
gttatggcag cactgcataa ttctcttact gtcatgccat ccgtaagatg cttttctgtg  1680
actggtgagt actcaaccaa gtcattctga gaatagtgta tgcggcgacc gagttgctct  1740
tgcccggcgt caatacggga taataccgcg ccacatagca gaactttaaa agtgctcatc  1800
attggaaaac gttcttcggg gcgaaaactc tcaaggatct taccgctgtt gagatccagt  1860
tcgatgtaac ccactcgtgc acccaactga tcttcagcat cttttacttt caccagcgtt  1920
tctgggtgag caaaaacagg aaggcaaaat gccgcaaaaa agggaataag ggcgacacgg  1980
aaatgttgaa tactcatact cttccttttt caatattatt gaagcattta tcagggttat  2040
tgtctcatga gcggatacat atttgaatgt atttagaaaa ataaacaaat aggggttccg  2100
cgcacatttc cccgaaaagt gccacctgag ctctaatacg actcactata ggataggaca  2160
tttgcttctg acacaactgt gttcactagc aacctcaaac agacaccatg gattggacat  2220
ggcgaatcct cttttggtc gcagcagcga cgggaacaca cgcagacatt caaatgactc  2280
agactacgag ctccctctcc gcatccctcg gcgaccgggt gactattagc tgccgcgcct  2340
ctcaagatat tagcaaatac cttaattggt accaacagaa gccggacgga acagtaaagc  2400
tcctgattta ccacacgtct cgacttcatt ccggcgtacc tagtaggttt tctggctctg  2460
gatctggtac cgactactcc ctcacaattt ccaatttgga acaagaagac attgccacct  2520
acttctgtca acagggcaat acgctgccat acacgttcgg cgggggtacc aaactggaga  2580
ttaccgggtc cacatctgga tccgggaagc cgggctccgg tgagggatca accaaaggcg  2640
aagtcaagtt gcaggaatct ggaccgggcc tcgttgcacc gtctcagtct ttgtccgtca  2700
cttgcacagt atcaggagtt tcccttcctg actacggggt atcttggatc cgacagccgc  2760
ccagaaaggg gctggagtgg ctcggagtga tatgggggtc tgaaaccacc tactataata  2820
gcgccctcaa gagtagactg actattatta aggataactc caagtctcag gtatttctca  2880
```

```
aaatgaacag tcttcagact gacgacacag ccatatacta ctgtgcgaaa cactattatt  2940
acggtggcag ttacgccatg gactactggg gccaggggac aagcgtaacc gtttcaagtg  3000
cagccgcaac aacgactcca gctcccagac caccgacccc agcaccaaca attgcgtccc  3060
aacctctctc ccttcgacct gaagcatgtc gaccggcagc gggcggagcc gtacacacca  3120
gggggcttga tttcgcttgt gacagacgac ctccatctaa accgttctgg gtgcttgtcg  3180
ttgtgggagg ggtgcttgcc tgctacagcc tcttggtgac tgtggcgttt attatctttt  3240
gggtgcgggc gtctctccgg gtaaaattct ccagaagtgc ggatgcccct gcctatcagc  3300
agggacaaaa tcaactttac aatgaactga acttgggcag gagggaggag tatgatgttc  3360
tcgacaagag gcgaggacgc gacccggaaa tgggaggtaa acctcaaagg cgcaagaatc  3420
cccaagaggg tctttataat gaattgcaga aagataagat ggccgaagcc tacagcgaga  3480
tcggtatgaa gggagagcga cggcgaggga agggtcacga cgggttgtac caaggactgt  3540
ccacggcgac taaggatacc tatgatgcgt tgcatatgca agcactgccc cccagggcaa  3600
gttaggctcg ctttcttgct gtccaatttc tattaaaggt tcctttgttc cctaagtcca  3660
actactaaac tgggggatat tatgaagggc cttgagcatc tggattctgc ctaataaaaa  3720
acatttattt tcattgcaa                                                3739

SEQ ID NO: 30          moltype = RNA  length = 1467
FEATURE                Location/Qualifiers
source                 1..1467
                       mol_type = other RNA
                       organism = synthetic construct
SEQUENCE: 30
atggattgga catggcgaat cctctttttg gtcgcagcag cgacgggaac acacgcagac  60
attcaaatga ctcagactac gagctccctc tccgcatccc tcggcgaccg ggtgactatt  120
agctgccgcg cctctcaaga tattagcaaa taccttaatt ggtaccaaca gaagccggac  180
ggaacagtaa agctcctgat ttaccacacg tctcgacttc attccggcgt acctagtagg  240
ttttctggct ctggatctgg taccgactac tccctcacaa tttccaattt ggaacaagaa  300
gacattgcca cctacttctg tcaacagggc aatacgctgc catacacgtt cggcgggggt  360
accaaactgg agattaccgg gtccacatct ggatccggga agccgggctc cggtgaggga  420
tcaaccaaag gcgaagtcaa gttgcaggaa tctggaccgg gcctcgttgc accgtctcag  480
tctttgtccg tcacttgcac agtatcagga gtttcccttc ctgactacgg ggtatcttgg  540
atccgacagc cgcccagaaa ggggctggag tggctcggag tgatatgggg gtctgaaacc  600
acctactata atagcgccct caagagtaga ctgactatta ttaaggataa ctccaagtct  660
caggtatttc tcaaaatgaa cagtcttcag actgacgaca cagccatata ctactgtgcg  720
aaacactatt attacggtgg cagttacgcc atggactact ggggccaggg gacaagcgta  780
accgtttcaa gtgcagccgc aacaacgact ccagctccca ggccgccgac tcctgctccg  840
acgatagcct cccaaccctt gtcactccgc cctgaagcat gtaggccagc cgcaggaggc  900
gctgttcata cccgaggatt ggatttcgct tgcgatattt atatctgggc accgttggca  960
gggacatgcg gcgtgctgtt gttgagcctc gtaataacgc tgtacaggtc caagaggtcc  1020
cgccttcttc attccgatta catgaacatg acccccagac gcccaggtcc aacacgaaaa  1080
cattatcaac catatgctcc acctagggac tttgcagcat accgatctcg cgtgaaattc  1140
agccgatctg ccgacgcacc ggcctatcag caaggccaga accaacttta caacgagctt  1200
aacttgggga gaagagagga atatgatgta ctggacaagc ggcgaggtcg ggatcctgag  1260
atgggaggta aacctcaacg gagaaaaaac ccacaagaag gtctctacaa cgagctgcaa  1320
aaggacaaga tggccgaggc atattcagaa attgggatga agggcgaacg acgccgaggc  1380
aaaggacatg atggattgta ccagggcctc tctaccgcaa ctaaagatac ctacgatgcc  1440
ctccatatgc aggcacttcc cccgcga                                      1467

SEQ ID NO: 31          moltype = RNA  length = 24
FEATURE                Location/Qualifiers
source                 1..24
                       mol_type = other RNA
                       organism = synthetic construct
SEQUENCE: 31
taatacgact cactatagga tagg                                         24

SEQ ID NO: 32          moltype = AA  length = 647
FEATURE                Location/Qualifiers
source                 1..647
                       mol_type = protein
                       organism = synthetic construct
SEQUENCE: 32
MKKTAIAIAV ALAGFATVAQ ADYKDDDDKL HHHHHHKLQV KLEESGTVLA RPGASVKMSC  60
KASGYRFTNY WMHWVKQRPG QGLEWIGVIY PGNSDTSYNQ KFKGKAKLTA VTSASTAYME  120
LSSLTNEDSA VYYCTREGEG SDYWGQGTTV TVSSGGGGSG GGGSGGGGSD IQLTQSPTTM  180
AASPGEKITI TCSASSSISS NYLHWYQQKP GFSPKLLIYR TSNLASGVPA RFSGSGSGTS  240
YSLTIGTMEA EDVATYYCQQ GSSIPYTFGT KLELKRLEHH HHHHLEGGSL AALTAHQACH  300
LPLETFTRHR QPRGWEQLEQ CGYPVQRLVA LYLAARLSWN QVDQVIRNAL ASPGSGGDLG  360
EAIREQPEQA RLALTLAAAE SERFVRQGTG NDEAGAANAD VVSLTCPVAA GECAGPADSG  420
DALLERNYPT GAEFLGDGGD VSFSTRGTQN WTVERLLQAH RQLEERGYVF VGYHGTFLEA  480
AQSIVFGGVR ARSQDLDAIW RGFYIAGDPA LAYAYAQDQE PDARGRIRNG ALLRVYVPRS  540
SLPGFYRTSL TLAAPEAAGE VERLIGHPLP LRLDAITGPE EEGGRLETIL GWPLAERTVV  600
IPSAIPTDPR NVGGDLDPSS IPDKEQAISA LPDYASQPGK PPREDLK                 647

SEQ ID NO: 33          moltype = AA  length = 303
FEATURE                Location/Qualifiers
source                 1..303
                       mol_type = protein
                       organism = synthetic construct
```

```
SEQUENCE: 33
MEIQLQQSGA ELVKPGASVK LSCTGPGFNI EDYYIHWVKQ RTEQGLEWIG RIDPENDETK  60
YGPIFQGRAT ITADTSSNTV YLQLSSLTSE DTAVYYCALR GGVYWGPGTT LTVSSGGGGS  120
GGGGSGGGGS HMDVVMTQSP LTLSVAIGQS ASISCKSSQS LLDSDGKTYL NWLLQRPGQS  180
PKRLISLVSK LDSGVPDRFT GSGSGTDFTL RISRVEAEDL GIYYCWQGTH FPGTFGGGTK  240
LEIKRSGGGG SGGGGSIMRG SHHHHHHGMA SMTGGQQMGR DLYDDDDKDP SSRSAAGTME  300
FEA                                                              303

SEQ ID NO: 34          moltype = AA  length = 287
FEATURE                Location/Qualifiers
source                 1..287
                       mol_type = protein
                       organism = synthetic construct
SEQUENCE: 34
MKYLLPTAAA GLLLLAAQPA MAEVQLVQSG GGLVKPGGSL RLSCAASGFT FSSYSMNWVR  60
QAPGKGLEWV SSISSSSSYI YYADSVKGRF TISRDNAKNS LYLQMNSLRA EDTAVYYCAR  120
VTDAFDIWGQ GTMVTVSSGL GGLGGGGSGG GGSGGSSGVG SDIQMTQSPS SVSASIGDRV  180
TITCRASQGI DNWLGWYQQK PGKAPKLLIY DASNLDTGVP SRFSGSGSGT YFTLTISSLQ  240
AEDFAVYFCQ QAKAFPPTFG GGTKVDIKRG GASLVEFEQK LISEEDL                287

SEQ ID NO: 35          moltype = AA  length = 241
FEATURE                Location/Qualifiers
source                 1..241
                       mol_type = protein
                       organism = synthetic construct
SEQUENCE: 35
MQVQLQQSGP ELEKPGASVK ISCKASGYSF TGYTMNWVKQ SHGKSLEWIG LITPYNGASS  60
YNQKFRGKAT LTVDKSSSTA YMDLLSLTSE DSAVYFCARG GYDGRGFDYW GQGTTVTVSS  120
GVGGSGGGGS GGGGSDIELT QSPAIMSASP GEKVTMTCSA SSSVSYMHWY QQKSGTSPKR  180
WIYDTSKLAS GVPGRFSGSG SGNSYSLTIS SVEAEDDATY YCQQWSGYPL TFGAGTKLEI  240
K                                                                241

SEQ ID NO: 36          moltype = AA  length = 234
FEATURE                Location/Qualifiers
source                 1..234
                       mol_type = protein
                       organism = synthetic construct
SEQUENCE: 36
QVKLQESGAE LVRPGSSVKI SCKASGYVFS NYWMNWVKQR PGQGLEWIGQ IFPGDGDSNY  60
NGKFKDKATL TADKSSTTAY MHLSSLTSED SAVYFCARLN WDSYAMDYWG QGTTGGGGSG  120
GGGSGGGGSE LTQSPAIMSA SPGEKVTMTC SASSSVVYIH WYQQKSGTSP KRWIYDTSKL  180
ASGVPARFSG SGSGTSYSLT ISSMEAEDAA TYYCQQWYSD PYTFGGGTKL EINN        234

SEQ ID NO: 37          moltype = AA  length = 251
FEATURE                Location/Qualifiers
source                 1..251
                       mol_type = protein
                       organism = synthetic construct
SEQUENCE: 37
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGQ GTKVEIKSGI LGTTAASGSS  120
GGSSSGAEVQ LVQSGAEVKK PGESLKISCK GSGYSFTSYW IGWVRQMPGK GLEWMGIIYP  180
GDSDTRYSPS FQGQVTISAD KSISTAYLQW SSLKASDTAV YYCARFTYYY YDYDYAGFDY  240
WGQGTLVTVS S                                                     251

SEQ ID NO: 38          moltype = AA  length = 248
FEATURE                Location/Qualifiers
source                 1..248
                       mol_type = protein
                       organism = synthetic construct
SEQUENCE: 38
QVQLQQSGPG LVKPWQTLSL TCGISGDSVS SNSVSWDWIR QSPSRGLEWL GRTYYRSKWY  60
NEYAVSVESR ITINPDTSKN QFSLQLNSVT PEDTAIYFCV RNNYFFDLWG RGTLVTVSSG  120
ILGSGGGGSG GGGSGGGGSE IVLTQSPATL SLSPGERATL SCRASQSVSS YLAWYQQKPG  180
QAPRLLIYDA SNRATGIPAR FSGSGSGTDF TLTISSLEPE DFAVYYCQQR SNWPPMYTFG  240
QGTKLEIK                                                         248

SEQ ID NO: 39          moltype = AA  length = 110
FEATURE                Location/Qualifiers
source                 1..110
                       mol_type = protein
                       organism = synthetic construct
SEQUENCE: 39
QSVLTQPPAS GTPGQRVTIS CTGSSSNIGN NDVSWYQQLP GTAPKLLIYD DNKRPSGVPD  60
RFSGSKSGTS ASLAISGLRS EDEADYYCGS WDASLNAYVF GGGTKLTVLG            110

SEQ ID NO: 40          moltype = AA  length = 301
FEATURE                Location/Qualifiers
source                 1..301
```

```
                      mol_type = protein
                      organism = synthetic construct
SEQUENCE: 40
MAADSQTPWL LTFSLLCLLW PQEAGALPLM DIQLTQSPAI LSASPGEKVT MTCRASSSLS  60
FMHWYQQKPG SSPKPWIYAT SNLASGVPAR FSGSGSGTSY SLTISTVEAE DAASYFCHQW  120
SSNPLTFGAG TKLEISSGGG GSGGGGSGDV MGVDSGGGLV QPGGSRKLSC AAPGFTFSSF  180
GMHWVRQAPE KGLEWVAYIS SPSSTLHYAD RVKGRFTISR DNPKNTLFLQ MKLPSLCYGL  240
LGPRDHVHRL LKHHHHHHLE YPYDVPDYAT TDAAHPGRSV VPALLPLLAG TLLLLETATA  300
P                                                                 301

SEQ ID NO: 41         moltype = AA  length = 542
FEATURE               Location/Qualifiers
source                1..542
                      mol_type = protein
                      organism = synthetic construct
SEQUENCE: 41
MGWSWIFLFL LSGRDGVLSD IELTQSPASL AVSLGQRATI SCRASESVEY YVTSLMQWYQ  60
QKPGQPPKLL IFAASNVESG VPARFSGSGS GTNFSLNIHP VDEDDVAMYF CQQSRKVPYT  120
FGGGTKLEIK RGGGGSGGGG SGGGGSQVKL QQSGPGLVTP SQSLSITCTV SGFSLSDYGV  180
HWVRQSPGQG LEWLGVIWAG GGTNYNSALM SRKSISKDNS KSQVFLKMNS LQADDTAVYY  240
CARDKGYSYY YSMDYWGQGT TVTVSSASTK GPSVFPLAPS SSGSGQVKLQ QSGPELVKPG  300
ASVKISCKAS GYAFSRSWMN WVKQRPGQGL EWIGRIYPGD GDTNYNGKFK GKATLTADKS  360
SSTAYMQVSS LTSVDSAVYF CARGNTVVVP YTMDYWGQGT TVTVSSGGGG SGGGGSGGGG  420
SDIELTQSPA SLAVSLGQRA TISCRASESV DSYGNSFMHW YQQKPGQPPK LLIYLASNLE  480
SGVPARFSGS GSRTDFTLTI DPVEADDAAT YYCQQNNEDP LTFGGGTKLE LKRAAAHHHH  540
HH                                                                542

SEQ ID NO: 42         moltype = AA  length = 242
FEATURE               Location/Qualifiers
source                1..242
                      mol_type = protein
                      organism = synthetic construct
SEQUENCE: 42
QVKLEESGGG LVQAGRSLRL SCAASEHTFS SHVMGWFRQA PGKERESVAV IGWRDISTSY  60
ADSVKGRFTI SRDNAKKTLY LQMNSLKPED TAVYYCAARR IDAADFDSWG QGTQVTVSSG  120
GGGSEVQLVE SGGGLVQAGG SLRLSCAASG RTFTMGWFRQ APGKEREFVA AISLSPTLAY  180
YAESVKGRFT ISRDNAKNTV VLQMNSLKPE DTALYYCAAD RKSVMSIRPD YWGQGTQVTV  240
SS                                                                242

SEQ ID NO: 43         moltype = AA  length = 243
FEATURE               Location/Qualifiers
source                1..243
                      mol_type = protein
                      organism = synthetic construct
SEQUENCE: 43
QVQLVQSGAE VKKPGASVKV SCKASGYTFT NHIIHWVRQA PGQGLEWMGY INPYPGYHAY  60
NEKFQGRATM TSDTSTSTVY MELSSLRSED TAVYYCARDG YYRDTDVLDY WGQGTLVTVS  120
SGGGGSGGGG SGGGGSDIQM TQSPSSLSAS VGDRVTITCQ ASQDISNYLN WYQQKPGKAP  180
KLLIYYTSRL HTGVPSRFSG SGSGTDFTFT ISSLEPEDIA TYYCQQGNTL PWTFGQGTKV  240
EIK                                                               243

SEQ ID NO: 44         moltype = RNA  length = 660
FEATURE               Location/Qualifiers
source                1..660
                      mol_type = other RNA
                      organism = synthetic construct
SEQUENCE: 44
acaactacta aacctgtgct tcggacaccc tcccctgttc accctactgg gacatcacag  60
ccccaaaggc cagaggattg tagaccaagg ggcagcgtca aggggaccgg gctggatttc  120
gcttgcgata tttacatatg ggccccattg gctggcatat gcgttgcttt gcttcttagt  180
ctcataatta ccctcatcaa ttcccgccga aaccggttgt tgcaaagcga ctatatgaac  240
atgactccta ggcgcccagg actgactagg aaaccctacc agccatacgc acccgccaga  300
gactttgctg catacagacc aagagctaaa ttcagtaggt ctgccgagac tgccgctaac  360
cttcaagatc ccaaccaact ctacaatgag ctgaatttgg gaaggcgcga agagtacgat  420
gtgctggaaa agaagcgagc ccgcgacccc gaaatgggtg ggaagcaaca gcgacgccgg  480
aatccccagg agggagtcta caacgccttg caaaaggata aaatggcaga agcttactct  540
gaaattggca ccaagggggga acgaagacga ggaaaagggc atgatggttt gtaccaaggt  600
cttagcacag ctactaagga tacctatgac gctttgcata tgcaaaccct ggccccacga  660
```

-continued

```
SEQ ID NO: 45           moltype = AA  length = 237
FEATURE                 Location/Qualifiers
source                  1..237
                        mol_type = protein
                        organism = synthetic construct
SEQUENCE: 45
IQMTQSPASL STSLGETVTI QCQASEDIYS GLAWYQQKPG KSPQLLIYGA SDLQDGVPSR  60
FSGSGSGTQY SLKITSMQTE DEGVYFCQQG LTYPRTFGGG TKLELKGGGG SGGGGSGGGG  120
SEVQLQQSGA ELVRPGTSVK LSCKVSGDTI TFYYMHFVKQ RPGQGLEWIG RIDPEDESTK  180
YSEKFKNKAT LTADTSSNTA YLKLSSLTSE DTATYFCIYG GYYFDYWGQG VMVTVSS     237
```